United States Patent
Boggs et al.

(10) Patent No.: US 9,925,433 B2
(45) Date of Patent: Mar. 27, 2018

(54) GOLF CLUBS AND GOLF CLUB HEADS

(71) Applicant: NIKE, Inc., Beaverton, OR (US)

(72) Inventors: Joshua M. Boggs, Aledo, TX (US);
Philip J. Hatton, Portland, OR (US);
Brian Kammerer, Fort Worth, TX (US);
Mario A. Lafortune, Fort Worth, TX (US);
Michael Wallans, Portland, OR (US);
Robert M. Boyd, Flower Mound, TX (US);
Jeffrey A. Hadden, Delaware, OH (US);
Sherry L. Jones, Pataskala, OH (US);
Gregory S. Kramer, Hilliard, OH (US);
James H. Lua, Columbus, OH (US);
John T. Stites, Sallisaw, OK (US);
Douglas A. Thornton, Columbus, OH (US);
Daniel F. Wisniewski, Columbus, OH (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 15/194,150

(22) Filed: Jun. 27, 2016

(65) Prior Publication Data
US 2016/0303443 A1 Oct. 20, 2016

Related U.S. Application Data

(63) Continuation-in-part of application No. 14/632,833, filed on Feb. 26, 2015, now Pat. No. 9,403,078, which
(Continued)

(51) Int. Cl.
*A63B 57/00* (2015.01)
*A63B 53/04* (2015.01)
(Continued)

(52) U.S. Cl.
CPC ........ *A63B 53/0487* (2013.01); *A61B 5/1122* (2013.01); *A61B 5/6895* (2013.01);
(Continued)

(58) Field of Classification Search
USPC .................................................. 473/222–226
See application file for complete search history.

(56) References Cited

U.S. PATENT DOCUMENTS

| | | |
|---|---|---|
| 3,270,564 A | 9/1966 | Evans |
| 3,788,647 A | 1/1974 | Evans |
(Continued)

FOREIGN PATENT DOCUMENTS

| | | |
|---|---|---|
| CA | 2139690 A1 | 7/1996 |
| CN | 2411030 Y | 12/2000 |
(Continued)

OTHER PUBLICATIONS

May 30, 2012—(WO) International Search Report and Written Opinion App. No. PCT/US2012/022021.

*Primary Examiner* — Ronald Laneau
(74) *Attorney, Agent, or Firm* — Banner & Witcoff, Ltd.

(57) ABSTRACT

Golf clubs according to at least some example aspects of this disclosure may include a golf club head and a shaft configured to engage with the golf club head which includes a grip engaged with the shaft. Further, the golf club may include a monitoring device, which includes a sensor and a transmitter. Additionally, the monitoring device may be configured to determine data related to the characteristics of a golf swing. Further, the monitoring device may be configured to transmit the data related to the characteristics of a golf swing to a remote computer.

18 Claims, 58 Drawing Sheets

Related U.S. Application Data is a continuation of application No. 13/828,793, filed on Mar. 14, 2013, now Pat. No. 8,986,130, which is a continuation-in-part of application No. 13/250,051, filed on Sep. 30, 2011, now Pat. No. 8,668,595, application No. 15/194,150, which is a continuation-in-part of application No. 14/632,829, filed on Feb. 26, 2015, now Pat. No. 9,440,127, which is a continuation of application No. 13/828,793, filed on Mar. 14, 2013, now Pat. No. 8,986,130, application No. 15/194,150, which is a continuation-in-part of application No. 13/907,366, filed on May 31, 2013, now Pat. No. 9,375,624, which is a continuation-in-part of application No. 13/250,051, application No. 15/194,150, which is a continuation-in-part of application No. 13/906,345, filed on May 31, 2013, now Pat. No. 9,409,076, which is a continuation-in-part of application No. 13/250,051, application No. 15/194,150, which is a continuation-in-part of application No. 13/906,346, filed on May 31, 2013, now Pat. No. 9,433,844, which is a continuation-in-part of application No. 13/250,051, application No. 15/194,150, which is a continuation-in-part of application No. 13/906,347, filed on May 31, 2013, now Pat. No. 9,433,845, which is a continuation-in-part of application No. 13/250,051, application No. 15/194,150, which is a continuation-in-part of application No. 13/906,348, filed on May 31, 2013, now Pat. No. 9,409,073, which is a continuation-in-part of application No. 13/250,051.

(60) Provisional application No. 61/665,834, filed on Jun. 28, 2012, provisional application No. 61/653,771, filed on May 31, 2012, provisional application No. 61/480,322, filed on Apr. 28, 2011.

(51) Int. Cl.
| | |
|---|---|
| *A63B 69/36* | (2006.01) |
| *A63B 71/06* | (2006.01) |
| *A63B 53/10* | (2015.01) |
| *A63B 53/14* | (2015.01) |
| *G06F 3/0346* | (2013.01) |
| *A63B 60/16* | (2015.01) |
| *A63B 60/50* | (2015.01) |
| *G01S 19/19* | (2010.01) |
| *G06K 9/00* | (2006.01) |
| *G06Q 50/00* | (2012.01) |
| *A61B 5/00* | (2006.01) |
| *A61B 5/11* | (2006.01) |
| *A63B 49/08* | (2015.01) |
| *A63B 102/24* | (2015.01) |
| *A63B 49/035* | (2015.01) |
| *A63B 59/70* | (2015.01) |
| *A63B 59/20* | (2015.01) |
| *A63B 102/18* | (2015.01) |
| *A63B 59/50* | (2015.01) |
| *A63B 71/00* | (2006.01) |

(52) U.S. Cl.
CPC ........ *A63B 53/047* (2013.01); *A63B 53/0466* (2013.01); *A63B 53/10* (2013.01); *A63B 53/14* (2013.01); *A63B 60/16* (2015.10); *A63B 60/50* (2015.10); *A63B 69/3632* (2013.01); *A63B 69/3685* (2013.01); *A63B 71/0619* (2013.01); *A63B 71/0622* (2013.01); *G01S 19/19* (2013.01); *G06F 3/0346* (2013.01); *G06K 9/00342* (2013.01); *G06Q 50/01* (2013.01); *A61B 2503/10* (2013.01); *A61B 2505/09* (2013.01); *A63B 49/035* (2015.10); *A63B 49/08* (2013.01); *A63B 53/04* (2013.01); *A63B 59/20* (2015.10); *A63B 59/50* (2015.10); *A63B 59/70* (2015.10); *A63B 2053/0433* (2013.01); *A63B 2053/0437* (2013.01); *A63B 2071/0063* (2013.01); *A63B 2071/068* (2013.01); *A63B 2071/0647* (2013.01); *A63B 2102/18* (2015.10); *A63B 2102/24* (2015.10); *A63B 2209/00* (2013.01); *A63B 2220/12* (2013.01); *A63B 2220/16* (2013.01); *A63B 2220/30* (2013.01); *A63B 2220/40* (2013.01); *A63B 2220/53* (2013.01); *A63B 2220/803* (2013.01); *A63B 2220/833* (2013.01); *A63B 2225/15* (2013.01); *A63B 2225/20* (2013.01); *A63B 2225/50* (2013.01); *A63B 2225/54* (2013.01)

(56) References Cited

U.S. PATENT DOCUMENTS

| | | |
|---|---|---|
| 3,792,863 A | 2/1974 | Evans |
| 3,806,131 A | 4/1974 | Evans |
| 3,945,646 A | 3/1976 | Hammond |
| 4,898,389 A | 2/1990 | Plutt |
| 4,940,236 A | 7/1990 | Allen |
| 4,991,850 A | 2/1991 | Wilhlem |
| 5,221,088 A | 6/1993 | McTeigue et al. |
| 5,233,544 A | 8/1993 | Kobayashi |
| 5,245,537 A | 9/1993 | Barber |
| 5,332,225 A | 7/1994 | Ura |
| 5,340,063 A * | 8/1994 | Hsieh ............... A63B 55/53 206/315.7 |
| 5,354,063 A | 10/1994 | Curchod |
| 5,364,093 A | 11/1994 | Huston et al. |
| 5,372,365 A | 12/1994 | McTeigue et al. |
| 5,413,345 A | 5/1995 | Nauck |
| 5,429,327 A | 7/1995 | Adams |
| 5,441,269 A | 8/1995 | Henwood |
| 5,478,082 A | 12/1995 | De Knight et al. |
| 5,507,485 A | 4/1996 | Fisher |
| 5,524,081 A | 6/1996 | Paul |
| 5,616,832 A | 4/1997 | Nauck |
| 5,634,855 A | 6/1997 | King |
| 5,681,993 A | 10/1997 | Heitman |
| 5,718,641 A | 2/1998 | Lin |
| 5,724,265 A | 3/1998 | Hutchings |
| 5,728,006 A | 3/1998 | Teitell et al. |
| 5,779,555 A | 7/1998 | Nomura et al. |
| 5,792,000 A | 8/1998 | Weber et al. |
| 5,792,001 A | 8/1998 | Henwood |
| 5,826,874 A | 10/1998 | Teitell et al. |
| 5,951,410 A | 9/1999 | Butler et al. |
| 5,955,667 A | 9/1999 | Fyfe |
| 5,973,596 A | 10/1999 | French et al. |
| 6,012,988 A | 1/2000 | Burke |
| 6,018,705 A | 1/2000 | Gaudet et al. |
| 6,044,704 A | 4/2000 | Sacher |
| 6,045,364 A | 4/2000 | Dugan et al. |
| 6,052,654 A | 4/2000 | Gaudet et al. |
| 6,196,932 B1 | 3/2001 | Marsh et al. |
| 6,224,493 B1 | 5/2001 | Lee et al. |
| 6,248,021 B1 | 6/2001 | Ognjanovic |
| 6,261,102 B1 | 7/2001 | Dugan et al. |
| 6,270,422 B1 | 8/2001 | Fisher |
| 6,299,553 B1 | 10/2001 | Petuchowski et al. |
| 6,402,634 B2 | 6/2002 | Lee et al. |
| 6,413,167 B1 | 7/2002 | Burke |
| 6,430,843 B1 | 8/2002 | Potter et al. |
| 6,431,990 B1 | 8/2002 | Manwaring |
| 6,441,745 B1 | 8/2002 | Gates |
| 6,456,938 B1 | 9/2002 | Barnard |
| 6,561,917 B2 | 5/2003 | Manwaring |
| 6,579,190 B2 | 6/2003 | Yamamoto |

(56) References Cited

U.S. PATENT DOCUMENTS

| | | |
|---|---|---|
| 6,607,450 B1 | 8/2003 | Hackman |
| 6,638,175 B2 | 10/2003 | Lee et al. |
| 6,648,769 B2 | 11/2003 | Lee et al. |
| 6,697,820 B1 | 2/2004 | Tarlie |
| 6,757,572 B1 | 6/2004 | Forest |
| 6,802,772 B1 | 10/2004 | Kunzle et al. |
| 6,819,247 B2 | 11/2004 | Bimbach et al. |
| 6,821,209 B2 | 11/2004 | Manwaring et al. |
| 6,876,947 B1 | 4/2005 | Darley et al. |
| 6,882,955 B1 | 4/2005 | Dhlenbusch et al. |
| 6,900,759 B1 | 5/2005 | Katayama |
| 6,923,729 B2 | 8/2005 | McGinty et al. |
| 6,929,558 B2 | 8/2005 | Manwaring et al. |
| 6,991,552 B2 | 1/2006 | Burke |
| 7,004,848 B2 | 2/2006 | Konow |
| 7,021,140 B2 | 4/2006 | Perkins |
| 7,037,198 B2 | 5/2006 | Hameen-Anttila |
| 7,041,014 B2 | 5/2006 | Wright et al. |
| 7,118,498 B2 | 10/2006 | Meadows et al. |
| 7,121,962 B2 | 10/2006 | Reeves |
| 7,125,340 B1 | 10/2006 | Priester et al. |
| 7,160,200 B2 | 1/2007 | Grober |
| 7,175,177 B2 | 2/2007 | Meifu et al. |
| 7,175,511 B2 | 2/2007 | Ueda et al. |
| 7,214,138 B1 | 5/2007 | Stivers et al. |
| 7,234,351 B2 | 6/2007 | Perkins |
| 7,235,020 B1 | 6/2007 | Christensen |
| 7,264,554 B2 | 9/2007 | Bentley |
| 7,264,555 B2 | 9/2007 | Lee et al. |
| 7,310,895 B2 | 12/2007 | Whittlesey et al. |
| 7,602,301 B1 | 10/2009 | Stirling et al. |
| 7,627,451 B2 | 12/2009 | Vock et al. |
| 7,647,071 B2 | 1/2010 | Rofougaran et al. |
| 7,691,004 B1 | 4/2010 | Lueders |
| 7,736,242 B2 | 6/2010 | Stites et al. |
| 7,771,263 B2 | 8/2010 | Telford |
| 7,780,535 B2 | 8/2010 | Hagood et al. |
| 7,789,742 B1 | 9/2010 | Murdock et al. |
| 7,800,480 B1 | 9/2010 | Joseph et al. |
| 7,801,575 B1 | 9/2010 | Balardeta et al. |
| 7,804,404 B1 | 9/2010 | Balardeta et al. |
| 7,811,182 B2 | 10/2010 | Ligotti, III et al. |
| 7,821,407 B2 | 10/2010 | Shears et al. |
| 7,825,815 B2 | 11/2010 | Shears et al. |
| 7,831,212 B1 | 11/2010 | Balardeta et al. |
| 7,837,574 B2 | 11/2010 | Brunner |
| 7,837,575 B2 | 11/2010 | Lee et al. |
| 7,853,211 B1 | 12/2010 | Balardeta et al. |
| 7,857,705 B1 | 12/2010 | Galloway |
| 7,881,499 B2 | 2/2011 | Bissonnette et al. |
| 7,883,428 B1 | 2/2011 | Balardeta et al. |
| 7,887,440 B2 | 2/2011 | Wright et al. |
| 7,892,102 B1 | 2/2011 | Galloway |
| 7,941,097 B2 | 5/2011 | Balardeta et al. |
| 7,946,926 B1 | 5/2011 | Balardeta et al. |
| 7,957,767 B2 | 6/2011 | Rofougaran |
| 7,978,081 B2 | 7/2011 | Shears et al. |
| 8,025,586 B2 | 9/2011 | Teramoto |
| 8,052,539 B2 | 11/2011 | Kimber |
| 8,117,903 B2 | 2/2012 | Golden et al. |
| 8,226,495 B2 | 7/2012 | Savarese et al. |
| 8,330,284 B2 | 12/2012 | Weston et al. |
| 8,337,335 B2 | 12/2012 | Dugan |
| 8,342,978 B2 | 1/2013 | Tamura |
| 8,430,770 B2 | 4/2013 | Dugan |
| 8,465,376 B2 | 6/2013 | Bentley |
| 8,534,121 B2 | 9/2013 | Golden et al. |
| 8,593,286 B2 | 11/2013 | Razoumov et al. |
| 8,696,450 B2 | 4/2014 | Rose et al. |
| 8,715,096 B2 | 5/2014 | Cherbini |
| 8,784,228 B2 | 7/2014 | Morin et al. |
| 8,801,532 B2 | 8/2014 | Katayama |
| 8,840,483 B1 | 9/2014 | Steusloff et al. |
| 8,894,502 B2 | 11/2014 | Rose |
| 8,941,723 B2 | 1/2015 | Bentley et al. |
| 8,994,826 B2 | 3/2015 | Bentley |
| 9,199,147 B2 | 12/2015 | Azizi |
| 2001/0005695 A1 | 6/2001 | Lee et al. |
| 2001/0035880 A1 | 11/2001 | Musatov et al. |
| 2001/0053720 A1 | 12/2001 | Lee et al. |
| 2002/0004723 A1 | 1/2002 | Meifu et al. |
| 2002/0019677 A1 | 2/2002 | Lee |
| 2002/0049507 A1 | 4/2002 | Hameen-Anttila |
| 2002/0052246 A1 | 5/2002 | Burke |
| 2002/0052750 A1 | 5/2002 | Hirooka |
| 2002/0072815 A1 | 6/2002 | McDonough et al. |
| 2002/0077189 A1 | 6/2002 | Tuer |
| 2002/0082775 A1 | 6/2002 | Meadows et al. |
| 2002/0107085 A1 | 8/2002 | Lee et al. |
| 2002/0123386 A1 | 9/2002 | Perlmutter |
| 2002/0151994 A1 | 10/2002 | Sisco |
| 2002/0160848 A1 | 10/2002 | Burke |
| 2002/0173364 A1 | 11/2002 | Boscha |
| 2002/0173365 A1 | 11/2002 | Boscha |
| 2002/0183657 A1 | 12/2002 | Socci et al. |
| 2003/0008722 A1 | 1/2003 | Konow |
| 2003/0009913 A1 | 1/2003 | Potter et al. |
| 2003/0014134 A1 | 1/2003 | Morgan |
| 2003/0036436 A1 | 2/2003 | Casanova et al. |
| 2003/0040380 A1 | 2/2003 | Wright et al. |
| 2003/0132844 A1 | 7/2003 | Walker |
| 2003/0191547 A1 | 10/2003 | Morse |
| 2003/0207718 A1 | 11/2003 | Perlmutter |
| 2004/0067797 A1 | 4/2004 | Knecht |
| 2004/0106460 A1 | 6/2004 | Lee et al. |
| 2004/0142603 A1 | 7/2004 | Walker |
| 2004/0177531 A1 | 9/2004 | DiBenedetto et al. |
| 2004/0204257 A1 | 10/2004 | Boscha et al. |
| 2004/0225199 A1 | 11/2004 | Evanyk et al. |
| 2004/0259651 A1 | 12/2004 | Storek |
| 2005/0017454 A1 | 1/2005 | Endo et al. |
| 2005/0032582 A1 | 2/2005 | Mahajan et al. |
| 2005/0037862 A1 | 2/2005 | Hagood et al. |
| 2005/0043109 A1 | 2/2005 | Buckley et al. |
| 2005/0054457 A1 | 3/2005 | Eyestone et al. |
| 2005/0079922 A1 | 4/2005 | Priester et al. |
| 2005/0096761 A1 | 5/2005 | Hanover et al. |
| 2005/0188566 A1 | 9/2005 | Whittlesey et al. |
| 2005/0215340 A1 | 9/2005 | Stites et al. |
| 2005/0227775 A1 | 10/2005 | Cassady et al. |
| 2005/0240294 A1 | 10/2005 | Jones et al. |
| 2005/0261073 A1 | 11/2005 | Farrington et al. |
| 2005/0282650 A1 | 12/2005 | Miettinen et al. |
| 2005/0288119 A1 | 12/2005 | Wang et al. |
| 2006/0025229 A1 | 2/2006 | Mahajan et al. |
| 2006/0029916 A1 | 2/2006 | Boscha |
| 2006/0040757 A1 | 2/2006 | Rosselli |
| 2006/0052173 A1 | 3/2006 | Telford |
| 2006/0063600 A1 | 3/2006 | Grober |
| 2006/0084516 A1 | 4/2006 | Eyestone et al. |
| 2006/0089845 A1 | 4/2006 | Marcell et al. |
| 2006/0094520 A1 | 5/2006 | Kostuj |
| 2006/0105849 A1 | 5/2006 | Brunner |
| 2006/0105853 A1 | 5/2006 | Glass |
| 2006/0109116 A1 | 5/2006 | Keays |
| 2006/0122002 A1 | 6/2006 | Konow |
| 2006/0166737 A1 | 7/2006 | Bentley |
| 2006/0166738 A1 | 7/2006 | Eyestone et al. |
| 2006/0184336 A1 | 8/2006 | Kolen |
| 2006/0194178 A1 | 8/2006 | Goldstein |
| 2006/0199659 A1 | 9/2006 | Caldwell |
| 2006/0224306 A1 | 10/2006 | Workman et al. |
| 2006/0276256 A1 | 12/2006 | Storek |
| 2006/0287118 A1 | 12/2006 | Wright et al. |
| 2007/0006489 A1 | 1/2007 | Case et al. |
| 2007/0010341 A1 | 1/2007 | Miettinen et al. |
| 2007/0011919 A1 | 1/2007 | Case |
| 2007/0087866 A1 | 4/2007 | Meadows et al. |
| 2007/0111811 A1 | 5/2007 | Grober |
| 2007/0129178 A1 | 6/2007 | Reeves |
| 2007/0135225 A1 | 6/2007 | Nieminen et al. |
| 2007/0135237 A1 | 6/2007 | Reeves |
| 2007/0145700 A1* | 6/2007 | Ambrose ............ A45C 5/145 280/47.26 |

(56) References Cited

U.S. PATENT DOCUMENTS

| | | |
|---|---|---|
| 2007/0191126 A1 | 8/2007 | Mandracken |
| 2007/0238538 A1 | 10/2007 | Priester |
| 2007/0270214 A1 | 11/2007 | Bentley |
| 2008/0039222 A1 | 2/2008 | Kiraly |
| 2008/0051208 A1 | 2/2008 | Lee et al. |
| 2008/0076580 A1 | 3/2008 | Murdock et al. |
| 2008/0085778 A1 | 4/2008 | Dugan |
| 2008/0085788 A1 | 4/2008 | Rainer et al. |
| 2008/0125288 A1 | 5/2008 | Case |
| 2008/0188310 A1 | 8/2008 | Murdock |
| 2008/0200275 A1 | 8/2008 | Wagen et al. |
| 2008/0218343 A1 | 9/2008 | Lee et al. |
| 2008/0242354 A1 | 10/2008 | Rofougaran |
| 2008/0287205 A1 | 11/2008 | Katayama |
| 2008/0318703 A1 | 12/2008 | Mooney |
| 2009/0018795 A1 | 1/2009 | Priester et al. |
| 2009/0048070 A1 | 2/2009 | Vincent et al. |
| 2009/0111602 A1 | 4/2009 | Savarese et al. |
| 2009/0120197 A1 | 5/2009 | Golden et al. |
| 2009/0131190 A1 | 5/2009 | Kimber |
| 2009/0131191 A1 | 5/2009 | Priester et al. |
| 2009/0163285 A1 | 6/2009 | Kwon |
| 2009/0165530 A1 | 7/2009 | Golden et al. |
| 2009/0165531 A1 | 7/2009 | Golden et al. |
| 2009/0203460 A1 | 8/2009 | Clark |
| 2009/0209358 A1 | 8/2009 | Niegowski |
| 2009/0247312 A1 | 10/2009 | Sato et al. |
| 2009/0254204 A1 | 10/2009 | Kostuj |
| 2009/0260426 A1 | 10/2009 | Lieberman et al. |
| 2009/0270743 A1 | 10/2009 | Dugan et al. |
| 2009/0321290 A1* | 12/2009 | Kuo ................ A63B 47/005 206/315.9 |
| 2010/0048314 A1 | 2/2010 | Hsu et al. |
| 2010/0049468 A1 | 2/2010 | Papadourakis |
| 2010/0063778 A1 | 3/2010 | Schrock et al. |
| 2010/0063779 A1 | 3/2010 | Schrock et al. |
| 2010/0067566 A1 | 3/2010 | Rofougaran et al. |
| 2010/0093457 A1 | 4/2010 | Ahem et al. |
| 2010/0093458 A1 | 4/2010 | Davenport et al. |
| 2010/0099509 A1 | 4/2010 | Ahem et al. |
| 2010/0113174 A1 | 5/2010 | Ahem |
| 2010/0117837 A1 | 5/2010 | Stirling et al. |
| 2010/0121227 A1 | 5/2010 | Stirling et al. |
| 2010/0121228 A1 | 5/2010 | Stirling et al. |
| 2010/0130298 A1 | 5/2010 | Dugan et al. |
| 2010/0144455 A1 | 6/2010 | Ahem |
| 2010/0144456 A1 | 6/2010 | Ahem |
| 2010/0154255 A1 | 6/2010 | Robinson et al. |
| 2010/0201512 A1 | 8/2010 | Stirling et al. |
| 2010/0210371 A1 | 8/2010 | Sato et al. |
| 2010/0216563 A1 | 8/2010 | Stites et al. |
| 2010/0216564 A1 | 8/2010 | Stites et al. |
| 2010/0216565 A1 | 8/2010 | Stites et al. |
| 2010/0222152 A1 | 9/2010 | Jaekel et al. |
| 2010/0255922 A1 | 10/2010 | Lueders |
| 2010/0304877 A1 | 12/2010 | Iwahashi et al. |
| 2010/0308105 A1 | 12/2010 | Savarese et al. |
| 2011/0028230 A1 | 2/2011 | Balardeta et al. |
| 2011/0053698 A1 | 3/2011 | Stites et al. |
| 2011/0081978 A1 | 4/2011 | Murdock et al. |
| 2011/0082571 A1 | 4/2011 | Murdock et al. |
| 2011/0087344 A1 | 4/2011 | Murdock et al. |
| 2011/0092260 A1 | 4/2011 | Murdock et al. |
| 2011/0130223 A1 | 6/2011 | Murdock et al. |
| 2011/0151977 A1 | 6/2011 | Murdock et al. |
| 2011/0212757 A1 | 9/2011 | Murdock et al. |
| 2011/0224011 A1 | 9/2011 | Denton et al. |
| 2011/0224025 A1 | 9/2011 | Balardeta et al. |
| 2011/0230273 A1 | 9/2011 | Niegowski et al. |
| 2011/0281621 A1 | 11/2011 | Murdock et al. |
| 2011/0306435 A1 | 12/2011 | Seo |
| 2012/0019140 A1 | 1/2012 | Maxik et al. |
| 2012/0052972 A1 | 3/2012 | Bentley |
| 2012/0120572 A1 | 5/2012 | Bentley |
| 2012/0191405 A1 | 7/2012 | Molyneux et al. |
| 2012/0289354 A1 | 11/2012 | Cottam et al. |
| 2013/0041590 A1 | 2/2013 | Burich et al. |
| 2013/0065711 A1 | 3/2013 | Ueda et al. |
| 2013/0260922 A1 | 10/2013 | Yontz et al. |
| 2013/0324274 A1 | 12/2013 | Stites |
| 2014/0228649 A1 | 8/2014 | Rayner et al. |
| 2014/0339110 A1* | 11/2014 | Soracco ................ A63B 55/00 206/315.3 |
| 2014/0364246 A1 | 12/2014 | Davenport |
| 2015/0340904 A1 | 11/2015 | Munson et al. |
| 2016/0190817 A1* | 6/2016 | Hartelt ................ H02J 7/0044 307/104 |

FOREIGN PATENT DOCUMENTS

| | | |
|---|---|---|
| CN | 2487416 Y | 4/2002 |
| CN | 2688331 Y | 3/2005 |
| CN | 1984698 A | 6/2007 |
| CN | 101352609 A | 1/2009 |
| CN | 101918090 A | 12/2010 |
| CN | 101927084 A | 12/2010 |
| DE | 202007013632 U1 | 12/2007 |
| EP | 2332619 A1 | 6/2011 |
| GB | 2517712 A | 3/2015 |
| JP | S62176470 A | 8/1987 |
| JP | H03-60680 A | 3/1991 |
| JP | H0355077 A | 3/1991 |
| JP | H06237 | 1/1994 |
| JP | H08000785 | 1/1996 |
| JP | H08131599 A | 5/1996 |
| JP | H08173586 | 7/1996 |
| JP | 2001264016 A | 9/2001 |
| JP | 2006247023 A | 9/2006 |
| JP | 2007530151 A | 11/2007 |
| JP | 2008506421 A | 3/2008 |
| JP | 2008073210 A | 4/2008 |
| JP | 2008289866 A | 12/2008 |
| JP | 2009534546 A | 9/2009 |
| JP | 06000237 B2 | 9/2016 |
| KR | 20060090501 A | 8/2006 |
| KR | 1020060114969 | 11/2006 |
| KR | 20070095407 A | 9/2007 |
| KR | 20090129246 A | 12/2009 |
| KR | 20100020131 A | 2/2010 |
| KR | 20100051153 A | 5/2010 |
| KR | 20100905917 A | 9/2010 |
| KR | 101002846 B1 | 12/2010 |
| KR | 20110005247 A | 1/2011 |
| WO | 1999065574 A2 | 12/1999 |
| WO | 0215993 A1 | 2/2002 |
| WO | 2004056425 A2 | 7/2004 |
| WO | 2005094953 A2 | 10/2005 |
| WO | 2005118086 A1 | 12/2005 |
| WO | 2006014459 A2 | 2/2006 |
| WO | 2007123970 A2 | 11/2007 |
| WO | 2009152456 A2 | 12/2009 |
| WO | 2012027726 A2 | 3/2012 |
| WO | 2012138543 A2 | 10/2012 |
| WO | 2012149385 A1 | 11/2012 |
| WO | 2016054249 A1 | 4/2016 |

* cited by examiner

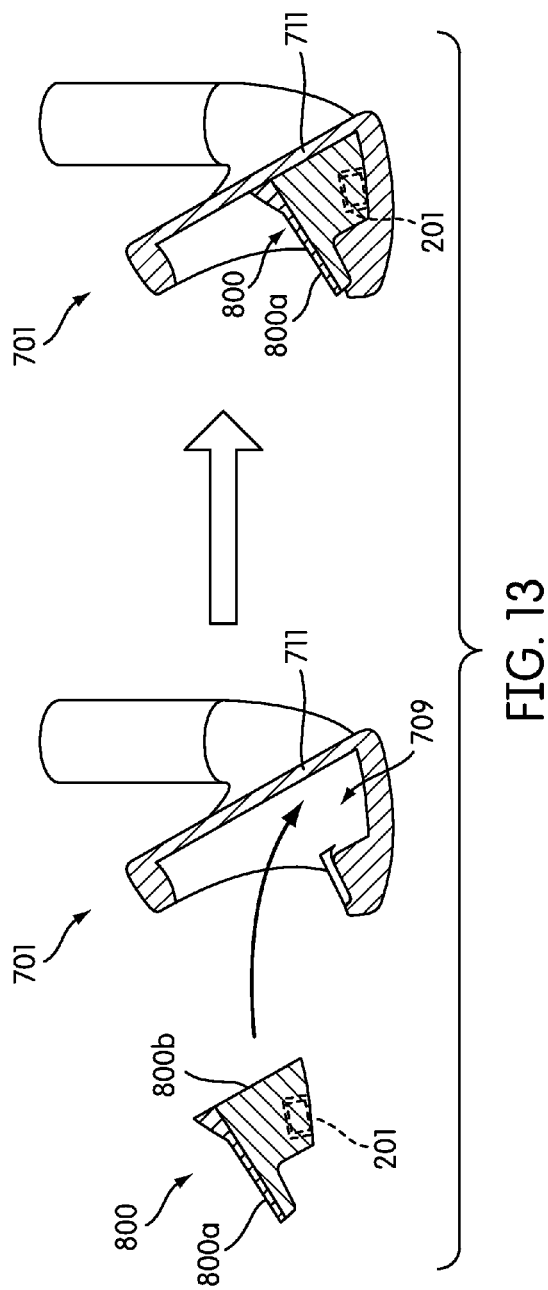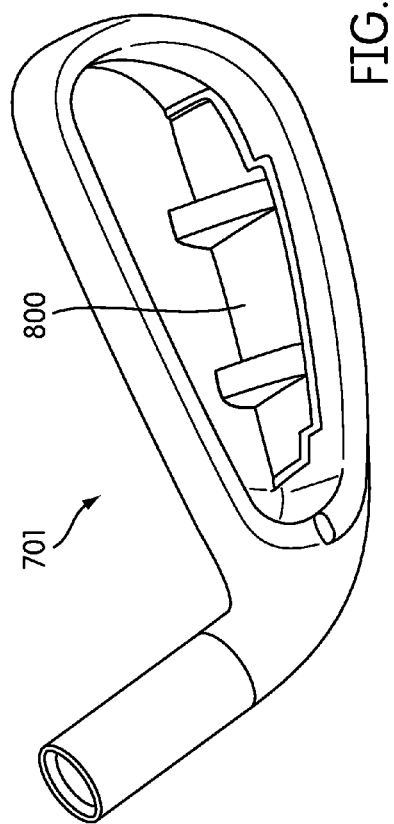
FIG. 13
FIG. 14

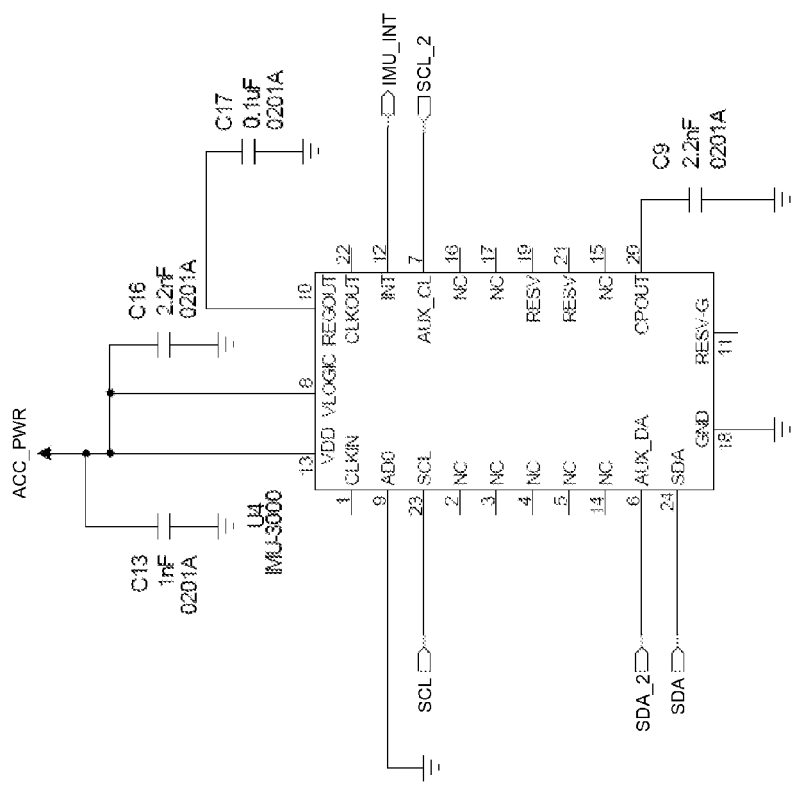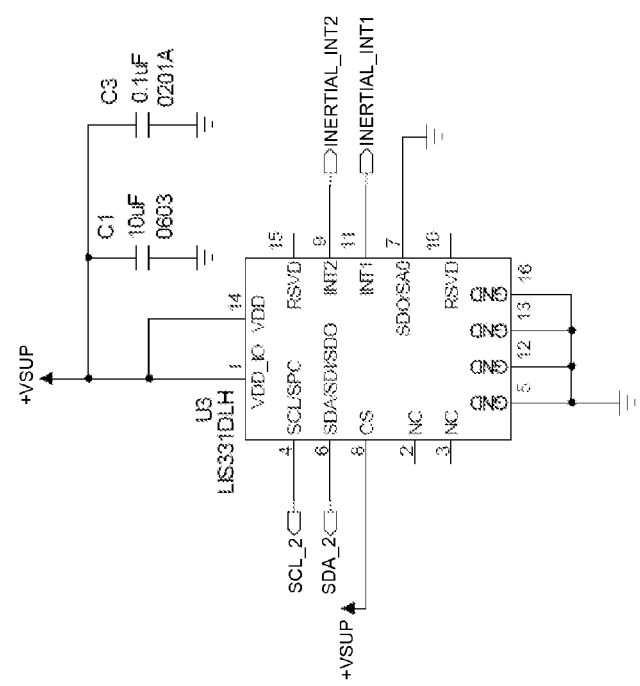
FIG. 18A

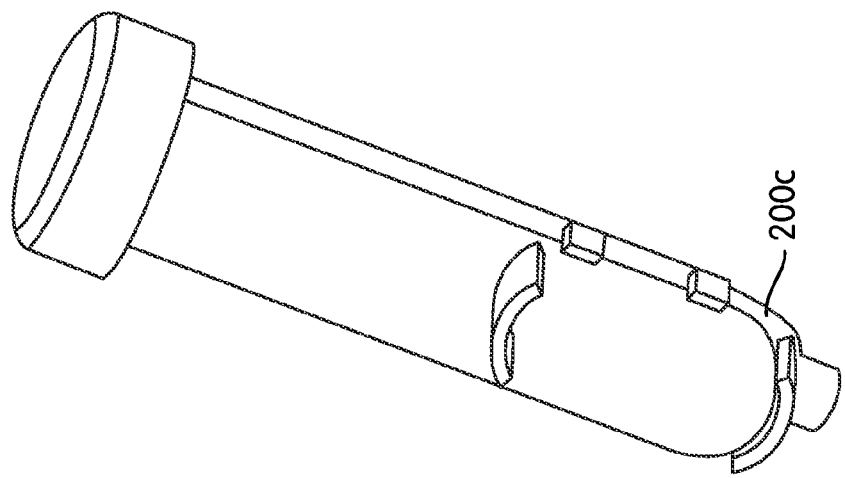
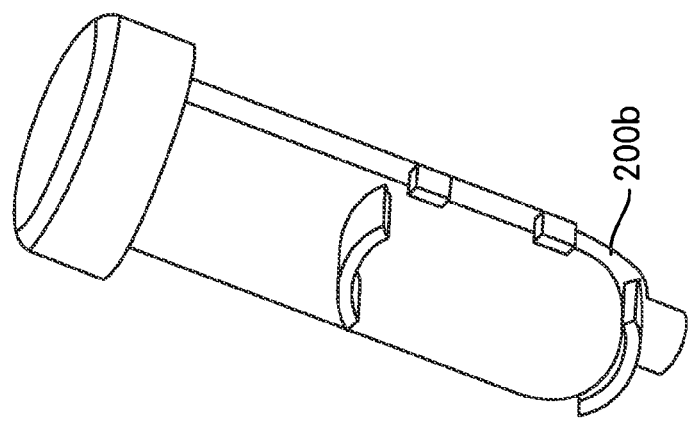
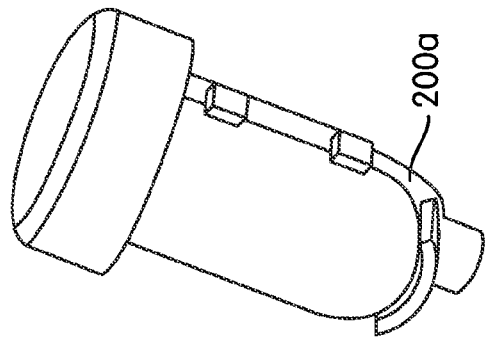
FIG. 23A

GOLF CLUBS AND GOLF CLUB HEADS

CROSS-REFERENCE TO RELATED APPLICATIONS

This application is a continuation-in-part application of U.S. patent application Ser. No. 13/906,345 filed on May 31, 2013, which claims priority to U.S. Patent Application No. 61/653,771 filed on May 31, 2012, and is also a continuation-in-part application of U.S. patent application Ser. No. 13/250,051 filed Sep. 30, 2011 now U.S. Pat. No. 8,668,595), which in turn claims the benefit of U.S. Provisional Application Ser. No. 61/480,322, filed Apr. 28, 2011.

This application is also a continuation-in-part application of U.S. patent application Ser. No. 13/906,346 filed on May 31, 2013, which claims priority to U.S. Provisional Application No. 61/653,771 filed May 31, 2012 and is also a continuation-in-part application of U.S. patent application Ser. No. 13/250,051 filed Sep. 30, 2011 (now U.S. Pat. No. 8,668,595), which in turn claims the benefit of U.S. Patent Application No. 61/480,322 filed Apr. 28, 2011.

This application is also a continuation-in-part application of U.S. patent application Ser. No. 13/906,347 filed on May 31, 2013, which claims priority to U.S. Provisional Application No. 61/653,771 filed May 31, 2012 and is also a continuation-in-part application of U.S. patent application Ser. No. 13/250,051 filed Sep. 30, 2011 (now U.S. Pat. No. 8,668,595), which in turn claims the benefit of U.S. Provisional Application Ser. No. 61/480,322, filed Apr. 28, 2011.

This application is also a continuation-in-part application of U.S. patent application Ser. No. 13/906,348 filed on May 31, 2013 which claims the benefit of U.S. Provisional Application No. 61/653,771 filed on May 31, 2012 and is also a continuation-in-part-application of U.S. patent application Ser. No. 13/250,051 filed Sep. 30, 2011 (now U.S. Pat. No. 8,668,595) which in turn claims the benefit of U.S. Provisional Application Ser. No. 61/480,322, filed Apr. 28, 2011.

This application is also a continuation-in-part application of U.S. patent application Ser. No. 13/907,366 filed on May 31, 2013 which claims the benefit of U.S. Provisional Application No. 61/653,771 filed on May 31, 2012 and is also a continuation-in-part-application of U.S. patent application Ser. No. 13/250,051 filed Sep. 30, 2011 (now U.S. Pat. No. 8,668,595), which in turn claims the benefit of U.S. Provisional Application Ser. No. 61/480,322 filed Apr. 28, 2011.

This application is also a continuation-in-part application of U.S. patent application Ser. No. 14/632,833 filed on Feb. 26, 2015, which claims the benefit of and is a continuation of U.S. patent application Ser. No. 13/828,793, filed Mar. 14, 2013 (now U.S. Pat. No. 8,986,130), which claims priority to both U.S. Provisional Application No. 61/665,834 filed Jun. 28, 2012 and U.S. Provisional Application No. 61/653,771 filed May 31, 2012 and is also a continuation-in-part application of U.S. patent application Ser. No. 13/250,051 filed Sep. 30, 2011 (now U.S. Pat. No. 8,668,595), which in turn claims priority to U.S. Provisional Application No. 61/480,322, filed Apr. 28, 2011.

This application is also a continuation-in-part application of U.S. patent application Ser. No. 14/632,829 filed on Feb. 26, 2015, which is a continuation of U.S. patent application Ser. No. 13/828,793 filed Mar. 14, 2013 (now U.S. Pat. No. 8,986,130), which claims priority to both U.S. Provisional Application No. 61/665,834 filed Jun. 28, 2012 and U.S. Provisional Application No. 61/653,771 filed May 31, 2012 and is also a continuation-in-part application of U.S. patent application Ser. No. 13/250,051 filed Sep. 30, 2011 (now U.S. Pat. No. 8,668,595), which in turn claims priority to U.S. Provisional Application No. 61/480,322, filed Apr. 28, 2011. The disclosures of the above noted applications are hereby incorporated by reference in their entirety.

TECHNICAL FIELD

The present disclosure relates to golf clubs and golf club heads. Particular example aspects of this disclosure relate to the golf clubs and golf club heads which may include monitoring devices for monitoring aspects of a golfer's swing or overall golf game.

BACKGROUND

Golf is enjoyed by a wide variety of players—players of different genders and dramatically different ages and/or skill levels. Golf is somewhat unique in the sporting world in that such diverse collections of players can play together in golf events, even in direct competition with one another (e.g., using handicapped scoring, different tee boxes, in team formats, etc.), and still enjoy the golf outing or competition. These factors, together with the increased availability of golf programming on television (e.g., golf tournaments, golf news, golf history, and/or other golf programming) and the rise of well known golf superstars, at least in part, have increased golf's popularity in recent years, both in the United States and across the world.

Golfers at all skill levels seek to improve their performance, lower their golf scores, and reach that next performance "level." Manufacturers of all types of golf equipment have responded to these demands, and in recent years, the industry has witnessed dramatic changes and improvements in golf equipment. For example, a wide range of different golf ball models now are available, with balls designed to complement specific swing speeds and/or other player characteristics or preferences, e.g., with some balls designed to fly farther and/or straighter; some designed to provide higher or flatter trajectories; some designed to provide more spin, control, and/or feel (particularly around the greens); some designed for faster or slower swing speeds; etc. A host of swing and/or teaching aids also are available on the market that promise to help lower one's golf scores.

Being the sole instrument that sets a golf ball in motion during play, golf clubs also have been the subject of much technological research and advancement in recent years. For example, the market has seen dramatic changes and improvements in putter designs, golf club head designs, shafts, and grips in recent years. Additionally, other technological advancements have been made in an effort to better match the various elements and/or characteristics of the golf club and characteristics of a golf ball to a particular user's swing features or characteristics (e.g., club fitting technology, ball launch angle measurement technology, ball spin rates, etc.). Further technological advancement in golf club design has also involved the incorporation of various types of monitoring devices or sensors in the golf club. Many such designs, however, have been cumbersome and unreliable. In addition, further processing of the data recorded by the sensors has been limited or not performed in a suitable manner to be most useful to golfers.

While the industry has witnessed dramatic changes and improvements to golf equipment in recent years, there is room in the art for further advances in golf club technology. Thus, while golf equipment according to the prior art provide a number of advantageous features, they nevertheless have certain limitations. The present invention seeks to overcome certain of these limitations and other drawbacks of the prior art, and to provide new features not heretofore available.

BRIEF SUMMARY

The following presents a general summary of aspects of the disclosure in order to provide a basic understanding of the disclosure and various aspects of it. This summary is not intended to limit the scope of the disclosure in any way, but it simply provides a general overview and context for the more detailed description that follows.

It would be advantageous to have the ability to monitor and analyze aspects of a golfer's golf game, such as a golfer's golf swing. For example, it would be beneficial to be able to monitor and analyze golf swings a golfer takes during practice (such as in a teaching facility or on a driving range) or golf swings a golfer takes while actually playing a round of golf on a golf course. Therefore, particular aspects of the disclosure are directed to a golf club which includes a monitoring device.

According to aspects of the disclosure, golf clubs may include a golf club head and a shaft configured to engage with the golf club head which includes a grip engaged with the shaft. The golf club may include a monitoring device, which may include a sensor and a transmitter. Additionally, the monitoring device may be configured to determine data related to the characteristics of a golf swing. Further, the monitoring device may be configured to transmit the data related to the characteristics of a golf swing to a remote computer.

According to aspects of the disclosure, the monitoring device may include one or more sensors for monitoring data related to aspects of a golfer's golf game (such as the golfer's golf swing) and a transmitter/transceiver configured to transmit such data. According to aspects of the disclosure, the transmitted data may be analyzed (as will be described in below) and used to aid a golfer in improving the golfer's abilities (e.g., the golfer's golf swing). It is noted that according to particular example aspects of the disclosure, other data (e.g., particular club data, on-course data (such as particular golf swings and the approximate location where the swings were taken on a golf course) may be monitored, transmitted and coordinated with the data regarding the aspects of a golfer's golf game (such as the golfer's golf swing) and analyzed as well. Further aspects of the disclosure may include sensing impact location on the golf club face upon a golfer impacting a golf ball during a golf swing. Communication of sensed data may be transmitted, wirelessly or via other means, to a remote location for further processing and display to the golfer.

Other aspects of this disclosure relate to an assembly comprising: a golf bag having a golf bag base with a first induction coil connected to a first power source; a container attached to the golf bag base wherein the container is configured to retain a golf club; a cartridge having a second induction coil, the cartridge engaged with a grip end of the golf club; and a monitoring device having a second power source, the monitoring device engaged with the cartridge, where when the grip end of the golf club is inserted into the container, a first electrical current flows in the first induction coil to induce a second electrical current into the second induction coil of the cartridge to charge the second power source. The first power source may be a battery contained within the golf bag or may be a plug connected to the golf bag that is connected to an external power source. The external power source may be contained on an apparatus for transporting the golf bag, the apparatus for transporting a golf bag having a platform for supporting the golf bag. The cartridge may comprise a first pair of electrical contacts that are in contact with a second pair of electrical contacts on an exterior of the monitoring device when the monitoring device is secured within the cartridge. Additionally, the cartridge may have an upper portion having a substantially cylindrical shape, and wherein the upper portion contains the second induction coil. When the second electrical current is induced into the second induction coil of the cartridge, the first induction coil is substantially parallel to the second induction coil. The golf bag further comprises a sensor configured to detect when the golf club is inserted into the golf bag and where the first electrical current in the first induction coil is configured to activate once the sensor detects the golf club has been inserted into the golf bag.

Still other aspects of this disclosure relate to an assembly comprising: a golf club having golf club head end and a grip end; a golf bag comprising: a golf bag base having a first induction coil connected to a first power source; a container attached to the golf bag base, the container configured to engage the golf club; and a monitoring device engaged with the grip end of the golf club, the monitoring device having a second induction coil and a second power source, where when the grip end of the golf club is inserted into the container, a first electrical current may flow in the first induction coil and induce a second electrical current into the second induction coil to charge a second power source within the monitoring device. The first power source may be a battery contained within the golf bag. The first power source may be an external power source that is connected to the first induction coil through a cable connected to the golf bag at a first end and connected to an external power source at a second end. The external power source may be contained on an apparatus for transporting the golf bag, the apparatus for transporting the golf bag having a platform for supporting the golf bag and a plug configured to engage a socket on the golf bag. The second electrical current may be induced into the second induction coil of the monitoring device, the first induction coil is substantially parallel to the second induction coil. The golf bag may further comprise a sensor configured to detect when the golf club is inserted into the golf bag, and where the first electrical current in the first induction coil is configured to activate once the sensor detects the golf club has been inserted into the golf bag.

Yet another aspect of this disclosure relates to an assembly comprising: an apparatus for transporting a golf bag comprising a platform to support the golf bag, and a first induction coil connected to a first power source, where the golf bag may comprise a golf bag base containing a second induction coil, and when the golf bag base is positioned adjacent the platform, a first electrical current in the first induction coil may induce a second electrical current in the second induction coil of the golf bag base to charge a second power source within the golf bag. The second induction coil may be positioned near a bottom surface of the golf bag base, and the golf bag base may further comprise a third induction coil positioned near an upper surface of the golf bag base; and the assembly further comprises: a monitoring device including a fourth induction coil, wherein the monitoring device engages a grip end of a golf club; and when the grip end of the golf club is inserted into the container of the golf bag, a third electrical current in the third induction coil may induce a fourth electrical current into the fourth induction coil of the monitoring device to charge a third power source within the monitoring device. The second induction coil may be positioned near a bottom surface of the golf bag base, and the golf bag base further comprises a third induction coil positioned near an upper surface of the golf bag base; and the assembly may further comprise: a cartridge having a fourth induction coil; a monitoring device carried by the cartridge, wherein the cartridge engages a grip end of a golf club; and when the grip end of the golf club is inserted into the container of the golf bag, a third electrical current in the third induction coil may induce a fourth electrical current into the fourth induction coil of the cartridge to charge a third power source within the monitoring device. The golf bag may further comprise a sensor configured to detect when the golf club is inserted into the golf bag, and where the third electrical current in the third induction coil is configured to activate once the sensor detects the golf club has been inserted into the golf bag.

Yet another aspect of this disclosure may relate to a golf bag comprising: a golf bag base; a pocket configured on an exterior of the golf bag with a first induction coil positioned beneath a wall of the pocket; and where the first induction coil may be connected to a power source. Also, the pocket may have a depth of less than 2.0 inches.

BRIEF DESCRIPTION OF THE DRAWINGS

The present disclosure is illustrated by way of example and not limited in the accompanying figures, in which like reference numerals indicate similar elements throughout, and in which:

FIG. 13 is an exploded view of the iron-type golf club head shown in FIG. 10;

FIG. 14 is a rear view of the iron-type golf club head shown in FIG. 10 wherein the cartridge is inserted the iron-type golf club head;

FIGS. 18A-D are illustrative embodiments of circuitry of a monitoring device according to aspects of the disclosure;

FIG. 23A shows illustrative removable sections of a golf club according to aspects of the disclosure;

Figure 1:
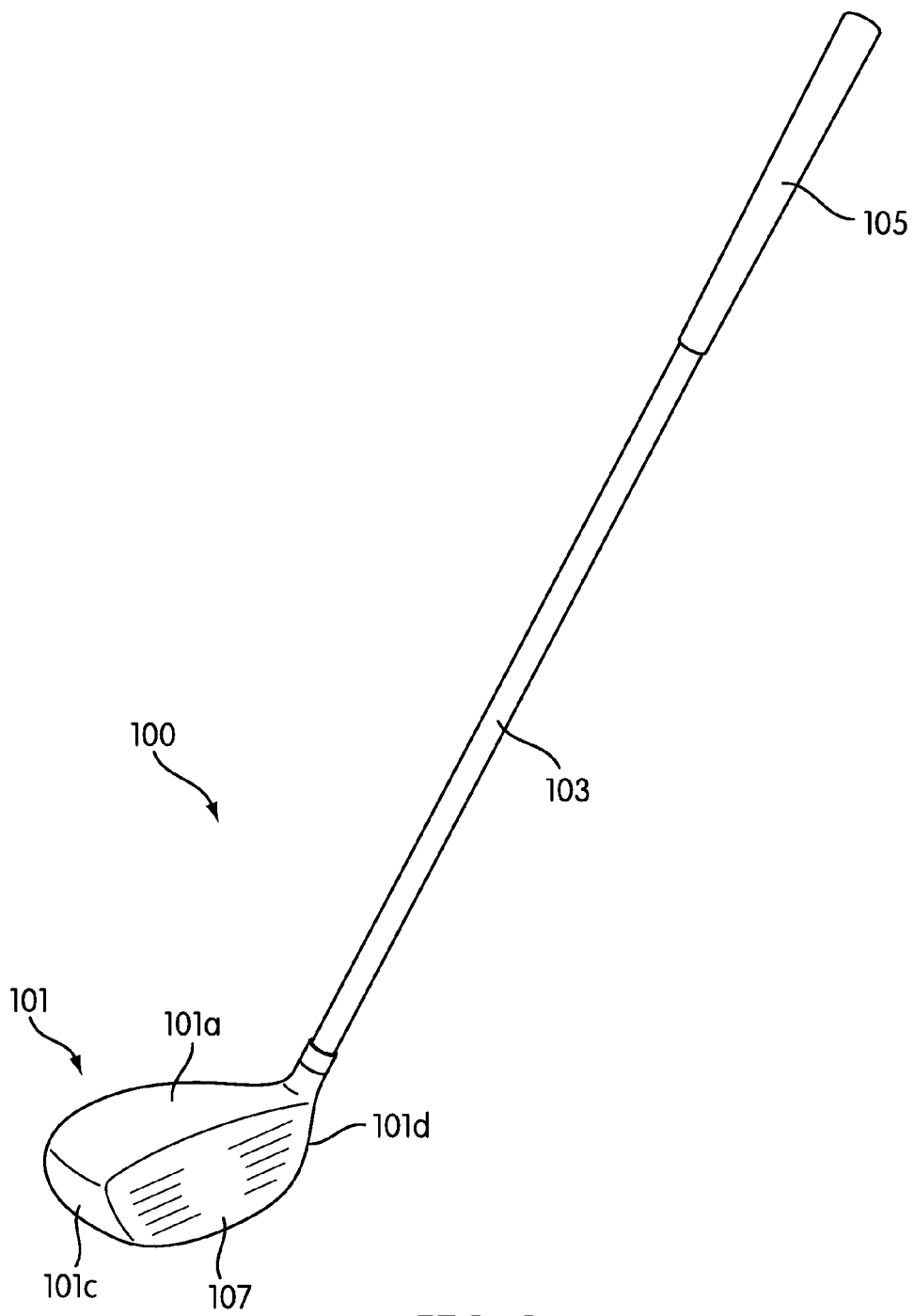
FIG. 1 is an illustrative embodiment of a wood-type golf club structure according to aspects of the disclosure.

The reader is advised that the various parts shown in these drawings are not necessarily drawn to scale.

DETAILED DESCRIPTION

The following description and the accompanying figures disclose features of golf club heads and golf clubs in accordance with examples of the present disclosure.

I. GENERAL DESCRIPTION OF EXAMPLE GOLF CLUB HEADS, GOLF CLUBS, AND METHODS IN ACCORDANCE WITH THIS DISCLOSURE

Aspects of this disclosure relate to golf club heads and golf clubs. Golf club heads according to at least some example aspects of this disclosure may include: (a) a golf club head body; and (b) a removable section or member which may include a monitoring device. Golf club heads according to at least some example aspects of this disclosure may also include: (c) one or more sensors and (d) a transmitter for transmitting data obtained by the one or more sensors. For example, the one or more sensors and the transmitter may be included in the monitoring device. According to some aspects of the disclosure, the golf club head may be configured to receive the removable section. Further, according to some aspects of the disclosure the golf club head may be configured to receive the monitoring device directly, without a removable section. Further, golf club heads of at least some example aspects of this disclosure may include wood-type golf club heads, iron-type golf club heads and putter type golf club heads.

Aspects of this disclosure also relate to golf club shafts and golf club grips. Golf club shafts according to at least some example aspects of this disclosure may include: (a) a grip portion; and (b) a removable section which may include a monitoring device. The monitoring device according to at least some example aspects of this disclosure may also include: (c) one or more sensors and (d) a transmitter for transmitting data obtained by the one or more sensors. According to some aspects of the disclosure, the grip portion or other portion of the shaft may be configured to receive the removable section. Further, according to some aspects of the disclosure the golf club shaft (e.g., the grip portion) may be configured to receive the monitoring device directly, without a removable section. Golf club shafts of at least some example aspects of this disclosure may include metal shafts, carbon fiber shafts, etc. and be directed to wood-type golf clubs, iron-type golf clubs and putter type golf clubs.

Additional aspects of this disclosure relate to golf club structures that include golf club heads or golf club shafts, e.g., of the types described above. Such golf club structures further may include one or more of: a shaft attached to the golf club head (optionally via a shaft engaging member (e.g., a hosel) or directly inserted otherwise engaged with the shaft); a grip or handle attached to the shaft; etc.

Still additional aspects of this disclosure relate to methods for producing golf club heads and golf club structures in accordance with examples of this disclosure. Such methods may include, for example, one or more of the following steps in any desired order and/or combinations: (a) providing a golf club head of the various types described above (including any or all of the various structures, features, and/or arrangements described above), e.g., by manufacturing or otherwise constructing the golf club head body, by obtaining it from a third party source, etc.; (b) engaging a shaft of the various types described above (including any or all of the various structures, features, and/or arrangements described above) with the golf club head; and (c) engaging a grip of the various types described above (including any or all of the various structures, features, and/or arrangements described above) with the shaft.

Given the general description of various example aspects of the disclosure provided above, more detailed descriptions of various specific examples of golf clubs and golf club head structures according to the disclosure are provided below.

II. DETAILED DESCRIPTION OF EXAMPLE GOLF CLUB HEADS, GOLF CLUB STRUCTURES, AND METHODS ACCORDING TO THE DISCLOSURE

As discussed above, it would be advantageous to have the ability to monitor and analyze aspects of a golfer's golf game, such as a golfer's golf swing. Therefore, particular aspects of the disclosure are directed to a golf club which includes a monitoring device. According to aspects of the disclosure, the monitoring device may include one or more sensors for monitoring data related to aspects of a golfer's golf game (such as the golfer's golf swing) and a transmitter configured to transmit such data. It is further understood that the data may be further processed if necessary or desired. According to aspects of the disclosure, the transmitted data may be analyzed (as will be described in below) and used to aid a golfer in improving the golfer's abilities (e.g., the golfer's golf swing). It is noted that in according to particular example aspects of the disclosure, other data (e.g., particular club data, on the course data (such as particular golf swings and the approximate location where the swings were taken on a golf course) may be monitored, transmitted and analyzed as well.

Further, it would also be beneficial to configure the golf club such that the monitoring device is able to be removable from the golf club. For example, if a golfer wanted to use the monitoring device during practice (e.g., on a driving range) and did not want to use it during play on a golf course, it would be beneficial to have a golf club configured to allow the monitoring device to be easily engageable with, and removable from, the golf club in order to allow the golfer to selectively configure the golf club to their particular preference at a given time. If the golfer did not wish to use the monitoring device during an actual round of golf, the cartridge with monitoring device could be removed from the club and replaced with a replacement member without a monitoring device wherein the monitoring device had characteristics such as weighting and aerodynamic features so as to not change the overall characteristics of the golf club from when the monitoring device was installed on the golf club.

Therefore, aspects of the disclosure are directed to a golf club which is configured to receive and secure the monitoring device, and is also configured to release the monitoring device. For example, aspects of the disclosure relate to a golf club which includes a golf club head which is configured to receive and secure the monitoring device in the golf club head. Further, example embodiments of the disclosure relate to golf club heads configured to receive and secure a removable section or a cartridge (e.g., a cartridge containing the monitoring device). Other aspects of the disclosure relate to a golf club which includes a golf club shaft which is configured to receive and secure the monitoring device in the golf club shaft. For example, the grip of the golf club shaft may be configured to receive and secure the monitoring device in the grip of the golf club shaft. Further, example embodiments of the disclosure relate to a golf club shaft configured to receive and secure a removable section or a cartridge (e.g., a cartridge containing the monitoring device).

The following discussion and accompanying figures describe various example golf clubs and golf club head structures in accordance with the present disclosure. When the same reference number appears in more than one drawing, that reference number is used consistently in this specification and the drawings to refer to the same or similar parts throughout.

More specific examples and features of golf club heads and golf club structures according to this disclosure will be described in detail below in conjunction with the example golf club structures illustrated in FIGS. 1-18.

FIG. 1 generally illustrates an example of a wood-type golf club 100 according to aspects of the disclosure. As seen in FIG. 1, the wood-type golf club may include a wood-type golf club head 101 in accordance with the present disclosure.

In addition to the golf club head 101, the overall golf club structure 100 may include a shaft 103 and a grip or handle 105 attached to the shaft 103. The shaft 103 may be received in, engaged with, and/or attached to the golf club head 101 in any suitable or desired manner, including in conventional manners known and used in the art, without departing from the disclosure. As more specific examples, the shaft 103 may be engaged with the golf club head 101 through a shaft-receiving sleeve or element extending into the club head 101 (e.g., a hosel), and/or directly to the club head structure 101, e.g., via adhesives, cements, welding, soldering, mechanical connectors (such as threads, retaining elements, or the like). If desired, the shaft 103 may be connected to the golf club head 101 in a releasable manner using mechanical connectors to allow easy interchange of one shaft for another on the head. The shaft 103 may be made from any suitable or desired materials, including conventional materials known and used in the art, such as graphite based materials, composite or other non-metal materials, steel materials (including stainless steel), aluminum materials, other metal alloy materials, polymeric materials, combinations of various materials, and the like.

The grip or handle 105 may be attached to, engaged with, and/or extend from the shaft 103 in any suitable or desired manner, including in conventional manners known and used in the art, e.g., using adhesives or cements, etc. As another example, if desired, the grip or handle 105 may be integrally formed as a unitary, one-piece construction with the shaft 103. Additionally, any desired grip or handle materials may be used without departing from this disclosure, including, for example: rubber materials, leather materials, rubber or other materials including cord or other fabric material embedded therein, polymeric materials, and the like.

Further, according to aspects of the disclosure, the golf club 100 may include a hosel. According to aspects of the disclosure, the shaft 103 may be received in and/or inserted into and/or through the hosel. If desired, the hosel may be configured such that the shaft 103 may be engaged with the hosel in a releasable manner using mechanical connectors to allow easy interchange of one shaft for another on the head. For example, threads, locking mechanisms, etc. may be incorporated into the hosel and the end of the shaft 103 that is to be engaged with the hosel may be configured with a corresponding configuration. Also, the shaft 103 may be secured to the hosel via bonding with adhesives or cements, welding (e.g., laser welding), soldering, brazing, or other fusing techniques, etc. Further, optionally, if desired, the hosel may be eliminated and the shaft 103 may be directly attached to the golf club head 101. For example, the shaft 103 may be directly engaged with the golf club head 101 (e.g., by bonding with adhesives or cements, welding (e.g., laser welding), soldering, brazing, or other fusing techniques, etc.).

According to aspects of the disclosure, the golf club head 101 may include a ball striking face (e.g., a ball striking face which includes a face plate) 107. The ball striking face 107 may be provided integrally with the golf club head 101. Also, the ball striking face 107 may include a separate element, such as a face plate, which is configured to be engaged with the golf club head. For example, the golf club head may include a structure, such as a recess, notch or other configuration for receiving the face plate. The face plate may be engaged with the golf club head in a variety of ways. For example, the face plate may be engaged with the golf club head by press fitting, bonding with adhesives or cements, welding (e.g., laser welding), soldering, brazing, or other fusing techniques, mechanical connectors, etc.

The ball striking face 107 may be comprised of one or more materials. The material(s) of the ball striking face should be relatively durable to withstand the repeated impacts with the golf ball. For example, the ball striking face 107 may comprise a high strength steel. Further, other materials, such as titanium or other metals or alloys may be used as well. Further, the ball striking face 107 may include one or more score lines which extend generally horizontally across the ball striking face 107.

According to aspects of the disclosure, the golf club head may include a crown 101a, a sole 101b, a toe 01c, and a heel 101d. Further, the golf club head 101 may be constructed in any suitable or desired manner and/or from any suitable or desired materials without departing from this disclosure, including from conventional materials and/or in conventional manners known and used in the art. In fact, it is noted that wide varieties of overall club head constructions are possible without departing from this disclosure. For example, if desired, some or all of the various individual parts of the club head body described above may be made from multiple pieces that are connected together (e.g., by adhesives or cements; by welding, soldering, brazing, or other fusing techniques; by mechanical connectors; etc.). The various parts (e.g., crown, sole, face, etc.) may be made from any desired materials and combinations of different materials, including materials that are conventionally known and used in the art, such as metal materials, including lightweight metal materials (e.g., titanium, titanium alloys, aluminum, aluminum alloys, magnesium, magnesium alloys, etc.), composite materials, polymer materials, etc. The club head 101 and/or its various parts may be made by forging, casting, molding, machining, and/or using other techniques and processes, including techniques and processes that are conventional and known in the art.

It is noted that a wide variety of overall club head constructions are possible without departing from this disclosure. For example, it is noted that the dimensions and/or other characteristics of the golf club head 101 according to examples of this disclosure may vary significantly without departing from the disclosure. For example, the above described features and configurations may be incorporated into any wood-type club heads including, for example: wood-type hybrid clubs, fairway woods, drivers, etc.

Figure 2:
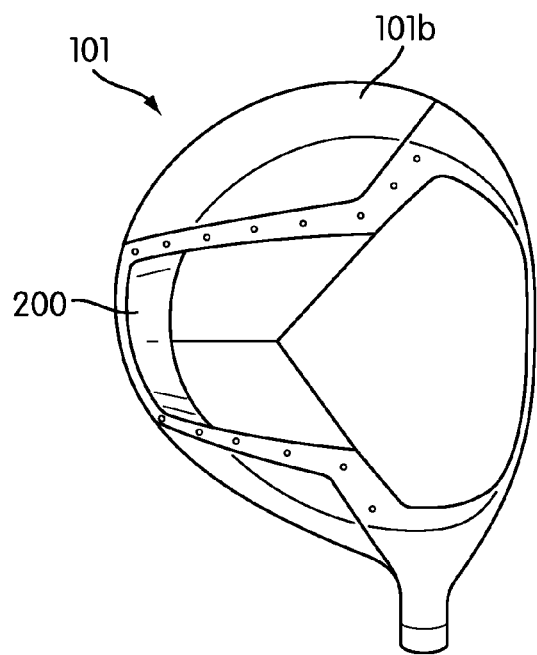
FIG. 2 is an enlarged bottom view of the wood-type golf club head shown in FIG. 1.
Figure 3:
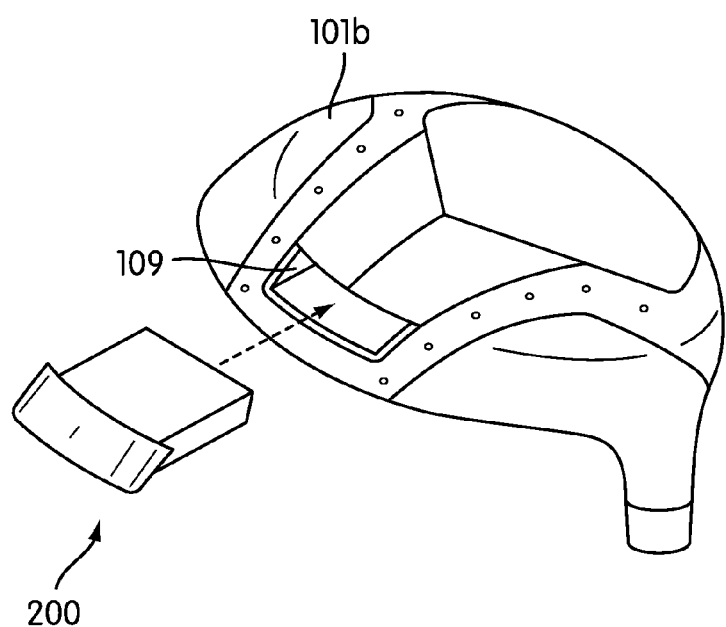
FIG. 3 is an exploded view of the wood-type golf club head shown in FIG. 2 and showing a monitoring device.

The depicted golf club 100 is an illustrative embodiment of a golf club which includes aspects of the disclosure. As seen in FIGS. 2 and 3, the golf club head 101 may include a port 109 configured to receive a section, member or cartridge, 200. The cartridge 200 may be configured to house the monitoring device 201. The monitoring device 201 may be configured to house at least one sensor 202 (FIG. 4) for determining various aspects of a golf swing. Further, if desired, the monitoring device 201 may be configured to house a transmitter 203 (or a transceiver). Such features of the golf club 100 will be described in detail below.

As seen in FIG. 3, the cartridge 200 may be configured to engage with the port 109 of the golf club head 100. For example, the cartridge 200 may be sized to directly engage with interior walls of the port 109, such that the cartridge 200 is firmly secured within the golf club head 101.

According to example embodiments of the disclosure, the cartridge 200 may be configured such that when the cartridge 200 is engaged with the port 109, the cartridge 200 becomes an exterior surface of the golf club head 101. For example, the cartridge 200 may be configured with a first portion (e.g., an exterior portion) 200a which is shaped so as to not protrude from the golf club head 101 and, instead, to fit seamlessly, or relatively seamlessly, with the exterior of the golf club head 101, once the cartridge 200 is engaged with the golf club head 101. For example, the first portion 200a of the golf club head 101 may form an exterior portion of the rear of the golf club head 101. Further, the first portion 200a of the golf club head 101 may form an exterior portion of crown 101a, sole 101b, toe 101c, heel 101d, etc. of the golf club head 101 or some combination thereof (e.g., the exterior of a rear portion and a sole portion of the golf club head 101), and depending on the location of the port 109. In such a configuration, wherein the first portion 200a, fits seamlessly, or relatively seamlessly, with the exterior of the golf club head 101, the aerodynamics of the golf club head 101 will be improved as compared with a golf club head wherein a sensor or transmitter protrudes beyond the surface of the exterior of the golf club head 101.

Further, according to example aspects of the disclosure, the cartridge 200 may include a second portion (e.g., an insert portion) 200b which is configured to be inserted into the interior of the port 109 of the golf club head 101. The second portion 200b may be configured to house a monitoring device 201 which, in turn, houses the at least one sensor 202 and the transmitter 203. As seen in the depicted embodiment, the monitoring device 201 may be secured within the second portion 200b such that the sensor 202 and the transmitter 203 are stationary with regard to the second portion 200b. In such a configuration wherein the sensor 202 and the transmitter 203 are held stationary with the second portion 200b and the second portion 200b is housed within the interior of the golf club head 101, the sensor 202 and transmitter 203 are relatively well protected (e.g., from the elements (water and other environmental conditions) encountered during use and from potential impacts the golf club head incurs during use of the golf club 100 or during typical storage or transport of the golf club 100 (e.g., in a golf bag).

According to aspects of the disclosure, the cartridge 200 may be made from any desired materials and combinations of different materials, including materials that are conventionally known and used in the art, such as metal materials, including lightweight metal materials (e.g., titanium, titanium alloys, aluminum, aluminum alloys, magnesium, magnesium alloys, etc.), composite materials, polymer materials, etc. For example, according to aspects of the disclosure, the first portion 200a of the cartridge 200 may be made from the same material from which the exterior of the golf club head 101 is made. In this way, when the cartridge 200 is engaged with the golf club head 101, the first portion of the cartridge 200 facilitates the appearance of the seamless, or relatively seamless, fit described above between the first portion of the cartridge 200 with the exterior of the golf club head 101. Further, the second portion 200b of the cartridge 200 may be a plastic or polymer. The second portion 200b may be configured to receive the monitoring device 201. Alternatively, if desired, the second portion 200b and the monitoring device 201 may be integral. Alternatively, if desired, the monitoring device 201 may be the second portion 200b. The sensor 201 and the transmitter 202 may be encased within the monitoring device 201 or the second portion 200b. Further, if desired, shock absorbers may be positioned in the monitoring device 201 or second portion 200b and configured to surround, or contact, the sensor 201 and the transmitter 202.

According to aspects of the disclosure, the first portion 200a may be curved to match the exterior portion of the portion of golf club head 101 with which it is engaged. Further, the first portion 200a may have a length of 1 inch, a width of ¾ inch and a thickness of 1/10 inch. According to aspects of the disclosure, the second portion 200b may be rectangular, or generally rectangular, extend from the center, or the relative center of the first portion 200a and may have a length of 1 inch, a width of ¾ inch and a height of ½ inch. Further, according to aspects of the disclosure, the cartridge 200 may have a relatively light weight.

According to aspects of the disclosure, the cartridge 200 may include one or more Light Emitting Diodes (LEDs). For example, the first portion 200a may be configured to be translucent and the one or more LEDs may be configured to emit light through the translucent first portion 200a. It is noted that, if desired, one or more indicators may be positioned on the cartridge. For example, logos may be inscribed on the first portion 200a of the cartridge 200. Further, such logos may be illuminated by the LEDs in particular embodiments of the disclosure.

As seen in the exploded view of FIG. 3, in the depicted embodiment, the port 109 is positioned in the rear or the sole 101b of the golf club head 101. However, the port 109 may be positioned in other areas of the golf club head 101 as well (e.g., the crown 101a). It is noted that according to aspects of the disclosure, the port 109 may be positioned within the golf club head 101 such that when the cartridge 200 is engaged with the golf club head, it less like to be contacted during use or transport. For example, the port 109 may be positioned near the rear of the golf club head wherein the cartridge 200 is less likely to contact the ground during a golf swing or when the golf club head 101 is inverted during transport in a golf bag. Such a configuration, wherein the cartridge is less likely to be contacted during the use or transport, reduces the likelihood that the cartridge 200 may be impacted or inadvertently dislodged from its engaged position.

Further, according to aspects of the disclosure, the port 109 may be configured with any size and shape adequate to receive the cartridge 200. For example, as seen in the depicted embodiment, the port 109 may be relatively rectangular. Further, according to particular embodiments of the disclosure, the port 109 may include a length of 1 inch, a width of ¾ inch and a height of ½ inch. Of course, such dimensions are merely exemplary and other sizes may be used as well. As long as the port 109 is configured to receive and securely hold the cartridge 200, the shape and size of the port 109 can be configured as desired.

It is noted that the port 109 may be configured with a recessed or lipped portion 109a at its exterior that is configured to receive or, engage with, the first portion 200a of the cartridge. In this way, the above described seamless, or relatively seamless, fit between with the exterior of the golf club head 101 and the cartridge 200 may be achieved when the cartridge 200 is engaged with the golf club head 101.

According to aspects of the disclosure, the port 109 may be made from any desired materials and combinations of different materials, including the materials described above with reference to the golf club head 101, such as metal materials, including lightweight metal materials (e.g., titanium, titanium alloys, aluminum, aluminum alloys, magnesium, magnesium alloys, etc.), composite materials, polymer materials, etc. It is noted that port 109 may be configured separately and then engaged with the golf club head 101 (e.g., by adhesives or cements; by welding, soldering, brazing, or other fusing techniques; by mechanical connectors; etc.) or, also, the port 109 may be integral with the golf club head (e.g., made during the manufacture of the golf club head 101 by forging, casting, molding, machining, and/or using other techniques and processes, including techniques and processes that are conventional and known in the art).

The cartridge 200 may be secured in the port 109 of the golf club head 101 in a variety of ways. For example, as discussed above, according to aspects of the disclosure, the cartridge 200 may be removably engaged with the golf club head 101. Therefore, mechanical fasteners may be used to secure the cartridge 200 in the port 109. For example, example embodiments of the disclosure may include a cartridge 200 which is configured to be engaged with the golf club head 101 via press fitting, snap fit mechanisms (e.g., spring loaded protrusions and corresponding detents), threaded fasteners, etc.

Further, one of the advantages of the golf club head 101 is that the cartridge 200 is easily removable from the golf club head 101. Therefore, according to aspects of the disclosure, the golf club head 101 may include a release mechanism for releasing the cartridge 200 from is secured position within the port 109. For example, according a particular embodiment of the disclosure, the port 109 and cartridge 200 are engaged via a mechanism which includes a spring loaded feature. The spring loaded feature of the release mechanism is configured such that when the cartridge 200 is secured in the port 109, the first portion 200a of the cartridge 200 is seamlessly, or relatively seamlessly, engaged with the exterior of the golf club head 101 as described above. In order to disengage the cartridge 200 from the port 109, the user will press the cartridge 200 which will be depressed a short distance into the golf club head 101. For example, the port 109 may include recessed portion along its exterior opening which allows the cartridge 200 to be depressed a short distance into the port 109. This movement of the cartridge 200 a short predetermined distance into the golf club head 101 disengages the cartridge 200 from its secured position within the golf club head 101. Subsequent to the user depressing the cartridge 200 the predetermined, short distance into the golf club head 101, the user releases the cartridge 200, and the spring loaded release mechanism ejects the cartridge 200 to a short, predetermined distance such that at least a portion of the cartridge 200 protrudes outside the golf club head 101 so that the user can easily grasp and remove the cartridge 200 from the golf club head 101.

As discussed above, the golf club head 101 may include other engagement and release mechanisms. Further, it is noted that the cartridge 200 and the port 109 may include guide features. For example, the port 109 may include one or more grooves and the cartridge 200 may include one or more protrusions which are configured to engage with and be guided by the grooves of the port 109. In example embodiments of the disclosure, the port 109 may include a groove on two or four of the interior walls of the port 109 and the second portion 200b of the cartridge 200 may include a corresponding number of protrusions.

As described above, aspects of the disclosure, are directed to a golf club configured to allow the one or more sensors and transmitter to be easily removable from the golf club head, so that the golfer can choose whether or not the golfer wants to have the one or more sensors and the transmitter engaged with the golf club head during golf swings. For example, as described above, a golfer may only want to use the one or more sensors and transmitter during practice (e.g., on a driving range or in a practice round) and not want the one or more sensors and transmitter engaged with the golf club head during play on a golf course during a round of golf.

Therefore, aspects of the disclosure relate to a weight cartridge 200' which is configured to be engaged with the port 109. The weight cartridge may be configured similarly to the cartridge 200 described above with the exception that the weight cartridge does not include a monitoring device 201 or a sensor 202 or a transmitter 203. Since the configuration of the weight cartridge is similar to the above described cartridge 200, the structure of the weight cartridge will not be recited here again for the sake or brevity. Further, it is noted that the weight cartridge may be configured to engage with the port 109 in the same manner as the corresponding cartridge 200. Hence, again, for the sake of brevity, the engaging and releasing structure of the weight cartridge and the port 109 will not be elaborated on here.

According to aspects of the disclosure, when the golfer does not want to have the monitoring device 201 housed within the golf club 100, the golfer may disengage and remove the cartridge 200 from the port 109 of the golf club head 101 and engage and secure the weight cartridge with the port 109 of the golf club head 101. By replacing the cartridge 200 with the weight cartridge 200', the golf club head 101 may retain the same exterior shape of the golf club head 101. The golf club 100 will also have the same weighting characteristics as the weight cartridge 200' is also weighted to correspond to the overall weight of the cartridge 200. Hence, the golf club 100 may be used just as it would be for any golf swing when the cartridge 200 is engaged with the golf club head 101 and the aerodynamics and weighting of the golf club head 101 will not be altered.

It is noted that the term weight cartridge is used merely to distinguish the weight cartridge from the cartridge 200 and does not necessarily imply that the cartridge 200 must be weighted. For example, according to aspects of the disclosure, the weight cartridge may have the same mass and weight as the cartridge 200. In such a configuration, the golfer's golf swing will not be affected regardless of which cartridge is engaged with the golf club head 101. However, if desired, the weight cartridge may include one or more weighted portions.

Therefore, based on the above disclosure, it is understood that aspects of the disclosure are directed to a golf club which is configured to receive interchangeable sections or cartridges, wherein one of the interchangeable cartridges may house the one or more sensors and the transmitter and a second of the interchangeable cartridges does not house a sensor or a transmitter. In this way, the golfer may selectively configure the golf club to include, or not include, the one or more sensors and the transmitter, at the golfer's discretion.

The monitoring device 201 may be configured to measure a multitude of different aspects of a golfer's golf game. For example, the monitoring device 201 may be configured to measure golf swing data. According to aspects of the disclosure, golf swing data may include information on a variety of different characteristics of a golf swing. Further, according to particular embodiments of the disclosure, the monitoring device 201 may also be configured to identify the particular golf club in which the sensor is positioned. For example, an RFID tag may be used. Further, according to particular embodiments of the disclosure, the monitoring device 201 may also be configured to identify a location where a particular golf swing was taken. For example, the monitoring device 201 may include Global Positioning Satellite (GPS) technology. Such information may be incorporated with maps of the golf course on which the golf shots were taken in order to provide a golfer with information on each shot during a round of golf. Each of these features will be described in further detail below.

Figure 4:
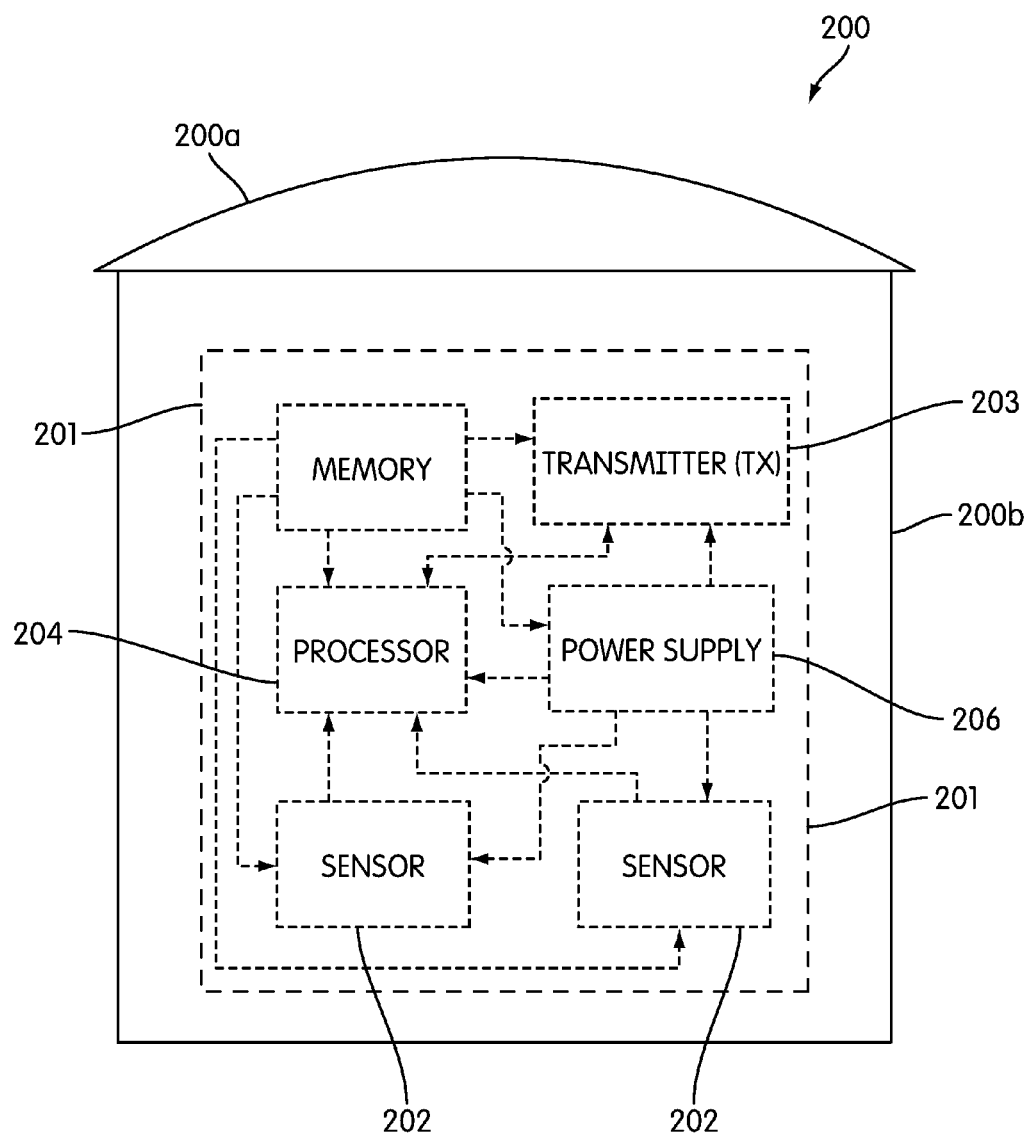
FIG. 4 is a cartridge according to an illustrative embodiment of the disclosure.

FIG. 4 illustrates one example of a monitoring device 201 that may be employed according to various examples of the disclosure to measure various aspects of a golfer's abilities and game. The monitoring device 201 may include a processor 204 for processing the electrical signals output by the sensors 202. With some implementations of the disclosure, the processor 204 may be a programmable microprocessor. For still other implementations of the invention, however, the processor 204 may be a purpose-specific circuit device, such as an ASIC. The processor 204 may be configured to perform any desired operation on the signals output from the sensors 202, such as curve smoothing, noise filtering, outlier removal, amplification, summation, integration, or the like. The processor 204 may be configured to provide the processed signals to transmitter 203 (or transceiver). Further, the monitoring device 201 may be configured to transmit the processed signals to a remote computer system 400 via the transmitter 203 (or transceiver), as will be discussed below. In one exemplary embodiment, the processed data may be transmitted wirelessly. The monitoring device 201 may also include a power supply 206, for providing power to the sensors 202, the processor 204, and the transmitter 203 (or transceiver) as needed. The power supply 206 may be, for example, a battery. Further, as discussed below, embodiments of the monitoring device 201 may include a memory (e.g., a flash memory). The memory may include both a read-only memory (ROM) and a random access memory (RAM). As will be appreciated by those of ordinary skill in the art, both the read-only memory (ROM) and the random access memory (RAM) may store software instructions for execution by the processor 204.

It is noted that while the depicted embodiment illustrates a processor 204, according to other aspects of the disclosure, the monitoring device 201 does not need to include a processor to process the data from the sensors 202. Instead, according to such aspects of the disclosure, the "raw" data from the sensors 202 may be transmitted, such as by wireless transmission, without being processed.

As discussed above, according to particular embodiments of the disclosure, the monitoring device 201 may be configured to measure golf swing data. Examples of golf swing data may include, the velocity of the golf club (or club head) during a golf swing, the acceleration of the club (or club head) during a golf swing, the angle of the golf club (or club head) during a golf swing (e.g., relative to one or more reference points), swing tempo, the impact of the ball with the golf club head during a golf swing, aspects of the impact of the ball with the golf club head during a golf swing (e.g., loft, etc.), etc. Further, the sensors may be configured to measure the position (e.g. a spatial position with regard to a particular frame of reference) of the golf club at various points in time in order to provide data on a golf swing. In this way, acceleration, velocity, positioning of the golf club may be determined and analyzed in 3 dimensions. Further, some or all of the above data may be leveraged to create a graphical representation (e.g., a picture or video) of the golf swing. For example, a swing path may be graphically represented in 3 dimensions along an X-Y-Z frame of reference. Further, areas of the "3D golf swing" during which acceleration is taking place may be represented differently than areas of constant velocity or deceleration. For example, high acceleration takes place may be shown in red, while areas in the swing path during which constant velocity or deceleration takes place may be shown in yellow.

According to aspects of the disclosure, the monitoring device 201 may include one or more sensors 202. It is noted that the sensors 202 may be accelerometers (such as piezo-electric accelerometers), magnetometers, or gyroscopes. Further, one skilled in the art will appreciate that numerous additional sensors may be used in connection with aspects of the disclosure (e.g., impact sensors, strain gauges, etc.).

According to particular embodiments of the disclosure, the sensors 202 may be similar to sensors used in the NIKE+™ athletic performance monitoring systems available from NIKE, Inc. of Beaverton, Oreg. For example, the sensors 202 may measure golf swing data in a manner akin to the measurement of data in NIKE+™ athletic performance monitoring systems (e.g., speed information, such as velocity and acceleration information, etc.). According to aspects of the disclosure, the sensors 202 will produce electrical signals corresponding to the specific golfing characteristic it is monitoring. As known in the art, these signals can then be used to generate data representative of the golfing activity performed by the golfer.

Figure 4A:
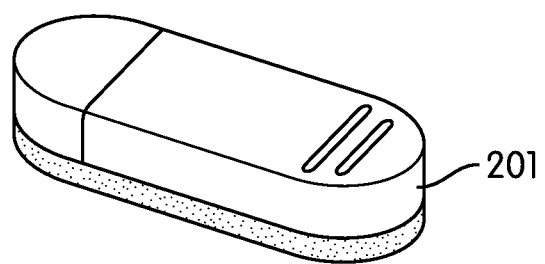
FIGS. 4A and 4B illustrate a monitoring device according to an illustrative embodiment of the disclosure.
Figure 4B:
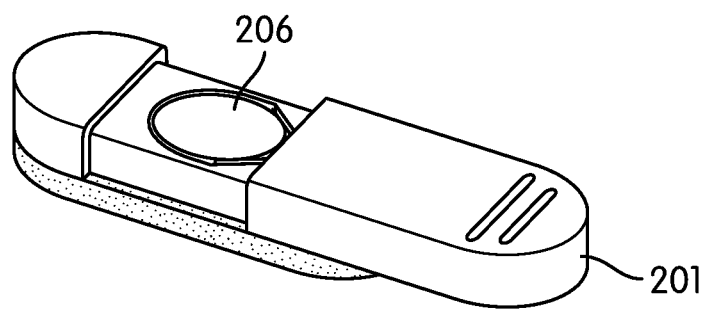

FIGS. 4A and 4B illustrate a particular embodiment of a monitoring device 201 according to aspects of the disclosure. As seen in FIGS. 4A and 4B, the monitoring device 201 may include a generally rectangular compartment in which sensors 202 are housed. The compartment may be similar to the compartment used to house sensors used in the NIKE+™ athletic performance monitoring systems available from NIKE, Inc. of Beaverton, Oreg. For example, according to aspects of the disclosure, the compartment may be rectangular with rounded ends and has a length in the range of 1.0-1.5 inches, a width of 0.4-1.0 inches and thickness of 0.2-0.45 inches. Other dimensions may be used as well. Further, the monitoring device 201 illustrated in FIGS. 5A-C may include three accelerometers, three gyroscopes and a magnetometer. Additionally, the monitoring device 201 illustrated in FIGS. 5A-C may include a transmitter 203 (or transceiver) for wirelessly transmitting data determined by the three accelerometers, three gyroscopes and a magnetometer.

According to aspects of the disclosure, the compartment of the monitoring device 201 may be made of plastic. It is noted that other materials may be used as well. The compartment of the monitoring device 201 may be opened to provide access to the sensors 202 and the other components housed inside the monitoring device 201. For example, as seen in FIGS. 4A and 4B, the compartment of the monitoring device 201 may include a cover which is configured to slide to provider access to various components of the monitoring device, such as the battery 206. Further, the compartment of the monitoring device 201 may house a circuit board or the like which may include various elements described above, such as the processor 204, sensors 202, transmitter 203, power supply 206, memory, etc.

Figure 5A:
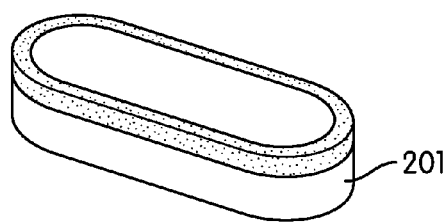
FIGS. 5A and 5B illustrate a monitoring device according to an illustrative embodiment of the disclosure.
Figure 5B:
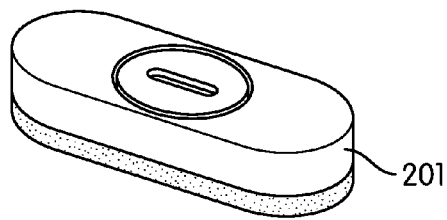
Figure 5C:
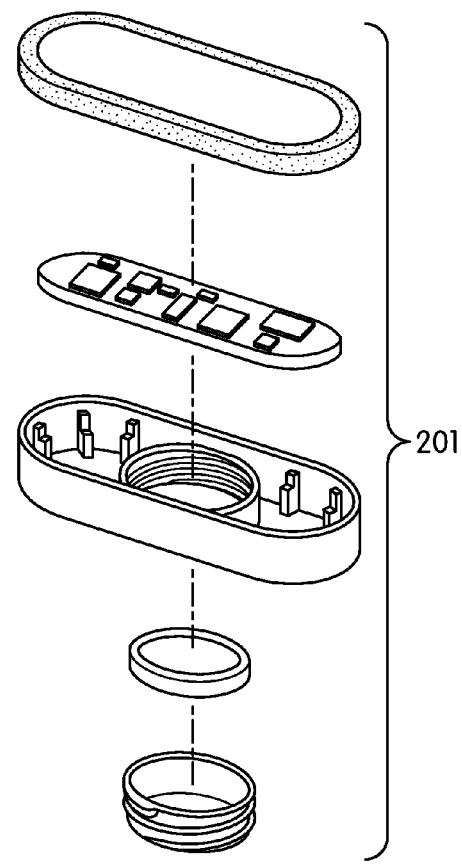
FIG. 5C is an exploded view of the monitoring device shown in FIGS. 5A and 5B.

FIGS. 5A-C illustrate a particular embodiment of the monitoring device 201. Specifically, FIG. 5A is a perspective view of the monitoring device 201. FIG. 5B is a perspective view of the bottom of the monitoring device 201. FIG. 5C is an exploded view of the monitoring device 201. As seen in FIGS. 5A-C, in the depicted embodiment, the monitoring device 201 includes a generally rectangular compartment in which sensors 202 are housed. The compartment may be similar to the compartment used to house sensors used in the NIKE+™ athletic performance monitoring systems available from NIKE, Inc. of Beaverton, Oreg. Further, the monitoring device 201 illustrated in FIGS. 5A-C may include three accelerometers, three gyroscopes and a magnetometer. Additionally, the monitoring device 201 illustrated in FIGS. 5A-C may include a transmitter 203 (or transceiver) for wirelessly transmitting data determined by the three accelerometers, three gyroscopes and a magnetometer.

According to aspects of the disclosure, the compartment of the monitoring device 201 may be made of plastic. It is noted that other materials may be used as well. As seen in FIG. 5C, the compartment of the monitoring device 201 may be opened to provide access to the sensors 202 and the other components housed inside the monitoring device 201. For example, as seen in FIG. 5B, the compartment of the monitoring device 201 may include a locking mechanism which allows the compartment to be unlocked and opened. As seen in FIG. 5C, the compartment of the monitoring device 201 may house a circuit board or the like which may include various elements described above, such as the processor 204, sensors 202, transmitter 203, power supply 206, memory, etc.

Figure 5D:
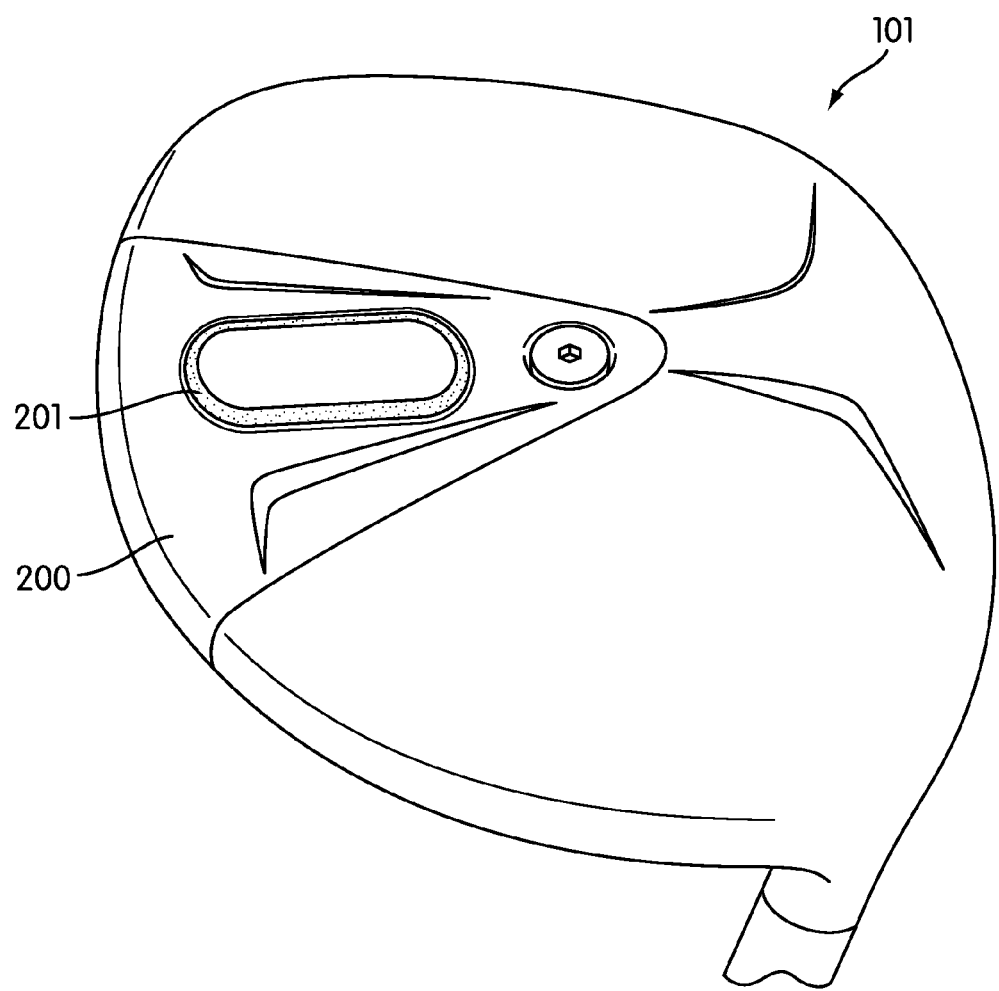
FIG. 5D is an illustrative embodiment of another wood-type golf club structure supporting a monitoring device according to aspects of the disclosure.
Figure 5E:
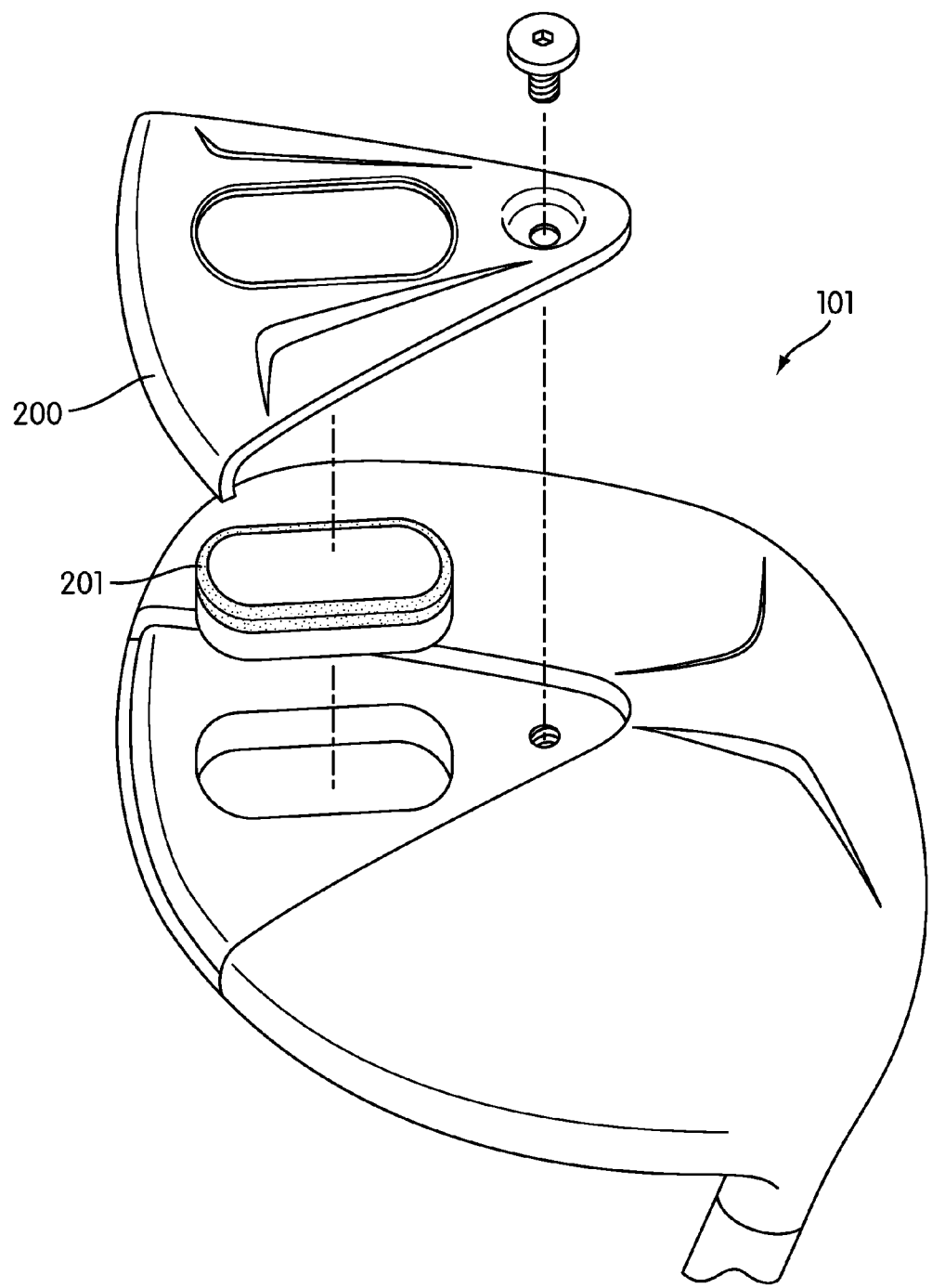
FIG. 5E is an exploded view of the wood-type golf club head shown in FIG. 5D.

According to the aspects of the disclosure, the monitoring device 201 may be configured to engage with the golf club head 101 in a variety of ways. FIGS. 5D-5G show various illustrative embodiments in which the monitoring device 201 is engage with the golf club head 101. For example, FIG. 5D illustrates an embodiment according to the disclosure, wherein the monitoring device 201 and a removable section 200 are engaged with the golf club head 101. FIG. 5E is an exploded view of the embodiment shown in FIG. 5E. As seen in FIGS. 5D and E, the removable section 200 is engaged with the golf club head via a threaded fastener. However, the removable section 200 may be configured to be engaged with the golf club head 101 via other methods as well, such as press fitting, snap fit mechanisms (e.g., spring loaded protrusions and corresponding detents), etc. As seen, the removable section 200 may include an opening configured to surround the monitoring device 201 and through which the monitoring device is visible. The removable section 200 may be configured to provide support and stability to the monitoring device 201.

Further, as seen in FIGS. 5D and 5E, the monitoring device 201 is engaged with the golf club head 101. The engagement of the monitoring device 201 with the golf club head 101 can be done in a variety of ways, e.g., mechanical fasteners, press fitting, snap fit mechanisms (e.g., spring loaded protrusions and corresponding detents), threaded fasteners, etc. As seen in FIG. 5E, the golf club head 101 may include a recess configured to receive the monitoring device 201. For example, the recess may be configured to surround and engage the monitoring device 201 in order to support and stabilize the monitoring device 201. Further, it is noted that the golf club head 101 may include a structure configured to receive the removable section 200. The golf club head 101, the removable section 200 and the monitoring device 201 may be configured so as not to affect the aerodynamics of the golf club head 101 during a golf swing. For example, the golf club head 101, the removable section 200 and the monitoring device 201 may be configured such that when engaged, the golf club head 101 resembles the sole of the traditional wood-type golf club head with a relatively seamless surface.

Figure 5F:
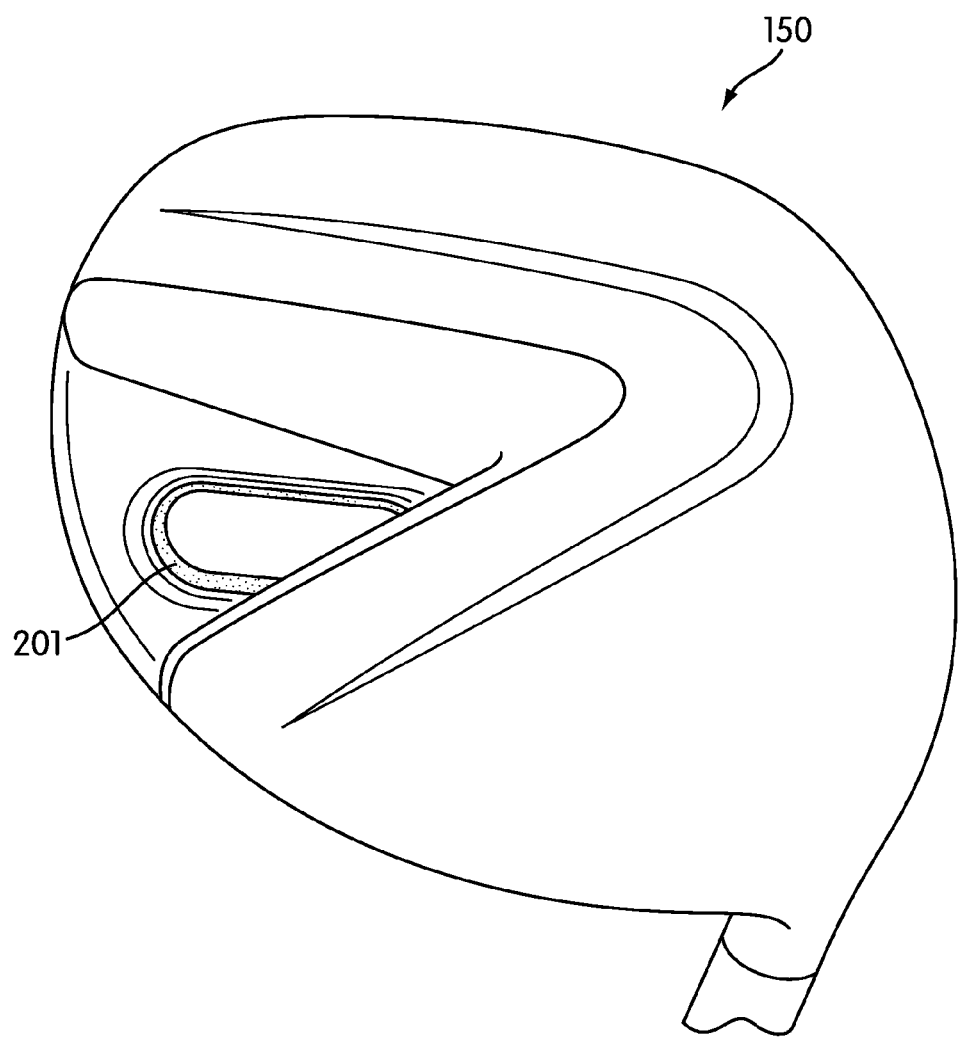
FIG. 5F is an illustrative embodiment of another wood-type golf club structure supporting a monitoring device according to aspects of the disclosure.

FIG. 5F illustrates another illustrative embodiment of a golf club head 150 according to aspects of the disclosure. As seen in FIG. 5F, the golf club head 150 includes a U or V-shaped sole structure between the sole of the golf club head 150 is configured to receive the monitoring device 201. For example, the portion of the of the sole of the golf club head 101 between the legs of the U or V-shaped sole structure may include a recess configured to receive the monitoring device 201. The engagement of the monitoring device 201 with the golf club head 150 can be done in a variety of ways, such as in the above described embodiments.

Figure 5G:
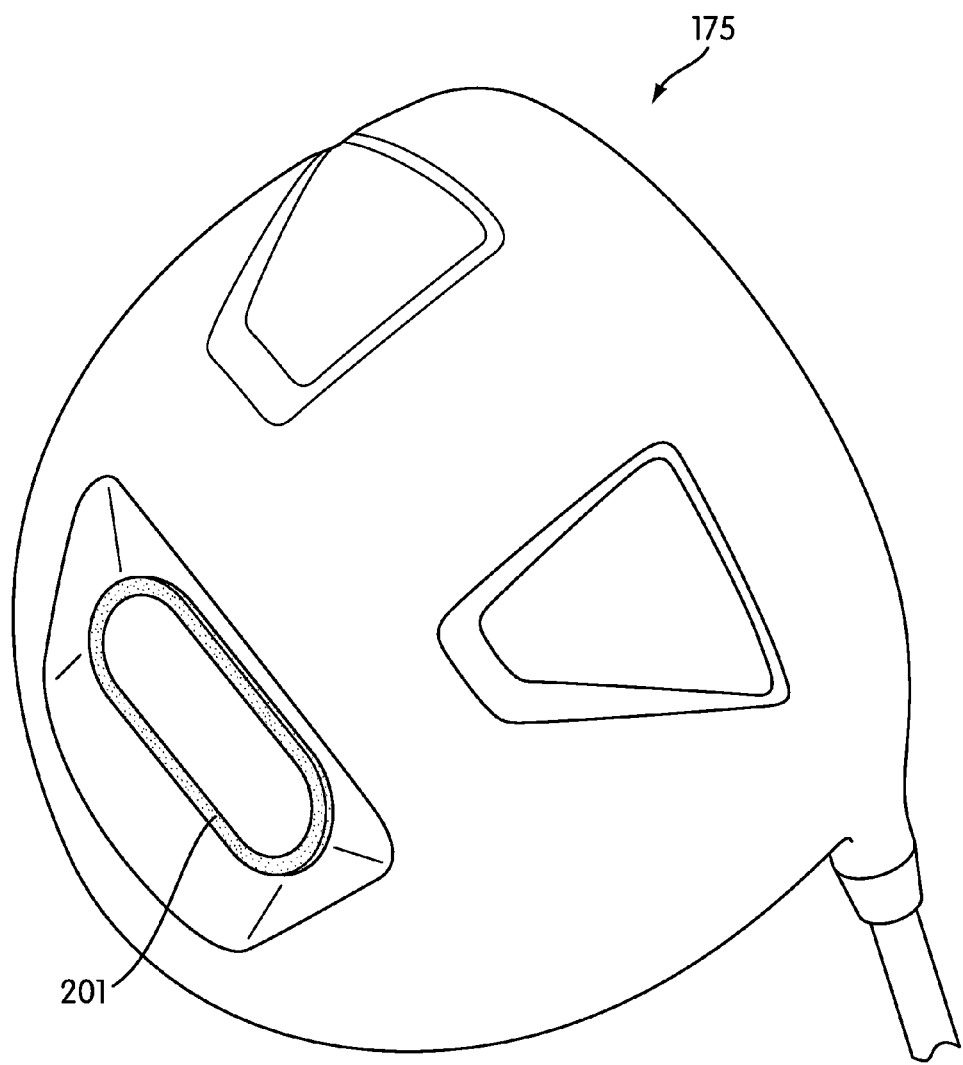
FIG. 5G is an illustrative embodiment of another wood-type golf club structure supporting a monitoring device according to aspects of the disclosure.

FIG. 5G illustrates another illustrative embodiment of a golf club head 175 according to aspects of the disclosure. As seen in FIG. 5G, the golf club head 175 includes a recess in the rear of the golf club head 175. The recess may be configured to receive the monitoring device 201. For example, the portion of the rear of the golf club head 101 may include a smaller recess configured to receive the monitoring device 201. The engagement of the monitoring device 201 with the golf club head 175 can be done in a variety of ways, such as in the above described embodiments.

According to aspects of the disclosure, the monitoring device 201 may include an activation system. The activation system may be used for selectively activating the monitoring device 201 and/or at least some functions of the monitoring device 201 (e.g., data transmission/reception functions, data storage functions, data calculation functions, etc.). A wide variety of different activation systems may be used without departing from this disclosure.

For example, input from the activation system may be provided in any desired form or format without departing from the disclosure. As some more specific examples, if desired, the activation system may include a simple button, switch, or other input source that simply provides an activation or deactivation signal to the monitoring device 201 (e.g., a logical "1" or "0"). If desired, in at least some examples according to this disclosure, the activation system may activate the monitoring device 201, based on input it receives from the remote computer 400 (described below). For example a golfer may manually activate the monitoring device 201 by providing input (e.g., pressing a button) on the remote computer 400. Alternatively, the activation system may activate the monitoring device 201 automatically upon a certain action being performed. For example, when a golfer moves the club in which the monitoring device 201 is inserted, the activation system may induce the monitoring device 201 or its functions to operate. For example, if the monitoring device 201 includes an accelerometer and the golfer waggles the club (e.g., moves the club) over a predefined speed or length of time, the activation system may automatically activate the monitoring device 201 and/or at least some functions of the monitoring device 201 (e.g., data transmission/reception functions, data storage functions, data calculation functions, etc.). Further, the activation system may activate the monitoring device 201 when the golf club expands on impact (e.g., an impact with a golf ball). Further, it is noted that a monitoring device 201 may be configured to enter a sleep mode to conserve battery power if the monitoring device 201 is not used for a predetermined amount of time.

As discussed above, according to aspects of the disclosure, one of the sensors 202 may be an accelerometer. An accelerometer is a device used to measure acceleration. For example, an accelerometer may measure the magnitude and the direction of acceleration. An accelerometer according to aspects of the disclosure may include a three-axis accelerometer for measuring acceleration along three orthogonal axes. According to aspects of the disclosure, one or more accelerometers may be included in the golf club 100. For example, one or more accelerometers may be included in the monitoring device 201 or other a micro-electromechanical system (MEMS) configured to be engaged within the golf club head body 101 or shaft 103/grip 105.

According to aspects of the disclosure, the accelerometer may be configured to measure the velocity of the golf club 100 (e.g., club head 101, shaft 103, grip 105) during a golf swing, the acceleration of the club 100 (e.g., club head 101, shaft 103, grip 105) during a golf swing, etc.

According to aspects of the disclosure, one of the sensors 202 may be a magnetometer. A magnetometer is an instrument used to measure the strength and or the direction of a magnetic field around the instrument. According to aspects of the disclosure, one or more magnetometers may be included in the golf club 100. For example, one or more magnetometers may be included in the monitoring device 201 or other MEMS configured to be engaged within the golf club head body 101 or shaft 103/grip 105.

Figure 5H:
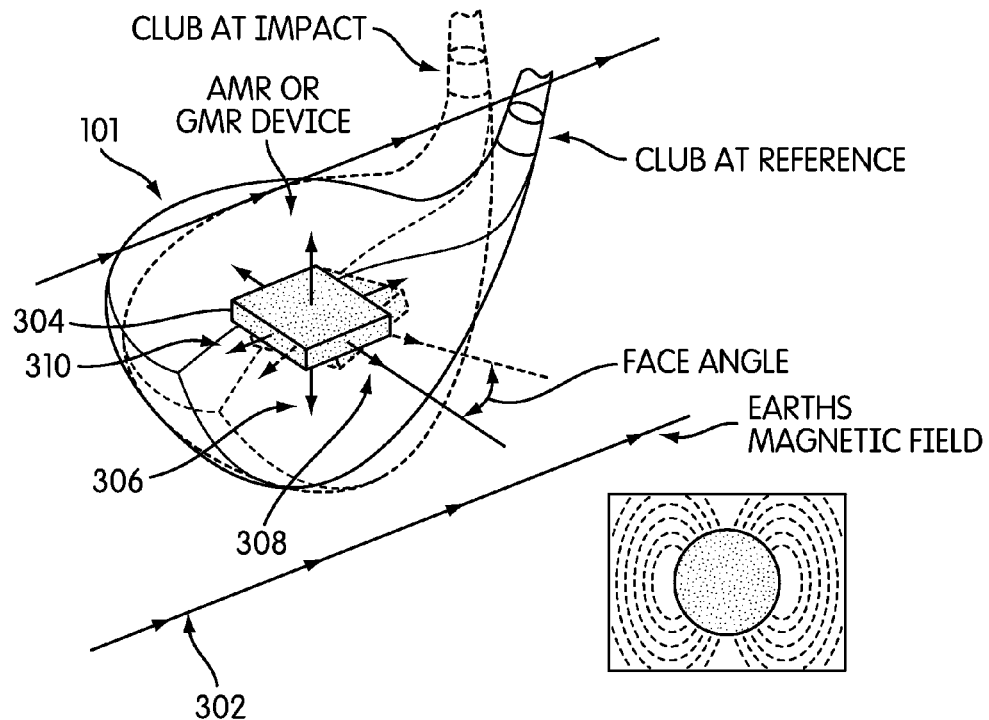
FIG. 5H illustrates an instrumented golf club that includes a magnetic field sensor, in accordance with an embodiment of the invention.

According to aspects of the disclosure, one or more magnetometers may also be used to determine golf swing parameters. As shown in FIG. 5H, the earth's magnetic field represented by vector 302 is relatively constant in the vicinity of a golfer. A magnetometer 304 resolves magnetic field vector 302 into three component vectors 306, 308 and 310. Magnetometer 304 may be implemented with an anisotropic magnetoresistive (AMR) device, a giant magnetoresistor (GMR) device or other suitable devices. As golf club head 101 moves, the magnetic field vector 302 is resolved into component vectors 306, 308 and 310 such that the respective components have different magnitudes. According to aspects of the disclosure, the changing magnitudes of the component vectors may then be used to determine golf swing parameters.

For example, a club head face angle may be determined by first taking a reference measurement of the magnetic field before the back swing and then taking another measurement of the magnetic field just prior to impact. For example, the magnitude of component vectors 306, 308 and 310 will have first values before the back swing and second values just prior to impact. The different component vector values can then be used to determine the face angle. If the magnetic field in the x-y plane is assumed to be 0.3 Gauss, the component X of the field with respect to component vector 308 (x axis) is determined by $X=0.3 \cos \theta$ and the component Y of the field with respect to component vector 310 (y axis) is determined by $Y=0.3 \sin \theta$.

A 1 degree difference would cause a change in the magnitudes of vector components 308 and 310 as follows:

$$\Delta X = 0.3(\cos\theta - \cos(\theta+1))$$

$$\Delta Y = 0.3(\sin\theta - \sin(\theta+1))$$

The smallest change that needs to be detected along each vector component may be determined by taking the derivative of each component and determining were the derivative crosses the 0 axis.

$$dX/d\theta = -0.3 \sin\theta = 0 \text{ at } \theta = 0 \text{ degrees}$$

$$dY/d\theta = 0.3 \cos\theta = 0 \text{ at } \theta = 90 \text{ degrees}$$

The highest resolution in the x-component is needed when the angle rotates from 0 to 1 degree and corresponds to 45.7 µG. The same resolution is needed when the y-component rotates from 89 to 90 degrees.

Other golf swing parameters may be determined by magnetometers. For example, according to aspects of the disclosure, swing tempo may be determined by using vector component 306 (z axis) as a tilt sensor. A reference measurement of vector component 306 may be recorded before the back swing. The period required for the club head to return to a position such that the vector component 306 returns to the measured reference value corresponds to the swing tempo. In an alternative embodiment, velocity information may also be just to determine impact time and the resulting swing tempo.

Figure 5I:
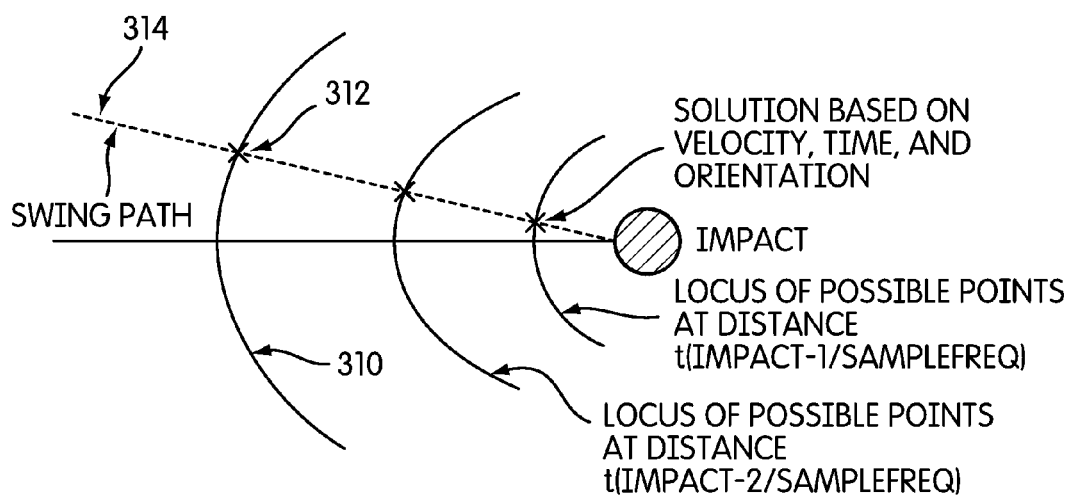
FIG. 5I illustrates how velocity, time and orientation measurements may be used to determine the swing path of a golf club, in accordance with an embodiment of the invention.

Further, several different measurements may be used to determine the swing path. For example, FIG. 5I shows a diagram of how velocity, time and orientation measurements may be used to determine the swing path. For example, velocity and time information measurements may be used to determine a first locus of points 310. Next, an orientation measurement may then be used to determine a first location 312 along first locus of points 310. The process of identifying club locations may be repeated several times to determine a swing path 314. In one embodiment, measurements are taken at least 1 kHz during a swing. Swing path 314 may be determined relative to a reference orientation and impact location.

According to aspects of the disclosure, one of the sensors 202 may be a gyroscope. A gyroscope is a device used to measure orientation and rotation. For example, a gyroscope may measure orientation based on the principles of the conservation of angular momentum. Further, according to aspects of the disclosure, a three-axis gyroscope may be used to increase accuracy. When combined with an accelerometer, the combination of the gyroscope and the accelerometer may provide a more accurate indication of movement within a 3-D space when compare to an accelerometer alone. According to aspects of the disclosure, one or more gyroscopes may be included in the golf club 100. For example, one or more gyroscopes may be included in the monitoring device 201 or other MEMS configured to be engaged within the golf club head body 101 or shaft 103/grip 105.

Figure 5J:
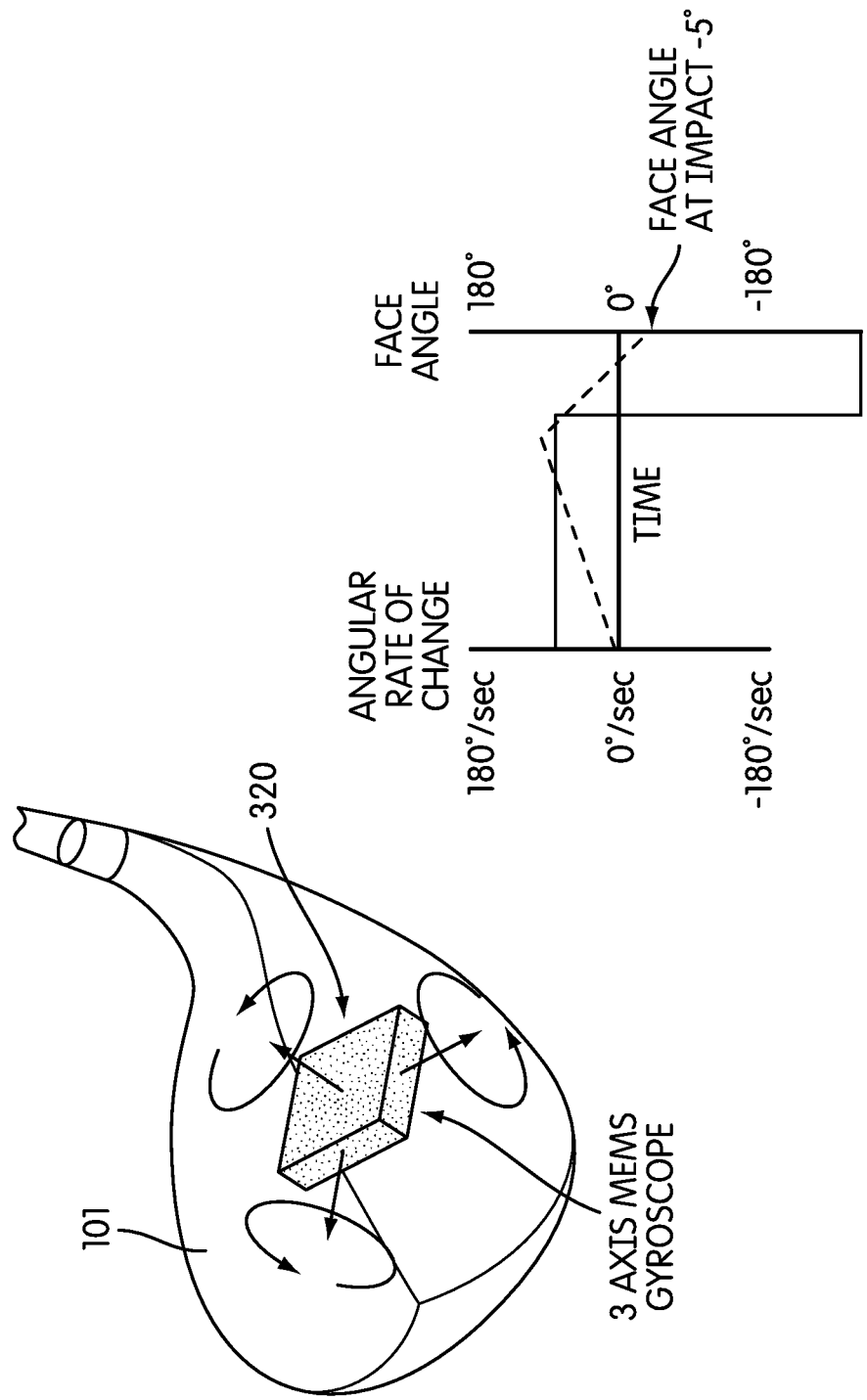
FIG. 5J illustrates an instrumented golf club that includes a gyroscope module, in accordance with an embodiment of the invention.

FIG. 5J shows an embodiment in which a gyroscope 320 is placed within a golf club head 101 to measure golf swing parameters. Gyroscope 320 may be implemented with a micro-electromechanical system (MEMS) or other device or module capable of fitting within golf club head 101. A three-axis gyroscope may be used to increase accuracy.

According to aspects of the disclosure, the gyroscope 320 may be configured to determine golf swing parameters by assuming that the point of rotation is a golfer's shoulders. Club head velocity may be determined by an accelerometer (such as described above) that is part of the same MEMS, an external accelerometer or some other device. For golf swing parameter determination purposes, in the proximity of a golf ball the movement of golf club head 101 may be modeled as an object moving on the surface of a sphere. The sphere has a radius equal to the length of the club plus the length of the golfer's arms. In one embodiment, a standard radius of 62.5 inches is used. In other embodiments, a golfer may provide his or her arm length and/or club length for more accurate determinations.

Figure 5K:
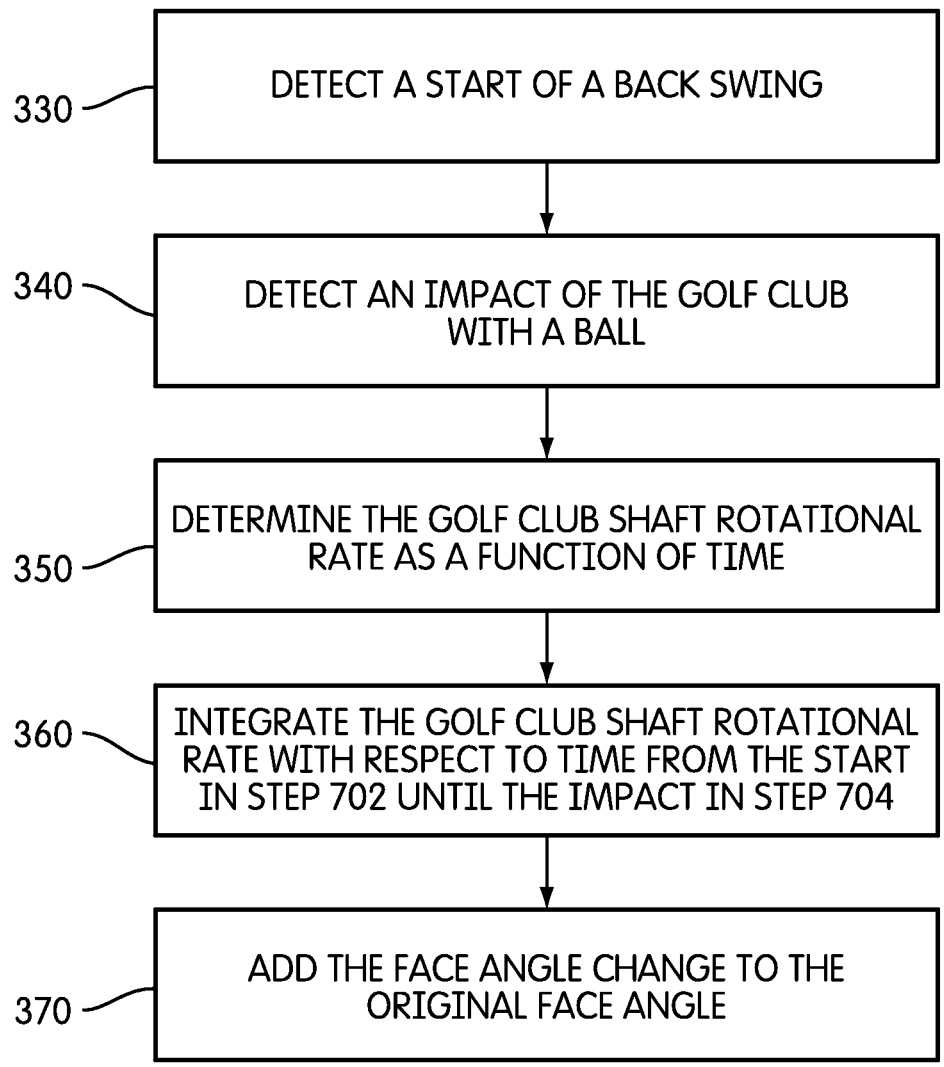
FIG. 5K illustrates a method of determining the face angle of a golf club with the use of a gyroscope, in accordance with an embodiment of the invention.

The face angle of golf club head 101 may be determined as a function of the shaft rotation rate. The shaft rotation rate may be determined by gyroscope 320. FIG. 5K illustrates one exemplary method of determining the face angle with the use of a gyroscope. First, in step 330 the start of the back swing is determined. A velocity sensor may be used to determine the start of the back swing. In step 340 impact of the golf club with a ball is detected. Step 350 may be performed by the impact sensors described above. The shaft rotational rate as a function of time may be determined by gyroscope 320 in step 350. Step 350 preferably includes determining the shaft rotational rate from at least the start in step 330 until at least the impact in step 340. Next, in step 360, the golf club shaft rotational rate is integrated with respect to time from the start in step 330 until the impact in step 340 in accordance with the following formula:

$$\text{Face Angle Change} = \int_{BackswingStart}^{Impact} \text{Shaft Rotation Rate}(t)\,dt$$

The face angle is then determined by adding the face angle change to the original face angle in step 370.

Club head speed may be determined as a function of the radius (arm length plus club length) and angular velocity. In particular, the club head speed is the product of the radius and the angular velocity of golf club head 101.

Swing tempo may be determined by first determining when the angular rate is zero and begins to increase at the start of the back swing. The time of impact may then be determined by a spike in the angular rate that accompanies the impact or from one or more other sensors, such as an accelerometer or impact sensor.

Rotational velocities may also be used to determine the swing path. In one embodiment in which gyroscope 320 is implemented with a three axis gyroscope and in which the z-axis is used to determine changes in face angle, the y-axis is used to determine motion in a target reference plane and the x-axis is used to determine motion parallel to the target reference plane, the swing path may be estimated by the following formula:

$$SwingPath = \operatorname{atan}\left(\frac{xAxisRotationalVelocity}{yAxisRotationalVelocity}\right)$$

Therefore, as demonstrated above, the monitoring device can determine various aspects of a golfer's golf swing, including: the velocity of the golf club (or club head) during a golf swing, the acceleration of the club (or club head) during a golf swing, the angle of the golf club (or club head) during a golf swing (e.g., relative to one or more reference points), swing tempo, the impact of the ball with the golf club head during a golf swing, etc.

As described above, the golf club 100 may include a transmitter 203. Further, it is noted that while a transmitter is the depicted embodiment, according to particular embodiments of the disclosure, the transmitter 203 may be a transceiver which is capable of receiving data as well as transmitting data. Data determined from each of the one or more sensors 202 may be communicated to the transmitter 203. For example, the one or more sensors 202 may be electrically connected to transmitter 203. Alternatively, data may be communicated wirelessly from the one or more sensors 201 to the transmitter 203. Regardless of how the data is communicated from the one or more sensors 202 to the transmitter 203, the transmitter 203 may be configured to transmit the data determined by the one or more sensors 202 to a remote computer system 400 (e.g., a portable computer device with a receiver configured to receive the data from the transmitter 203). While not shown, according to aspects of the disclosure, the monitoring device 201 may include a memory. The memory may be configured to store data from the one or more sensors 202. More specifically, the memory may store data while the golfing activity takes place and save it for later transmission to the remote computer system 400 (as discussed below).

While the data may be transmitted from the transmitter 202 in any desired manner, wireless type transmissions may be used in embodiments of the disclosure. Any desired wireless transmission system and method may be used without departing from the scope of the disclosure, including the use of any desired wireless data transmission format or protocol, including the transmission systems and protocols currently in use in NIKE+™ athletic performance monitoring systems. According to example aspects of the disclosure, the transmitter 203 may be configured to transmit data using a variety of conventional protocols. For example, the monitoring device 201 may be configured to communicate using the Bluetooth wireless communication protocol, so that it can be employed with Bluetooth-capable mobile telephones, personal digital assistants, watches or personal computers. Further, other methods of transmitting may be used as well, such as Bluetooth2, RFID, infrared transmission, cellular transmissions, etc.

Further, according to example aspects of the disclosure, the transmitter 203 may be configured to transmit data via an antenna. For example, in one embodiment of the invention, a ferrule is used as an antenna. The ferrule may be formed of a metal material or other type of antenna material. In another embodiment, shaft 103 may function as an antenna. An antenna may also be plated onto shaft 103, embedded under grip 105 or placed in any other location that does not interfere with a golf swing. The monitoring device 201 and the golf club head 101 may be configured such that a connection is made between the transmitter 203 and the antenna when the monitoring device 201 is engaged with the golf club head 101.

While wireless communication between the monitoring device 201 and the remote computer system 400 is described above, it is noted that any desired manner of communicating between the monitoring device 201 and the remote computer system 410 may be used without departing from the scope of the disclosure, including wired connections. For example, if desired, monitoring device 201 may include its own data storage system for storing data from the one or more sensors 202. Further, the monitoring device 201 may be configured to be engaged with the remote computer system 400 in order to transmit data to the remote computer 400. For example, monitoring device 201 may include an interface (e.g., a USB connection) configured to engage with a port of the remote computer system 400 in order to transmit data to the remote computer 400.

According to aspects of the disclosure, data collected from the sensors 202 may be stored during a practice session or a round of golf. Then, at a convenient time, such as after the practice session or round of golf, the golfer may disengage the monitoring device 201 from the golf club head and engage it with the remote computer system 400 in order to transmit the data to the remote computer system 400. Any type of connection system may be used without departing from the scope of the disclosure, including a wireless connection, a hardwired connection, connection via an input port (such as a USB port, or the like), etc.

Other data storage and/or transmission arrangements also are possible without departing from the scope of the invention. For example, any desired way of placing data derived from the physical data from the monitoring device 201 in the proper form or format for communication to the remote computer system 400 may be provided without departing from the invention. For example, as discussed above, the monitoring device 201 may include a receiver (e.g., the transmitter 203 may be a transceiver) which determines whether a transmission from transmitter 203 has been or is being received by the remote computer 400. If the transmission from transmitter 203 is not received by the remote computer 400, the monitoring device 201 may be configured to store the data on the memory (e.g., if the remote computer system 400 is not in range or is turned off). In this way, data collected by the sensors 202 will be stored locally so that it will not be lost and can be downloaded later to the remote computer system 400.

The remote computer system 400 may be any desired type of computer system, at any desired location, without departing from the scope of the disclosure.

An example remote computer 400 may include a processor system (which may include one or more processors or microprocessors, which may be configured to execute software instructions), a memory, a power supply, an output device, other user input devices, and data transmission/reception system (e.g., a wireless transceiver). The processor system and the memory may be connected, either directly or indirectly, through a bus or alternate communication structure to one or more peripheral devices. For example, the processor system or the memory may be directly or indirectly connected to additional memory storage, such as a hard disk drive, a removable magnetic disk drive, an optical disk drive, and a flash memory card. The processor system and the memory also may be directly or indirectly connected to one or more input devices and one or more output devices. The input devices may include, for example, a keyboard, touch screen, a remote control pad, a pointing device (such as a mouse, touchpad, stylus, trackball, or joystick), a scanner, a camera or a microphone. The output devices may include, for example, a monitor display, speakers, etc.

Still further, the processor system may be directly or indirectly connected to one or more network interfaces for communicating with a network. This type of network interface, also sometimes referred to as a network adapter or network interface card (NIC), translates data and control signals from the processor system into network messages according to one or more communication protocols, such as the Transmission Control Protocol (TCP), the Internet Protocol (IP), and the User Datagram Protocol (UDP). These protocols are well known in the art, and thus will not be discussed here in more detail. The data transmission/reception system may employ any suitable connection agent for connecting to a network, including, for example, a wireless transceiver, a power line adapter, a modem, or an Ethernet connection.

It should be appreciated that, in addition to the input, output and storage peripheral devices specifically listed above, the computing device may be connected to a variety of other peripheral devices, including some that may perform input, output and storage functions, or some combination thereof.

Of course, still other peripheral devices may be included with or otherwise connected to the remote computer system 400, as is well known in the art. In some cases, a peripheral device may be permanently or semi-permanently connected to the processor system. For example, as with many computers, the processor system, the hard disk drive, the removable optical disk drive and a display are semi-permanently encased in a single housing. Still other peripheral devices may be removably connected to the remote computer system. The remote computer system may include, for example, one or more communication ports through which a peripheral device can be connected to the processor unit (either directly or indirectly through the bus). These communication ports may thus include a parallel bus port or a serial bus port, such as a serial bus port using the Universal Serial Bus (USB) standard or the IEEE 1394 High Speed Serial Bus standard (e.g., a Firewire port). Alternately or additionally, the remote computer system 400 may include a wireless data "port," such as a Bluetooth interface, a Wi-Fi interface, an infrared data port, or the like.

According to aspects of the disclosure, the transmission/reception system may be configured for communication with the transmitter 203 of the monitoring device via the above described transmission/reception systems and/or through any type of known electronic communications. If desired, in accordance with at least some examples of this invention, the remote computer system 400 may include a display and/or a user input system, such as one or more rotary input devices, switches, buttons, mouse or trackball elements, touch screens, or the like, or some combination thereof.

The display may be employed to show, for example, information relating to the golfing information signals being received by the remote computer system 400, etc. The user input system may be employed, for example: to control one or more aspects of the processing of the input data received, to control input data receipt (e.g., timing, types of information received, on-demand data requests, etc.), to control data output, to control the monitoring device, etc. Alternatively or additionally, if desired, the input system on the remote computer system 400 (e.g., buttons, a touch screen, a digitizer/stylus based input, a rotary input device, a trackball or roller ball, a mouse, etc.), may be used to provide user input data to the monitoring device 201. As still another example, if desired, a voice input system may be provided with the interface device and/or the remote computer system 400, e.g., to enable user input via voice commands. Any other desired type of user input system, for control of any system elements and/or for any purpose, may be provided without departing from the scope of the disclosure. For example, the remote computer system 400 may include additional input and/or output elements, e.g., such as ports e.g., for headphones (or other audio output), power supplies, wireless communications, infrared input, microphone input, or other devices.

According to aspects of the disclosure, the remote computer system 400 may be, for example, portable audio and/or video players, cellular telephones, personal digital assistants, pagers, beepers, palm top computers, laptop computers, desktop computers, servers, or any type of computer controlled device, optionally a computer controlled device that generates or displays a human perceptible output and/or interface.

Figure 6B:
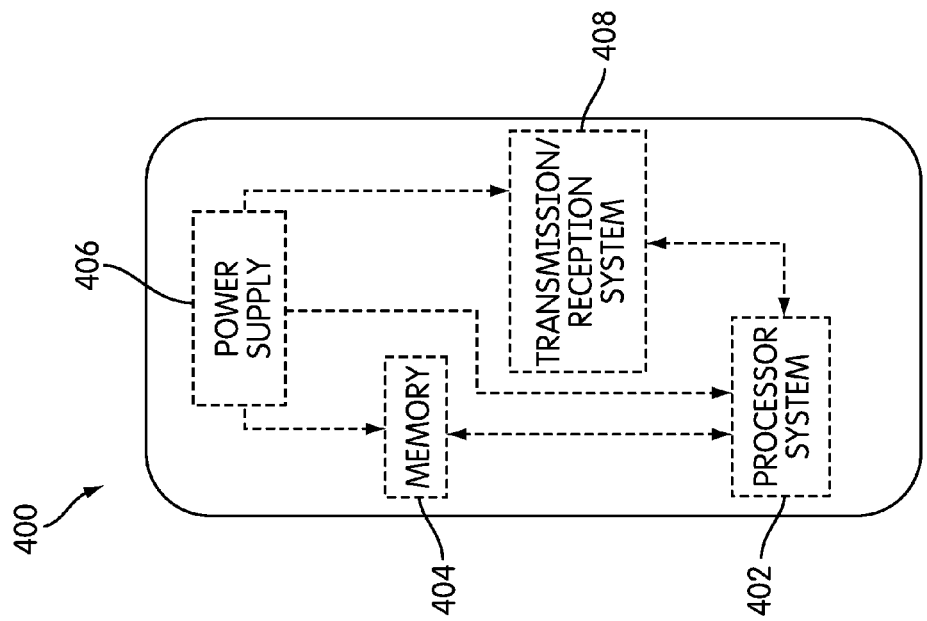
FIGS. 6A and 6B illustrate a remote computer system according to an illustrative embodiment of the disclosure.
Figure 6A:
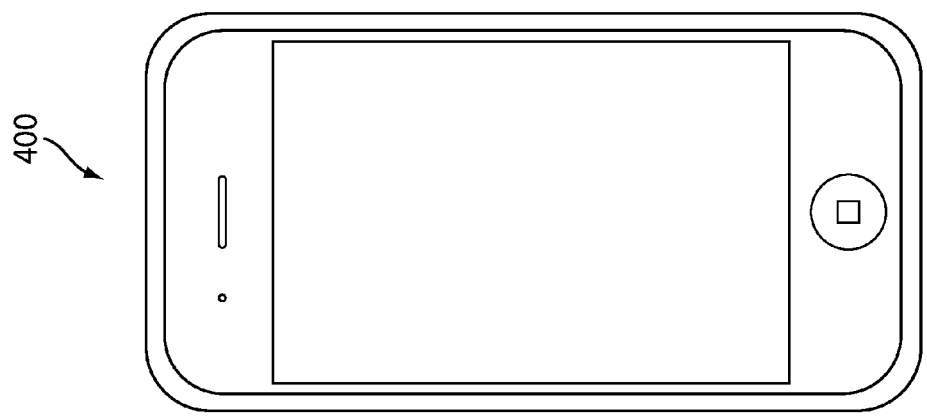

FIG. 6 illustrates one example of a remote computer system 400 that may be employed according to various examples of the invention to measure various information corresponding a golfer's abilities and game. As shown in this figure, the remote computer system 400 may be a cellular telephone (e.g., a Bluetooth enabled cellular telephone, such as an IPHONE®, BLACKBERRY®, DROID®, or other smart phone, etc.). FIG. 6 also illustrates a schematic rendering of the remote computer system 400. As seen in FIG. 6, the cellular telephone may include a processor system 402, a memory 404, a power supply 406, and a data transmission/reception system (e.g., a wireless receiver or transceiver) 408. The memory 404 may include both a read-only memory (ROM) and a random access memory (RAM). As will be appreciated by those of ordinary skill in the art, both the read-only memory (ROM) and the random access memory (RAM) may store software instructions for execution by the processor system 400. The data transmission/reception system 408 may be configured to receive, from the transmitter 203, data that corresponds to the measured golfing parameter. Further, as shown, the data transmission/reception system 408 may be configured to provide the received data to the processor 402.

For example, according to aspects of the disclosure, the data transmission/reception system 408 receives the signals (e.g., processed or unprocessed signals) transmitted by the transmitter 203 in the monitoring device 201. The data transmission/reception system 408 may be configured to relay the signals to the processor 402, which processes the signals further. Like the processor 204, the processor 402 may perform any desired operation on the processed signals, such as curve smoothing, noise filtering, outlier removal, amplification, summation, integration, or the like.

According to aspects of the disclosure, the processor 402 may initially store the processed signals in a memory 404. Further, with some implementations of the disclosure, the processor 402 may operate on the processed signals provided by the monitoring device 201 to generate a set of data corresponding to the golf activity performed by the golfer. For example, if the monitoring device 201 includes accelerometers for measuring the acceleration of the golf club head 101, the processor 402 may analyze the signals from the monitoring device 201 to generate a set of data describing the acceleration of the golf club head 101 at specific instances during the golf swing. It is noted that the transmitted data set may also include a time value associated with each speed value.

Once the processor 402 has generated a set of data from the information provided by the monitoring device 201, the processor 402 may store the data set in the memory 404. As will be discussed in more detail below, when the remote computer system 400 subsequently is connected to a second computing device 500 implementing a golf information collection tool, the computing unit 404 may be configured download the data to a display configuration tool.

It is noted that the above described monitoring system (which includes the monitoring device 201 and the remote computer system 400) may be configured to be active, real-time transmitting systems that provides data to the remote computer system 400 as the golf activity is taking place. Optionally, if desired, the remote computer system 400 may be configured to provide the golfer with real-time performance feedback (e.g., velocity of the golf club head, acceleration of the golf club head, the impact position of the golf ball on the ball striking face, path of the swing path of a particular swing, face angle of the ball striking face of the club head throughout the swing (e.g., during impact), etc.) while the golfing performance is taking place. The real-time performance feedback could be in the form of an audio or visual message. For example, if desired, the remote computer system 400 may be configured to provide an output based on the received data from the sensors 202, wherein the output provides feedback to the golfer in real time, such as when the athletic performance is taking place. For example, the output may be as a visual display such as an alphanumeric, video, or textual output. Additionally, or alternatively, the output may be an audio output, such as an audio tone, message, etc.

According to example aspects of the disclosure, the output may include a visual display provided on the display screen of the cellular telephone, wherein the visual display includes one of: an illustration of a swing path of a golf swing, a numeric value of a maximum acceleration of the golf club head 101 during a golf swing (and, if desired, at a particular time relative to the duration of the golf swing when that maximum acceleration was reached), a numeric value of the acceleration or velocity of the golf club head 101 at a particular time relative to the duration of the golf swing (e.g., the acceleration or velocity of the golf club head 101 during impact or on the backswing), the angle of the ball striking face 107 at a particular time relative to the duration of the golf swing (e.g., the angle of the ball striking face 107 during impact; this may be represented with characters (e.g., "Open Face", "Closed Face", etc.) or graphically (e.g., pictures of a golf club head with an "Open Face", "Closed Face", etc.), the impact location of the golf ball on ball striking face, messages (e.g., "Great Shot!" or "You Hit a Slice"), etc. Similarly, audio messages may be employed as well. For example, recorded messages (e.g., recorded by well known golfers) may be stored in the memory and played based on predefined circumstances being achieved.

It should be appreciated that, while some specific embodiments of the invention described above relate to a cellular telephone, alternate examples of the disclosure may be implemented using other portable electronic device. For example, with some implementations of the invention, the monitoring device 201 may be used in conjunction with a digital music or video player, a watch, a personal digital assistant, another type of music player (such as a compact disc or satellite radio music player), a portable computer, or any other desired electronic device. For example, remote computer system 400 may be in the form of a wrist band, such as a watch or other wrist borne data receiving device, or an arm band, or other apparel. Therefore, it is understood that while several examples of the remote computer system 400 are described above, the remote computer system 400 may take on a variety of different forms without departing from the scope of the disclosure.

It is noted, that if the remote computer system 400 does not have an internal electronic interface device (e.g., if the remote computer 400 is a digital music player, such as an iPod®, the data transmission/reception system 408 (e.g., the receiver or transceiver) may be a separate device which is configured to engage with the remote computer system 400. For example, the data transmission/reception system 408 may include a connector system that physically plugs into and connects with a conventional input port provided on remote computer system 400. The input port into which the connector system of the data transmission/reception system 408 connects may be any desired type of input port for transferring data, such as a parallel data port, a serial data port, an earphone or microphone jack, etc. The connector system may include any suitable connecting devices, such as wires, pins, electrical connectors, and the like, so as to make an electrical connection or other suitable connection with corresponding elements provided in the input port of the remoter computer system 400 (e.g., to allow electronic and/or data communications between the remote computer system and the electronic interface device). If necessary or desired, additional securing elements may be provided to securely connect the interface device to the remote computer system 400, such as straps, hooks, buckles, clips, clamps, clasps, retaining elements, mechanical connectors, and the like. In this way, when the external data transmission/ reception system 408 is engaged with the remote computer system 400, the remote computer system 400 may communicate wirelessly with the monitoring device 201.

Figure 7A:
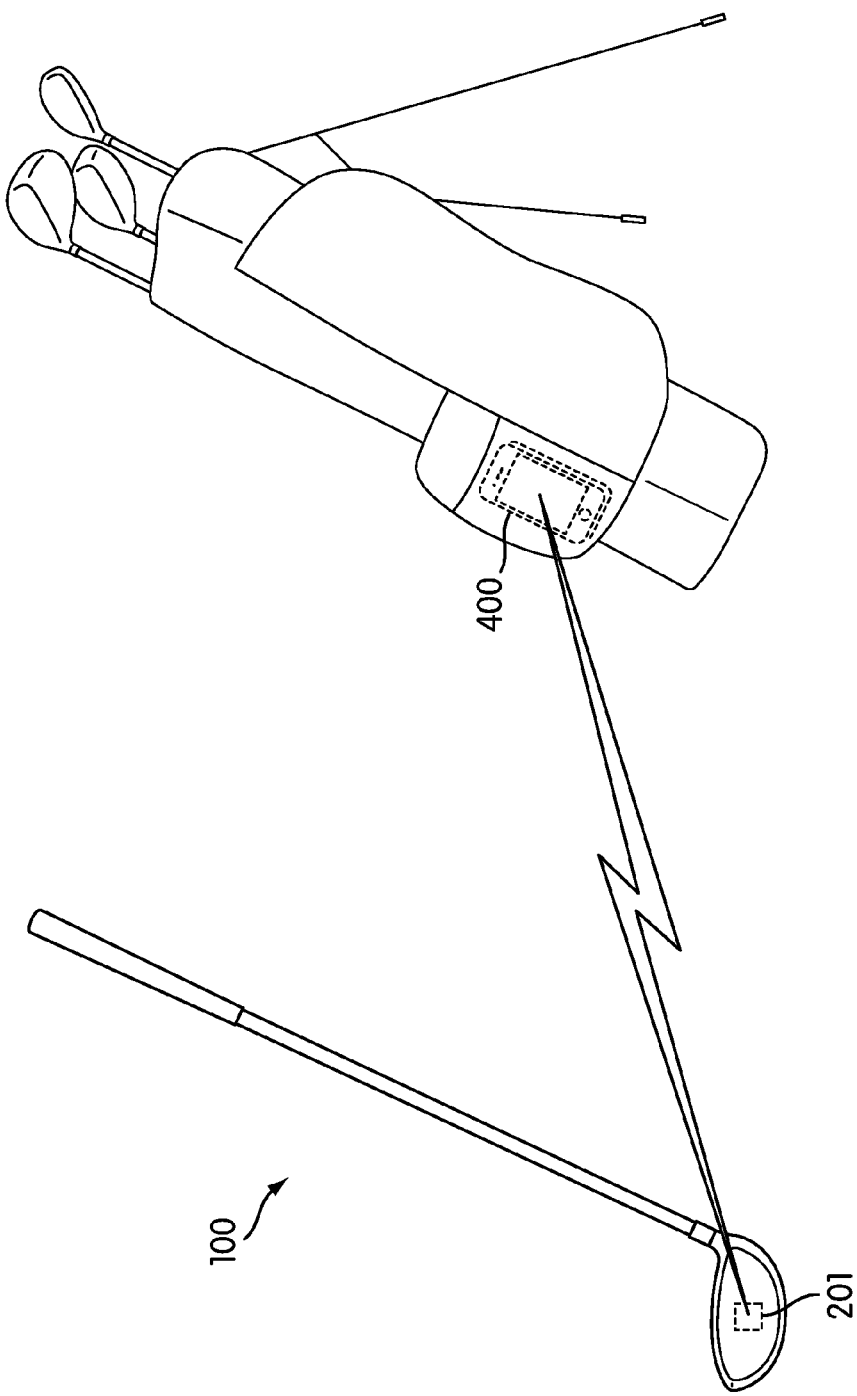
FIGS. 7A and 7B illustrate wireless communication between the monitoring device and the remote computer system according to an illustrative embodiment of the disclosure.
Figure 7B:
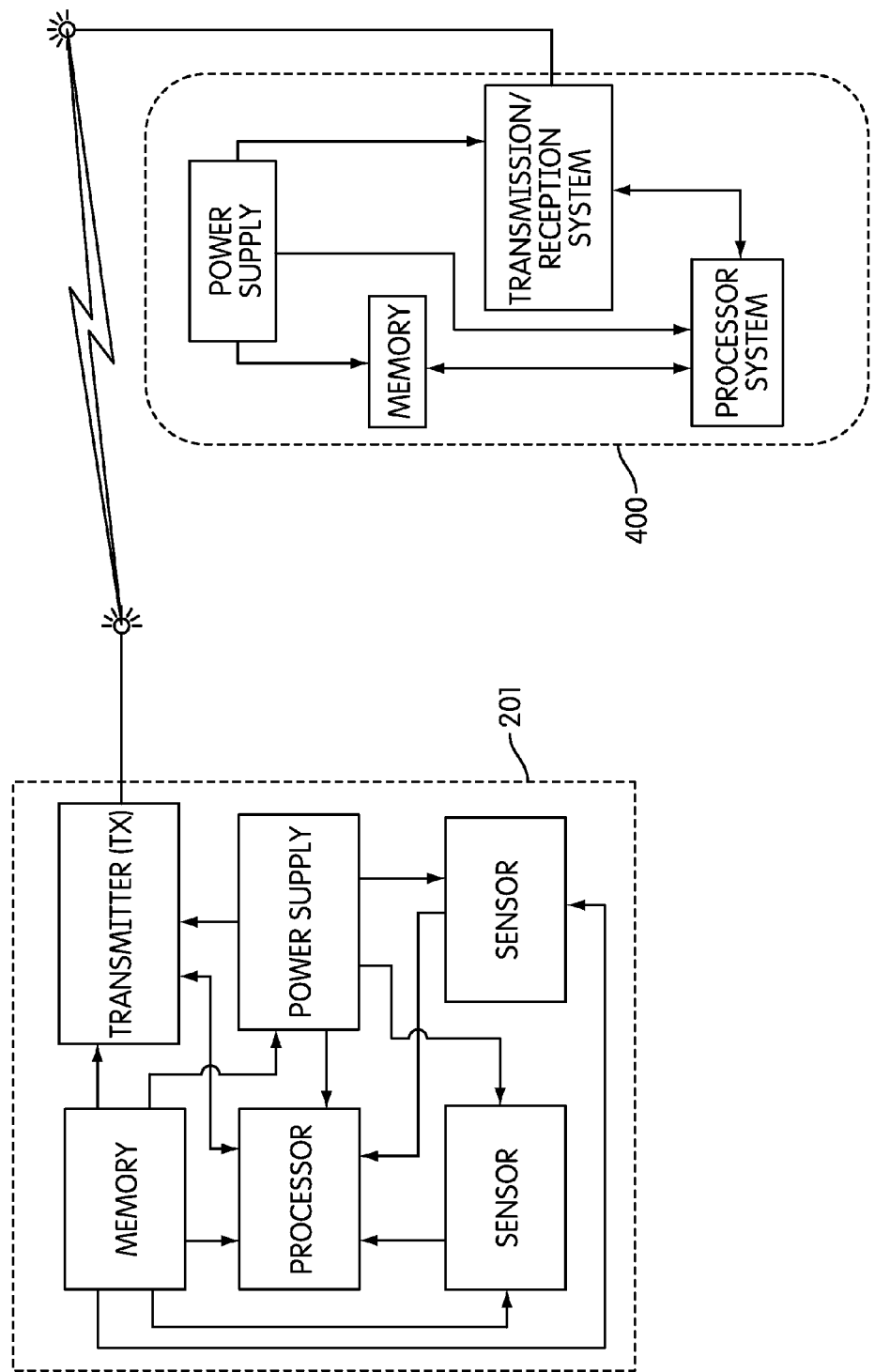

FIGS. 7A and 7B show an illustrative transmission from the monitoring device 201 to the remote computer system 400 according to aspects of the disclosure. Specifically, FIG. 7B illustrates the transmitter (or transceiver) 203 of the monitoring device 201 communicating with the transmission reception system 408 of the remote computer 400. As described above, in embodiments in which the monitoring device 201 includes a transceiver 203, the communication may be two-way, i.e., from the transceiver 203 to the transmission reception system 408 of the remote computer 400 and, also, from the transmission reception system 408 to the transceiver 203. However, in embodiments in which the monitoring device 201 includes a transmitter 203, the communication will be one way, i.e., from the transmitter 203 to the transmission reception system 408 of the remote computer 400.

According to aspects of the disclosure, the determination of data by the monitoring device 201 and the transmission of data between the monitoring device 201 and the remote computer 400 may be performed in a variety of ways.

For example, according to a first method in which the monitoring device 201 determines data and then communicates the data to the remote computer 400, the monitoring device 201 includes sensors 202 (e.g., one or more accelerometers, one or more gyroscopes, and/or one or more magnetometers), a transmission module 203 (e.g., a transmitter or transceiver configured to transmit/receive data wirelessly (e.g., through RF, Bluetooth, Bluetooth2, etc.)), a processor 204 (e.g., microprocessor) and a power source 206 (e.g., a battery). Further, according to such a method, data determined by the monitoring unit is transmitted to the remote computer 400 (e.g., a portable telephone, a computer (e.g., a PC), a sport tablet, an electronic range finder, such as SKY CADDIE® available from SKY GOLF®), etc. Further, according to such a method, data may be determined by the sensors 202. Once the data is determined by the sensors, the processor 204 in the monitoring device 201 may use the data to calculate golf metrics or variables (e.g., a swing path representation as discussed) According to aspects of the method, the golf metrics or variables may be transmitted wirelessly via the transmission module 203 to the remote computer 400. Alternatively, according to other aspects of the method, the golf metrics or variables may be stored in a memory in the monitoring device 201. Afterwards, (e.g., after a number of golf shots), the golf metrics or variables may be transmitted wirelessly via the transmission module 203 to the remote computer 400. According to aspects of this method, the remote computer 400 may be configured to store the golf metrics or variables, communicate the golf metrics or variables to the user, e.g., through video or audio means, and/or further transmit the golf metrics or variables to other devices.

According to another method in which the monitoring device 201 determines data and then communicates the data to the remote computer 400, the monitoring device 201 includes sensors 202 (e.g., one or more accelerometers, one or more gyroscopes, and/or one or more magnetometers), a transmission module 203 (e.g., a transmitter or transceiver configured to transmit/receive data wirelessly (e.g., through RF, Bluetooth, Bluetooth2, etc.)), a processor 204 (e.g., a microprocessor) and a power source 206 (e.g., a battery). Further, according to such a method, data determined by the monitoring unit is transmitted to the remote computer 400 (e.g., a portable telephone, a computer (e.g., a PC), a sport tablet, an electronic range finder, such as SKY CADDIE® available from SKY GOLF®), etc. Further, according to such a method, data may be determined by the sensors 202. Once the data is determined by the sensors, the processor 204 in the monitoring device 201 may use the data to calculate kinematics (e.g., computed acceleration data). According to aspects of the method, the kinematics may be transmitted wirelessly via the transmission module 203 to the remote computer 400. For example, the kinematics may be transmitted during each golf shot or after each golf shot. Alternatively, according to other aspects of the method, the kinematics may be stored in a memory in the monitoring device 201. Afterwards, (e.g., after a number of golf shots or whenever the golfer desires), the kinematics may be transmitted wirelessly via the transmission module 203 to the remote computer 400. Regardless of when the kinematics are transmitted from the monitoring device 201 to the remote computer 400, once the kinematics are received by the remote computer 400 (e.g., via the transmission reception system 408), the remote computer 400 may be configured to process the kinematics to calculate golf metrics or variables. According to aspects of this method, the remote computer 400 may be configured to store the golf metrics or variables, communicate the golf metrics or variables to the user, e.g., through video or audio means, and/or further transmit the golf metrics or variables to other devices.

According to another method in which the monitoring device 201 determines data and then communicates the data to the remote computer 400, the monitoring device 201 includes sensors 202 (e.g., one or more accelerometers, one or more gyroscopes, and/or one or more magnetometers), a transmission module 203 (e.g., a transmitter or transceiver configured to transmit/receive data wirelessly (e.g., through RF, Bluetooth, Bluetooth2, etc.)), a processor 204 (e.g., a microprocessor) and a power source 206 (e.g., a battery). Further, according to such a method, data determined by the monitoring unit is transmitted to the remote computer 400 (e.g., a portable telephone, a computer (e.g., a PC), a sport tablet, an electronic range finder, such as SKY CADDIE® available from SKY GOLF®), etc. Further, according to such a method, data may be determined by the sensors 202. Once the data is determined by the sensors, the processor 204 in the monitoring device 201 may use the data to calculate individual processed sensor signals (e.g., processed electrical signals from the sensors). According to aspects of the method, the individual processed sensor signals may be transmitted wirelessly via the transmission module 203 to the remote computer 400. For example, the individual processed sensor signals may be transmitted during each golf shot or after each golf shot. Alternatively, according to other aspects of the method, the individual processed sensor signals may be stored in a memory in the monitoring device 201. Afterwards, (e.g., after a number of golf shots or whenever the golfer desires), the individual processed sensor signals may be transmitted wirelessly via the transmission module 203 to the remote computer 400. Regardless of when the individual processed sensor signals are transmitted from the monitoring device 201 to the remote computer 400, once the individual processed sensor signals are received by the remote computer 400 (e.g., via the transmission reception system 408), the remote computer 400 may be configured to process the individual processed sensor signals to calculate golf metrics or variables. According to aspects of this method, the remote computer 400 may be configured to store the golf metrics or variables, communicate the golf metrics or variables to the user, e.g., through video or audio means, and/or further transmit the golf metrics or variables to other devices.

According to another method in which the monitoring device 201 determines data and then communicates the data to the remote computer 400, the monitoring device 201 includes sensors 202 (e.g., one or more accelerometers, one or more gyroscopes, and/or one or more magnetometers), a transmission module 203 (e.g., a transmitter or transceiver configured to transmit/receive data wirelessly (e.g., through RF, Bluetooth, Bluetooth2, etc.)), a power source 206 (e.g., a battery). Further, according to such a method, data determined by the monitoring unit 201 is transmitted to the remote computer 400 (e.g., a portable telephone, a computer (e.g., a PC), a sport tablet, an electronic range finder, such as SKY CADDIE® available from SKY GOLF®), etc. Further, according to such a method, data may be determined by the sensors 202. Once the data is determined by the sensors, data may be transmitted wirelessly via the transmission module 203 to the remote computer 400. For example, the data may be transmitted to the remote computer 400 without being processed (e.g., raw data such as electrical signals from the sensors). According to such a method, the unprocessed data may be transmitted during each golf shot or after each golf shot. Alternatively, according to other aspects of the method, the unprocessed data may be stored in a memory in the monitoring device 201. Afterwards, (e.g., after a number of golf shots or whenever the golfer desires), the unprocessed data may be transmitted wirelessly via the transmission module 203 to the remote computer 400. Regardless of when the unprocessed data is transmitted from the monitoring device 201 to the remote computer 400, once the unprocessed data is received by the remote computer 400 (e.g., via the transmission reception system 408), the remote computer 400 may be configured to process the unprocessed data to calculate golf metrics or variables. According to aspects of this method, the remote computer 400 may be configured to store the golf metrics or variables, communicate the golf metrics or variables to the user, e.g., through video or audio means, and/or further transmit the golf metrics or variables to other devices.

While the above methods described various methods for determining data by the monitoring device 201 and the communicating the data between the monitoring device 201 and the remote computer 400, they should not be construed as limiting. In contrast, they are provided to assist the reader with understanding the disclosure and other methods for determining data by the monitoring device 201 and the communicating the data between the monitoring device 201 and the remote computer 400 may be considered within the scope of the disclosure.

It also should be appreciated that, while specific examples of monitoring devices 201 have been described above for ease of understanding, any type of desired monitoring device 201 can be employed with various embodiments of the disclosure. For example, according to aspects of the disclosure, the monitoring device 201 may be configured to engage with the shaft 103 of the golf club 100. For example, the monitoring device 201 may be configured with a shape and size such that the monitoring device 201 is able to be positioned within the grip 105 of the golf club.

Figure 8:
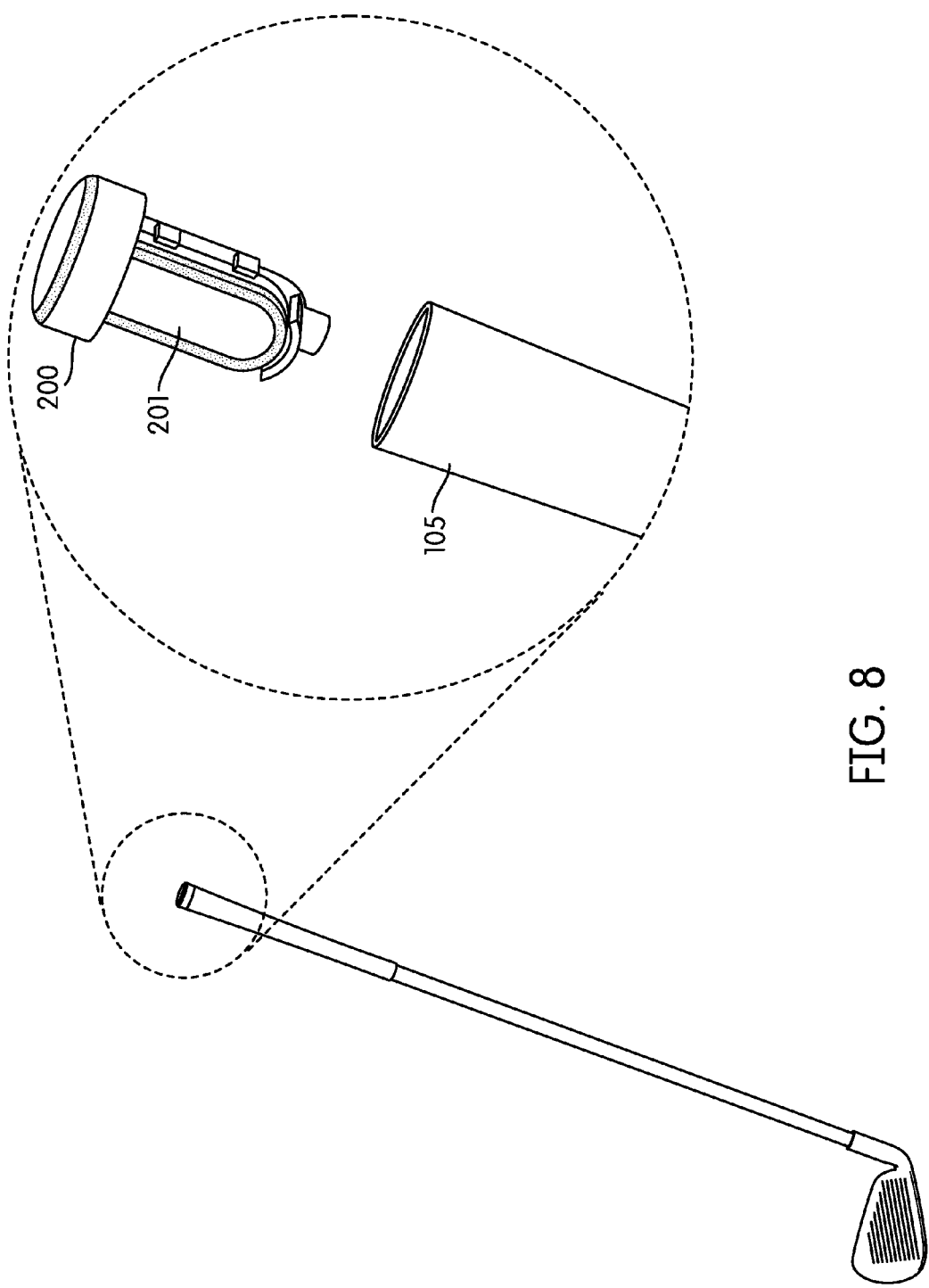
FIG. 8 is a perspective view of another embodiment of a golf club according to an illustrative embodiment of the disclosure, including an exploded view of a grip portion of the golf club having a cartridge supporting a monitoring device.

For example, according to aspects of the disclosure, the grip 105 may be configured to receive a removable section or cartridge 200. Further, the removable section 200 may be configured to receive the monitoring device 201. FIG. 8 shows an illustrative embodiment of such aspects of the disclosure.

As seen in FIG. 8, the removable section 200 may include a circular portion which forms the top of the shaft and, also, an elongated portion configured to house the monitoring device 201. According to aspects of the disclosure, the elongated portion of the removable section 200 may include guides to aid in positioning and securing the monitoring device 201 within the removable section 200. It is noted that the removable section 200 may be configured to secure the monitoring device 201 in such a way that the monitoring device 201 does not move within the removable section 200. For example, the removable section 200 may be configured to engage with the monitoring device 201 (e.g., a compartment which includes the exterior of the monitoring device 201) via press fitting, snap fit mechanisms (e.g., spring loaded protrusions and corresponding detents), mechanical fasteners, etc. For example, the elongate portion may include a first arched end configured to engage a first rounded end of the compartment, a second arched end configured to engage a second rounded end of the compartment and a back portion which extends between the first arched portion and the second arched portion and is configured to engage a side of the compartment. In this way, the removable section 200 may be configured to support and stabilize the monitoring device 201. For example, the elongate portion may be configured to secure the compartment which may be rectangular with first and second rounded ends and have a length in the range of 1.0-1.5 inches, a width of 0.4-1.0 inches and thickness of 0.2-0.45 inches. According to aspects of the disclosure, the removable section 200 may be made of plastic. It is noted that other materials, such as rubber, or combinations thereof may be used as well.

The removable section or cartridge 200 may be configured to be engaged with the grip 105 in a variety of ways. For example, the grip 105 may be configured with an opening at its terminal end that is configured to receive the removable section 200. Further, the grip 105 may be configured with guides within the interior of the grip 105 that guide the removable section during insertion into the grip 105. Also, the grip may be configured with a locking mechanism, such as threads which line the interior of the grip 105. The removable section 200 may include a corresponding structure through which the removable section 200 is engaged and locked with the grip 105 upon twisting the removable section 200 into the grip 105. Alternatively, the removable section 200 may be configured to engage with the grip 105 via press fitting, snap fit mechanisms (e.g., spring loaded protrusions and corresponding detents), other mechanical fasteners, etc.

Figure 8A:
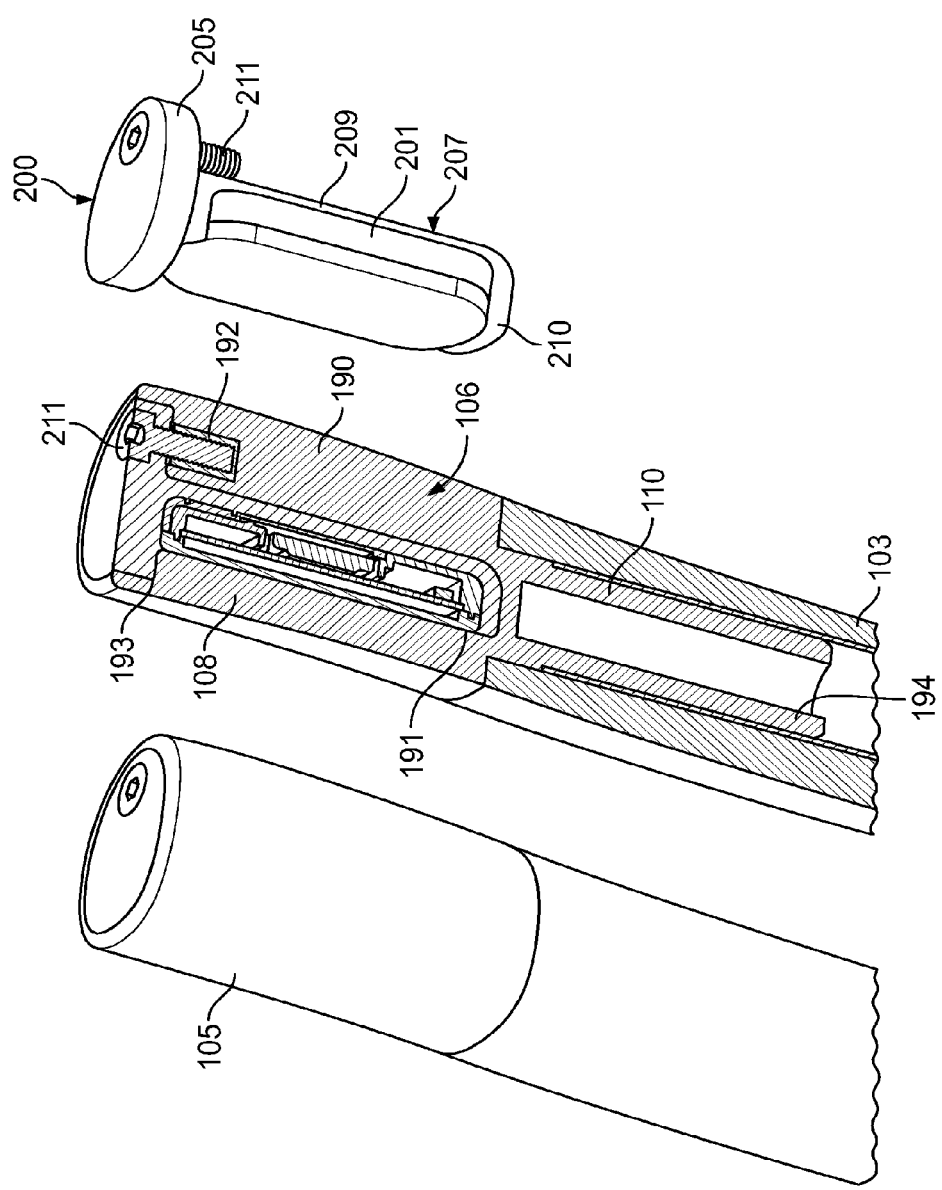
FIG. 8A is a perspective view of another embodiment of a golf club according to an illustrative embodiment of the disclosure, including an exploded view of a grip portion of the golf club configured to receive a monitoring device.

FIG. 8A illustrates an exploded view of another embodiment of a removable section or cartridge according to aspects of the disclosure. For example, as seen in FIG. 8A, the cartridge 200 may be configured to fit within a top portion of the grip 105, or distal end of the grip 105. The top portion of the grip 105 may be configured to removably fit within the golf club shaft 103. The removable top portion of the grip 105 and the cartridge 200 may be configured to be attached to each other as explained below.

Hence, in an exemplary embodiment, the top portion of the grip 105 may be considered a cartridge holder 106. The cartridge holder 106 generally includes a first portion 108 which is configured to receive the cartridge 200 supporting the monitoring device 201 and a second portion 110 configured to engage with the interior of the shaft 103 of the golf club.

The first portion 108 has a main body portion 190 having a first opening 191 therein and a second opening 192. The first opening 191 is generally an elongated slot that extends generally longitudinally into the main body portion 190. The first opening 191 can vary in length and width and is generally dimensioned to receive the portion of the cartridge 200 holding the sensor 201 as described in greater detail below. The first opening 191 is dimensioned such that there minimum play between the cartridge 200 and the main body portion 190. The second opening 192 is a threaded opening in an exemplary embodiment. The main body portion 190 further defines a recessed portion 193 at a distal end and the first opening 191 and the second opening 192 open at the recessed portion 193. The second portion 110 has a protrusion 194 that extends from the main body portion 190 of the first portion 108. The protrusion 194 may be hollow and is dimensioned to fit within and extend into the shaft 103. In an exemplary embodiment, the cartridge member 106 is an integral member and can be formed from a variety of materials known in the art. In addition, an outer surface of the main body portion 190 may be formed with the material identical to the remaining portions of the grip member to provide a uniform surface as desired.

As further shown in FIG. 8A, the removable cartridge 200 has a cap member 205 having a clip member 207 depending from the cap member 205. The cap member 205 has an orifice 208 extending therethrough and adjacent to the clip member 207. The clip member 207 has a base 209 and a resilient finger 210 extending generally transversely from the base 209. The base is dimensioned to accommodate the length of the sensor 201. The resilient finger 210 engages an end of the sensor 201. Thus, it is understood that the sensor 201 is inserted into the cartridge 200 wherein the sensor 201 is secured generally in an interference fit. One end of the sensor 201 is engaged by the resilient finger 210 and another end of the sensor 201 is engaged by an underside of the cap member 205. Accordingly, the sensor 201 can be snapped into the clip member 207. If desired, additional fingers or other retaining elements can be incorporated with the clip member 207. For example, additional retaining elements may be employed when a longer base 209 is utilized thus spacing the sensor 201 further away from the cap member 205.

As further shown in FIG. 8A, the cartridge holder 106 is secured to the shaft 103. The second portion 110 is inserted and secured to the shaft 103. This connection may be a permanent connection or a releasable connection. The removable cartridge 200 is inserted into the cartridge holder 106. The base 209 and finger 210 holding the sensor 201 are inserted into the first opening 191. The structure of the main body portion 190 surrounds and securely holds the cartridge 200 and thereby further protects the monitoring device 201 from damage due to impact or the elements. It is further understood that the first opening 191 is generally non-circular wherein the clip member 207 holding the sensor 201 must be inserted into the first opening 191 in a set, fixed orientation. Further, with minimum play around the sensor 201, the position of the sensor 201 is always known. This aids in the ability to record and analyze data in a desired fashion.

The cap member 205 is received in the recessed portion 193. The cap member 205 is generally flush with the end of the cartridge holder 106. The orifice 208 on the cap member 205 is aligned with the second opening 192. A threaded fastener 211 is inserted through the orifice 208 and secured in the second opening 192. Thus, removable cartridge 200 is thus secured in the grip of the club by a single fastener. It is understood that other fastening mechanisms could be utilized between the removable cartridge 200 and the cartridge holder 106, or otherwise the grip 105. The other fastening mechanisms include snap-fitting configurations or interference fittings as well as other mechanical configurations. With such configuration, the cartridge holder 106 holding the cartridge 200 is seamlessly integrated into the grip 105 and is virtually undetectable. The golf club appears like any traditional golf club that does not incorporate any sensor technology.

It is further understood that the removable cartridge 200 may utilize features of other embodiments described herein. For example, the clip member 207 may have different lengths such as shown in FIG. 23A. The cartridge holder 106 may then have corresponding structure to cooperate with a cartridge 200 with such dimensions. The cartridge 200 may also employ the various lock-out or other identifying structures described herein.

Figure 9:
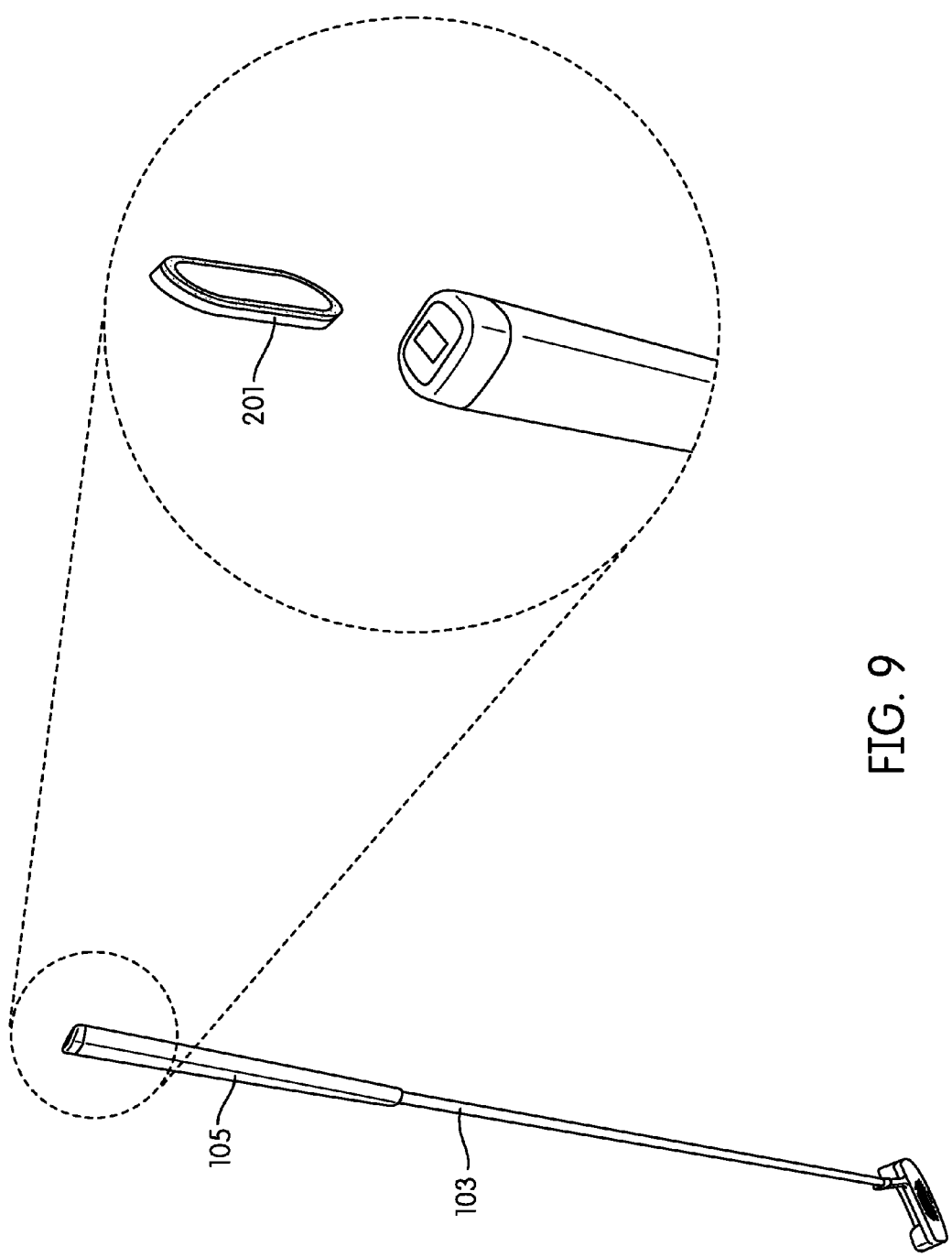
FIG. 9 is a perspective view of another embodiment of a golf club according to an illustrative embodiment of the disclosure, including an exploded view of a grip portion of the golf club having a monitoring device.

According to other aspects of the disclosure, the grip 105 may be configured to receive and secure the monitoring device 201 directly, without the inclusion of a separate removable section or cartridge 200. FIG. 9 shows an illustrative embodiment of such aspects of the disclosure.

The monitoring device 201 may be configured to be engaged with the grip 105 in a variety of ways. For example, the grip 105 may be configured with an opening at its terminal end that is configured to receive the monitoring device 201. For example, as seen in FIG. 9, the grip 105 may include a slit that is configured to receive the monitoring device 201 when the monitoring device 201 is inserted into the grip along the monitoring device's longitudinal axis. The slit may be configured to provide a tight interference fit with the monitoring device 201. It is noted that in this way, the grip 105 may be configured to secure the monitoring device 201 such that the monitoring device 201 does not move within the grip 105. In this way, the removable section 200 may be configured to support and stabilize to the monitoring device 201.

Further, the grip 105 may be configured with guides within the interior of the grip 105 that guide the monitoring device 201 during insertion into the grip 105. Also, the grip may be configured with a locking mechanism, such as a cover which includes flaps through which the monitoring device is inserted. It is noted that monitoring device 201 may be configured to engage with the grip 105 via other methods as well, including snap fit mechanisms (e.g., spring loaded protrusions and corresponding detents), other mechanical fasteners, etc.

While, the engagement of the monitoring device 201 and the removable section 200 with the shaft is described above with respect to the grip 105, it is noted that, alternatively, the shaft 103 may be configured to receive the monitoring device 201 and/or the removable section 200 at the butt end of the shaft 103. Further, the interior of the shaft 103 may be configured to position the monitoring device 201 at any point along the length of the shaft 103 (e.g., at the butt end, the grip end, the center, etc.).

According to aspects of the disclosure, the grip end of the shaft 103 (or a portion thereof) may be removable to allow the monitoring device 201 to be inserted. Additionally, or alternatively, as described above, the butt end of the shaft may be removably engaged with the golf club head 101. Hence, the monitoring device 201 may be inserted into that end of the shaft 103 as well. Further, it is noted that, if desired, more than one monitoring device 201 may be inserted into the shaft 103 in order to measure various different locations or different portions of the shaft 103 during the golf swing.

According to aspects of the disclosure, golf club 101 may include a monitoring device 201 in both the shaft 103 and in the golf club head 101. For example, the golf club 101 may include two monitoring devices 201, such as a first monitoring device 201 which is positioned in the grip 105 (such as shown in FIG. 8) and a second monitoring device 201 which is positioned in the golf club head 101 such as shown in FIG. 5D. In such embodiments, wherein the golf club 101 includes a first monitoring device 201 positioned in the grip 105 and a second monitoring device 201 positioned in the golf club head 101, data may be collected from both monitoring devices and used together in one of the manners described above with regard to providing golf metrics and variables. For example, the first monitoring device 201 positioned in the grip 105 and a second monitoring device 201 positioned in the golf club head 101 may be configured to collect data related to different aspects of a golf swing. For example, first monitoring device 201 positioned in the grip 105 may collect data regarding acceleration while the second monitoring device 201 positioned in the golf club head 101 may collect data regarding the angle of the golf club (or club head) during a golf swing (e.g., relative to one or more reference points), or the impact of the ball with the golf club head during a golf swing. Such data may be combined in calculating the golf metrics in order to provide more detailed feedback to the golfer. It is noted that according to other aspects of the disclosure, the first monitoring device 201 positioned in the grip 105 and a second monitoring device 201 positioned in the golf club head 101 may be configured to collect data related to the same or similar aspects of a golf swing. For example, both the first and second monitoring devices 201 may be configured to collect data related to acceleration. Again, such data may be combined in calculating the golf metrics in order to provide more detailed feedback to the golfer. Such golf metrics that may be determined by one or more of the monitoring devices may include bending, torsion, deflection, kick, etc. of the shaft during a golf swing.

Regardless of how many monitoring devices 201 are included in the golf club and the positioning of the monitoring devices 201 on or within the golf club, according to aspects of the disclosure, a first monitoring device 201 may be configured to be a "master" monitoring device 201 and the other monitoring devices 201 may be configured to communicate data to the "master" monitoring device 201. Further, the "master" monitoring device 201 may be configured to receive, from the other monitoring devices 201, the data determined by such monitoring devices 201 and perform any necessary calculations, comparisons, etc. as described in this disclosure and/or transmit the data to the remote computer 400.

The "master" monitoring device 201 and other monitoring devices may communicate wirelessly (e.g., through RF, Bluetooth, Bluetooth2, etc.) or may be hardwired to each other. Although it is noted that if the "master" monitoring device 201 and other monitoring devices communicate via wiring, the wiring may be removable connected via ports or other interfaces. Further, according to aspects of the disclosure, the "master" monitoring device 201 and other monitoring devices may not have the same configuration. For example, the "master" monitoring device 201 may include a processor 204 such as a programmable microprocessor, a purpose-specific circuit device (e.g., an ASIC), etc. Further, the "master" monitoring device 201 may also include sensors 202, a transmitter 203 (or transceiver) configured to transmit the processed signals to a remote computer system 400, a power supply 206, and a memory (e.g., a flash memory). According to aspects of the disclosure, the other monitoring devices 201 may or may not have the same structure as the "master" monitoring device 201. For example, the other monitoring devices 201 may not include the same processor 204 which performs any necessary calculations, comparisons, etc. as described in this disclosure. Further, other monitoring devices 201 may not include the same transmitter 203 (or transceiver) configured to transmit the data to the remote computer 400. In some embodiments, the other monitoring devices 201 may be configured to submit the "raw" data from the sensors 202 to the "master" monitoring device 201, such as by wireless transmission, without being processed.

For example, according to an illustrative embodiment, a "master" monitoring device 201 such as described above may be included in the shaft 103 in a first position (e.g., the grip) and another monitoring device 201 such as one of the other monitoring devices 201 described above may be included at a second position in the shaft 103 which is different from the first position. Additionally, monitoring device 201 such as one of the other monitoring devices 201 described above may be included at other locations in the golf club 100 (e.g., in the golf club head 101 or at other positions in the shaft 103). It is further understood that the exemplary embodiments of the golf club 100 described herein can also cooperate with golf balls having various types of sensors operably associated therewith.

Further, is noted that, if desired, strain gauges may be used in conjunction with the monitoring device 201 in order to provide measurements regarding the axial strain, bending moments or other characteristics of the shaft 103 or other features of the golf swing. Such data may be combined in calculating the golf metrics in order to provide more detailed feedback to the golfer. Such strain gauges are known in the art and will not be elaborated on here for the sake of brevity.

As discussed above, according to particular embodiments of the disclosure, the monitoring device 201 may also be configured to identify the particular golf club in which the monitoring device 201 is engaged. For example, golf club 100 may include a chip (e.g., an RFID chip) which communicates with the monitoring device 201 when the cartridge 200 or the monitoring device 201 is engaged with the golf club 100. This could be through direct electrical connection, wireless transmission, etc. The chip may be configured to indicate to the monitoring device 201 with which golf club the monitoring device 201 is engaged. Of course, other methods of identification may be used as well. For example, prior to use, the monitoring device 201 may be programmed such that it reflects the golf club with which it will be used prior to even being engaged with the golf club head 202.

Regardless of how the monitoring device 201 is aware of the particular golf club with which it is engaged, according to aspects of the disclosure, such information may be incorporated with the data collected from the sensors 202 of the monitoring device 201. For example, the characteristics of a particular golf shot (e.g., the velocity of the golf club (or club head) during a golf swing, the acceleration of the club (or club head) during a golf swing, the angle of the golf club (or club head) during a golf swing (e.g., relative to one or more reference points), swing tempo, the impact of the ball with the golf club head during a golf swing, etc.) may be coordinated with the particular golf club with which the shot was made (e.g., the processor 204 of the monitoring device may be configured to calculate and coordinate such data).

Such coordinated identification information may then be transmitted by the transmitter 203 and/or stored in a memory (if applicable) along with the data from the sensors 202 (e.g., through methods such as discussed above). Of course, the identification information and the data from the sensors 202 may be coordinated at the remote computer system 400 if desired (e.g., through methods such as discussed above). Regardless of where the identification information and data from the sensors or golf metrics are coordinated, such coordinated information may be included with a data set generated from the information provided by the monitoring device 201.

According to aspects of the disclosure, the processor 204 of the monitoring device 201 or remote computer system 400 may use such golf club identification information and data from the sensors 202 of the monitoring device 201 to determine an estimated distance of the golf shot. For example, the remote computer system 400 may be configured to use characteristics of the golf swing (e.g., velocity of the golf club head at impact, the angle of the golf club head at impact, etc.) and the particular golf club which the golf shot was taken in order to estimate the distance and the direction the golf ball will travel. Such information may be useful to the golfer. For example, if the remote computer system 400 is a portable electronic device that the golfer has during a round of golf, the golfer may consult a remote computer system and use such information to potentially find a lost golf ball. Of course, the data may be used for other purposes as well. For example, the golfer's round of golf may be tracked and used for later analysis, such as to determine potential tendencies or habits in a golfer's swing of a particular golf club.

As discussed above, according to aspects of the disclosure, the monitoring device 201 may include a GPS technology. For example, the monitoring device 201 may include a GPS device which determines the location of the golf club 100 in which the monitoring device 201 is engaged. Alternatively, the golf club 100 may include a separate GPS device (e.g., a GPS transmitter/transceiver and, if desired, a processor). According to aspects of the disclosure, the location information may be incorporated with data determined by the sensors of monitoring device 201. For example, the action of a golf swing may be determined by the sensors 202 of the monitoring device 201). Hence, by coordinating such data with the location information from the GPS device (in a manner similar to the methods described above), the location of each golf shot taken during a round of golf may be determined.

Further, according to aspects of the disclosure, the above described location of each golf shot may be incorporated with maps of the golf course on which the golf shots were taken in order to provide a golfer with information on each golf shot during a round of golf. For example, according to aspects of the disclosure, maps of the golf course may be downloaded to the remote computer system 400. Thereafter, the golf shots (determined in a manner such as described above) may be superimposed or otherwise represented on the maps of the golf course in order to represent the golfer's round of golf.

Further, according to aspects of the disclosure, the above described location of a particular golf shot on the golf course may be incorporated with the data collected from the sensors 202. For example, the characteristics of a particular golf shot (e.g., the velocity of the golf club (or club head) during a golf swing, the acceleration of the club (or club head) during a golf swing, the angle of the golf club (or club head) during a golf swing (e.g., relative to one or more reference points), swing tempo, the impact of the ball with the golf club head during a golf swing, etc.) may be coordinated with the location on the golf course at which that particular golf shot was taken.

Further, according to aspects of the disclosure, the above described location of a particular golf shot on the golf course may be incorporated with information about the particular golf club with which the golf shot was taken. For example, such aspects of the determining the particular golf club with which a shot is take are described above and may be used in combination with the above described GPS technology. Further, such coordinated information may be included with a data set generated from the information provided by the monitoring device 201. For example, based on the data transmitted by the monitoring device 201, it may be determined that a golfer used a 3-iron to make a golf shot at a point 170 yards from the flag at the $2^{nd}$ hole of a golf course.

Some or all of the above described determining information, such as determined golf swing characteristics (e.g., the velocity of the golf club (or club head) during a golf swing, the acceleration of the club (or club head) during a golf swing, the angle of the golf club (or club head) during a golf swing (e.g., relative to one or more reference points), swing tempo, the impact of the ball with the golf club head during a golf swing, etc.), golf club identification, location of the golf shot, golf course positioning information, etc., (including combinations and permutations thereof) may be coordinated and the coordinated information may be included with a data set generated from the information provided by the monitoring device 201. Therefore, according to aspects of the disclosure, detailed information of the practice session or round of golf may be recorded and analyzed.

According to aspects of the disclosure, the remote computer system 400 does not have to be a portable computer system. For example, as discussed above, the remote computer system 400 may be a desktop computer or other type of computer system. In such embodiments, the data collected by the monitoring device 201 may be stored locally in a memory as described above.

When the golfer has finished the practice session or round, the golfer may disengage the monitoring device 201 from the golf club head and engage it with the remote computer system 400 in order to transmit the data to the remote computer system 400. It is noted, that any type of connection system may be used without departing from the scope of the disclosure, including a wireless connection, a hardwired connection, connection via an input port (such as a USB port, or the like), etc. For example, according to some aspects of the disclosure, the monitoring device 201 does not have to be disengaged from the golf club head 101 and instead can transmit the data to the remote computer system 400 wirelessly. Other data storage and/or transmission arrangements also are possible without departing from the scope of the invention. For example, any desired way of placing data derived from the physical data from the monitoring device 201 in the proper form or format for communication to the remote computer system 400 may be provided without departing from the invention.

It is noted that according to some aspects of the disclosure, the monitoring device 201 may be configured to transmit data to the remote computer system 400 (e.g., a portable computer system, such as a cellular telephone) and the remote computer system 400 may be configured to transmit data to a secondary computer system (such as a desktop computer) or a network as described below. For example, the remote computer system 400 may be connected to the secondary computer via a USB cable or other connection. Alternatively, a wireless connection such as described above (e.g., telecommunication means of a smartphone) may be used as well. In such a configuration, wherein the remote computer system 400 is portable, it could be used during play (e.g., at a practice session on a driving range or on the course during play) to give real time feedback to the golfer (e.g., during the round or practice session). Thereafter or in real-time, the data from the portable remote computer system 400 may be downloaded or uploaded to the secondary computer system for further analysis. For example, the data could be uploaded over telecommunication lines (e.g., through a smart phone) to a network which could compare the uploaded data with predetermined tables, charts, etc. and provide appropriate feedback based on the comparisons. For example, a system according to an exemplary embodiment can provide coaching videos, drills, challenges, product selection recommendations, etc. as described in detail below based on the uploaded data and comparisons of the uploaded data with predetermined data. It is noted that in some embodiments (e.g., wherein the secondary computer system is a network), the secondary computer system may include databases which are configured to store profiles for an individual golfer and update the profile of the golfer based on the uploaded data.

Additional aspects of this disclosure relate to the presentation of data to the golfer, coach, or other person(s). Such systems help the golfer measure and track his or her capabilities, mark improvements over time, determine areas that require additional work, etc. Data can be collected over single rounds of golf, portions of rounds of golf, single practices, portions of practices, multiple rounds of golf (or portions thereof), multiple practices (or portions thereof), multiple seasons (or portions thereof), etc.

Figure 9A:
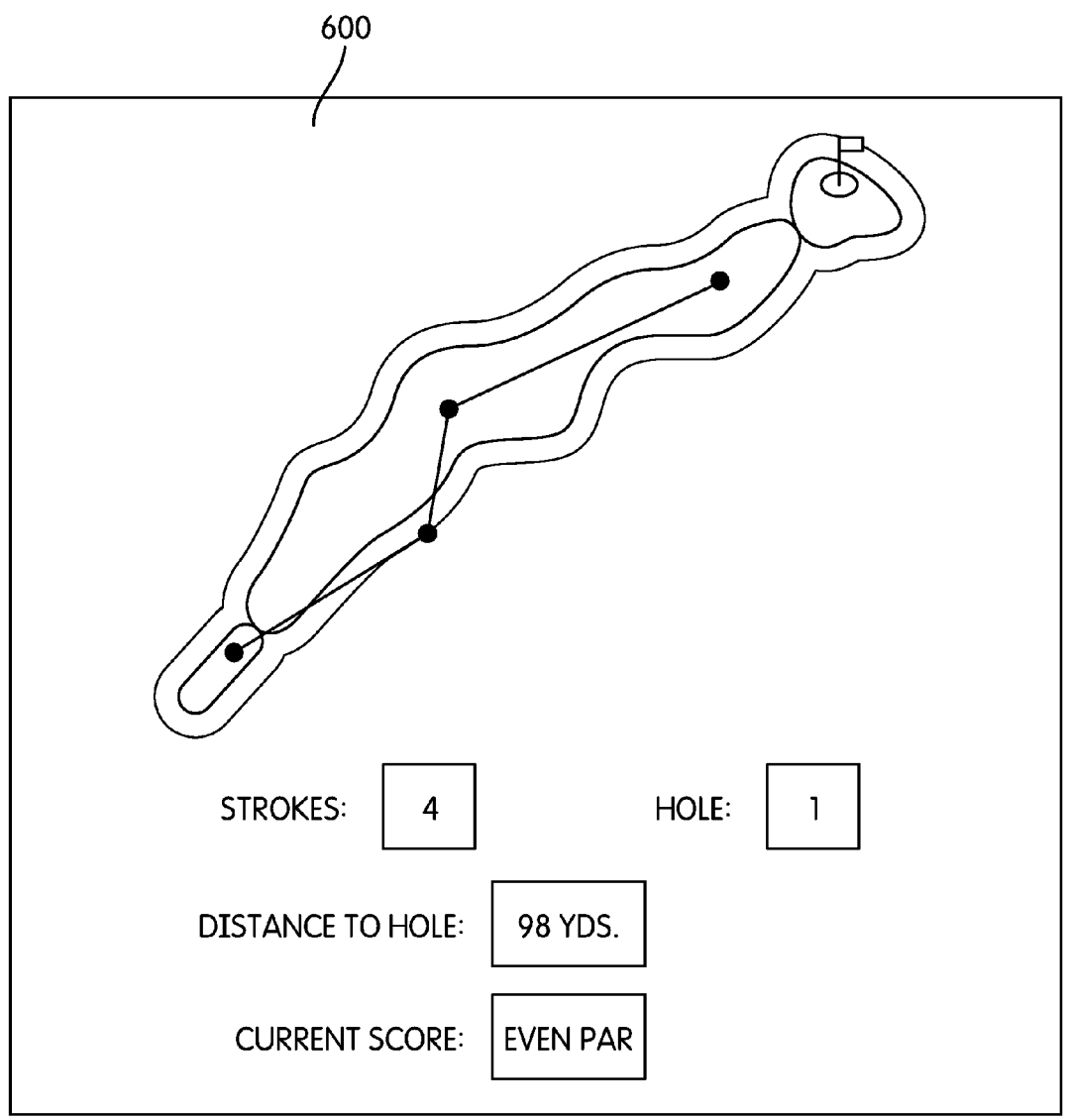
FIG. 9A is an illustrative user interface according to an embodiment of the disclosure.

FIG. 9A illustrates an example user interface screen 600 that may be used in systems and methods in accordance with at least some examples of this disclosure. As shown in FIG. 9A, the interface screen 600 may present much information to the player, including information relating to a specific round of golf or practice session, as well as information relating to more long term use of systems and methods in accordance with this disclosure. For example, as shown in FIG. 9A, user interface 600 may provide a display of the above described location of each golf shot incorporated with a map of the golf course on which the golf shots were taken in order to provide a golfer with information on each golf shot during a round of golf. For example, according to aspects of the disclosure, maps of the golf course may be downloaded to the remote computer system 400 and the golf shots (determined in a manner such as described above) have been superimposed on the map of the golf course in order to represent the golfer's round of golf. Further additional data may be displayed as shown.

Additionally, in accordance with this disclosure, other interfaces may provide information relating to: the overall total number of rounds of golf and/or practice sessions played by the golfer, the total overall strokes logged by the golfer using the system, the golfer's handicap over that time period, the golfer's top swing speed during those rounds or practice sessions, the number of times the golfer had an open club face during impact, the number of times the golfer had a closed club face during impact, the number of strokes that the club head was within a predetermined angle during a predetermined portion of the golf swing (e.g., the backswing or downswing), etc., the number of strokes that the club head was within a predetermined velocity or acceleration range during the entire or a predetermined portion of the golf swing, etc.

The interface may also provide information for an individual round or practice session (with the ability to select among the various stored rounds of golf or practice sessions on the system). For example, the interface may display information relating to the speed of the golf swing during this specific practice session. Also, if desired, the user interface could be adapted to allow user selection of various different metrics or information to be displayed.

Systems and methods in accordance with at least some examples of this disclosure may include "goals" or "challenges." While the goals may be set by the individual golfer for himself or herself, optionally, the goals or challenges may be set by others (e.g., a coach, etc.). For example, a user interface may present one or more data metric which includes "grayed out" blocks that represent a player's "goal" or "challenge" for that metric. For example, the data from a round of golf may be displayed with an indication of the player's performance in that round of golf (e.g., in blackened in boxes) along with an indication of where the golfer's performance stood with respect to their "goal" or "challenge" levels (e.g., in grayed out boxes). The specific metric for the "goal" or "challenge" may be displayed in any desired manner, e.g., by clicking on the last box associated with the goal or challenge, by hovering over a grayed-out box, through a continuous display, etc. For example, the system may indicate that the player's overall top swing speed goal or challenge is 70 mph, while in the present round they had only run at a top swing speed of 65 mph.

In the next round, however, if the golfer achieved his or her speed goal by swinging at 70 mph, the systems and methods in accordance with at least some examples of this disclosure may provide a congratulatory message (e.g., textually, visually, audibly, etc., note the changes in the display. Furthermore, if desired, in an effort to keep the golfer motivated, a new "goal" or "challenge" can be calculated and displayed for the golfer. Also, if desired, when presented as a challenge from a coach, systems and methods in accordance with at least some examples of this disclosure may send a message to the golfer (or offer to let the golfer compose a message to others (e.g., a coach)) to advise that the challenge had been met. Other "rewards," motivational information, or other interaction may be provided, if desired, without departing from the scope of this disclosure.

User interfaces for athletic performance monitoring systems and methods in accordance with this invention may take on a wide variety of forms and formats and provide a variety of different types of displays and information without departing from this invention. Displays of other metrics or combinations of metrics are possible without departing from the scope of this disclosure. Other graphical or other displays of the desired metric information also may be provided without departing from the scope of this disclosure.

According to aspects of the disclosure, data collected from the above described system and metrics determined by the above described system may be uploaded to a network. For example, similar to aspects of the NIKE+™ athletic performance monitoring systems, such data may be uploaded to and shared on various social networking sites like FACEBOOK® or TWITTER®. In particular, the user may be able to enable or disable activity broadcasts. Activity broadcasts may include the automatic sharing of completed rounds of golf, goals and challenges. Additionally or alternatively, the user may enable or disable a function that notifies other users (e.g., placing a post or status update on the user's network site page) whenever the user playing a round of golf or practicing at a driving range. This may enable other users to post messages of encouragement and to track the user's progress during the round of golf or the practice session. Golf data may also be posted to social network sites and social networking feeds mid-run and in real-time. Various other features and functions may also be configured by the user for sharing information.

Golfers may choose to share information or portions thereof with one or more other users, friends or through a social networking site. If the golfer chooses to share workout data through a social network site such as FACEBOOK® or TWITTER®, an interface may be displayed. Such an interface may include an automatically generated round of golf update message and allow the golfer to include additional information or notes. Upon approving the message, the user may publish the data to the social networking site by selecting publish option of the interface.

Figure 10:
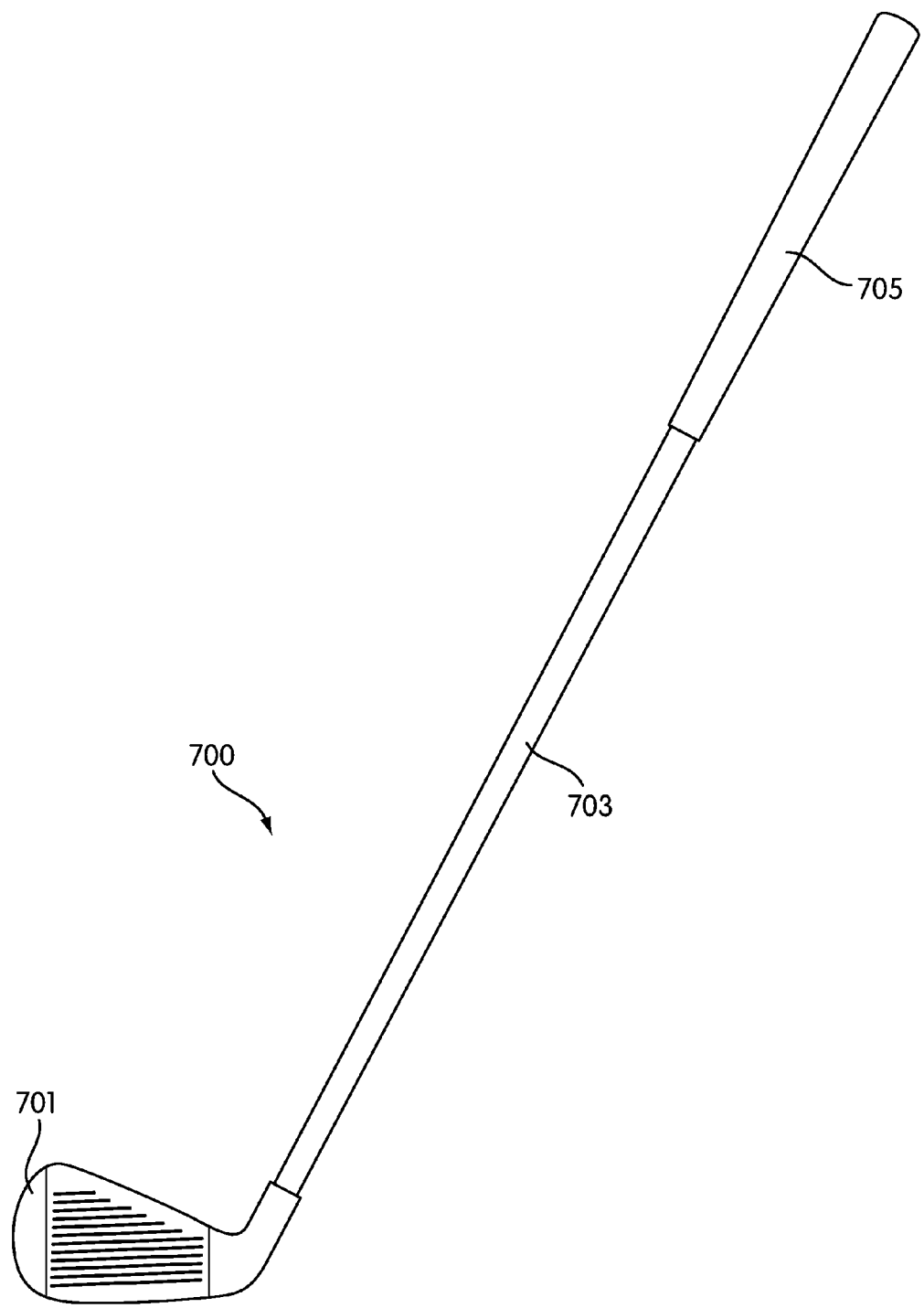
FIG. 10 is an illustrative embodiment of an iron-type golf club structure according to aspects of the disclosure.

While wood-type golf clubs and wood-type golf club heads have been described in detail above, other aspects of this disclosure relate to iron-type golf club heads and iron-type golf clubs. For example, FIG. 10 illustrates an example of an iron-type golf club 700 according to aspects of the disclosure. As seen in FIG. 10, the iron-type golf club 700 may include an iron-type golf club head 701 in accordance with the present disclosure.

In addition to the golf club head 701, the overall golf club structure 400 may include a shaft 703 and a grip or handle 705 attached to the shaft 703. The shaft 703 may be received in, engaged with, and/or attached to the golf club head 701 in any suitable or desired manner, including in conventional manners known and used in the art, without departing from the disclosure. As more specific examples, the shaft 703 may be engaged with the golf club head 701 through a shaft-receiving sleeve or element extending into the club head 701 (e.g., a hosel), and/or directly to the club head structure 701, e.g., via adhesives, cements, welding, soldering, mechanical connectors (such as threads, retaining elements, or the like). If desired, the shaft 703 may be connected to the golf club head 701 in a releasable manner using mechanical connectors to allow easy interchange of one shaft for another on the head. Also, the grip or handle 705 may be attached to, engaged with, and/or extend from the shaft 703 in any suitable or desired manner, including in conventional manners known and used in the art, e.g., using adhesives or cements, etc. The shaft 703 and the grip or handle 705 may be made from any suitable materials such as those described above with regard to the wood type golf club 100.

According to aspects of the disclosure, the golf club head 701 may also include a ball striking face (e.g., a ball striking face which includes a face plate) 711. According to aspects of the disclosure, the golf club head 701 may be constructed in any suitable or desired manner and/or from any suitable or desired materials without departing from this disclosure, including from conventional materials and/or in conventional manners known and used in the art. For example, the club head 701 and/or its various parts may be made by forging, casting, molding, and/or using other techniques and processes, including techniques and processes that are conventional and known in the art. According to aspects of the disclosure, the golf club head 701 may be a blade type iron golf club head. According to other aspects the golf club head 701 may be a perimeter weighted and/or cavity back type golf club head or other iron type golf club head structure.

Figure 11:
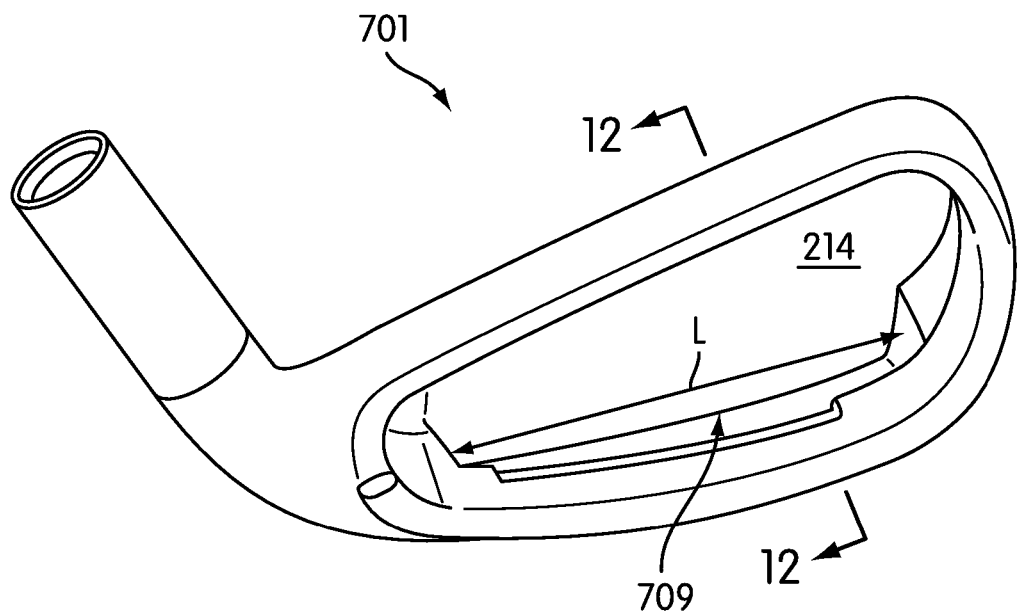
FIG. 11 is a rear view of the iron-type golf club head shown in FIG. 10 wherein a cartridge is removed from the iron-type golf club head.
Figure 12:
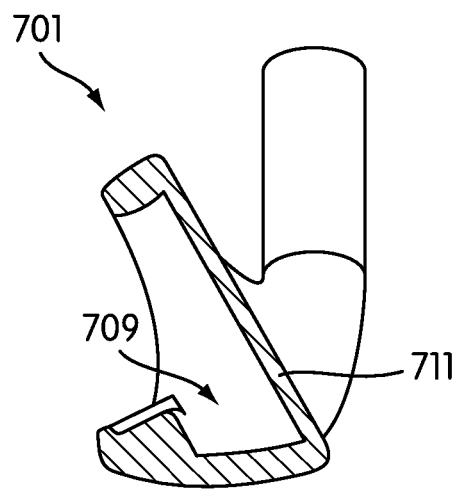
FIG. 12 is a cross-sectional view along line 12-12 of the iron-type golf club head shown in FIG. 11.

According to aspects of the disclosure, the golf club head 701 may include a crown, a sole, a toe end, and a heel end. Further, as seen in FIGS. 11 and 12 the golf club head 701 may include a cavity, or port, 709 behind the ball striking face 711. The port 709 may extend substantially along the length of the rear of the ball striking face 711.

According to aspects of the disclosure, and as seen in FIGS. 13 and 14, the port 709 may be configured to receive a cartridge 800. Further, if desired, cartridge 800 may be secured within to the golf club head 701 by securing means. It is noted, that the cartridge 800 may be secured in the port 709 of the golf club head 701 in a variety of ways. For example, as discussed above, according to aspects of the disclosure, the cartridge 800 may be removably engaged with the golf club head 701. Therefore, mechanical fasteners may be used to secure the cartridge 800 in the port 709. For example, example embodiments of the disclosure may include a cartridge 800 which is configured to be engaged with the golf club head 701 via press fitting, snap fit mechanisms (e.g., spring loaded protrusions and corresponding detents), threaded fasteners, etc. Other securing means, such as described above with regard to wood-type golf club, may be used as well.

According to example embodiments of the disclosure, the cartridge 800 may be configured with a first portion (e.g., an exterior portion) 800a. Further, according to example aspects of the disclosure, the cartridge 800 may include a second portion (e.g., an insert portion) 800b which is configured to be inserted into the interior of the port 709 of the golf club head 701. The cartridge 800 may be made from any desired materials and combinations of different materials such as described above with regard to cartridge 200.

The second portion may be configured to house a monitoring device 201 similar to the one described above with regard to the wood-type golf club. For example, the monitoring device 201 may be configured to house the sensors 202, the transmitter/transceiver 203, processor 204, power supply 206, memory, etc. The monitoring device 201, its capabilities and functions are similar to the monitoring device 201 described above and, therefore, for the sake of brevity, will not be elaborated on here. Further, the above described methods for determining and transmitting data to the remote computer 400 are applicable with the iron-type golf clubs as well and, therefore, will not be repeated for the sake of brevity.

While not shown in the depicted embodiment, aspects of the disclosure, relate to a weight cartridge which is configured to be engaged with the port 709. The weight cartridge may be configured similarly to the cartridge 800 described above with the exception that the weight cartridge does not include a monitoring device 201. It is noted that the weight cartridge may be configured to engage with the port 709 in the same manner as the corresponding cartridge 800. Hence, again, for the sake of brevity, the engaging and releasing structure of the weight cartridge and the port 709 will not be elaborated on here.

According to aspects of the disclosure, when the golfer does not want to have the monitoring device 201 housed within the golf club 700, the golfer may disengage and remove the cartridge 800 from the port 709 of the golf club head 701 and engage and secure the weight cartridge with the port 709 of the golf club head 701. It is noted that according to aspects of the disclosure, the weight cartridge may be configured to act as a dampening member.

Based on the above disclosure, it is understood that aspects of the disclosure are directed to a golf club configured to receive interchangeable sections or cartridges, wherein one of the interchangeable cartridges may house a monitoring device 201 and a second of the interchangeable cartridges does not house a monitoring device. In this way, the golfer may selectively configure the golf club to include, or not include, the monitoring device 201 at the golfer's discretion. It is noted that, if desired, neither the cartridge 800 or the weight cartridge has to be included in the golf club head 701 and, instead, the golfer may remove the cartridge 800 and play with the port 709 being open and unfilled.

Figure 14A:
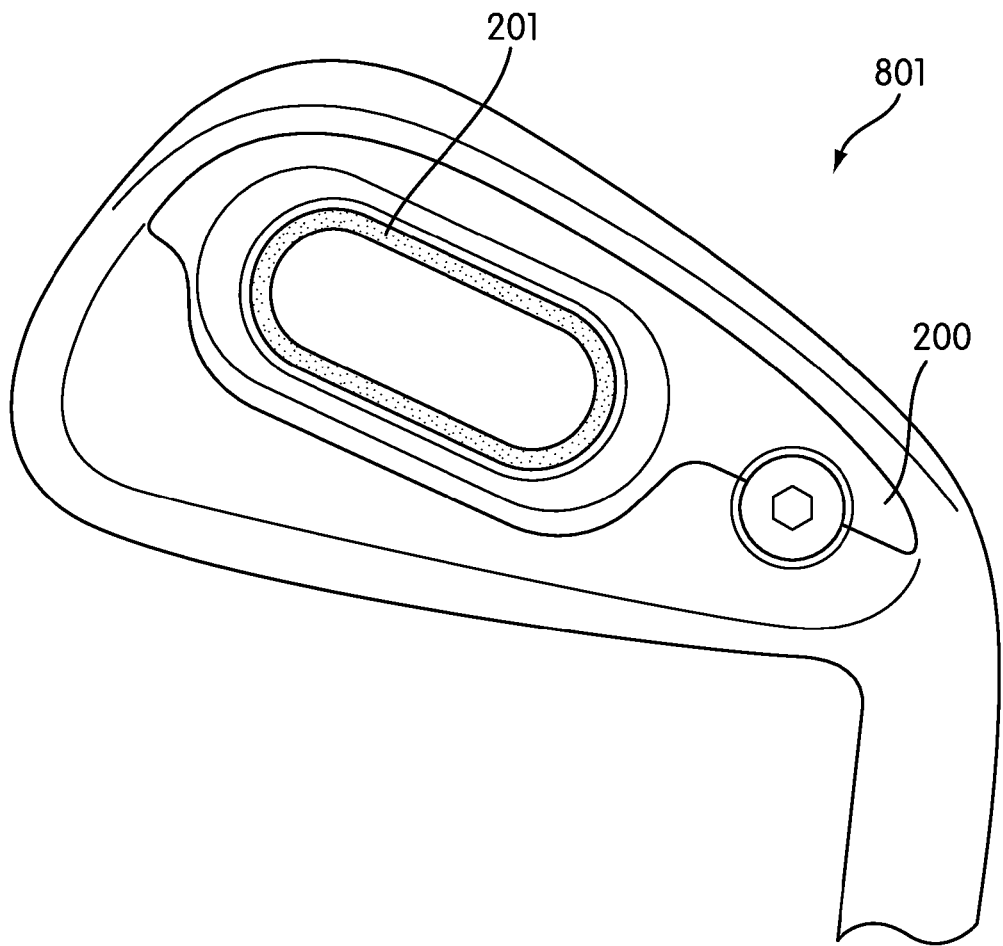
FIG. 14A is an illustrative embodiment of another iron-type golf club structure supporting a monitoring device according to aspects of the disclosure.

FIG. 14A shows another iron-type golf club 800 according to aspects of the disclosure. As seen in FIG. 14A, the iron-type golf club 800 may include an iron-type golf club head 801 in accordance with the present disclosure. Further, the iron-type golf club 800 may be configured to engage with a removable section or cartridge 200 and a monitoring device 201.

According to the aspects of the disclosure, the monitoring device 201 may be configured to engage with the golf club head 801 in a variety of ways. For example, as seen in FIG. 14A, the removable section 200 is engaged with the golf club head 801 via a threaded fastener. However, the removable section 200 may be configured to be engaged with the golf club head 801 via other methods as well, such as press fitting, snap fit mechanisms (e.g., spring loaded protrusions and corresponding detents), etc. As seen, the removable section 200 may include an opening configured to surround the monitoring device 201 and through which the monitoring device is visible. The removable section 200 may be configured to provide support and stability to the monitoring device 201. According to aspects of the disclosure, the removable section 200 may be made of plastic or other materials.

Further, as seen in FIG. 14A, the monitoring device 201 is engaged with the golf club head 801. The engagement of the monitoring device 201 with the golf club head 801 can be done in a variety of ways, e.g., mechanical fasteners, press fitting, snap fit mechanisms (e.g., spring loaded protrusions and corresponding detents), threaded fasteners, etc. The golf club head 801 may include a recess configured to receive the monitoring device 201. For example, the recess may be configured to surround and engage the monitoring device 201 in order to support and stabilize the monitoring device 201.

The golf club head 801, the removable section 200 and the monitoring device 201 may be configured to provide desirable weight placement in the club head 801. For example, the golf club head 101, the removable section 200 and the monitoring device 201 may be configured such that when engaged, the golf club head 801 it is in the lower portion of the golf club head 801.

A wide variety of overall club head constructions are possible without departing from this disclosure. For example, it is noted that the dimensions and/or other characteristics of the golf club heads 701, 801 according to examples of this disclosure may vary significantly without departing from the disclosure. For example, the above described features and configurations may be incorporated into any iron-type club heads including, for example: wedges (e.g., pitching wedges, lob wedges, gap wedges, sand wedges, etc.), iron-type hybrid clubs, driving irons, 0 through 10 irons, etc.

Further, the above described features and configurations in the aspects of the disclosure may be incorporated into a blade type golf club heads, a perimeter weighted and/or cavity back type golf club head or other iron type golf club head structure without departing from this disclosure. For example, a perimeter weighted and/or cavity back type golf club head including the golf club heads 701, 801 according to aspects of the disclosure, may include a rear surface opposite the ball striking face 711 which includes a perimeter weighting member extending rearward from the ball striking face and along at least a portion of a circumferential area of the golf club head body.

While wood-type golf clubs and iron-type golf clubs have been described in detail above, other aspects of this disclosure relate to putter type golf club heads and putters. For example, FIGS. 15A and 15B generally illustrate an example of a putter-type golf club head 1001 according to aspects of the disclosure. The putter-type golf club head 1001 may be included in a putter which includes a shaft and a grip or handle (not shown). It is noted that the shaft and the grip or handle may be configured and attached to, or engaged with, the putter-type golf club head 1001 any suitable or desired manner such as those described above with regard to the wood type golf club 100 and iron-type golf club 700.

According to aspects of the disclosure, the golf club head 1001 may also include a ball striking face (e.g., a ball striking face which includes a face plate) 1111. According to aspects of the disclosure, the golf club head 1001 may be constructed in any suitable or desired manner and/or from any suitable or desired materials without departing from this disclosure, including from conventional materials and/or in conventional manners known and used in the art. For example, the club head 1001 and/or its various parts may be made by forging, casting, molding, and/or using other techniques and processes, including techniques and processes that are conventional and known in the art.

Figure 15A:
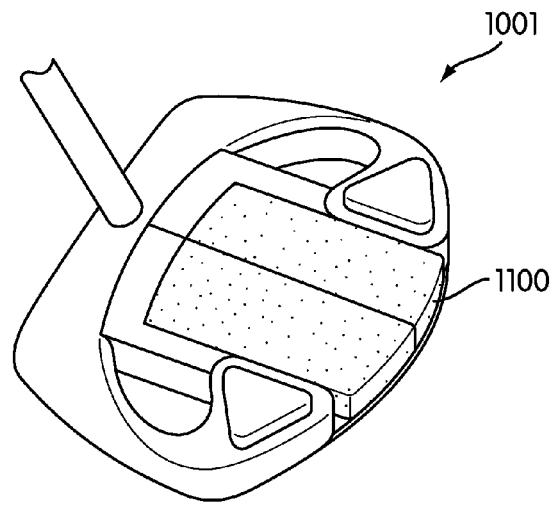
FIG. 15A is an illustrative embodiment of an putter golf club head structure supporting a monitoring device according to aspects of the disclosure.
Figure 15B:
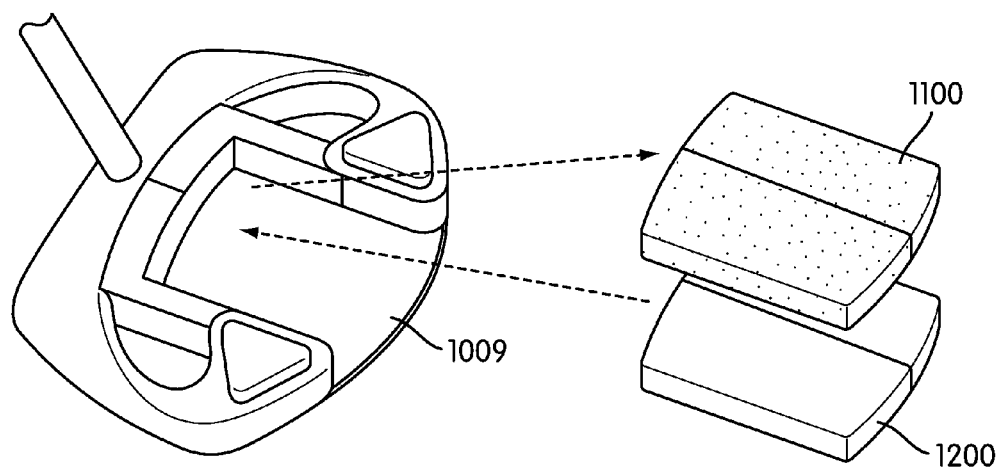
FIG. 15B is an exploded view of the putter golf club head shown in FIG. 15A.

According to aspects of the disclosure, the golf club head 701 may include a crown, a sole, a toe end, and a heel end. Further, as seen in FIG. 15B the golf club head 1001 may include a cavity, or port, 1009 behind the ball striking face 1011. The port 1009 may be positioned centrally in the golf club head 1001 and behind the rear of the ball striking face 1011.

According to aspects of the disclosure, and as seen in FIG. 15B, the port 1009 may be configured to receive a cartridge 1100. Further, if desired, the cartridge 1100 may be secured within the golf club head 1001 by securing means. It is noted, that the cartridge 1100 may be secured in the port 1009 of the golf club head 1001 in a variety of ways. For example, as discussed above, according to aspects of the disclosure, the cartridge 1100 may be removably engaged with the golf club head 1001. Therefore, mechanical fasteners may be used to secure the cartridge 1100 in the port 1009. For example, example embodiments of the disclosure may include a cartridge 1100 which is configured to be engaged with the golf club head 1001 via press fitting, snap fit mechanisms (e.g., spring loaded protrusions and corresponding detents), threaded fasteners, etc. Other securing means, such as described above with regard to wood-type golf club, may be used as well.

According to aspects of the disclosure, the cartridge 1100 may be made from any desired materials and combinations of different materials such as described above with regard to cartridge 200. Further, according to example embodiments of the disclosure, the cartridge 1100 may be configured with configured to house a monitoring device 201 similar to the one described above with regard to the wood-type golf club. For example, the monitoring device 201 may be configured to house the sensors 202, the transmitter/transceiver 203, processor 204, power supply 206, memory, etc. The monitoring device 201, its capabilities and functions are similar to the monitoring device 201 described above and, therefore, for the sake of brevity, will not be elaborated on here. Further, the above described methods for determining and transmitting data to the remote computer 400 are applicable with the iron-type golf clubs as well and, therefore, will not be repeated for the sake of brevity.

As seen in FIG. 15B, aspects of the disclosure, relate to a weight cartridge 1200 which is configured to be engaged with the port 1009. The weight cartridge 1200 may be configured similarly to the cartridge 1100 described above with the exception that the weight cartridge 1200 does not include a monitoring device 201. It is noted that the weight cartridge 1200 may be configured to engage with the port 1009 in the same manner as the corresponding cartridge 1100. Hence, again, for the sake of brevity, the engaging and releasing structure of the weight cartridge 1200 and the port 1009 will not be elaborated on here.

According to aspects of the disclosure, when the golfer does not want to have the monitoring device 201 housed within the golf club 1000, the golfer may disengage and remove the cartridge 1100 from the port 1009 of the golf club head 1001 and engage and secure the weight cartridge 1200 with the port 1009 of the golf club head 1001. It is noted that according to aspects of the disclosure, the weight cartridge 1100 may be weighted as desired to provide appropriate balancing to the putter-type golf club head 1001.

Therefore, based on the above disclosure, it is understood that aspects of the disclosure are directed to a golf club configured to receive interchangeable sections or cartridges, wherein one of the interchangeable cartridges may house the monitoring device 201 and a second of the interchangeable cartridges does not house the monitoring device 201. In this way, the golfer may selectively configure the golf club to include, or not include, the monitoring device 201 at the golfer's discretion.

A wide variety of overall club head constructions are possible without departing from this disclosure. For example, it is noted that the dimensions and/or other characteristics of the golf club heads 1001 according to examples of this disclosure may vary significantly without departing from the disclosure. For example, the above described features and configurations may be incorporated into any putter-type club heads including, for example: mallet heads, blade-type putters, etc.

Figure 16A:
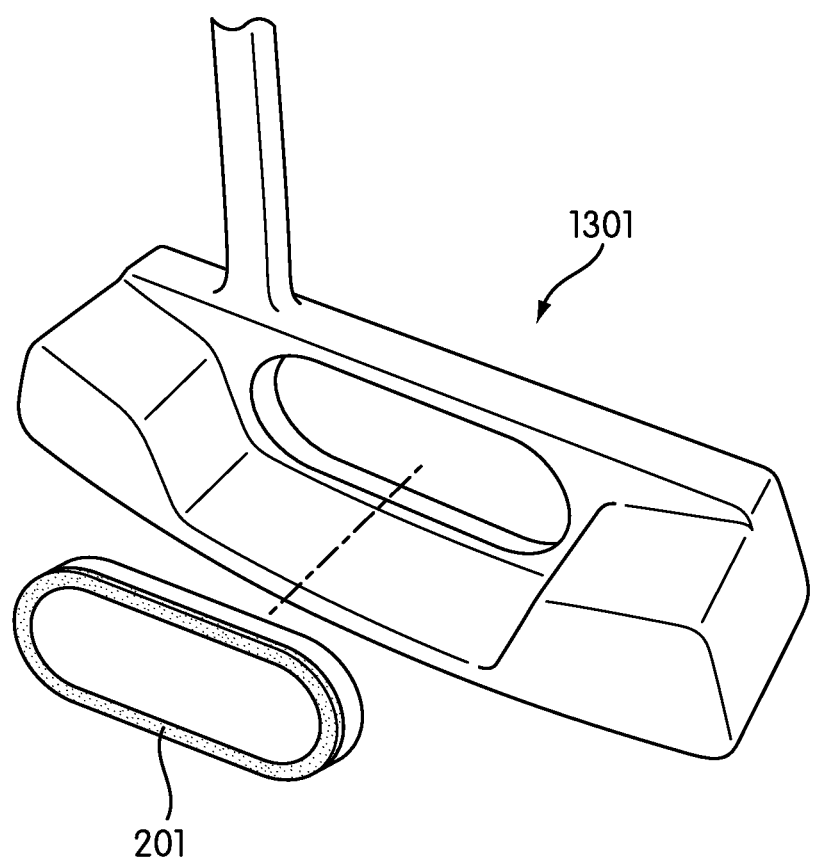
FIG. 16A is an exploded view of an illustrative embodiment of an putter golf club head structure having a monitoring device according to aspects of the disclosure.
Figure 16B:
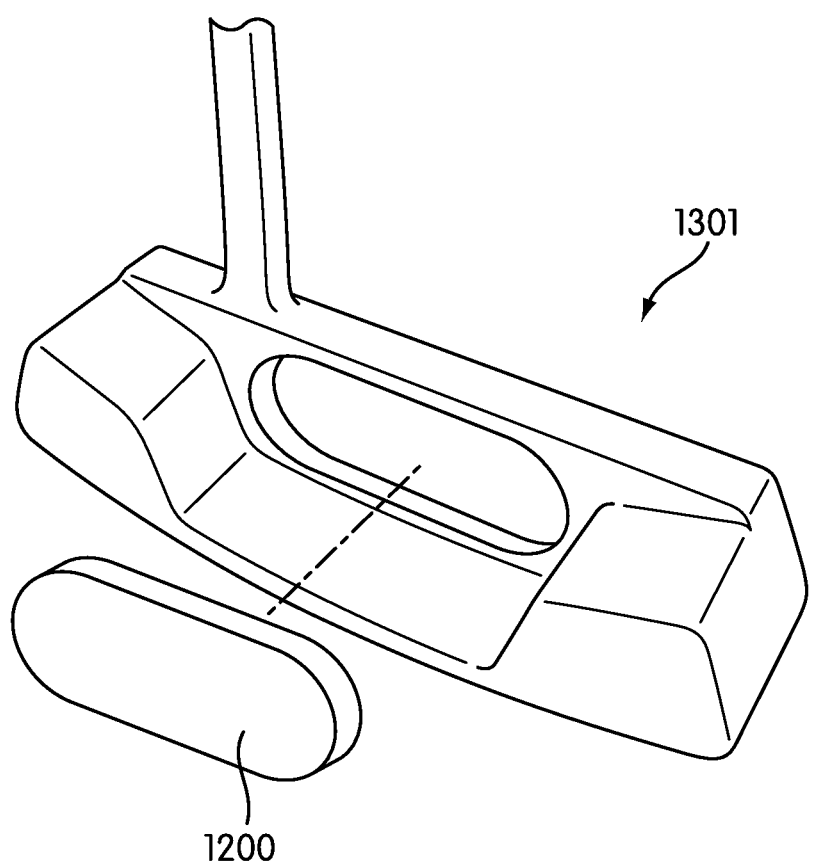
FIG. 16B is an exploded view of the putter golf club head shown in FIG. 16A wherein the weight is attached the golf club head.

For example, FIGS. 16A and 16B show an alternative embodiment of a putter-type golf club according to aspects of the disclosure. FIG. 16A is an exploded view of an illustrative embodiment of a putter golf club head structure according to aspects of the disclosure wherein a monitoring device 201 is used. FIG. 16B is an exploded view of the putter golf club head shown in FIG. 16A wherein the weight cartridge 1200 is used instead of the monitoring device 201.

As seen in FIGS. 16A and 16B, the putter-type golf club may include a putter-type golf club head 1301 in accordance with the present disclosure. The golf club head 1301 may include a recess configured to receive the monitoring device 201. For example, the recess may be configured to surround and engage the monitoring device 201 in order to support and stabilize the monitoring device 201. As seen in FIG. 16A, the recess may be configured in the rear of the golf club head 1301 behind the ball striking face of the golf club head 1301. According to the aspects of the disclosure, the monitoring device 201 may be configured to engage with the golf club head 1301 in a variety of ways, such as mechanical fasteners, press fitting, snap fit mechanisms (e.g., spring loaded protrusions and corresponding detents), threaded fasteners, interference fit configurations etc. The mechanical fasteners could also include additional fastening mechanisms such as bar members dimensioned to be placed across the monitoring device 201. The monitoring device 201 can also engage with the golf club head 1301 via adhesive members. For example, a double-sided tape could secure the monitoring device 201 in the recess. The adhesive member or double-sided tape may utilize a low-tack adhesive wherein the monitoring device 201 is releasably engageable in the recess. It is further understood that the recess shown in the golf club head 1301 could be positioned in other locations on the head. For example, the recess could be located in the sole of the golf club head 1301 or further in a top surface or crown of the club head 1301. The recess could also be positioned in a heel or toe of the club head 1301. Thus, the monitoring device 201 can be received in the recess at these alternative locations on the head 1301.

The golf club head 1301 and the monitoring device 201 may be configured to provide desirable weight placement in the club head 1301. For example, the golf club head 1301, and the monitoring device 201 may be configured such that when engaged, the golf club head 1301 is directly behind the center of the ball striking face of the golf club head 1301. While not illustrative, it is noted that in alternative embodiments, the removable section 200 may be used to engage the monitoring device with the golf club head 1301.

As seen in FIG. 16B, aspects of the disclosure, relate to a weight cartridge 1200 which is configured to be engaged with the recess. The weight cartridge 1200 may be configured similarly to the monitoring device 201 described above with the exception that the weight cartridge 1200 does not include a monitoring device 201. It is noted that the weight cartridge 1200 may be configured to engage with the recess in the same manner as the monitoring device 201. Hence, for the sake of brevity, the engaging and releasing structure of the weight cartridge 1200 and the recess will not be elaborated on here.

Figure 16C:
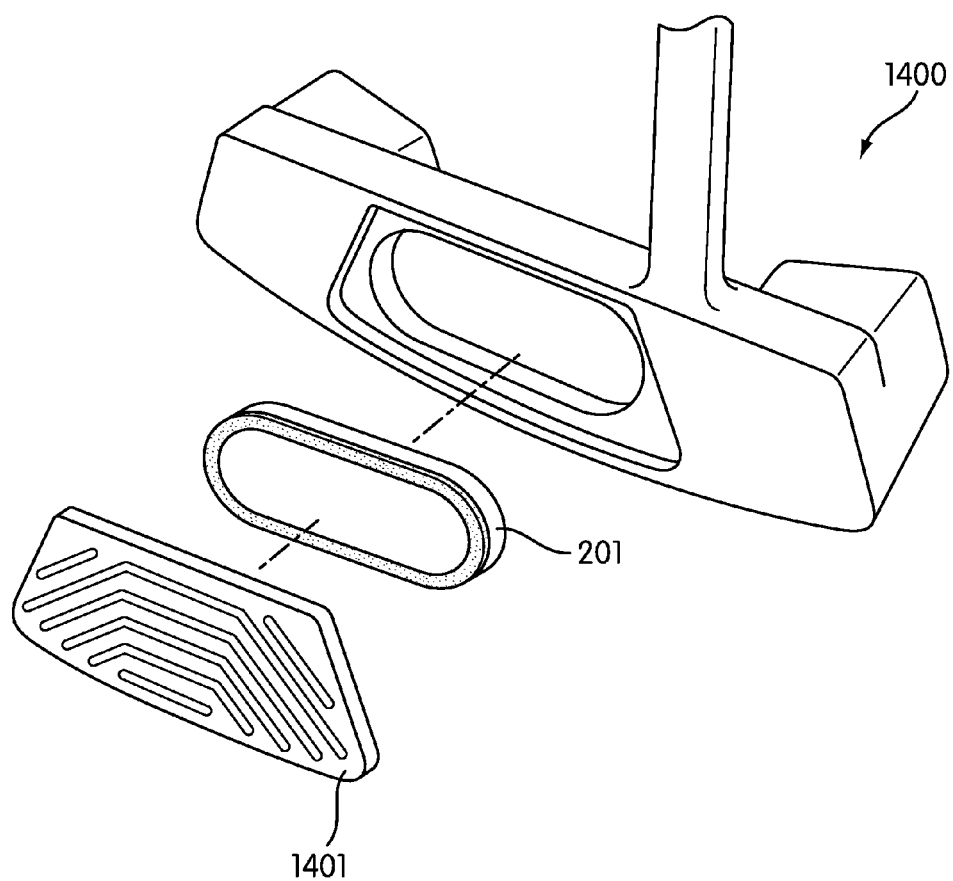
FIG. 16C is an exploded view of an illustrative embodiment of another putter golf club head structure supporting a monitoring device according to aspects of the disclosure.

FIG. 16C shows an alternative embodiment of a putter-type golf club according to aspects of the disclosure. FIG. 16C is an exploded view of an illustrative embodiment of a putter golf club head structure according to aspects of the disclosure wherein a monitoring device 201 is used.

As seen in FIG. 16C, the putter-type golf club may include a putter-type golf club head 1400 in accordance with the present disclosure. The golf club head 1400 may include a recess configured to receive the monitoring device 201. For example, the recess may be configured to surround and engage the monitoring device 201 in order to support and stabilize the monitoring device 201. As seen in FIG. 16C, the recess may be configured in the ball striking face of the golf club head 1400. According to the aspects of the disclosure, the monitoring device 201 may be configured to engage with the golf club head 1400 in a variety of ways, such as mechanical fasteners, press fitting, snap fit mechanisms (e.g., spring loaded protrusions and corresponding detents), threaded fasteners, etc. As further shown in FIG. 16C, a ball striking face insert 1401 is received in the recess of the golf club head 1400 and is positioned over the monitoring device 201.

The golf club head 1400 and the monitoring device 201 may be configured to provide desirable weight placement in the club head 1400. For example, the golf club head 1400 and the monitoring device 201 may be configured such that when engaged, the monitoring device 201 is generally in a center of the ball striking face of the golf club head 1400. While not illustrative, it is noted that in alternative embodiments, the removable section 200 may be used to engage the monitoring device with the golf club head 1400.

Figure 16D:
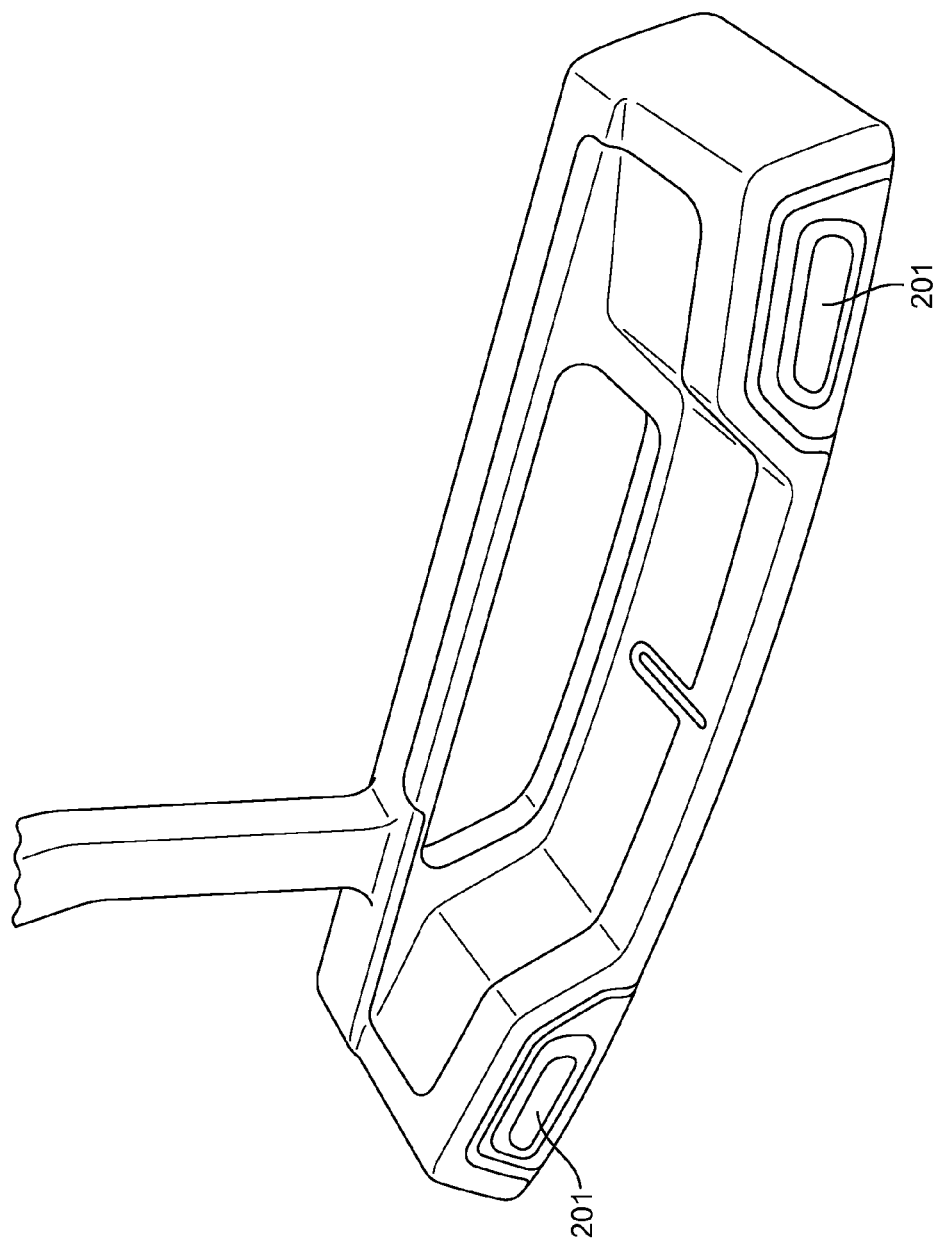
FIG. 16D is a view of an illustrative embodiment of another putter golf club head structure according to aspects of the disclosure.

FIG. 16D shows an alternative embodiment of a putter-type golf club according to aspects of the disclosure. FIG. 16D is a view of an illustrative embodiment of a putter golf club head structure according to aspects of the disclosure wherein two monitoring devices 201 are used. For example, as seen in FIG. 16, a first monitoring device 201 may be positioned in a heel of the putter-type golf club head and a second monitoring device 201 may be positioned in a toe of the putter-type golf club head. According to aspects of the disclosure, by using data from both the first and second monitoring devices 201, the position of where the golf ball impacts the face of the golf club head may be determined. It is noted that while this feature of having two monitoring devices 201 in a golf club head is depicted in a putter, this feature is applicable to any type of golf club head, including: wood-type golf club heads, iron-type golf club heads, hybrid-type golf club heads, etc. It is further understood that the pair of monitoring devices 201 may be positioned proximate the face of the club head and proximate the heel and toe of the club head.

Figure 16E:
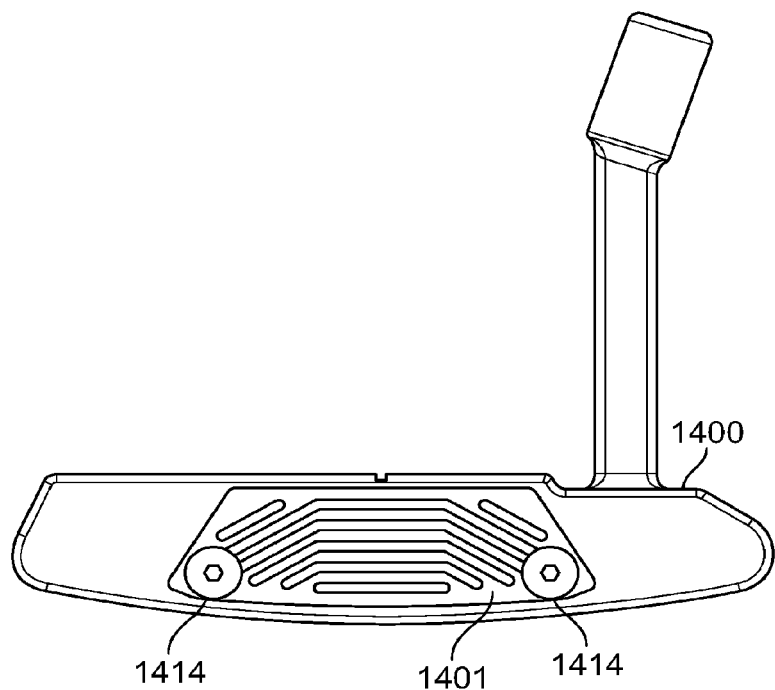
FIGS. 16E-G are views of an illustrative embodiment of another golf club head structure supporting a monitoring device according to aspects of the disclosure, which embodiment is similar to the embodiment of FIG. 16C.
Figure 16F:
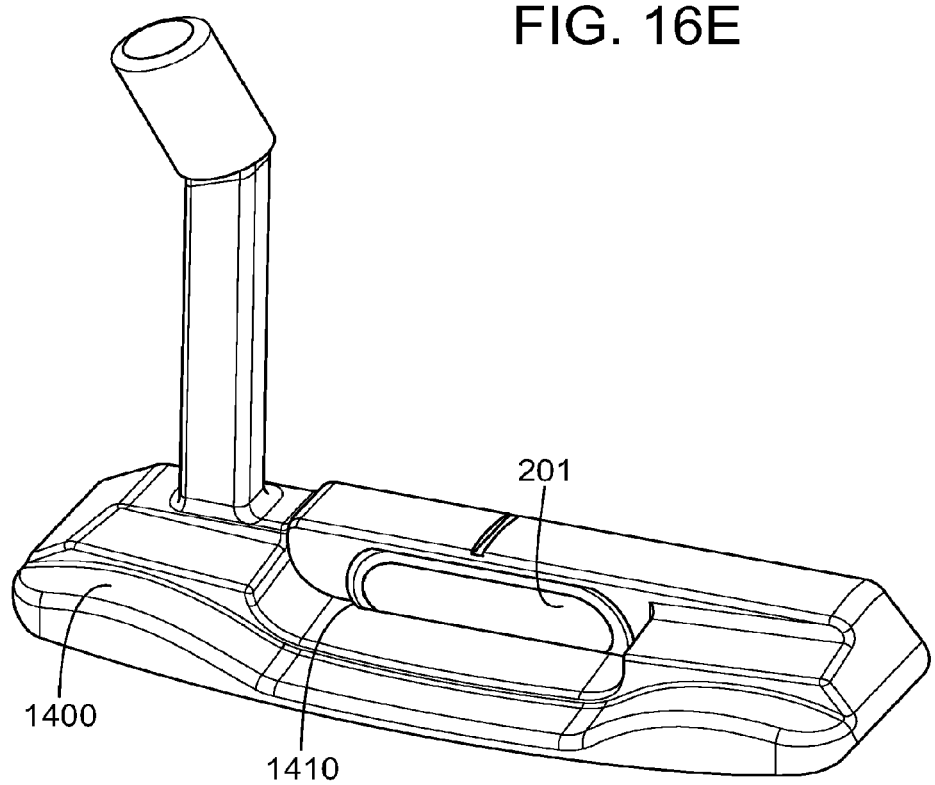
Figure 16G:
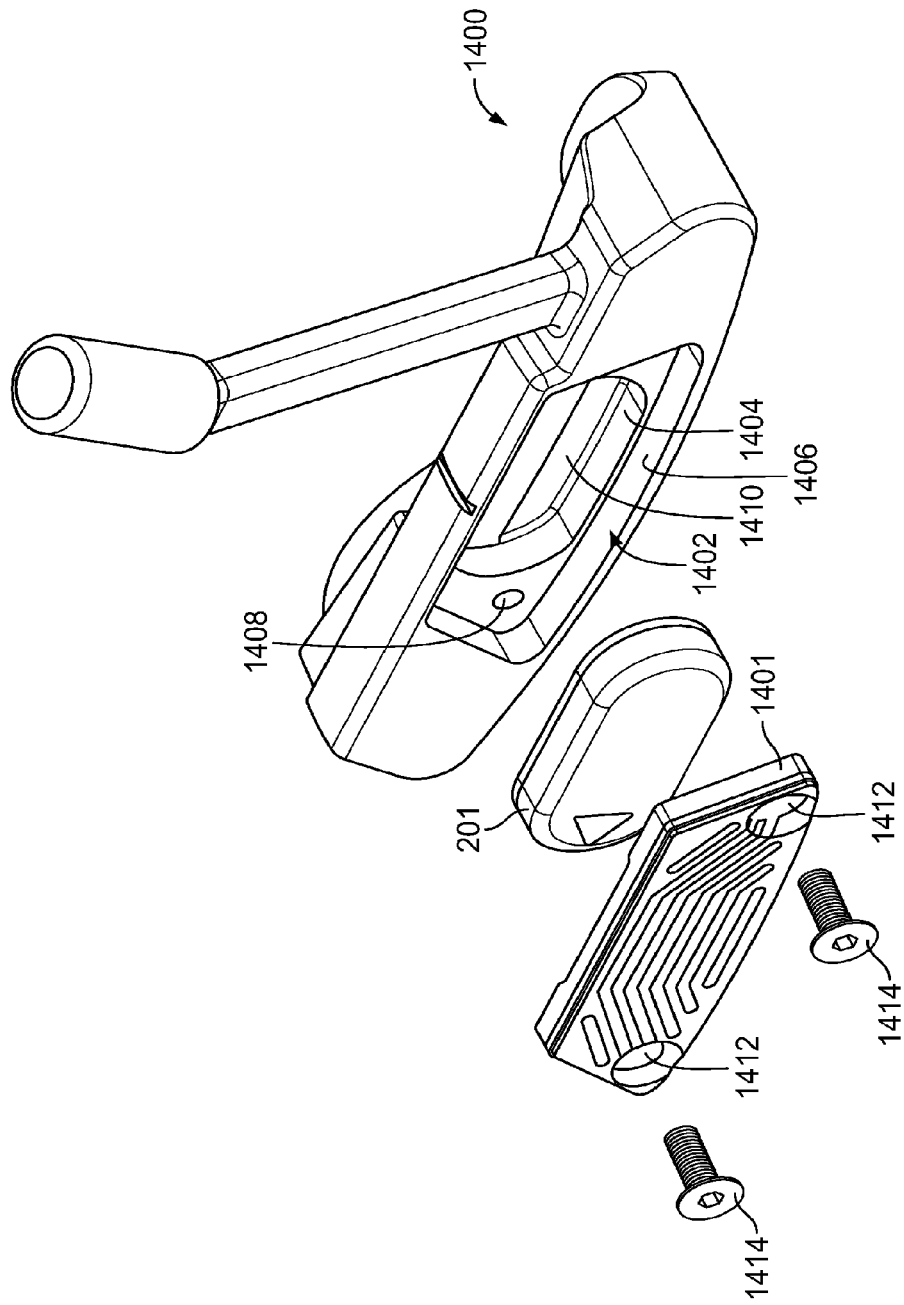

FIGS. 16E-G illustrate another alternative embodiment of a putter-type golf club head according to aspects of the disclosure. This embodiment is similar to the embodiment disclosed in FIG. 16C and similar reference numerals will be used. The putter golf club head 1400 has a recess 1402 that in this particular embodiment extends completely through the golf club head 1400. The recess 1402 has a first section 1404 and a second section 1406. A platform 1405 is defined in the recess 1402. A pair of threaded apertures 1408 is defined in the platform 1405. The first section 1404 of the recess 1402 opens to a rear of the golf club head 1400. In alternative embodiments, a floor may be provided wherein the recess does not extend completely through the club head. A ledge 1410 is defined at the rear and faces a rear of the first section 1404. As further shown in FIG. 16G, the ball striking face insert 1401 has threaded apertures 1412 therein. The monitoring device 201 is inserted into the recess 1402 and is received by the first section 1404. The monitoring device 201 abuts against the ledge 1410. The ball striking face insert 1401 is inserted into the recess 1402 and is received by the second section 1406. Fasteners 1414 are inserted into the aligned apertures 1408,1412 to secure the monitoring device 201 and the face insert 1401 to the golf club head 1400 (FIG. 16E). It is appreciated from FIGS. 16F and 16G that the monitoring device 201 is sandwiched between the ledge 1410 and the face insert 1401. The monitoring device 201 is visible from a rear of the golf club head 1400 but can only be removed from a front of the golf club head 1400 by removing the face insert 1401 via the fasteners 1414.

According to aspects of the disclosure, monitoring devices 201 may include one or more sensors configured to detect the impact of the golf ball with the golf club head 101. For example, a force sensor, a pressure sensor (e.g., a piezoelectric sensor), or the like may be configured to detect the location of the impact on the ball striking face 107 of the golf club head and, further, the force generated from the impact. Such data generated from the impact sensors may be communicated through the monitoring device 201 and, further, transmitted via the transmitter 203 along with the other data from the other one or more sensors of the monitoring device 201 described above. Further, according to embodiments of such a disclosure, the data from the impact sensors can be incorporated with data from the above described sensors. For example, the data from the impact sensors can be used to determine various characteristics of the golf swing such as described above. Further, according to aspects of the disclosure, by using data from one or more impact sensors, the position of where the golf ball impacts the face of the golf club head may be determined.

According to aspects of the disclosure, embodiments of the disclosure may include one or more monitoring devices 201 located in various positions throughout the golf club. For example, according to aspects of the disclosure, the first and second monitoring devices 201 may be positioned at or near the ball striking face of the golf club head. However, according to other aspects of the disclosure, embodiments may have one or more monitoring devices 201 positioned away from the ball striking face of the golf club head. For example, in the embodiment depicted in FIG. 16D, the first and second monitoring devices 201 are positioned in the rear of the golf club head.

It is noted that in embodiments wherein the sensors are not positioned at the ball striking face, the data determined by sensors may need to be manipulated or adjusted in order to provide accurate measurements. For example, in the embodiment shown in FIG. 16D, because sensors are positioned in the rear of the golf club head, they may provide data that is different from data determined by sensors in monitoring devices 201 positioned at or near the ball striking face of the golf club head. Therefore, data collected from sensors of the embodiment shown in FIG. 16D may be manipulated (e.g., recalculated or otherwise modified) in order to account from the positioning of the sensors within the rear of the golf club head. In this way, the manipulated data can be used to determine accurate golf metrics, variables and kinematics, such as described above.

It is noted that while the above description of manipulating data is with respect to a distance from the ball striking face of the golf club head, any reference point may be used. Accordingly, the data collected from sensors positioned away from that particular reference point may be manipulated (e.g., recalculated or otherwise modified) in order to account from the positioning of those sensors away from the particular reference point.

According to aspects of the disclosure, the data from sensors may be subjected a transformation matrix which manipulates the data (e.g., recalculates or modifies the data) in order to account for the exact positioning of the sensor within the golf club. The transformation matrix may be a series of calculations which modifies that data according to the exact positioning of the sensor within the golf club. Therefore, it is understood that a different transformation matrix may be required for each of individual sensors positioned at different locations within the golf club. For example, in the embodiment shown in FIG. 16D, a first transformation matrix may be used to calculate data obtained the first sensor in the heel of the golf club head and a second, different, transformation matrix may be used to calculate data obtained the second sensor in the toe of the golf club head.

The transformation matrix may be included in a software package that may be downloaded to the remote computer 400 to which the data from the monitoring device 201 is transmitted. For example, the software package may be available for download from a website. For example, a website may include software packages or applications designed for particular golf clubs of sets of golf clubs. Those software packages may contain transformation matrices designed for the specific positions of sensors and remote monitoring devices 201 in the respective golf clubs.

Therefore, if a golfer was using a particular putter (e.g., putter A), the golfer could download the particular software package or application designed for putter A to the remote computer 400. Hence, when data (obtained by the sensors of the remote monitoring device(s) 201 in that particular golf club) is transmitted to the remote computer 400, the downloaded software package or application for that particular golf club would recalculate the obtained data and output accurate measurements, golf metrics, variables and kinematics.

According to aspects of the disclosure, a monitoring device 201 may contain identification codes which allow data transmitted from a particular monitoring device 201 to synchronize with the remote computer 400 used by the golfer. For example, the upon downloading the software package or application for the particular golf club to the remote computer 400, the golfer may manually enter an identification code into the remote computer 400 to synchronize the monitoring device 201 with the remote computer 400. Hence, by allowing the particular monitoring device 201 to be synchronized with the remote computer 400, the monitoring devices could be interchangeable within various golf clubs.

For example, a golfer may download an application or software package which contains transformation matrices for each golf clubs that a golfer owns. By synchronizing the monitoring device(s) 201 in each of the golf clubs (e.g., the monitoring device(s) 201 in each of: a pitching wedge, a sand wedge, a 10-iron, a 9-iron . . . a 3-wood, a driver, etc.), with the remote computer 400, the remote computer 400 would recognize the data from a particular monitor device 201 and associate that data with the respective golf club and, additionally, appropriate location of the sensor within the respective golf club. Hence, using the transformation matrix for the respective golf club, the remote computer 400 would output correct measurements, golf metrics, variables and kinematics. Therefore, as demonstrated, provided that the monitoring device(s) 201 are synchronized correctly, the monitoring device(s) 201 may be interchangeable within golf clubs. It is noted that, if desired, the identification code could be transmitted to the remote computer 400 by the monitoring device 201 along with the data. In this way, the identification code would not have entered by the golfer and, instead, the synchronization and coordination of the monitoring device 201 with remote computer 400 could be done automatically.

Figure 17A:
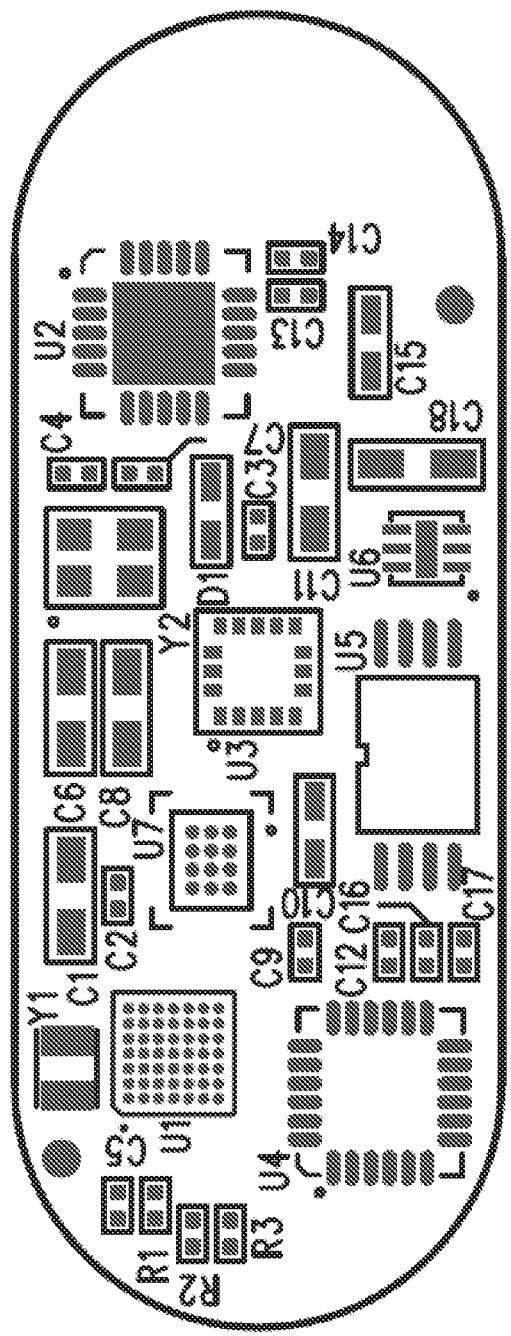
FIGS. 17A and 17B are an illustrative embodiment of the interior of an embodiment of a monitoring device according to aspects of the disclosure.
Figure 17B:
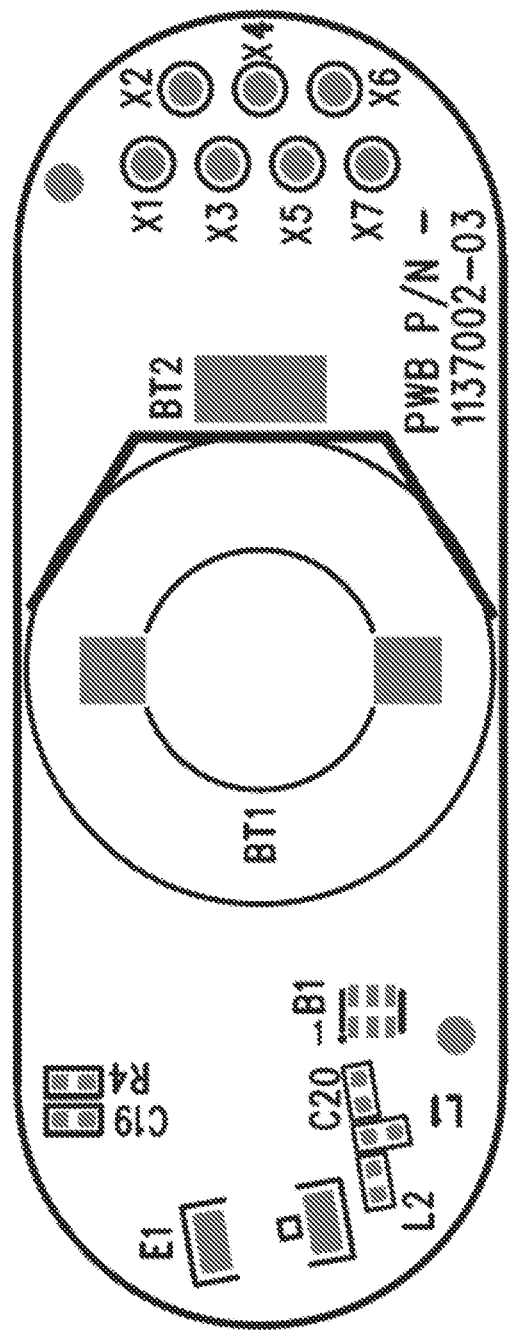
Figure 18B:
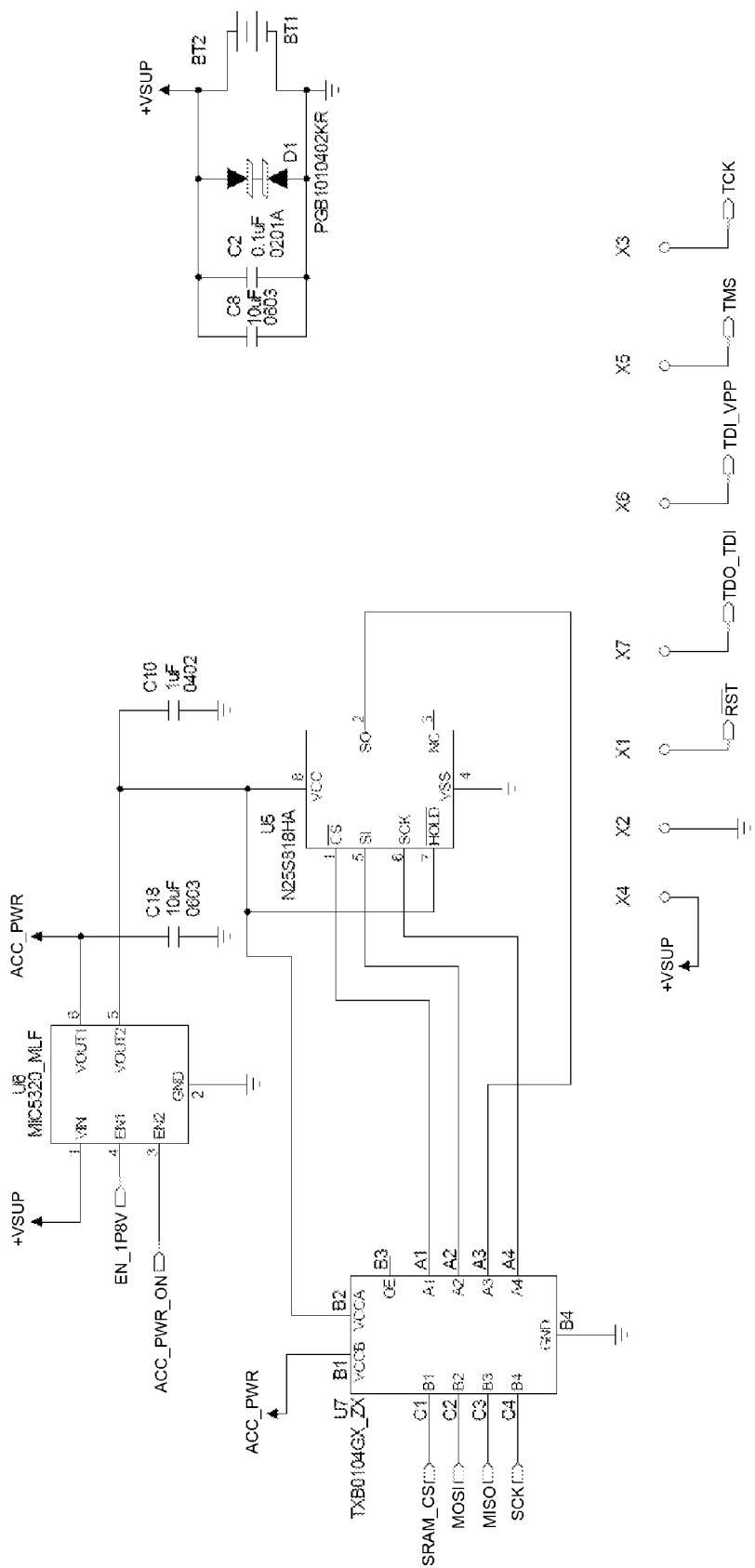
Figure 18C:
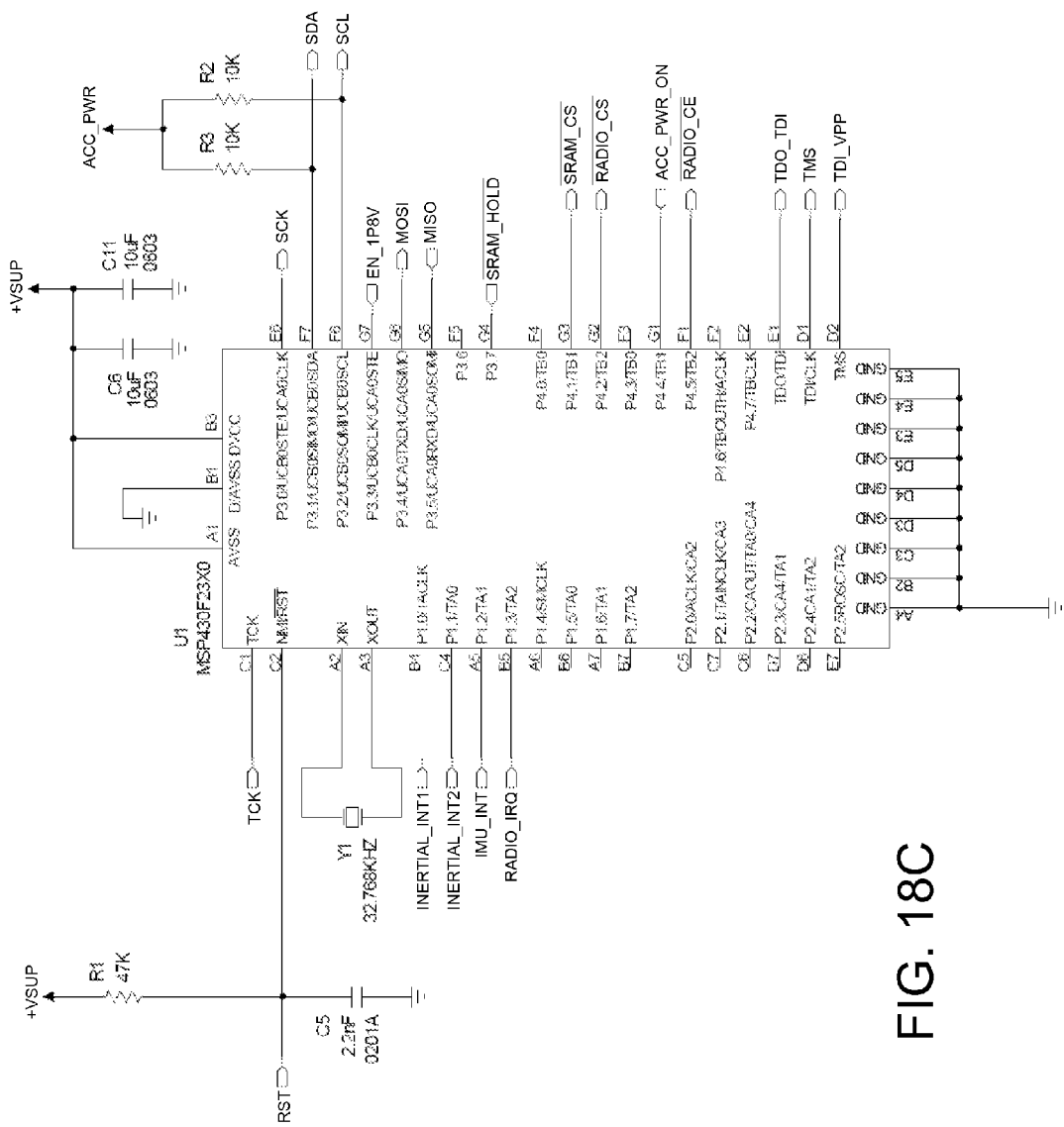
Figure 18D:
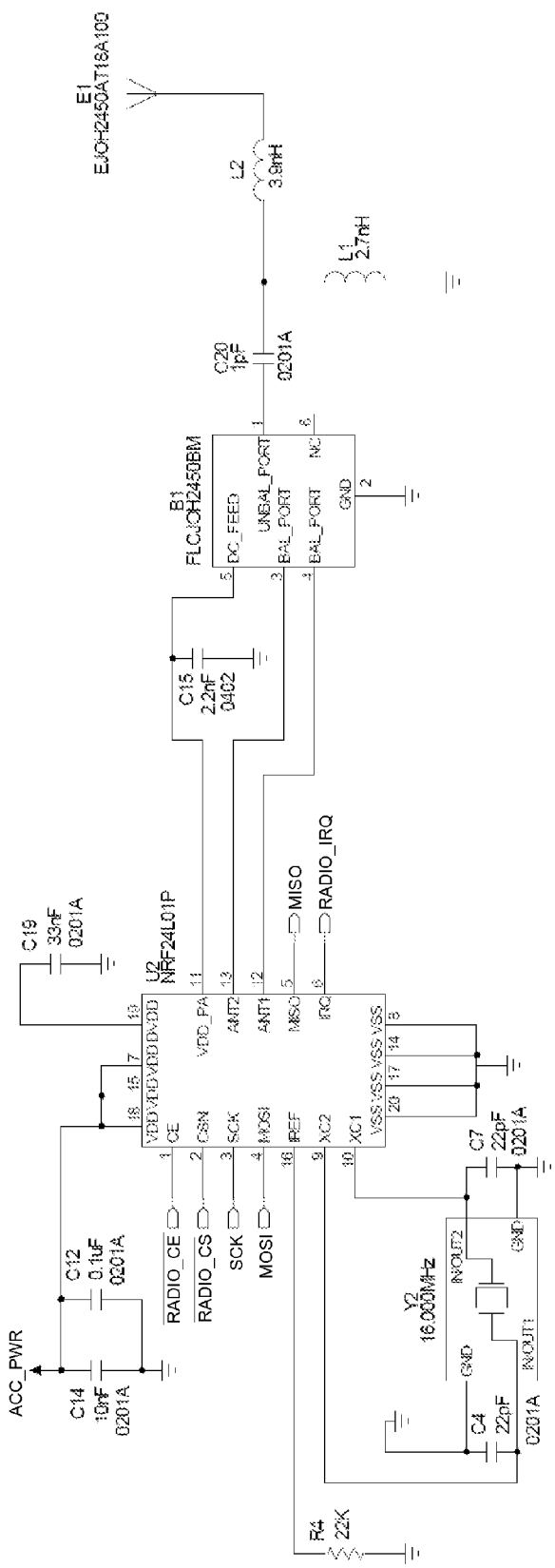

FIGS. 17A and 17B are an illustrative embodiment of the interior of an embodiment of a monitoring device 201, or general schematic sensor layout, according to aspects of the disclosure. For example, as seen in FIGS. 17A and B, a monitoring device 201 may include a power source, a transceiver, an accelerometer (e.g., 3-axis accelerometer), one or more: capacitors, diodes, antennas, inductors, resistors, filters, integrated circuits for controllers (e.g., mixed signal controllers), transceivers, memory and digital motion sensors, voltage regulators, inertial measurement units, etc. One of ordinary skill in the art would realize that modification to, or exclusion of, one or more of the above components or the inclusion of additional components in monitoring device may be used as desired to configure the monitoring device to function as described above. Such inclusions, modifications, etc. are considered within the scope of the disclosure. FIGS. 18A-D are illustrative embodiments of circuitry of a monitoring device according to aspects of the disclosure. It is understood that various components as described above can be incorporated into the schematic layouts and circuitry disclosed herein.

Sensivity Ranges

As discussed above, aspects of the disclosure relate to a monitoring device 201 that is configured to measure displacement, position, orientation, velocity, acceleration or other characteristics of associated with a golf stroke. According to further aspects of the disclosure, a monitoring device 201 may be configured to fit in any golf club of a set of golf clubs in accordance with one or more embodiments of the disclosure. In other words, a monitoring device 201 according to aspects of the disclosure may be "universal" with respect to the golf clubs in such a set of golf clubs. For example, the monitoring device 201 may be configured to fit in a putter of the golf club set, an iron-type golf club of the golf club set and in a wood-type golf club of the golf club set.

However, the displacement, velocity, acceleration or other characteristics associated with a golf stroke may vary dramatically depending on the particular golf stroke. For example, velocity, acceleration or other characteristics associated with a putt may vary dramatically from the velocity, acceleration or other characteristics associated with the golf swing of a driver or iron.

For example, during a golf swing with a driver, the velocity of the club head may be between 0-125 miles per hour (mph) (roughly about 0-56 meters per second). In contrast, during a putt with a putter, the velocity of the club head may be between 0-7 miles per hour (roughly 0-3.0 meters per second). Further, during a golf swing with a driver, the angular velocity of the club head may be between 0-3000 degrees per second (roughly about 0-52 radians per second). In contrast, during a putt with a putter, the angular velocity of the club head may be between 0-150 degrees per second (roughly 0-3 radians per second).

Similarly, during a golf swing with a driver, the acceleration of the club head may be between 0-3000 feet/sec$^2$ (roughly about 0-1000 meters per second$^2$ (m/s$^2$)). In contrast, during a putt with a putter, the acceleration of the club head may be between 0-3000 feet/sec$^2$ (roughly about 0-15.0 m/s$^2$).

Figure 19A:
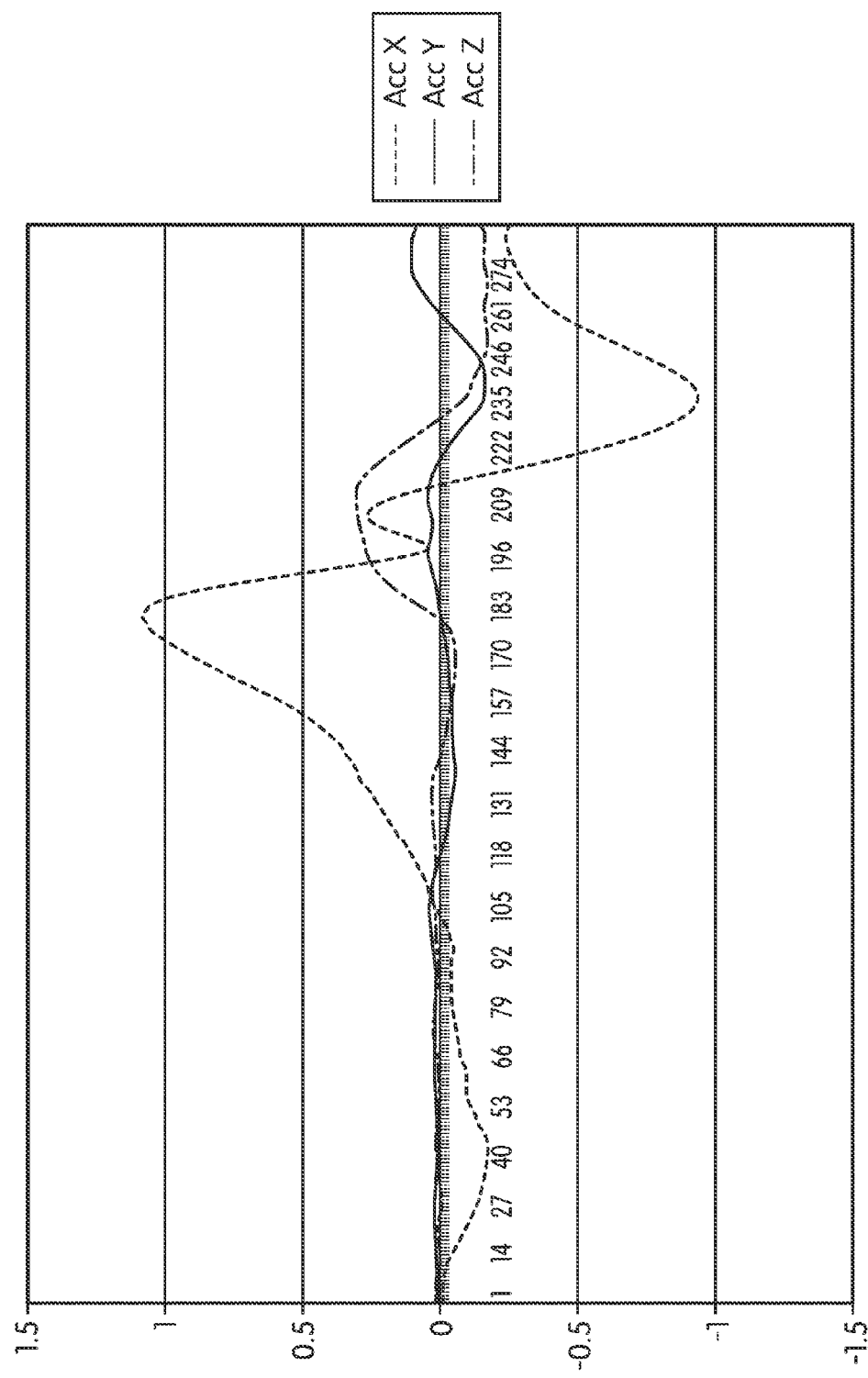
FIGS. 19A-B are graphs illustrating the magnitude of acceleration and angular velocities for a typical putt.
Figure 19B:
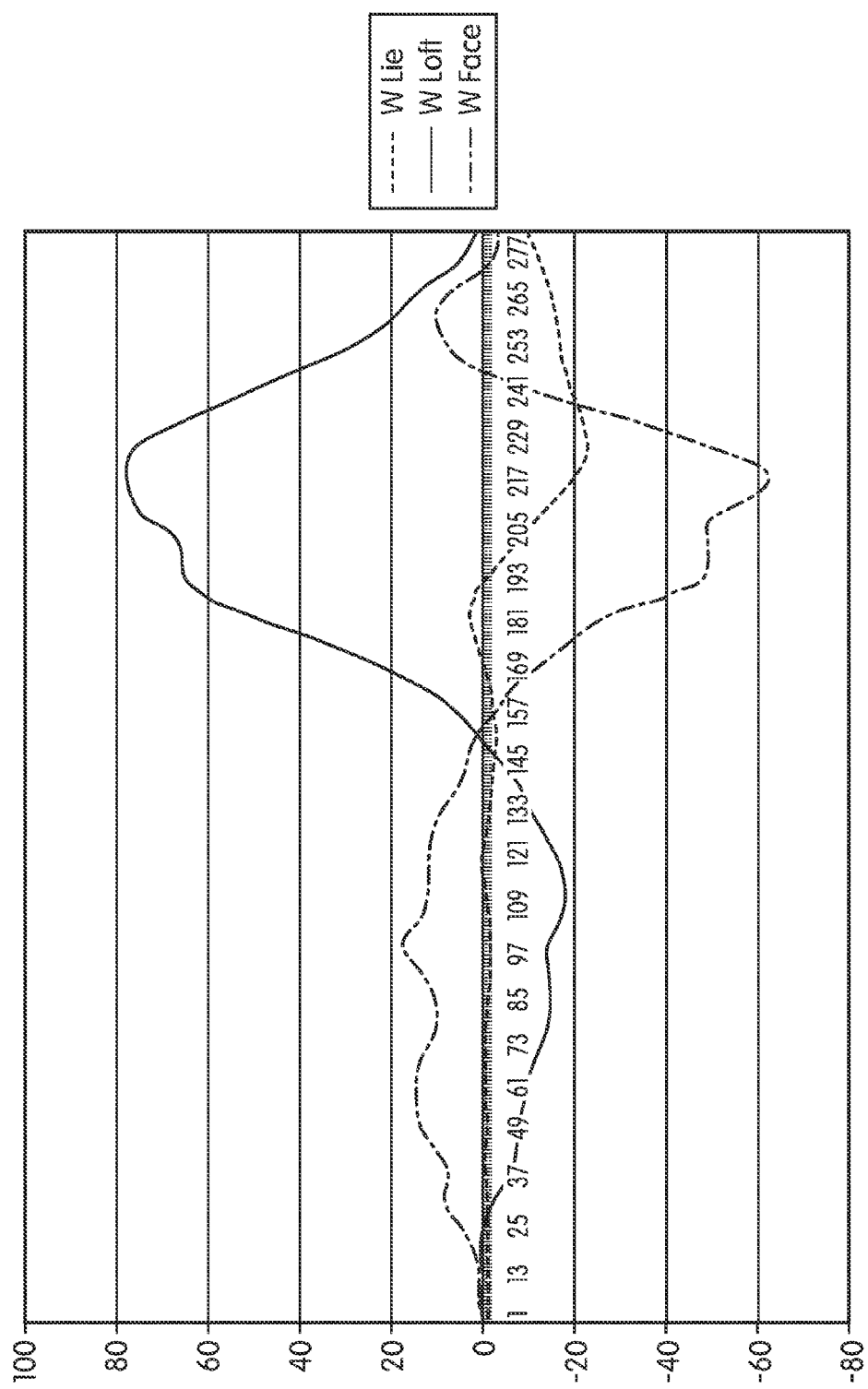
Figure 19C:
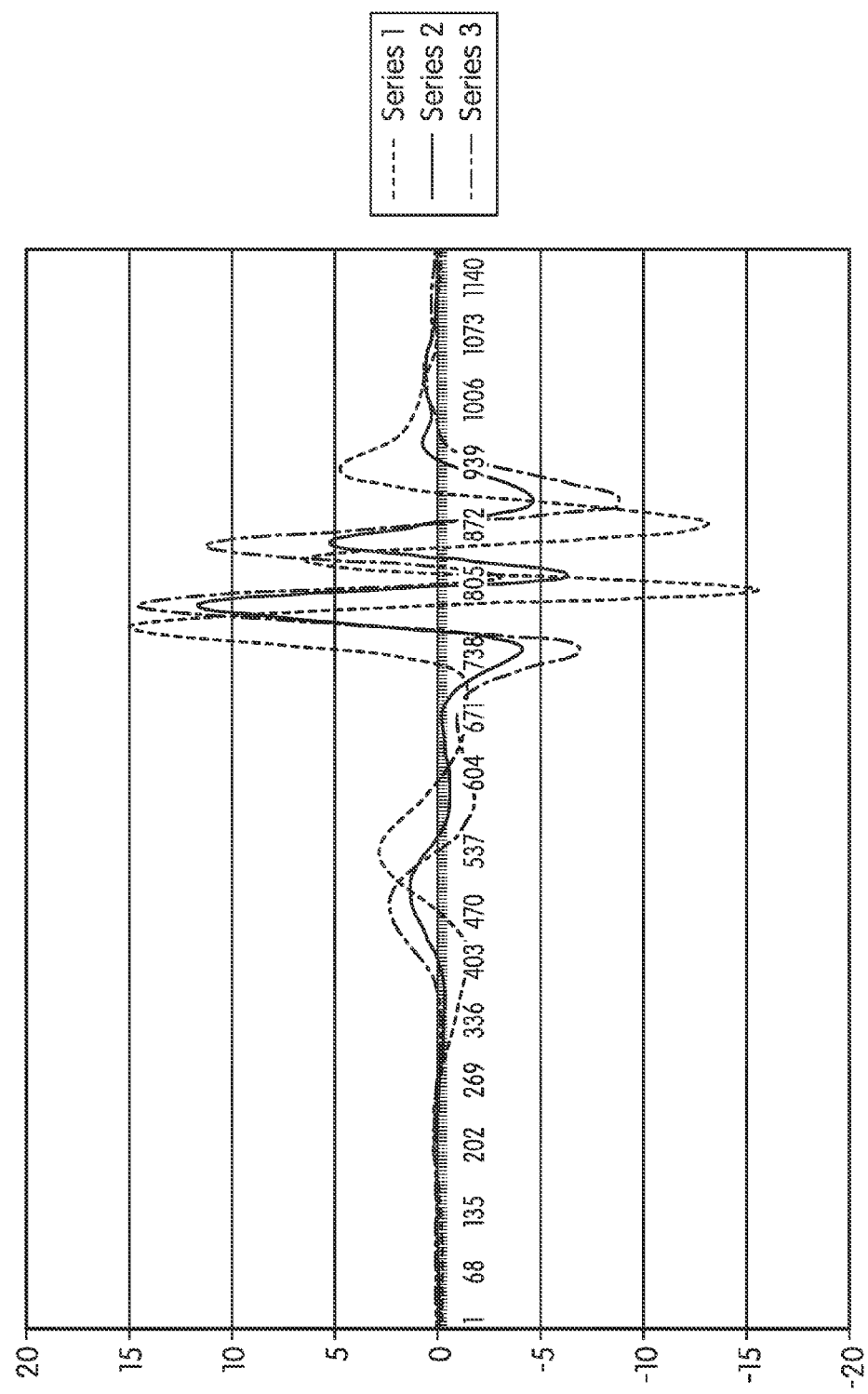
FIGS. 19C-D are graphs illustrating the magnitude of acceleration and angular velocities for a typical golf swing associated with a driver.
Figure 19D:
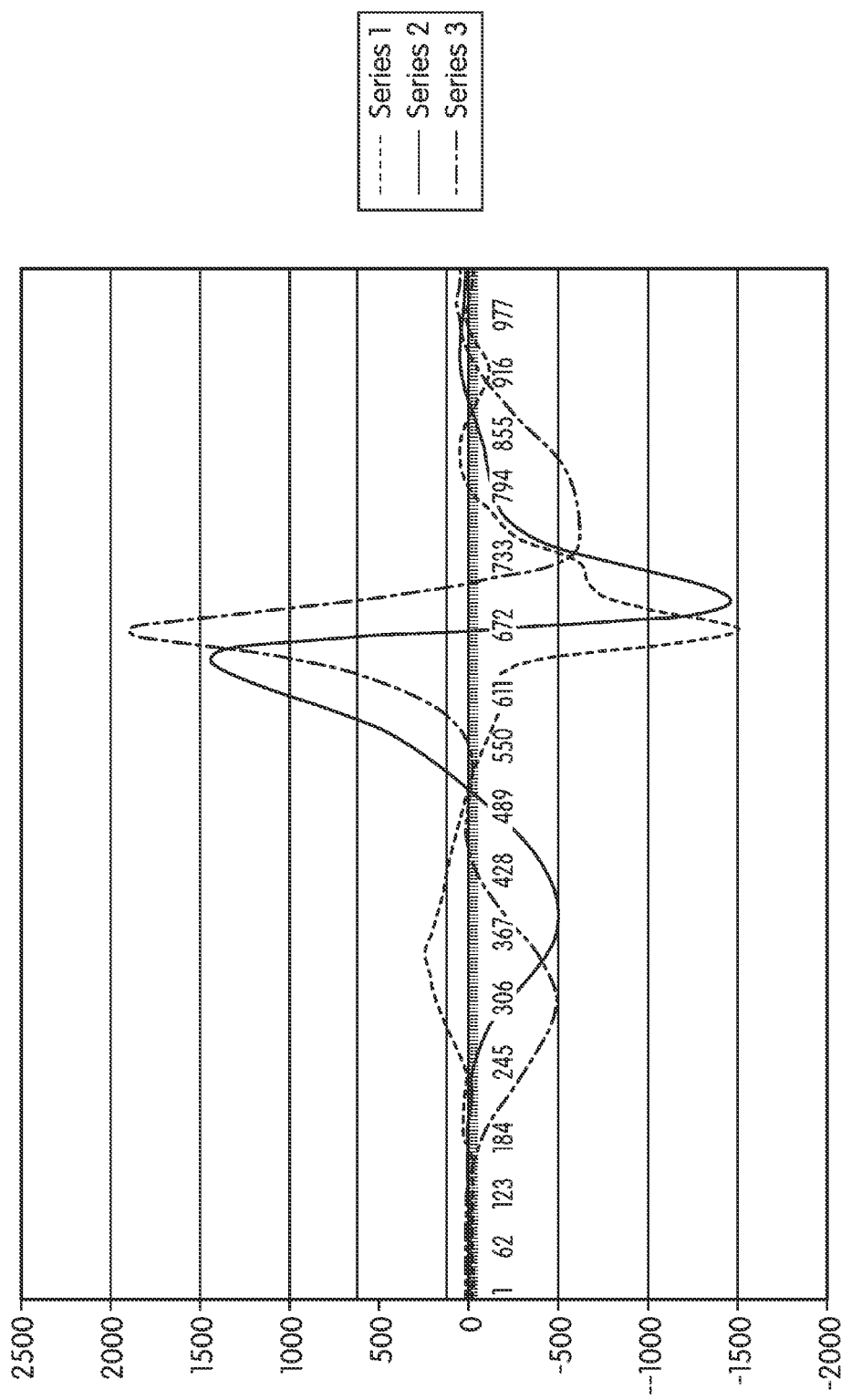

For example, according to an illustrate embodiment, FIGS. 19A-B show graphically the magnitude of acceleration and angular velocities for a typical putt. As seen in FIGS. 19A-B, the acceleration during a putt may be 1.1 g (11 m/s$^2$). Further, the angular velocity during a putt may be 80 dps (1.5 rad/second). In contrast, FIGS. 19C-D, show graphically the magnitude of acceleration and angular velocities for an illustrative golf swing with a driver. As seen in FIG. 19C, the acceleration during a golf swing with the driver may be 15 g (150 m/s$^2$. Further, the angular velocity during the golf swing with a driver may be 1500 dps (26 rad/second). Hence, it is understood, that as discussed above, velocity, acceleration or other characteristics associated with a putt may vary dramatically from the velocity, acceleration or other characteristics associated with a golf swing of a driver.

As described above, a monitoring device 201 may include one or more sensors 202 and the sensors 202 may be accelerometers (such as piezoelectric accelerometers), magnetometers, or gyroscopes which are configured to measure a plurality of data including velocity, acceleration, orientation, gravitational forces, etc. Hence, a monitoring device 201 according to aspects of the disclosure may include an Inertial Measuring Unit (IMU) which is one or more sensors (e.g., accelerometers and/or gyroscopes, or some combination thereof in an exemplary embodiment) that are configured to measure velocity, acceleration, orientation, gravitational forces, etc.

Given the above described disparity in velocity ranges between the different types of golf stroke, it may be difficult for a single IMU to accurately determine the displacement, velocity and acceleration of the club during the golf stroke. For example, in order to achieve an accurate reading of the angular velocity of a putting stroke, an IMU configured to measure a putt may be extremely sensitive to small changes in angular velocity, wherein small is relative to the velocity ranges discussed above with respect to a putting stroke (e.g., fractions of a meter per second). Similarly, in order to achieve an accurate reading of the velocity of a golf swing for an iron-type golf club or a wood-type golf club, an IMU configured to measure such a golf swing may be less sensitive to small changes in velocity and able to determine larger changes in velocity, wherein large is relative to the velocity ranges discussed above with respect to a golf swing of an iron-type golf club or a wood-type golf club (e.g., at least several meters per second).

Similarly, given the disparity in acceleration ranges between the different types of golf stroke, it may be difficult for a single IMU to accurately determine the acceleration of the club during the golf stroke. For example, in order to achieve an accurate reading of the acceleration of a putting stroke, an IMU configured to measure a putt may be extremely sensitive to small changes in acceleration, wherein small is relative to the acceleration ranges discussed above with respect to a putting stroke (e.g., 0-15 m/s$^2$). Similarly, in order to achieve an accurate reading of the acceleration of a golf swing for an iron-type golf club or a wood-type golf club, an IMU configured to measure such a golf swing may be less sensitive to small changes in acceleration and able to determine larger changes in acceleration, wherein large is relative to the acceleration ranges discussed above with respect to a golf swing of an iron-type golf club or a wood-type golf club (e.g., 0-1000 m/s$^2$).

As aspects of the disclosure are directed to a monitoring device 201 which is "universal" with respect to engaging with any of the golf clubs in the golf club set, a monitoring device 201 according to aspects of the disclosure may include more than one IMU, wherein each of the IMUs is configured differently in order to accurately measure a particular type of golf stroke. For example, one of the IMUs may be configured to measure angular velocity and/or acceleration and may be extremely sensitive to small changes in velocity and/or acceleration (e.g., fractions of a meter per second or m/s$^2$). As discussed above, such an IMU may be beneficial in determining characteristics associated with a putting stroke. Further, another of the IMUs may be configured to measure velocity and/or acceleration and may be may be less sensitive to small changes in velocity and/or acceleration (as compared with the first IMU) and able to more accurately determine larger changes in velocity and/or acceleration (e.g., at least several meters per second or m/s$^2$). As discussed above, such an IMU may be beneficial in determining characteristics associated with a golf swing for an iron-type golf club or a wood-type golf club.

Therefore, according to aspects of the disclosure a single monitoring device 201 may be configured to include a first IMU directed to determining data associated with a putting stroke and a second IMU, which is different from the first IMU, and is directed to determining data associated with a golf swing for an iron-type golf club or a wood-type golf club.

Aspects of the disclosure are directed to determining which of the one or more IMUs to use in collecting data related to the golf stroke. For example, aspects of the disclosure are directed to selectively using data (e.g., for calculations as will be described below) from the first IMU instead of the second IMU or the second IMU instead of the first IMU based on the type of club with which the monitoring device 201 is engaged. Further aspects of the disclosure are directed to receiving data (related to the golf stroke) collected from each (or more than one) of the IMUs and then determining which of data from the one or more IMUs to use (e.g., for calculations as will be described below) based on the type of club with which the monitoring device 201 is engaged. For example, the data from a particular IMU may be selected for use in calculations and/or for transmission to the remote computer 400 based on the data received from each of the IMUs and the type of golf club or other information indicated by the data received from each of the IMUs. In this way, the monitoring device 201 may switch between using and/or transmitting data from a first IMU and a second IMU based on data received from both IMUs.

For example, according to one embodiment of the disclosure, the monitoring device 201 may be configured to be engaged with a golf club of a set of golf clubs which are each configured to receive the monitoring device 201 and the engagement between the monitoring device 201 and the particular golf club of the set causes the selection of the appropriate IMU to be used in conjunction with that particular golf club of the set. In other words, the one or more IMUs that is selected to be used to capture data associated with the golf stroke is determined by the engagement of the monitoring device 201 with the particular golf club. Further, in another example wherein data is collected from each IMU of the golf club, the monitoring device 201 may be configured to be engaged with a golf club of a set of golf clubs which are each configured to receive the monitoring device 201 and the engagement between the monitoring device 201 and the particular golf club of the set causes the selection the appropriate IMU from which the data should be used for a particular purpose in conjunction with that particular golf club of the set. In other words, data from one of the IMUS (and associated with the golf stroke) is selected to be used for a particular purpose based on the engagement of the monitoring device 201 with the particular golf club. For example, while data is collected from both a first and second IMU, based on the engagement of the monitoring device 201 with the particular golf club, data from the first IMU, instead of the second IMU may be used for determining angular velocity of the golf swing.

By way of example, the grips of each of the golf clubs in the set of golf clubs may be configured to receive the monitoring device 201 in a manner discussed above with regard to FIGS. 8-9. For example, as discussed above, according to particular embodiments of the disclosure, monitoring device 201 may be similar to those used in the NIKE+™ athletic performance monitoring systems available from NIKE, Inc. of Beaverton, Oreg. For example, as seen in FIGS. 4A and 4B, the monitoring device 201 may include a generally rectangular compartment which may be similar to the compartment used to house sensors used in the NIKE+™ athletic performance monitoring systems available from NIKE, Inc. of Beaverton, Oreg. Further, the compartment of the monitoring device 201 may house various elements described above, such as the processor 204, sensors 202, transmitter 203, power supply 206, memory, etc. Further, as described above, according to aspects of the disclosure, the monitoring device 201 may be configured to engage with the grip 105 of the golf club. For example, as described with regard to FIG. 8, the grip 105 may be configured to receive a removable section or cartridge 200 and the removable section 200 may be configured to receive the monitoring device 201.

Figure 20:
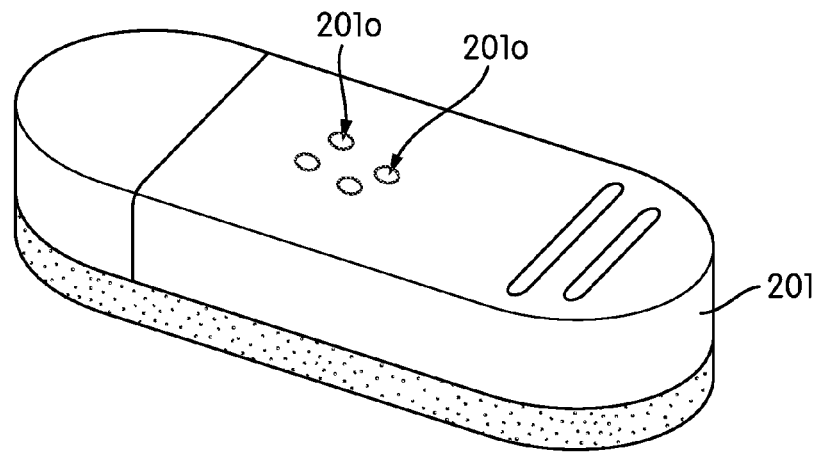
FIG. 20 is an illustrative monitoring device with openings according to aspects of the disclosure.

According to aspects of the disclosure, the engagement between the monitoring device 201 and removable section 200 the particular golf club may cause a particular IMU of the monitoring device 201 to be selectively activated. For example, as seen in FIG. 20, in one such embodiment, the monitoring device 201 may include one or more openings 201o configured to receive one or more protrusions (e.g., prongs) that extend from the removable section 200 of the particular golf club. According to aspects of the disclosure, a particular IMU of the monitoring device 201 may be activated based on which of the openings in the monitoring device 201 receive a protrusion of the removable section 200.

Figure 21A:
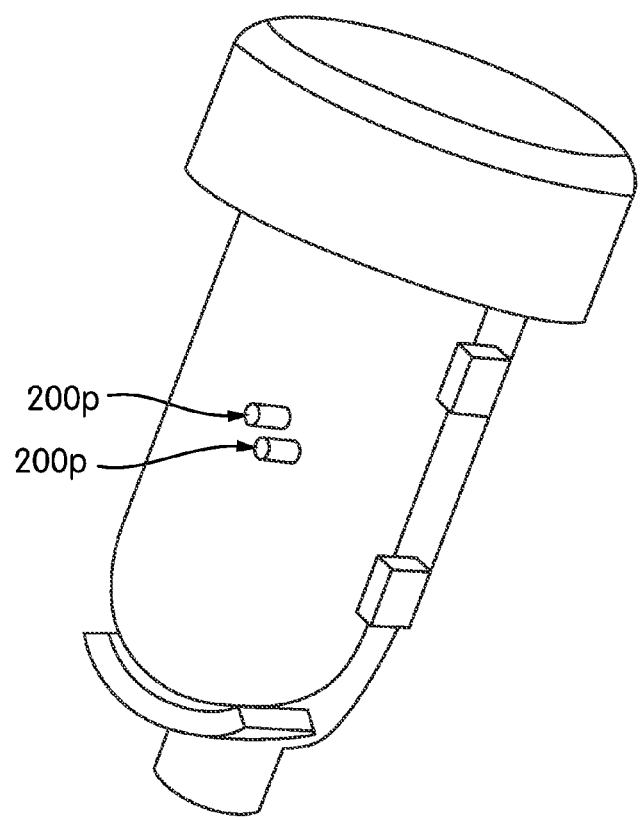
FIGS. 21A-B are illustrative removable sections of a golf club according to aspects of the disclosure.

For example, the monitoring device 201 may include four openings 201o. Further, as seen in FIG. 21A, a removable section 200 of a putter of the set of golf clubs may have two protrusions 200p that are configured to engage with the first and second of the four openings 201o of monitoring device 201. When the first and second holes are engaged by the two protrusions of the a removable section 200 of a putter, a first IMU of the monitoring device 201 that is configured to measure velocity and/or acceleration associated with a putting stroke (e.g., an IMU that may be extremely sensitive to small changes in velocity and/or acceleration (e.g., fractions of a meter per second or m/s$^2$)) may be selected and/or activated.

Figure 21B:
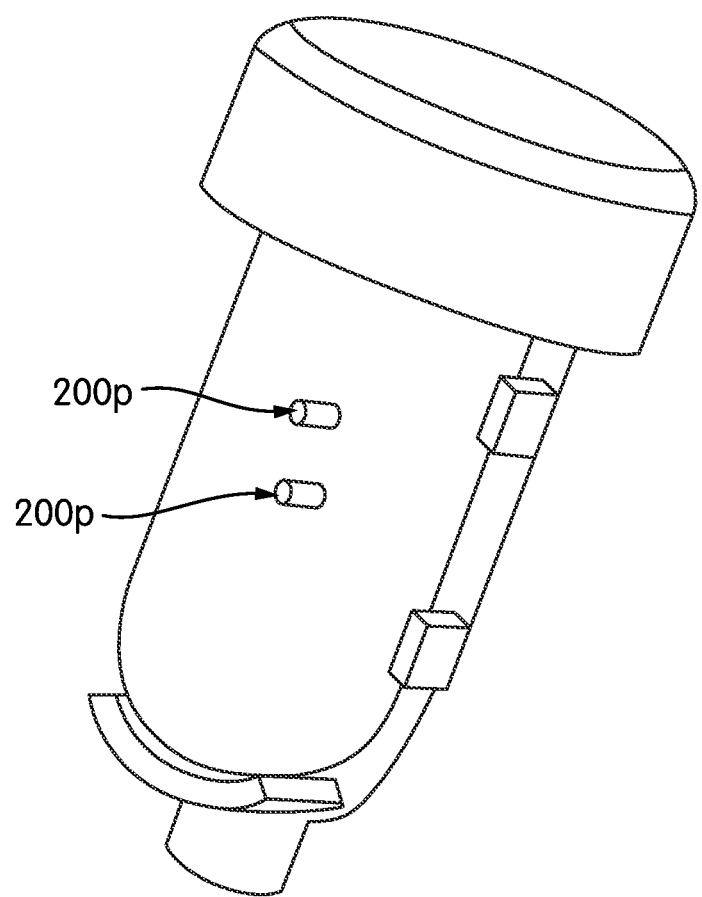

Conversely, as seen in FIG. 21B, a removable section 200 of an iron-type golf club or a wood-type golf club of the set of golf clubs may have two protrusions that are configured to engage with the third and fourth of the four openings 201o of monitoring device 201. When the third and fourth openings 201o are engaged by the two protrusions of the a removable section 200 of the iron-type golf club or the wood-type golf club, a second IMU of the monitoring device 201 that is configured to measure velocity and/or acceleration associated with a golf swing for the iron-type golf club or the wood-type golf club (e.g., an IMU that may be may be less sensitive to small changes in velocity and/or acceleration (as compared with the first IMU) and able to more accurately determine larger changes in velocity and/or acceleration (e.g., at least several meters per second or m/s$^2$)) may be activated.

It is noted that in some embodiments, the protrusions of the removable section 200 may be configured to activate detecting switches within monitoring device 201 which cause the processor 204 to determine which of the IMUs to use. For example, engagement of the protrusions 200p with the openings 201o of the removable section 200 may cause the detecting switches within the openings 201o to move from a first position to second position. The processor 204 may be configured to recognize this movement and activate either the first or second IMU depending on which of the detecting switches have been moved. Alternatively, there may be electrical connections made between the protrusions and the elements (e.g., leads) within the opening openings 201o of the removable section 200. The processor 204 may be configured to recognize these connections and activate either the first or second IMU depending on which of the elements are contacted. Of course, such embodiments are just examples and other methods of selectively determining which of the IMUs to use in capturing data associated with the golf stroke may be used.

Other embodiments may be implemented as well. For example, while the above embodiment describes selectively activating either the first or second IMU based on the processor 204 being able to recognize movement of the detecting switches or insertion of the protrusions, in other embodiments, each of the first or second IMU may be already activated, and the processor 204 may be configured to selectively use data from each (or more than one) of the IMUs based of the recognition of movement of the detecting switches or insertion of the protrusions. For example, based on the processor's recognition of movement of the detecting switches or insertion of the protrusions, data from the first IMU may be used for determining angular velocity while data from a second IMU may be used for other purposes (e.g., confirming velocity is above or below a predetermined range, determining other characteristics of the golf swing, etc.). In this way, the protrusions, detecting switches, etc. may be used as an information source for determining aspects of the golf club and which data from the IMUs to use for predetermined purposes or calculations (e.g., the processor/firmware may be configured to use data from a first IMU instead of a second IMU for determining velocity when data received from the first IMU and/or the second IMU is within a predetermined range) rather than a physical switching or selectively activating a particular IMU. These features may be used in any of the embodiments described herein.

As seen in FIGS. 21A and 21B, the removable section 200 may include an elongated portion configured to aid in housing the monitoring device 201. As described above, the elongated portion may include a first arched end configured to engage a first rounded end of the compartment, a second arched end configured to engage a second rounded end of the compartment and a back portion which extends between the first arched portion and the second arched portion and is configured to engage a side of the compartment. According to aspects of the disclosure, the elongated portion of the removable section 200 may include the protrusions 200p.

Further, the flat side of the compartment of the monitoring device 201 may be configured to include the openings 201o. Additionally, or alternatively, one or both of the rounded ends of the compartment of the monitoring device 201 may be configured to include the openings 201o which are configured to receive the protrusions 200p which are positioned on the first arched portion and/or the second arched portion of the removable section 200.

The protrusions 200p and openings 201o may be arranged such that the monitoring device 201 can only be engaged with the removable section in an intended orientation. For example, while the "universal" monitoring device 201 may have four holes, the protrusions 200p on the removable section 200 and openings 201o on the monitoring device 201 are arranged such that they will align only when the monitoring device 201 is engaged with the removable section 200 in the intended orientation.

It is noted that according to other aspects of the disclosure, and as shown in FIG. 9, the grip 105 may be configured to receive and secure the monitoring device 201 directly, without the inclusion of a separate removable section. As discussed above, the monitoring device 201 may be configured to be engaged with the grip 105 in a variety of ways. For example, the grip 105 may be configured with an opening at its terminal end that is configured to receive the monitoring device 201. However, regardless of how the monitoring device 201 is engaged with the grip 105, the grip 105 itself may be configured with the above discussed protrusions 200p configured to engage with the openings 201o in the monitoring device 201 to selectively determine which of the IMUs of the monitoring device 201 to use in capturing data associated with the golf stroke. For example, the grip 105 may include a slit that is configured to receive the monitoring device 201 when the monitoring device 201 is inserted into the grip along the monitoring device's longitudinal axis. Further, one or both of the rounded ends of the compartment of the monitoring device 201 may be configured to include the openings 201o which are configured to receive the protrusions 200p and the lower end of the slit may include the one or more protrusions 200p. Additionally, or alternatively, the protrusions 200p may positioned on the sides of the slit and may be spring loaded, flexible, etc. in order to accommodate the insertion and removable of the monitoring device 201.

It is noted that while four openings 201o and four protrusion 200p are discussed in the illustrative embodiment, it is clear that any combination of openings 201o and protrusions 200p may be used provided the combination will sufficiently allow the monitoring device 201 to selectively determine which of the IMUs of the monitoring device 201 to use in capturing data associated with the golf stroke.

Memory Wire

In addition to the above described embodiment which includes protrusions for activating detection switches, shape memory alloy may be used as well. Shape memory alloy is a substance which is configured to return to its original shape upon heating.

RFID Technology

Further, while the above embodiment discussed the structural engagement between the monitoring device 201 and the golf club 100 as a means of allowing the monitoring device 201 to selectively determine which of the IMUs of the monitoring device 201 to use in capturing data associated with the golf stroke, other methods and means may be used as well.

For example, as discussed above, according to particular embodiments of the disclosure, the monitoring device 201 may also be configured to identify the particular golf club in which the monitoring device 201 is engaged. For example, golf club 100 may include a chip (e.g., an RFID chip) which communicates with the monitoring device 201 when the monitoring device 201 is engaged with the golf club 100. This could be through direct electrical connection, wireless transmission, etc. The chip may be configured to indicate to the monitoring device 201 with which golf club the monitoring device 201 is engaged. For example, the transceiver of the monitoring device 201 may be configured to receive or "read" ID data from the chip which indicates which golf club of the golf club set the monitoring device is engaged. Accordingly, once the monitoring device 201 has determined the golf club with which it is engaged (based on the data provided from the chip), the processor of the monitoring device 201 can selectively chose one of the IMUs of the monitoring device 201 to use to capturing data associated with the golf stroke.

For example, when the monitoring device 201 has received data from the chip (e.g., RFID chip) engaged with golf club, that the golf club is a putter, the processor may select, activate, and/or use the data from a first IMU of the monitoring device 201 that is configured to measure velocity and/or acceleration associated with a putting stroke (e.g., an IMU that may be extremely sensitive to small changes in velocity and/or acceleration (e.g., fractions of a meter per second or m/s$^2$)). Conversely, when the monitoring device 201 has received data from the chip (e.g., RFID chip) engaged with golf club, that the golf club is an iron-type golf club or a wood-type golf club, the processor may selected, activate, and/or use the data from a second IMU of the monitoring device 201 that is configured to measure velocity and/or acceleration associated with a golf swing for the iron-type golf club or the wood-type golf club (e.g., an IMU that may be may be less sensitive to small changes in velocity and/or acceleration (as compared with the first IMU) and able to more accurately determine larger changes in velocity and/or acceleration (e.g., at least several meters per second or m/s$^2$)).

Sensor Self-Awareness Based on Speed

Further, while the above embodiments discussed the structural engagement between the monitoring device 201 and the golf club 100 or the use of a chip (e.g., an RFID chip) as means of allowing the monitoring device 201 to selectively determine which of the IMUs of the monitoring device 201 to use in capturing data associated with the golf stroke (or selectively determine, from the data collected by each of the IMUs, which IMU's data to use in calculating or transmitting data to the remote computer), other methods and means may be used as well. For example, according to aspects of the disclosure, the monitoring device 201 may be configured to selectively determine which of the IMUs of the monitoring device 201 to use in capturing data associated with the golf stroke (or selectively determine, from the data collected by each of the IMUs, which IMU's data to use in calculating or transmitting data to the remote computer) based on the movement of the golf club. Further, the monitoring device 201 may be configured to determine the golf club with which the monitoring device 201 has been engaged based on the movement of the golf club.

According to aspects of the disclosure, the processor 204 may be configured to receive data from each of the IMUs in the monitoring device 201. If the data indicates that a characteristic is above a predetermined value (or within a predetermined range), the processor 204 may be configured to use the data from a corresponding, predefined IMU as the determined data and discard the data from the other IMU(s).

Conversely, if the data indicates that a characteristic is below that predetermined value (or within a predetermined range), the processor 204 may be configured to use the data from a second corresponding, predefined IMU as the determined data and discard the data from the other IMU(s).

For example, if the processor 204 receives data from the IMUs which indicates the club was swung at a velocity that is below a predefined value (e.g., 3 mph), then the processor 204 of the monitoring device 201 will assume the golf club with which the monitoring device 201 is engaged is a putter. Therefore, the processor 204 may use the data received from a first IMU of the monitoring device 201 that is configured to measure velocity and/or acceleration associated with a putting stroke (e.g., an IMU that may be extremely sensitive to small changes in velocity and/or acceleration (e.g., fractions of a meter per second or m/s$^2$)) and discard the data from other IMU(s).

Conversely, if the processor receives data from the IMUs which indicates the club was swung at a velocity that is above a predefined value (e.g., 3 mph), then the processor 204 of the monitoring device 201 will assume the golf club with which the monitoring device 201 is engaged is an iron-type golf club or a wood-type golf club. Therefore, the processor 204 may use the data received from a second IMU of the monitoring device 201 that is configured to measure velocity and/or acceleration associated with a golf swing for the iron-type golf club or the wood-type golf club (e.g., an IMU that may be may be less sensitive to small changes in velocity and/or acceleration (as compared with the first IMU) and able to more accurately determine larger changes in velocity and/or acceleration (e.g., at least several meters per second or m/s$^2$)) and discard the data from other IMU(s).

According to additional aspects of the disclosure, the processor 204 may be configured to receive data from each (or more than one) of the IMUs in the monitoring device 201 and compare that data with predetermined values or ranges to determine the data from which IMU to use for a particular purpose. For example, as discussed above with regard to FIGS. 19A and 19B, the acceleration and angular velocity for a putting stroke may be have a particular graphical range or "signature." Similarly, as discussed above with regard to FIGS. 19C and 19D, the acceleration and angular velocity for a golf swing associated with a driver may have a particular graphical range or "signature." Such graphical range or "signature" may be stored in a memory which the processor 204 may access. Therefore, in some embodiments of the disclosure, the processor 204 may be configured to receive data from each of the IMUs in the monitoring device 201 and compare that data with the stored graphical ranges or "signatures." If the data matches a particular graphical range or "signature" associated with the putting stroke, the processor may determine that the swing was a putting stroke and accordingly use data from a first IMU in making particular calculations (or transmitting that data to the remote computer). Alternatively, if the data matches particular graphical range or "signature" associated with a swing of a driver, the processor may determine that the swing was associated with a driver and accordingly use data from a second IMU in making particular calculations (or transmitting that data to the remote computer). It is noted that while the above embodiment discusses graphical ranges or "signatures" other data could be used instead (e.g., numerical ranges or values may be used as "signatures"). Further, it is noted that tolerances may be incorporated into the comparison of the collected data with saved values, ranges, "signatures", etc. such that the collected data does not have to match exactly in order for the swing to be identified. For example, either the processor 204 may be configured to account for a predefined tolerance when comparing the data with the saved values, ranges, "signatures", etc. or the saved values, ranges, "signatures", etc. may already include a predefined tolerance. Accordingly, if the receive data from each of the IMUs in the monitoring device 201 does not exactly match the signature of a particular predetermined swing with a predetermined club, but is still within a tolerance or predetermined range of the particular predetermined swing with a particular club, then the monitoring device 201 may be configured to identify the club with which pending swing was produced as the particular club associated with the signature.

It is noted that while a swing with a driver and a stroke with a putter are described above, such features (e.g., signatures, predetermined ranges for particular swings, etc.) may be used for any type of golf club (or other sporting equipment as described below).

If the data indicates that a characteristic is above a predetermined value (or within a predetermined range), the processor 204 may be configured to use the data from a corresponding, predefined IMU as the determined data (and perhaps discard the data from the other IMU(s)). Conversely, if the data indicates that a characteristic is below that predetermined value (or within a predetermined range), the processor 204 may be configured to use the data from a second corresponding, predefined IMU as the determined data (and perhaps discard the data from the other IMU(s)).

It is noted that the above described aspects of having the processor (or other firmware) receive data from each of the IMUs and then use the data to determine with which type of club the monitoring device 201 is engaged (and thereby determine which of the particular IMU's data to use and/or transmit) may be applied to or used in combination with the other features in the other embodiments described herein. For example, in the above described embodiments, which include prongs and detecting switches to determine with which type of club the monitoring device 201 is engaged, the processor (or other firmware) may still collected data from each IMU and then use or transmit such data accordingly. For example, data from each IMU may still be relevant for various characteristics of the golf swing and even though data from one IMU is selected for determining a particular characteristic based on the above described methods, data from other IMUs may still be used for determining other characteristics and/or transmitted to the remote device.

The above discussed embodiments do not preclude other means of allowing the monitoring device 201 to selectively determine which of the IMUs of the monitoring device 201 to use in capturing data associated with the golf stroke. Instead, other methods and means may be used as well.

For example, while the above discussed embodiments describe features which "automatically" determine which of the IMUs of the monitoring device 201 to use in capturing data associated with the golf stroke (i.e., without the user taking an affirmative step to manually choose between the different IMUs), this should not be interpreted to mean that embodiments which allow the user to manually determine and select which of the IMUs of the monitoring device 201 to use in capturing data associated with the golf stroke are precluded. Instead, according to aspects of the disclosure, the monitoring device 201 may be configured to receive instructions from the user to use a particular IMU of the monitoring device 201 to use in capturing data associated with the golf stroke.

For example, according to an embodiment of the disclosure, the monitoring device 201 could include a switch which the user can manually move between different positions. Further, the processor 204 of the monitoring device 201 may be configured to interpret the different positions of the switch as instruction to use a particular IMU (e.g., the first IMU instead of the second IMU) in capturing data associated with the golf stroke.

Alternatively, the processor 204 of the monitoring device 201 could receive instructions from the remote computer 400 discussed above, to use a particular IMU (e.g., the first IMU instead of the second IMU) in capturing data associated with the golf stroke. For example, the particular IMU (e.g., the first IMU instead of the second IMU) whose data is collected and used may be chosen by the user affirmatively instructing the processor 204 via the remote computer 400. Alternatively, the particular IMU (e.g., the first IMU instead of the second IMU) whose data is collected and used may be chosen/dictated by the particular software application being run by the remote computer. In other words, a particular software application may require that data from first IMU instead of a second IMU to be used to calculate the particular value (even though data from the second IMU may still be collected and stored or used for other purposes). For example, the application directed to determining driver angular velocity may specify that the processor 204 use data from the first IMU instead of the data from the second IMU. It is noted that such instructions could be stored in the memory until the monitoring unit 201 receives other instructions which override such instructions.

Voice Commands

Alternatively, the particular IMU (e.g., the first IMU instead of the second IMU) whose data is collected and used may be chosen/dictated by the user through voice commands. For example, the remote computer 400 (e.g., a mobile telephone, such as a smart phone as described above) may be positioned near the golfer when the golfer is preparing to make a golf shot. The remote computer 400 may include a particular software application that transmits instructions to the processor of the monitoring device 201 to use a particular IMU (e.g., the first IMU instead of the second IMU) based on the remote computer 400 receiving a predetermined voice command. For example, the remote computer 400 may have voice recognition software which interprets the golfer's command of "Driver", "I am using a driver" of other predetermined phrases as an instruction to transmit data to the remote computer 400 to use a first IMU. Further, the remote computer 400 may interpret the golfer's command of "Putter", "I am using a putter" of other predetermined phrases as an instruction to transmit data to the remote computer 400 to use a second IMU. Alternatively, the golf club 100 itself could be configured to have the voice recognition software and a microphone for receiving the voice commands. Hence, in such an embodiment, the golf club 100 itself may be receive the voice commands and interpret them to activate or use a particular IMU (e.g., the first IMU instead of the second IMU).

As described in the above discussed embodiments, according to aspects of the disclosure, one of the IMUs in the monitoring device 201 is used in capturing data associated with the golf stroke. In some embodiments, this may include receiving data from each IMU in the monitoring device 201 and then using or transferring the data collected from only the selected IMU (i.e., selected according to one of the above described embodiments).

Alternatively, according to aspects of the disclosure, selecting one of the IMUs in the monitoring device 201 to be used in capturing data associated with the golf stroke includes using and transferring the data collected from each of the IMUs and then specifying in the data transmission to the remote computer 400 which data in the transmission is the data from the selected IMU.

Alternatively, the remote computer 400 may receive the data and be configured to determine which data is from the selected IMU. Alternatively, according to aspects of the disclosure, selecting one of the IMUs in the monitoring device 201 to be used in capturing data associated with the golf stroke includes determining data with only a single IMU (e.g., the IMU selected according to one of the above described embodiments) and not determining data with the other IMU(s). For example, the other IMUs may not be activated. Further, it is noted that various combinations of the above described embodiments of selecting one of the IMUs in the monitoring device 201 to be used in capturing data associated with the golf stroke may be used.

It is noted that while the measured characteristics described above have related to velocity, position, orientation, angular velocity, acceleration and angular acceleration, the above described features are not limited to measuring these feature and other characteristics of the golf stroke may be measured as well. Also, it is noted that regardless of how the IMU in the monitoring device 201 that is to be used in capturing data associated with the golf stroke is selected, once the IMU is selected, data can be determined, processed, transmitted, etc. according to any of the above discussed aspects of the disclosure.

Single IMU with Different Sensitivty Ranges

It is noted that while the above embodiments describe choosing to use a particular IMU (e.g., a first IMU instead of a second IMU) to collect data or, alternatively, receiving data from more than one IMU and choosing to use data from a particular IMU (e.g., a first IMU instead of a second IMU), other aspects of the disclosure relate to a monitoring device 201 which includes an IMU which has more than one sensitivity range. Therefore, rather than selectively choosing between different IMUs or between data from different IMUs, aspects of the disclosure are directed to selectively choosing between different sensitivity ranges in a single IMU. For example, aspects of the disclosure relate to a single IMU which includes a first sensitivity range configured to measure angular velocity and/or acceleration and may be extremely sensitive to small changes in velocity and/or acceleration (e.g., fractions of a meter per second or $m/s^2$). Such a sensitivity range may be beneficial in determining characteristics associated with a putting stroke. Further, the IMU may include a second sensitivity range configured to measure velocity and/or acceleration and may be may be less sensitive to small changes in velocity and/or acceleration (as compared with the first sensitivity range) and able to more accurately determine larger changes in velocity and/or acceleration (e.g., at least several meters per second or $m/s^2$). Such a sensitivity range may be beneficial in determining characteristics associated with a golf swing for an iron-type golf club or a wood-type golf club. Therefore, according to aspects of the disclosure a single monitoring device 201 may be configured to include a first IMU which is both directed to determining data associated with a putting stroke and is also directed to determining data associated with a golf swing for an iron-type golf club or a wood-type golf club.

Aspects of the disclosure are directed to a monitoring device 201 which is configured to choose a particular sensitivity range (e.g., a first sensitivity range instead of a second sensitivity range). Any of the above described methods for choosing to use a particular IMU (e.g., a first IMU instead of a second IMU) to collect data or, alternatively, receiving data from more than one IMU and choosing to use data from a particular IMU (e.g., a first IMU instead of a second IMU), may be used to select the particular sensitivity range (e.g., a first sensitivity range instead of a second sensitivity range) of the single variable IMU. For example, selecting the particular sensitivity range (e.g., a first sensitivity range instead of a second sensitivity range) of the single variable IMU may be done via the above described: structural engagement (e.g., protrusions 200*p* activating detection switches), RFID techniques, based on the movement of the golf club (e.g., if the signature of the current swing matches, or falls within a tolerance of, a predetermined signature stored in a memory), commands from the remote computer 400 (e.g., manual commands, such as voice commands, automatic commands from a software application), manual commands based on activation of a switch on the club or monitoring device itself, etc.

"Waking Up" Golf Club

According to aspects of the disclosure, the monitoring device 201 may be activated during insertion of the monitoring device 201 into golf club. Further, the monitoring device 201 may be continuously sensing and collecting data. However, according to other aspects of the disclosure, the monitoring device 201 may be selectively activated. For example, the monitoring device 201 may be configured to enter a "sleep" or "hibernation" state when the monitoring device has not been active for a predetermined amount of time (e.g., 1 minute, 5 minutes, 1 or 5 seconds after the monitoring device 201 determines that golf shot is completed (as will be described below), etc.). It is noted that in some embodiments, the IMU of the monitoring device 201 may recognize that the golf club has been held in an inverted state for a predetermined amount of time (e.g., indicating that the golf club has been placed in the golf bag) and enter a "sleep" or "hibernation" state once that predetermined amount of time has elapsed. In this "sleep" or "hibernation" state only the components needed for determining activation of the monitoring device 201 may continue to receive power. In other embodiments of the "sleep" or "hibernation" state, components may receive less power than they do in a use state. Further, the monitoring device may be selectively activated manually, or automatically upon the occurrence of an event (e.g., movement of the club or movement of the club in a particular fashion, such as a pre-shot routine). Other structures for detecting "sleep" or "hibernation" may be associated with the golf club 100 as well.

For example, in an illustrative embodiment of the disclosure, the movement of the club may act as a trigger to cause the monitoring device 201 to exit the "sleep" or "hibernation" state and/or fully activate (i.e., "wake up"). For example, the monitoring device 201 may be configured to receive data from the IMUs that the golf club has been moved and based on the data exit the "sleep" or "hibernation" state and/or fully activate (i.e., "wake up"). According to aspects of the disclosure, the monitoring device 201 may be configured to compare the data from the IMUs with a predetermined threshold and only exit the "sleep" or "hibernation" state and/or fully activate (i.e., "wake up") if the data from the IMUs is above the predetermined threshold. For example, the data from the IMUs must be above a predetermined angular velocity or acceleration in order to "wake up" the monitoring device 201. In this way, incidental movement (e.g., golf clubs jostling in the golf bag while being carried) will not "wake up" the monitoring device 201.

In an illustrative embodiment of the disclosure, the predetermined movement of the club may act as a trigger to cause the monitoring device 201 to exit the "sleep" or "hibernation" state and/or fully activate (i.e., "wake up"). For example, as discussed above, the monitoring device 201 may be configured to receive data from the IMUs that the golf club has been moved in a predetermined movement (e.g., a pre-shot routine) and based on the data, exit the "sleep" or "hibernation" state and/or fully activate (i.e., "wake up"). According to aspects of the disclosure, the monitoring device 201 may be configured to compare the data from the IMUs with a predetermined range(s) or value(s) (e.g., such as the above discussed graphical or numerical range or signatures which indicate a driver swing or putting stroke) and only exit the "sleep" or "hibernation" state and/or fully activate (i.e., "wake up") if the data from the IMUs is above the predetermine threshold. For example, the predetermined range(s) or value(s) may be a "signature" which indicates a practice swing. Therefore, when the data from the IMUs match (or are within a tolerance or the signature) the monitoring device 201 "wakes up".

In another illustrative embodiment, the user may manually cause the monitoring device 201 to enter to exit the "sleep" or "hibernation" state. For example, the user may use the remote computer 400 (e.g., a smart phone with a software application that configures the smartphone to receive and transmit data to the monitoring device 201) to cause the monitoring device to enter or to exit the "sleep" or "hibernation" state. This could be done by inputting data to the smartphone (e.g., voice commands or touching a touch screen) which instructs the monitoring device 201 to enter or to exit the "sleep" or "hibernation" state.

Zeroing

According to aspects of the disclosure, similar methods may be used to correlate data to a particular swing and, thereby, indicate individual golf swings/distinguish between different golf swings. For example, in embodiments where the monitoring device 201 may be activated and continually receiving data from the IMUs during the entire time the monitoring device 201 is activated, aspects of the disclosure are directed to correlating data for a particular golf stroke (e.g., as distinguished from a practice swing or movement not related to the swing, such as when the club is removed from the bag or being carried to the location of the shot).

According to particular aspects of the disclosure, the pre-shot routine (e.g., the end of a pre-shot routine) may "zero" the monitoring device 201 (i.e., cause the monitoring device 201 to recognize that the upcoming movement is the beginning of an individual golf swing). For example, as discussed above, the monitoring device 201 may be configured to receive data from the IMUs that the golf club has been moved in a predetermined movement, such as pre-shot routine. The monitoring device 201 may be configured to recognize the predetermined range(s) or value(s) as the "signature" which indicates the pre-shot routine and determine that any movement after (or subsequent to a predetermined time after) the recognized pre-shot routine is part of golf swing or stroke. Accordingly, only movement of the golf club after (or subsequent to a predetermined time after) the pre-shot routine will be correlated with the particular golf stroke. In other words, only movement of the golf club which occurs after the IMUs provide data to the monitoring device 201 that the golf club is at rest in the address position after having completed the pre-shot routine will be correlated with the particular golf stroke.

It is noted that the monitoring device 201 may be configured to account for, or include, a predetermined time after the pre-shot routine is completed and after the golf swing is completed in determining which data is related to the golf swing or stroke. For example, the monitoring device 201 may be configured to allow for a predetermined time (e.g., 1 or 2 seconds) once the monitoring device 201 has determined that the pre-shot routine has been completed (i.e., the IMUS provide data to the monitoring device 201 that the golf club is at rest in the address position after having completed the pre-shot routine) before beginning to associate data with the particular golf stroke. Similarly, the monitoring device 201 may be configured to allow for a predetermined time (e.g., 1 or 2 seconds) once the monitoring device 201 has determined that the golf swing or stroke has been completed (i.e., the IMUS provide data to the monitoring device 201 that the golf club has completed the stroke (e.g., the follow through of the golf swing or stroke has been completed) as defined by the stored signature of the typical swing or stroke) before ending the association data with the particular golf stroke.

In some embodiments, the pre-shot routine may include one or more practice swings. Further, it is noted that the pre-shot routine may be customized to the particular golfer. For example, the pre-shot routine may include one or more "waggles" of the golf club after the one or more practices swing(s) and prior to the golf club coming to rest in the address position after having completed the pre-shot routine depending on the particular golfer's habits. It is further understood that the pre-shot routine could comprise a combination of practice swings, waggles etc. and also could comprise holding the golf club 100 stationary at the address position for a predetermined amount of time. Such information regarding the pre-shot routine may be stored on in the monitoring device. For example, the particular signature of a golfer's pre-shot routine may be stored to the monitoring device 201 (e.g., uploaded to the memory of the monitoring device 201 via the remote computer 400 or the remote computer 400 could instruct the monitoring device 201 to record data from the IMU for a particular amount during which the golfer performs the pre-shot routine and then store the recorded data as the signature of the pre-shot routine). According to aspects of the disclosure, a the monitoring device 201 may be configured to determine a practice swing as a swing whose signature is within a particular range relative to the signature of an actual swing. For example, a practice swing may be defined as a predetermined amount or range which corresponds to predetermined value (e.g., 70% of the angular velocity of an actual swing or 70% of the radial length of an actual swing). Alternatively, a practice swing may be defined with its own digital signature which identifies the swing as a practice swing as described above.

According to some embodiments of the disclosure, the golfer may manually correlate data to a particular swing and, thereby, indicate individual golf swings/distinguish between different golf swings. For example, the golfer may activate a switch which "zeros" the monitoring device 201 (i.e., cause the monitoring device 201 to recognize that the upcoming movement is the beginning of an individual golf swing). For example, the golfer may activate a switch on the golf club itself the transmits information to the monitoring device 201 that causes the monitoring device 201 to recognize that the upcoming movement is the beginning of an individual golf swing. Further, the golfer may activate a switch on the remote computer 400 (e.g., pressing a button on a smart phone) that causes the monitoring device 201 to recognize that the upcoming movement is the beginning of an individual golf swing. Further, the golfer may use voice commands to zero the monitoring device 201. For example, the remote computer 400 (e.g., a smart phone) may be configured to receive the voice commands from the golfer and transmit data to the monitoring device which indicates the beginning and end of the golf shot. For instance, the remote computer 400 may be configured to interpret the golfer saying "begin" or "start" as the beginning of the golf shot and transmit instructions to the remote computer to begin recording data from the IMUs or being associating data from the IMUs as a particular, individual golf shot. Conversely, the remote computer 400 may be configured to interpret the golfer saying "done" or "end" as the end of the golf shot and transmit instructions to the remote computer to stop recording data from the IMUs or stop associating data from the IMUs as a particular, individual golf shot. Other structures are possible such as sensors located in the grip of the golf club that are configured to detect a squeeze or tightened grip by the user for activation.

In some embodiments of the disclosure impact sensors such as described above may be used to determine a recordable golf shot. For example, if a particular swing has characteristics which resemble both a practice swing and an actual swing (e.g., above a threshold angular velocity), the monitoring device 201 may be configured to receive data from an impact sensor which indicates whether impact with the golf ball was made during the golf swing. In such embodiments, the occurrence of an impact may serve as validating that the swing should not be interpreted as a practice swing, but instead a particular golf swing for which characteristics of the swing should be measured/determined.

Charging

According to aspects of the disclosure, the monitoring device 201 may be configured to be charged. As described above, the monitoring device 201 may include a power supply (e.g., a battery). Further, the monitoring device 201 may be configured to receive a charging cable which will provide power to recharge the power supply. In some embodiments, the monitoring device 201 may be configured to receive the charging cable while the monitoring device 201 is in the golf club itself. For example, in embodiments where the monitoring device 201 is positioned in the shaft/grip of the golf club, the end of the golf club may be removed and the charging cable may be hooked into the monitoring device 201.

Alternatively, according to aspects of the disclosure, the monitoring device 201 may be configured to be charged via induction charging.

According to aspects of the disclosure, the monitoring device 201 is configured to receive information via a charging cable. For example, the charging cable may be a USB cable which is configured to connect the monitoring device 201 with computer (e.g., the remote computer 400) or other data source. Accordingly, during the connected with the computer, the monitoring device 201 can update firmware, reboot the system, and conduct other diagnostic checks and updates as needed or instructed.

Sensor Orientation Determination

As discussed above, according to aspects of the disclosure, the data from sensors in the monitoring device 201 may be subjected a transformation matrix which manipulates the data (e.g., recalculates or modifies the data) in order to account for the exact positioning of the sensor within the golf club. As discussed, the transformation matrix may be a series of calculations which modifies that data according to the exact positioning of the sensor within the golf club. Therefore, in an embodiment such as discussed above, wherein the monitoring device 201 (which includes the sensors) is positioned in the grip 105 or the shaft of the golf club, the data from the sensors of the monitoring device may be subjected to a transformation matrix in order to provide feedback to the golfer.

As discussed above, the transformation matrix may be included in a software package that may be downloaded to the remote computer 400 to which the data from the monitoring device 201 is transmitted. Alternatively, according to some aspects of the disclosure, the transformation matrix may be included as firmware in the monitoring device 201 (e.g., in the memory of the monitoring device). As discussed above, such transformation matrices may be designed for the specific positions of sensors and remote monitoring devices 201 in the respective golf clubs. Accordingly, if the sensor is not provided in the appropriate location, the feedback may be incorrect. For example, if the monitoring device 201 is inserted into the removable section 200 in an orientation that is different the intended position (e.g., inverted from the intended position or backwards to the intend position), the sensors within the monitoring device 200 may provide inaccurate data to the transformation matrix.

Hence, as described above, according to some embodiments of the disclosure, the grips 105 or the removable section 201 are configured with structure that prevents the monitoring device 201 from being inserted into the removable section 200 or the grip 105 in an orientation other than the intended orientation. However, according to embodiments of the disclosure (e.g., which do not have such structure), when the monitoring device 201 is inserted into the removable section 200 in an orientation that is different the intended position, the monitoring device 201 can be configured to recognize the incorrect positioning of the monitoring device 201. Further, according to aspects of the disclosure, when the monitoring device 201 recognizes the incorrect positioning of the monitoring device 201, the monitoring device may be configured to correct the data by applying an alternate transformation matrix to the data (e.g., prior to transmitting the data to the remote computer 400).

For example, according to aspects of the disclosure, the memory in the monitoring device may be configured to store a predetermined range of values which correspond to "acceptable" values for the data received from the sensors when the monitoring device is positioned in the correct position and orientation. If the processor receives data from the sensors, compares the data with the "acceptable" range of values and determines that the data is outside the range of "acceptable" values, the processor 204 may be configured to determine that the monitoring device 201 is in an incorrect orientation. Upon recognizing that the monitoring device 201 is positioned in an incorrect orientation, the monitoring device may receive that data and apply a transformation matrix to the data in order to correct the data.

For example, if the monitoring device 201 is inserted into the removable section 200 inverted from the intended position, the monitoring device 201 may receive data from the one or more sensors, compare the received data with the "acceptable" range of values and determine that the data is outside the range of "acceptable" values. According to aspects of the disclosure, the processor may then access a transformation matrix from the memory, wherein the transformation matrix accounts for the altered distance of the sensors in the inverted state as compared with the intended positioning of sensors. The process may then apply such a transformation matrix to the data to thereby calculate "correct" feedback (i.e., the corrected data may be used according to the above described methods for calculations to determine properties and characteristics associated with a swing to the user), even though the monitoring device 201 is still in the "incorrect" (e.g., inverted) orientation. Thereafter, in some embodiments the processor may cause the data to be transmitted to the remote computer 400. Further, according to some aspects of the disclosure, upon the monitoring device 201 recognizing that it is positioned in an "incorrect" orientation, it may send a message to the remote computer indicating such, in order to provide notification to the user. This message could be in addition to, or as an alternative to, providing the correct feedback and data from the transformation matrix described above.

It is noted that, if desired, the above described corrective transformation matrix which is configured to account for incorrect positioning of the sensor(s) may be used in conjunction with the previously discussed transformation matrices specific to the individual golf club which recalculate the obtained data (obtained by the sensors of the remote monitoring device(s) 201 in that particular golf club) and output accurate measurements, golf metrics, variables and kinematics. Further, it is noted that these previously discussed transformation matrices may also be firmware stored in the monitoring device 201 instead of software downloaded onto the remote computer. In this way, feedback may be calculated by the processor 204 in the monitoring device 201 and then transmitted to the remote computer 400. Further, such feedback could include an identification of the club from which it is being transmitted.

Left Vs. Right Hand Golf Clubs

According to aspects of the disclosure, similar features may be used to differentiate between left handed golf clubs and right handed golf clubs. For example, according to aspects of the disclosure, left handed golf clubs may have a structure (e.g., a removable section) which is configured to receive the monitoring device 201 in a first orientation. In contrast, right handed golf clubs may have a structure (e.g., a removable section) which is configured to receive the monitoring device 201 in a second orientation different from the first orientation of that for left handed golf clubs. As described above, when the monitoring device 201 is inserted into the removable section in the first orientation, the monitoring device 201 can be configured to recognize the first orientation of the monitoring device 201 and determine that the golf club is a left handed golf club. Further, when the monitoring device 201 is inserted into the removable section in the second orientation, the monitoring device 201 can be configured to recognize the second orientation of the monitoring device 201 and determine that the golf club is a right handed golf club.

Hence, according to aspects of the disclosure, the monitoring device 201 may be configured to distinguish between a right handed golf club and a left handed golf club. Further, according to aspects of the disclosure, when the monitoring device 201 recognizes the orientation of the monitoring device 201, the monitoring device 201 may be configured to manipulate the data from the sensors (e.g., by applying a particular transformation matrix to the data (e.g., prior to transmitting the data to the remote computer 400).

It is noted that, according to aspects of the disclosure, other methods in which the monitoring device 201 distinguishes between a right handed golf club and a left handed golf club may be used as well. For example, the protrusions 200p discussed above could be configured to engage with and activate detection switches which indicate whether the club is right handed or left handed. Additionally, the RFID methods of identifying a club may include right handed and left handed information regarding the particular club.

Grip End Cap

According to aspects of the disclosure, a set of golf clubs which are configured to receive and hold a monitoring device (such as monitoring device 201 described above) may be configured such that each of the golf clubs in the set secures its respective monitoring device 201 at a common point respective to each of the golf clubs in the set. Further, according to aspects of the disclosure, each of the golf clubs in the set may be configured to secure its respective monitoring device 201, such that the monitoring device 201 is offset by a specified distance from a reference point which is common to each of the golf clubs in the set. The specified distance from the reference point may be identical for each of the clubs.

For example, according to an illustrative embodiment of the disclosure, each of the golf clubs in the set may be configured to position the monitoring device 201 such that it is located a distance X (e.g., 20 inches) from the center of mass of the respective golf club. The center of mass of the golf club is the point (e.g., a point in space) wherein the entire mass of the golf club is concentrated. For a golf club (as with all rigid bodies), the center of mass is a fixed point in relation to the golf club. In a set of golf clubs, which includes different types of golf clubs (e.g., a 14 club set of the golf clubs which includes putter, iron-type golf club heads, wood type golf club heads, etc.) the center of mass of each of the different golf clubs will be different. Accordingly, in such an embodiment, each golf club in the set may have the monitoring device 201 secured at a different position along its respective shaft, however, the distance between the monitoring device 201 in each golf club and the fixed center of mass of each golf club would be constant (e.g., 20 inches from the center of mass of the respective golf club).

Figure 22:
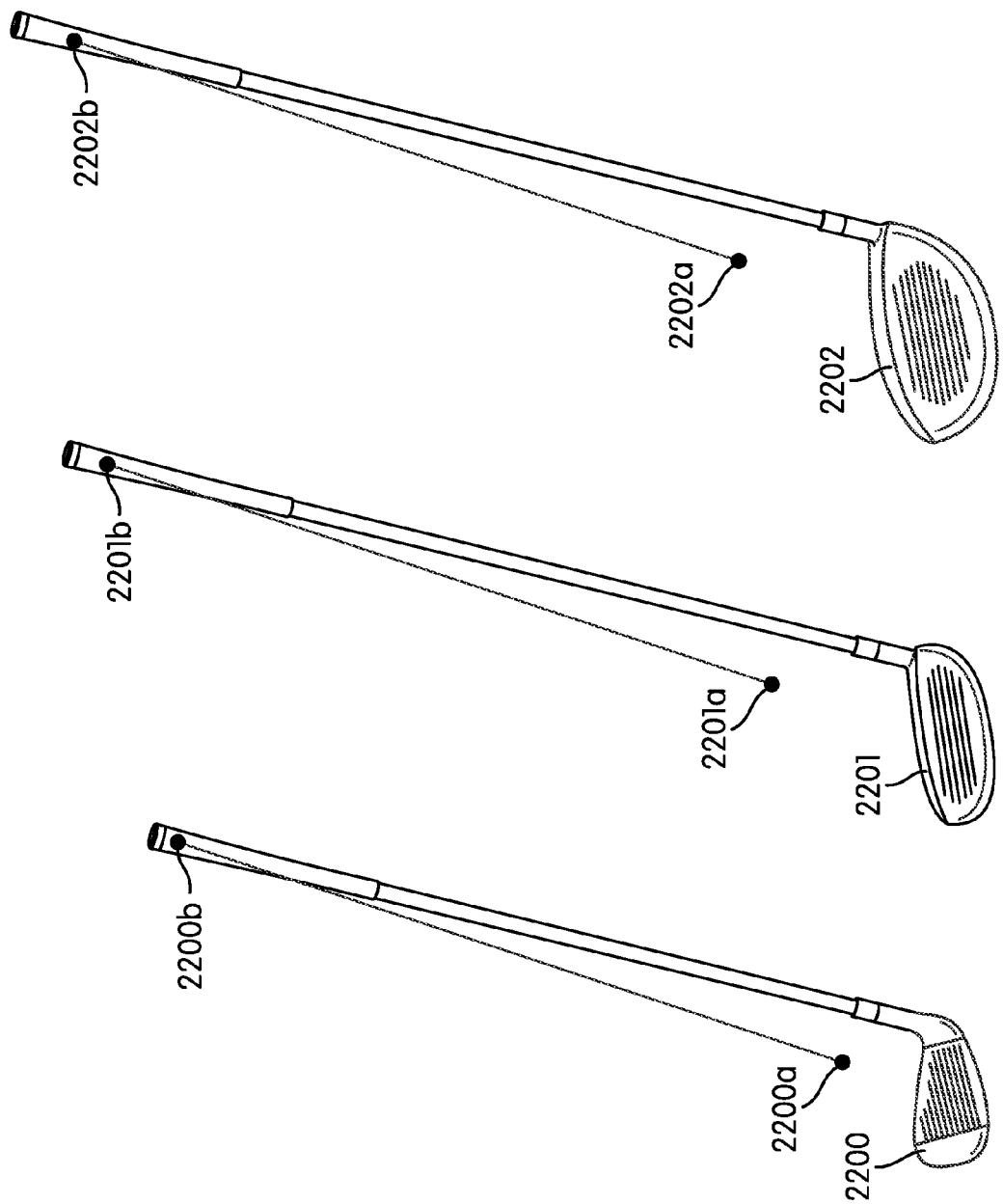
FIG. 22 illustrates golf clubs with have an identical distance between their respective centers of mass and monitoring devices according to aspects of the disclosure.

FIG. 22 illustrates an example set of golf clubs according to aspects of the disclosure. As seen in FIG. 22, a shorter club, such as a wedge (e.g., a pitching wedge) 2200 has a center of mass indicated by the point 2200a. Further, the point where the monitoring device 201 is located is indicated by the point 2200b. Similarly, a longer club, such as a hybrid club 2201, has a center of mass indicated by the point 2201a. Further, the point where the monitoring device 201 is located is indicated by the point 2201b. Also, an even longer club of the set, such as a driver 2202, has a center of mass indicated by the point 2202a. Further, the point where the monitoring device 201 is located is indicated by the point 2202b. As seen in FIG. 22, the distance between the center of mass for each of the respective clubs and the positioning of monitoring devices 201 for each of the respective clubs is indicated by the lines drawn between the points. This distance is identical for each of the clubs 2200, 2201 and 2202.

The above described feature of positioning the monitoring device 201 in each of the golf clubs in the set such that the monitoring device 201 is offset by the identical specified distance from a reference point which is common to each of the golf clubs in the set may be accomplished in many ways according to aspects of the disclosure. For example, as described above, each of the golf clubs in the set of golf clubs may include a removable section 200 of the type discussed above with regard to FIGS. 8 and 8A that is configured to be engaged with the grip 105 of the respective golf club. Further, as discussed above the removable section 200 may be configured to receive the monitoring device 201 wherein according to particular embodiments of the disclosure, the monitoring device 201 may be similar to those used in the NIKE+™ athletic performance monitoring systems available from NIKE, Inc. of Beaverton, Oreg.

As seen in FIGS. 21A and B, the removable section 200 may include a circular portion which forms the top of the shaft and, also, an elongated portion configured to house the monitoring device 201. According to aspects of the disclosure, the elongated portion of the removable section 200 may include guides to aid in positioning and securing the monitoring device 201 within the removable section 200. It is noted that the removable section 200 may be configured to secure the monitoring device 201 in such a way that the monitoring device 201 does not move within the removable section 200. For example, the removable section 200 may be configured to engage with the monitoring device 201 (e.g., a compartment which includes the exterior of the monitoring device 201) via press fitting, snap fit mechanisms (e.g., spring loaded protrusions and corresponding detents), mechanical fasteners, etc. For example, the elongated portion may include a first arched end configured to engage a first rounded end of the compartment, a second arched end configured to engage a second rounded end of the compartment and a back portion which extends between the first arched portion and the second arched portion and is configured to engage a side of the compartment. In this way, the removable section 200 may be configured to support and stabilize the monitoring device 201. For example, the elongate portion may be configured to secure the compartment which may be rectangular with first and second rounded ends and have a length in the range of 1.0-1.5 inches, a width of 0.4-1.0 inches and thickness of 0.2-0.45 inches.

According to aspects of the disclosure, the elongate portion of the removable section 200 may be configured to have a particular length such that when the removable section 200 is engaged with the grip of the golf club, the removable section 200 positions the monitoring device 201 within the shaft such that the monitoring device 201 is offset by a specified distance from a reference point. For example, according to one embodiment, the elongate portion of the removable section 200 may include the first arched end configured to engage a first rounded end of the compartment, the second arched end configured to engage a second rounded end of the compartment and the back portion which extends between the first arched portion and the second arched portion and is configured to engage a side of the compartment, but the first arched end, second arched end and back portion are spaced further away from the round portion of the removable section which forms the end cap. For example, the first arched end, second arched end and back portion may be spaced from the round portion by a section of the elongate portion that extends between the round portion and the upper arched end of the guide for receiving the monitoring device.

The section of the elongate portion that extends between the round portion and the upper arched end of the guide may be a particular length such that when the removable section 200 is engaged with the shaft, of the golf club, the removable section 200 positions the monitoring device 201 within the shaft such that the monitoring device 201 is offset by a specified distance from a reference point. Further, as each different golf club in the set of golf club has a center of mass that is in a different location than the other golf clubs in the set, the removable section 200 associated with each of the respective, different golf clubs in the set may have to be configured differently in order to ensure the that the respective monitoring device 201 is positioned within the shaft, such that the monitoring device 201 is offset by a specified distance from a reference point. For example, the length of the section of the elongate portion that extends between the round portion and the upper arched end of the guide may be a different for each of the respective removable sections 200 in the golf club set in order to ensure the that the respective monitoring device 201 is positioned within the shaft, such that the monitoring device 201 is offset by a specified distance from a reference point.

FIG. 23A illustrates embodiments of such removable sections 201. As seen in FIG. 23, according to a particular embodiment of the disclosure, a first removable section 200 associated with a first golf club of the set of golf clubs may have a first elongate portion that has a first length, while a second removable section 200 associated with a second, different golf club of the set of golf clubs may have a second elongate portion that has a second length which is different (e.g., longer) from the first length. Further, as seen in FIG. 23A, according to a particular embodiment of the disclosure, a third removable section 200 associated with a third, different golf club of the set of golf clubs may have a third elongate portion that has a third length, which is different (e.g., longer) than the first or second lengths. For example, a shorter club (e.g., a pitching wedge) may have the removable section 200 with the elongate portion that has the first length while a longer club (e.g., a long iron or hybrid type golf club) may have the removable section 200 with the elongate portion that has the second length. Further, an even longer club (e.g., a driver) may have the removable section 200 with the elongate portion that has the third length. It is noted that while only three embodiments are shown in FIG. 23A, each of the golf clubs in the set could have a removable section 200 with an elongated portion of a different length (e.g., increasing longer as the length of the club increases) in order to position the monitoring device 201 in the correct positioning.

Figure 23B:
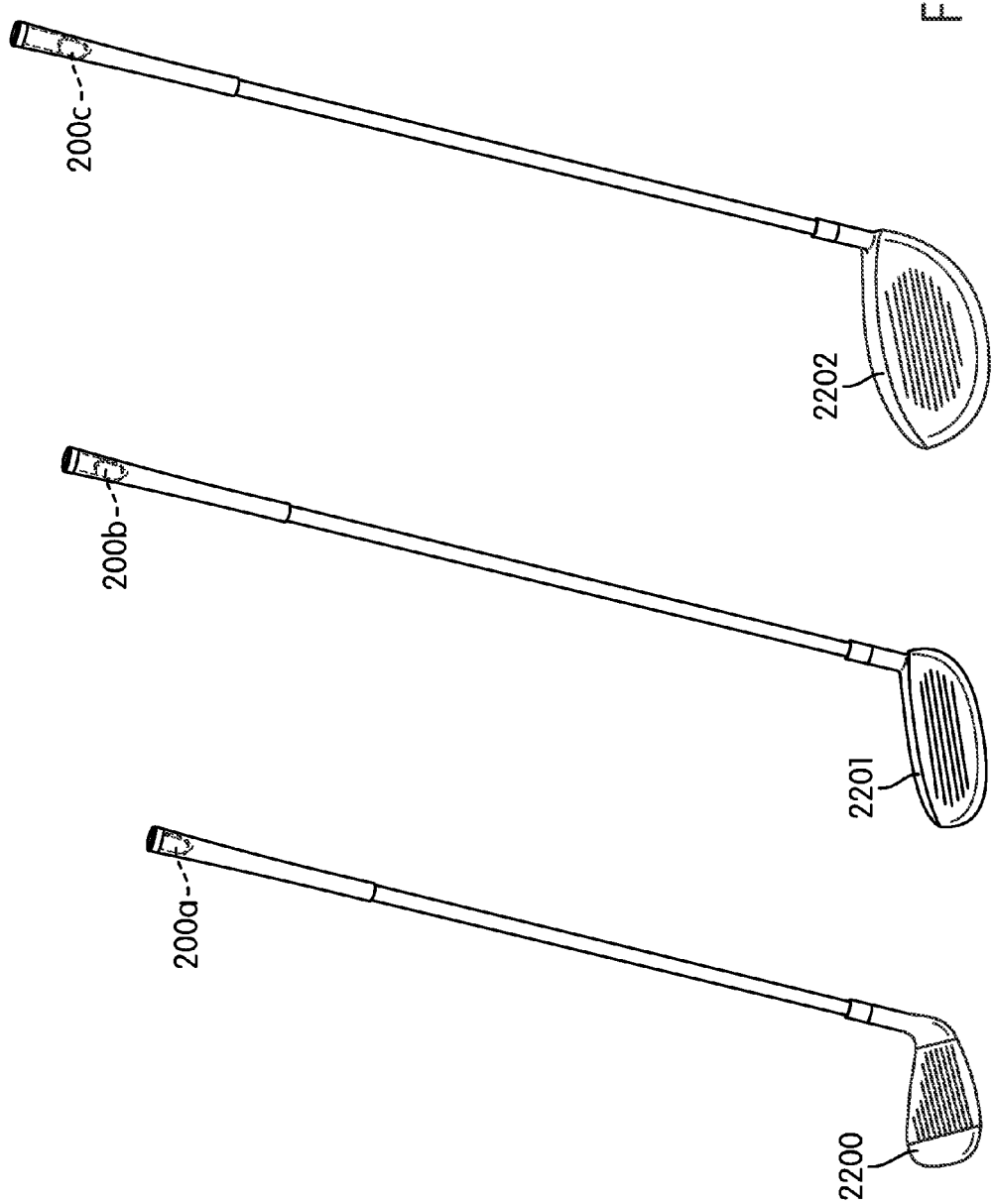
FIG. 23B shows the illustrative removable sections of 23A in combination with their respective golf clubs according to aspects of the disclosure.

For example, as seen in FIG. 23B, the wedge 2200 (e.g., pitching wedge) may have a removable section 200 with the elongate portion that has the first length. The hybrid club 2201 may have a removable section 200 with the elongate portion that has the second length. The wood-type club 2201 (e.g., a driver) may have the removable section 200 with the elongate portion that has the third length. As seen in FIG. 22, the third length of the elongate portion of the removable section 200 associated with the wood-type club 2202 is longer than the second length of the elongate portion of the removable section 200 associated with the hybrid 2201. Further, the second length of the elongate portion of the removable section 200 associated with the hybrid 2201 is longer than the first length of the elongate portion of the removable section 200 associated with the wedge 2200.

As seen in FIGS. 23A and B, each of the removable sections 201 are configured (e.g., the length of the elongate portion of the removable sections is configured) in order to ensure the that the respective monitoring device 201 is positioned within the shaft, such that the monitoring device 201 is offset by an identical specified distance from a reference point. In this case, the monitoring devices 201 of the wedge, the hybrid 2201 and the wood-type club 2202 are positioned such that they are offset by an identical specified distance from the center of mass of the respective golf club. While only three club of the set are illustrated, it is understood that similar structures may be applied to each of the golf clubs in the set. For example, the removable section 200 of each of a lob wedge, sand wedge, pitching wedge, 10 iron and 9 iron of a set of golf clubs may have an elongated portion of a different length (e.g., increasing longer as the length of the club increases) in order to position the monitoring device 201 in the correct positioning.

According to other embodiments of the disclosure, the removable sections 200 may have other structures as well. For example, according to some embodiments of the disclosure, the removable sections 200 may be a self-locating, conical structure in which the monitoring device 201 is received. The conical structure may be configured to engage with the interior of the shaft 103 of the golf club 100 in order to position the monitoring device 201 in the appropriate position within the shaft 103. For example, the multitude of conical removable sections 200 for engagement with the different clubs in a set of golf clubs may be longer and wider (e.g., have an increased diameter) to position the monitoring device 201 in the appropriate position within the shaft 103. According to some embodiments of the disclosure, the interior of the golf club shaft 103 may include a structured (e.g., positioning recesses/protrusions or ledges) which are configured to engage with the removable sections 200 and position the monitoring device 201 in the appropriate position within the shaft 103.

While the concept of a set of golf clubs in which each club may be configured such that it secures its respective monitoring device 201 at a common point respective to each of the golf clubs in the set (e.g., such that the monitoring device 201 is offset by an identical specified distance from a reference point which is common to each of the golf clubs in the set) has been illustrated with respect to a removable section 200, it is noted that other means may be used as well.

For example, instead of a removable section configured as described above, a plurality of inserts with other structures that hold the monitoring device 201 may be employed to achieve the above described goal. For example, one or more of the inserts may each have varying lengths which are based on the golf club with which the inserts are associated such that the inserts secures its respective monitoring device 201 at a common point respective to each of the golf clubs in the set (e.g., such that the monitoring device 201 is offset by an identical specified distance from a reference point which is common to each of the golf clubs in the set). The particular structure of the group of inserts may vary provided the group of inserts achieves the above recited goal of securing its respective monitoring device 201 at a common point respective to each of the golf clubs in the set.

While the concept of a set of golf clubs in which each club may be configured such that it secures its respective monitoring device 201 at a common point respective to each of the golf clubs in the set (e.g., such that the monitoring device 201 is offset by an identical specified distance from a reference point which is common to each of the golf clubs in the set) has been illustrated with respect to removable sections and inserts, it is noted that the grip 105 itself may be configured to receive and secure the monitoring device 201 directly, without the inclusion of a separate removable section or cartridge 200.

For example, as discussed with regard to FIG. 9, the grip 105 may be configured with an opening at its terminal end that is configured to receive the monitoring device 201. For example, the grip 105 may include a slit that is configured to receive the monitoring device 201 when the monitoring device 201 is inserted into the grip along the monitoring device's longitudinal axis. The slit may be configured to provide a tight interference fit with the monitoring device 201. Further, the one or more of the slits may each have varying depths that are based on their respective golf clubs. In this way, the depth of the slits may be configured such that each of the slits secures the monitoring device 201 it receives at a common point respective to each of the golf clubs in the set (e.g., such that the monitoring device 201 is offset by an identical specified distance from a reference point which is common to each of the golf clubs in the set).

It is noted that monitoring device 201 may be configured to engage with the grip 105 via other methods as well, including snap fit mechanisms (e.g., spring loaded protrusions and corresponding detents), other mechanical fasteners, etc. provided that the respective monitoring devices 201 are secured at a common point respective to each of the golf clubs in the set (e.g., such that the monitoring device 201 is offset by an identical specified distance from a reference point which is common to each of the golf clubs in the set).

It is noted that while the center of mass has been discussed above with respect to the illustrative embodiments, this is not meant to suggest that other reference points may be used. On the contrary, other fixed reference points of the golf club, such as the center of gravity of the club head, the hosel, the top of the grip, etc. may be used as well.

It is noted that by providing a set of golf clubs in which each golf club secures its respective monitoring device 201 at a common point respective to each of the golf clubs in the set (e.g., such that the monitoring device 201 is offset by an identical specified distance from a reference point which is common to each of the golf clubs in the set), the data received from each monitor device 201 can be interpreted relative to the common reference point. For example, in an embodiment wherein the reference point is the center of mass, each of the monitoring devices 201 in the golf clubs may be offset from the center of mass of the respective golf club by an identical distance. Hence, in calculating data (e.g., such as when using transformation matrices as discussed above) data can be interpreted without having to account for a different distance from the center of mass for each club. For example, in some embodiments of the disclosure, formulas and transformation matrices used to calculate data and provide feedback can be uniformly applied for the set of golf clubs.

It is noted that according to aspects of the disclosure, the structure of the golf club and/or the separate removable section or cartridge 200 may be configured so that the swing weight of the club may be chosen as desired. For example, the longer separate removable section or cartridge 200 described above may be formed of a material of a lighter weight/density than the shorter separate removable section or cartridge 200 described above. Further, the structure of the separate removable sections or cartridges may be varied throughout the set of golf clubs. For example, the longer separate removable sections or cartridges 200 may include openings to remove weight and the thickness of shorter separate removable sections or cartridges 200 may be increased to add weight. In these ways, consistency in the swing weight may be achieved throughout the set of golf clubs.

Interchangeable Puck for Different Sports Equipment

As discussed above, a monitoring device 201 according to aspects of the disclosure may be "universal" with respect to the golf clubs in such a set of golf clubs. For example, the monitoring device 201 may be configured to fit in a putter of the golf club set, an iron-type golf club of the golf club set and in a wood-type golf club of the golf club set. According to further aspects of the disclosure, a monitoring device 201 may be "universal" with respect to other sports equipment. For example, a monitoring device 201 according to aspects of the disclosure may be "universal" with respect to the golf clubs, tennis racquets, bats (e.g., baseball, softball, cricket, etc.), hockey sticks (e.g., ice hockey, field hockey), lacrosse sticks, etc. Thus, exemplary embodiments described herein are applicable to any implements that incorporate monitoring devices etc.

However, the characteristics to be measured for each piece of sports equipment may vary dramatically. For example, the rotation of the piece of sports equipment around its longitudinal axis may be more relevant in some sports than in others. For example, the rotation of a golf club around its longitudinal axis during a golf swing (e.g., which may be used to provide information about the angle club face throughout the swing) may be more valuable information for the user's feedback than the rotation of a baseball bat around its longitudinal axis during a swing of the baseball bat. Similarly, the rotation of a tennis racquet around its longitudinal axis during a tennis stroke (e.g., which may provide information about the angle of the face of the tennis racquet throughout the swing) may be more valuable information for the user's feedback than the rotation of a baseball bat around its longitudinal axis during a swing of the baseball bat.

Therefore, aspects of the disclosure are directed to a monitoring device 201 (and/or system) that is configured to determine different characteristics of a swing or stroke according on the type of sports equipment with which the monitoring device 201 is engaged. For example, aspects of the disclosure are directed to a monitoring device 201 (and/or system) that is configured with the ability to selectively collect particular data based on the type of sports equipment with which the monitoring device 201 is engaged. Further, according to aspects of the disclosure, the monitoring device 201 may be configured to automatically determine the type of sports equipment with which the monitoring device 201 is engaged and automatically configure itself to selectively collect particular data based on that type of sports equipment.

For example, according to aspects of the disclosure, if the monitoring device 201 (and/or system) determines that the monitoring device 201 is engaged with a golf club, the monitoring device 201 (and/or system) may configure itself to measure various characteristics, such as angular rotation about the longitudinal axis of the golf club. Further, the monitoring device 201 may configure itself to measure velocity, acceleration, etc. at a first rate (e.g., a first refresh rate). In contrast, according to aspects of the disclosure, if the monitoring device 201 (and/or system) determines that the monitoring device 201 is engaged with a baseball bat, the monitoring device 201 (and/or system) may configure to measure various characteristics that do not include angular rotation about the longitudinal axis of the baseball bat. Further, the monitoring device 201 may configure to measure velocity, acceleration, etc. at a second rate (e.g., a second refresh rate) which is different from the first rate used for the golf club. While these examples are merely illustrative, it is understood that according to aspects of the disclosure, the monitoring device 201 (and/or system) is configured to determine the piece of sports equipment with which the monitoring device 201 is engaged, differentiate that piece of sports equipment with which the monitoring device 201 is engaged from other pieces of sports equipment, change the characteristics that the monitoring device 201 will measure and/or the data the monitoring device 201 will collect based on the piece of sports equipment with which the monitoring device 201 is engaged.

Further, in addition to changing the characteristics that the monitoring device 201 will measure and/or the data the monitoring device 201 will collect based on the piece of sports equipment with which the monitoring device 201 is engaged, other aspects of the disclosure are directed to determining which of one or more IMUs in the piece of sports equipment to use in collecting data related to the swing or stroke. For example, aspects of the disclosure are directed to selectively using data (e.g., for calculations such as described above) from the first IMU instead of the second IMU or the second IMU instead of the first IMU based on the type of sports equipment with which the monitoring device 201 is engaged.

Further aspects of the disclosure are directed to receiving data (related to the stroke or swing) collected from each (or more than one) of the IMUs in the sports equipment and then determining which of data from the one or more IMUs to use (e.g., use for calculations as will be described below) based on the type of sports equipment with which the monitoring device 201 is engaged. For example, the data from a particular IMU may be selected for use in calculations and/or for transmission to the remote computer 400 based on the data received from each of the IMUs and the type of sports equipment or other information indicated by the data received from each of the IMUs. In this way, the monitoring device 201 may switch between using and/or transmitting data from a first IMU and a second IMU based on data received from both IMUs.

It is noted that while the above embodiments describe choosing to use a particular IMU (e.g., a first IMU instead of a second IMU) to collect data or, alternatively, receiving data from more than one IMU and choosing to use data from a particular IMU (e.g., a first IMU instead of a second IMU), other aspects of the disclosure relate to a monitoring device 201 which includes an IMU which has more than one sensitivity range. Therefore, rather than selectively choosing between different IMUs or between data from different IMUs, aspects of the disclosure are directed to selectively choosing between different sensitivity ranges in a single IMU.

For example, aspects of the disclosure relate to a single IMU which includes a first sensitivity range configured to measure angular velocity and/or acceleration and may be extremely sensitive to small changes in velocity and/or acceleration (e.g., fractions of a meter per second or m/s$^2$). Such a sensitivity range may be beneficial in determining characteristics associated with a particular piece of sports equipment. Further, the IMU may include a second sensitivity range configured to measure velocity and/or acceleration and may be may be less sensitive to small changes in velocity and/or acceleration (as compared with the first sensitivity range) and able to more accurately determine larger changes in velocity and/or acceleration (e.g., at least several meters per second or m/s$^2$). Such a sensitivity range may be beneficial in determining characteristics associated with a different piece of sports equipment. Therefore, according to aspects of the disclosure a single monitoring device 201 may be configured to include a first IMU which is both directed to determining data associated with a piece of sports equipment and is also directed to determining data associated with a second piece of sports equipment.

Figure 24:
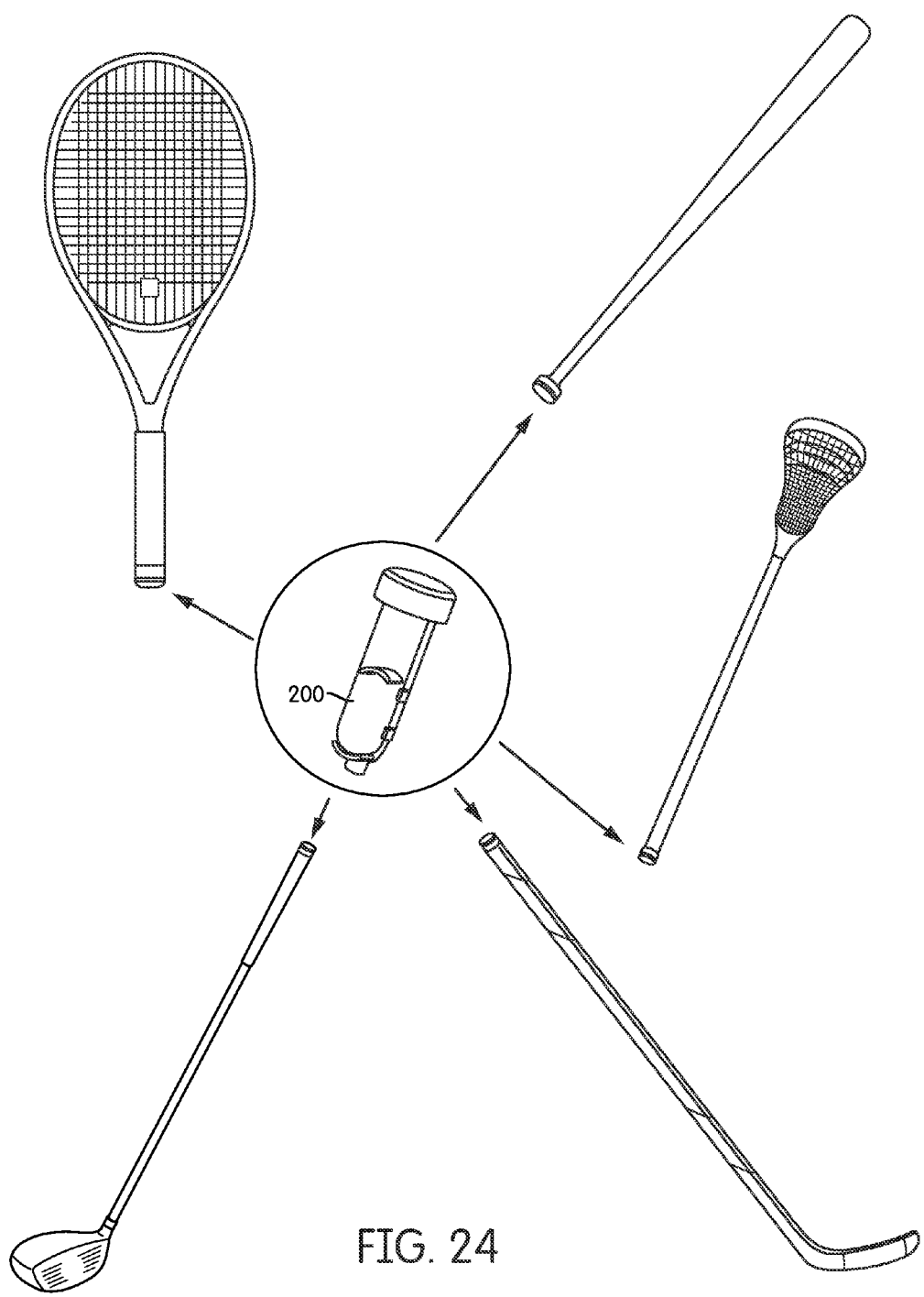
FIG. 24 is illustrates a monitoring device configured to be engaged with various different pieces of sports equipment according to aspects of the disclosure.

Aspects of the disclosure are directed to a monitoring device 201 which is configured to choose a particular sensitivity range (e.g., a first sensitivity range instead of a second sensitivity range). Any of the above or below described methods for choosing to use a particular IMU (e.g., a first IMU instead of a second IMU) to collect data or, alternatively, receiving data from more than one IMU and choosing to use data from a particular IMU (e.g., a first IMU instead of a second IMU), may be used to select the particular sensitivity range (e.g., a first sensitivity range instead of a second sensitivity range) of the single variable IMU. For example, selecting the particular sensitivity range (e.g., a first sensitivity range instead of a second sensitivity range) of the single variable IMU may be done via the above described: structural engagement (e.g., protrusions 200*p* activating detection switches), RFID techniques, based on the movement of the sports equipment (e.g., if the signature of the current swing matches, or falls within a tolerance of, a predetermined signature stored in a memory), commands from the remote computer 400 (e.g., manual commands, such as voice commands, automatic commands from a software application), manual commands based on activation of a switch on the sports equipment or monitoring device itself, etc. It is noted that, as discussed above, the monitoring device 201 may be engaged with a golf club in any of the manners described above (e.g., removable section 200, other types of inserts which hold the monitoring device 201, the monitoring device 201 may be engaged directly with the grip of the grip club, etc.). According to aspects of the disclosure, and as shown in FIG. 24, the monitoring device 201 may be engaged with the handle of a tennis racquet similarly to any of the manners described above (e.g., a similar removable section 200 configured to engage with the handle of the tennis racquet, other types of inserts which hold the monitoring device 201, or the monitoring device 201 may be engaged directly with the handle of the tennis racquet). Further, according to aspects of the disclosure, and as shown in FIG. 24, the monitoring device 201 may be engaged with the grip of a baseball bat or a hockey or lacrosse stick similarly to any of the manners described above (e.g., a similar removable sections 200 configured to engage with the grip of the baseball bat or hockey stick, other types of inserts which hold the monitoring device 201, or the monitoring device 201 may be engaged directly with the grip of the baseball bat or hockey or lacrosse stick).

Further, as discussed above, aspects of the disclosure relate to determining the type of sports equipment with which the monitoring device 201 is engaged. According to one embodiment of the disclosure, the engagement between the monitoring device 201 and the particular piece of sports equipment causes the monitoring device 201 to determine the piece of sports equipment with which the monitoring device 201 is engaged and, further, configure the monitoring device 201 to select the particular characteristics it will measure and data it will collect.

By way of example, the grips or handles of each of the pieces of sports equipment (e.g., the golf clubs, tennis racquets, bats, hockey sticks, etc.) may be configured to receive the monitoring device 201 in a manner discussed above with regard to FIGS. 8-9. For example, as discussed above, according to particular embodiments of the disclosure monitoring device 201 may be similar to those used in the NIKE+™ athletic performance monitoring systems available from NIKE, Inc. of Beaverton, Oreg. For example, as seen in FIGS. 4A and 4B, the monitoring device 201 may include a generally rectangular compartment which may be similar to the compartment used to house sensors used in the NIKE+™ athletic performance monitoring systems available from NIKE, Inc. of Beaverton, Oreg. Further the compartment of the monitoring device 201 may house various elements described above, such as the processor 204, sensors 202, transmitter 203, power supply 206, memory, etc. Further, as described above, according to aspects of the disclosure, the monitoring device 201 may be configured to engage with the grip 105 of the respective piece of sports equipment. For example, as described above, the grip 105 may be configured to receive a removable section or cartridge 200 and the removable section 200 may be configured to receive the monitoring device 201.

According to aspects of the disclosure, the engagement between the monitoring device 201 and removable section 200 the particular piece of sports equipment may cause the monitoring device 201 to determine the piece of sports equipment with which the monitoring device 201 has been engaged and, further, configure the monitoring device 201 to select the particular characteristics that the monitoring device 201 will measure and the data that monitoring device 201 will collect. For example, the engagement between the monitoring device 201 and removable section 200 may cause the monitoring device 201 to selectively activate different components of the monitoring device 201 (e.g., different IMUS) or collect data at different rates (e.g., slower or faster data refresh rates).

In one embodiment of the disclosure, the "universal" monitoring device 201 may be configured with one or more openings 201o configured to receive one or more protrusions 200p (e.g., prongs) that extend from the removable section 200 of the particular piece of sports equipment. According to aspects of the disclosure, the monitoring device 201 based on which of the openings 201o in the monitoring device 201 receive a protrusion 200p of the removable section 200, the monitoring device 201 determines the piece of sports equipment with which the monitoring device 201 has been engaged and, further, is configured to select the particular characteristics it will measure and the data it will collect.

For example, the monitoring device 201 may include have plurality of 201o. Further, a removable section 200 of one piece of sports equipment may have a set of protrusions 200p that are configured to engage with some of the holes of the plurality of openings 201o of monitoring device 201. When that particular combination of opening 201o is engaged by the respective protrusions 200p of the removable section 200 of particular piece of sports equipment, the monitoring device 201 determines the piece of sports equipment with which the monitoring device 201 has been engaged and, further, is configured to select the particular characteristics it will measure and the data it will collect. Similarly, a removable section 200 of a second, different, piece of sports equipment may have a different set of protrusions 200p that are configured to engage with some of the openings 201o of the plurality of openings of monitoring device 201. When that particular combination of openings 201o is engaged by the respective protrusions 200p of the removable section 200 of second, different piece of sports equipment, the monitoring device 201 determines the second, different piece of sports equipment with which the monitoring device has 201 been engaged and, further, is configured to select the particular (and potentially different) characteristics the monitoring device 201 will measure and the particular (and potentially different) data the monitoring device will collect.

Figure 25A:
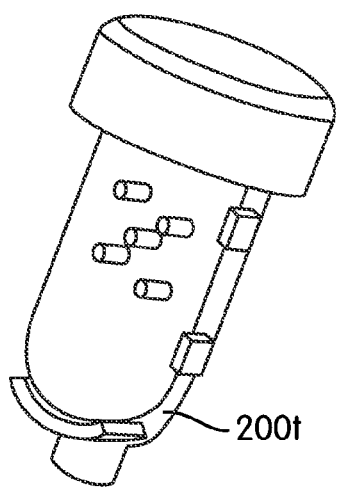
FIGS. 25A-C show illustrative removable sections of pieces of sports equipment according to aspects of the disclosure.
Figure 25B:
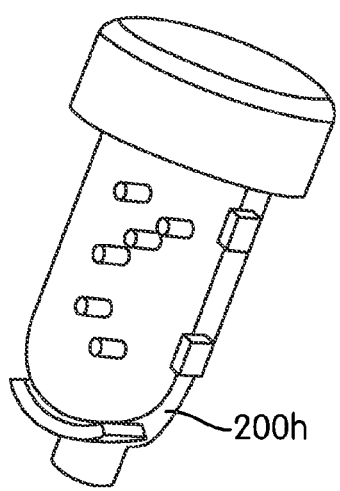
Figure 25C:
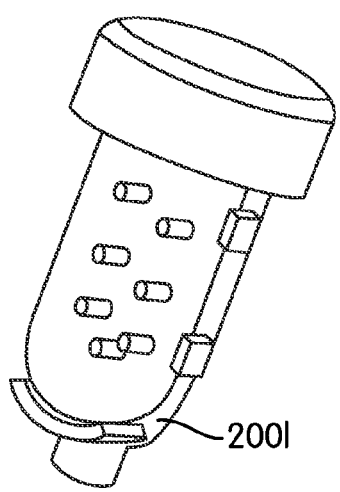

FIGS. 25A-C show illustrative removable sections 200 according to aspects of this disclosure. As seen in FIGS. 25A-C, each of the removable sections 200 may include an elongated portion configured to aid in housing the monitoring device 201. As described above, each of the elongate portions may include a first arched end configured to engage a first rounded end of the compartment, a second arched end configured to engage a second rounded end of the compartment and a back portion which extends between the first arched portion and the second arched portion and is configured to engage a side of the compartment of the monitoring device 201. According to aspects of the disclosure, the elongated portion of each of the removable section 200 may include the one or more protrusions 200p. As seen FIG. 25A, the illustrative removable section 200T includes a plurality of protrusions 201p which are arranged in unique positioning. In this case there are five protrusions 200p arranged in the unique positioning. It is noted that the number of protrusions 200p and the unique positioning of those protrusions 200p may be configured such that when engaged with the monitoring device 201, they indicate to the monitoring device to the piece of sports equipment with which the monitoring device 201 is engaged. For example, the number of protrusions 200p and the unique positioning of those protrusions 200p in illustrative removable section 200T may indicate to the monitoring device 201 that the monitoring device 201 is engaged with a tennis racquet.

Similarly, FIGS. 25B-C each show other illustrative removable sections 200 with their own respective plurality of protrusions 201p which are arranged in unique arrangements. For example, as seen in FIG. 25B, the illustrative removable section 200H may include six protrusions 200p arranged in a unique positioning which may indicate to the monitoring device 201 that the monitoring device 201 is engaged with a hockey stick. Further, as seen in FIG. 25C, the illustrative removable section 200L may include seven protrusions 200p arranged in a unique positioning which may indicate to the monitoring device 201 that the monitoring device 201 is engaged with a lacrosse stick.

Figure 26:
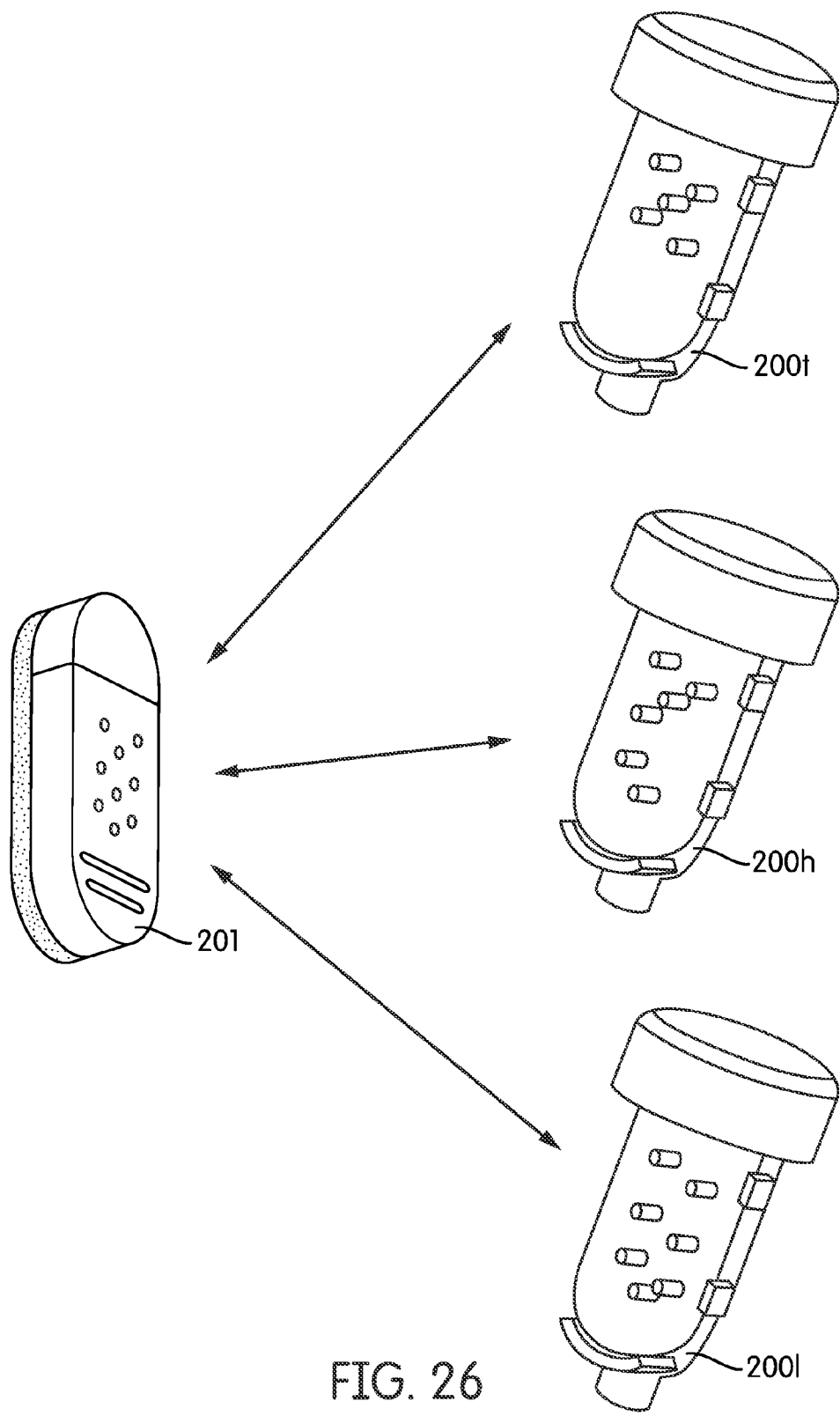
FIG. 26 is an illustrative monitoring device with openings according to aspects of the disclosure configured to be engaged with the removable sections of FIGS. 25A-C.

FIG. 26 shows an illustrative monitoring device 201 according to aspects of this disclosure. As seen in FIG. 26, the flat side of the compartment of the monitoring device 201 may be configured to include the one or more openings 201o (which are configured to receive the protrusions 200p. Additionally, or alternatively, one or both of the rounded ends of the compartment of the monitoring device 201 may be configured to include the openings 201o which are configured to receive the protrusions 200p which are positioned on the first arched portion and/or the second arched portion of the removable section 200.

As seen FIG. 26, the illustrative monitoring device 201 includes a plurality of openings 201o which are arranged such that the openings 201o can accommodate each of the unique arrangements of the protrusions of the various removable sections 200. In this example, there are nine opening 201o which are configured to receive the protrusions of the various removable sections 200. Further, as seen in FIG. 26, the openings 201o can receive each of the unique arrangements of the protrusions of the various removable sections 200T, 200H, 200L.

It is noted that these embodiments are merely illustrative and not meant to be limiting. For example, while nine openings and 5-7 protrusions are discussed in the illustrative embodiments, it is clear that any combination of openings and protrusions may be used provided the combination will sufficiently allow the monitoring device 201 to selectively determine the piece of sports equipment with which the monitoring device 201 has been engaged and, further, select the particular characteristics it will measure and the data it will collect. For example, other protrusions 200p (e.g., number of protrusions, arrangements of protrusions) and sets of openings 201o (e.g., number of openings, arrangements of openings) may be used in accordance with aspects of the disclosure.

It is noted that in some embodiments, the protrusions of the removable sections 200 may be configured to activate detecting switches within monitoring device 201 which cause the processor 204 to determine the piece of sports equipment with which the monitoring device 201 has been engaged and, further, is configured to select the particular characteristics it will measure and the data it will collect. For example, engagement of the protrusions with the openings of the removable section 200 may cause the detecting switches within the openings to move from a first position to second position. The processor 204 may be configured to recognize this movement and depending on which of the detecting switches have been moved, determine the piece of sports equipment with which the monitoring device 201 has been engaged and, further, is select the particular characteristics it will measure and the data it will collect. Alternatively, there may be electrical connections made between the protrusions and the elements (e.g., leads) within the opening of the removable section 200. The processor 204 may be configured to recognize these connections and depending on which of the elements are contacted and, thereby, determine the piece of sports equipment with which the monitoring device 201 has been engaged and, further, select the particular characteristics it will measure and the data it will collect. Of course, these are just examples and other methods of selectively determining the piece of sports equipment with which the monitoring device 201 has been engaged and, further, selecting the particular characteristics it will measure and the data it will collect may be used.

The protrusions and openings may be arranged such that the monitoring device 201 can only be engaged with the removable section in an intended orientation. For example, while the "universal" monitoring device 201 may have nine holes, the protrusions on the removable section 200 and holes on the monitoring device 201 are arranged such that they will align only when the monitoring device 201 is engaged with the removable section 200 in the intended orientation.

It is noted that as discussed above, according to other aspects of the disclosure, the grip 105 may be configured to receive and secure the monitoring device 201 directly, without the inclusion of a separate removable section or cartridge 200. As discussed above, the monitoring device 201 may be configured to be engaged with the grip 105 in a variety of ways. For example, the grip 105 may be configured with an opening at its terminal end that is configured to receive the monitoring device 201. However, regardless of how the monitoring device 201 is engaged with the grip 105, the grip 105 itself may be configured with the above discussed protrusions configured to engage with the openings in the monitoring device 201 to selectively determine the piece of sports equipment with which the monitoring device 201 has been engaged and, further, select the particular characteristics it will measure and the data it will collect accordingly. For example, the grip 105 may include a slit that is configured to receive the monitoring device 201 when the monitoring device 201 is inserted into the grip along the monitoring device's longitudinal axis. Further, one or both of the rounded ends of the compartment of the monitoring device 201 may be configured to include the openings which are configured to receive the protrusions and the lower end of the slit may include the one or more protrusions. Additionally, or alternatively, the protrusions may positioned on the sides of the slit and may be spring loaded, flexible, etc. in order to accommodate the insertion and removable of the monitoring device 201.

In addition to the above described embodiment which includes protrusions for activating detection switches, shape memory alloy may be used as well. Shape memory alloy is substance which is configured to return to its original shape upon heating.

Further, while the above embodiment discussed the structural engagement between the monitoring device 201 and the piece of sports equipment as a means of allowing the monitoring device 201 to selectively determine the piece of sports equipment with which the monitoring device 201 has been engaged and, further, select the particular characteristics it will measure and the data it will collect, other methods and means may be used as well.

For example, the piece of sports equipment may include a chip (e.g., an RFID chip) which communicates with the monitoring device 201 when the monitoring device 201 is engaged with the piece of sports equipment. This could be through direct electrical connection, wireless transmission, etc. The chip may be configured to indicate to the monitoring device 201 with which piece of sports equipment the monitoring device 201 is engaged. For example, the transceiver of the monitoring device 201 may be configured to receive or "read" ID data from the chip which indicates which piece of sports equipment the monitoring device 201 is engaged. Accordingly, once the monitoring device 201 has determined the piece of sports equipment with which it is engaged (based on the data provided from the chip), the processor 204 of the monitoring device 201 can selectively determine the piece of sports equipment with which the monitoring device 201 has been engaged and, further, select the particular characteristics it will measure and the data it will collect.

For example, when the monitoring device 201 has received data from the chip (e.g., RFID chip) engaged with golf club, the processor 204 of the monitoring device 201 (and/or system) may configure the monitoring device 201 to measure various characteristics, such as angular rotation about the longitudinal axis of the golf club. Further, the monitoring device 201 (and/or system) may configure the monitoring device 201 to measure velocity, acceleration, etc. at a first rate (e.g., a first refresh rate). In contrast, according to aspects of the disclosure, when the monitoring device 201 has received data from the chip (e.g., RFID chip) that the monitoring device 201 is engaged with a baseball bat, the monitoring device 201 (and/or system) may configure the monitoring device 201 to measure various characteristics that do not include angular rotation about the longitudinal axis of the baseball bat. Further, the monitoring device 201 (and/or system) may configure the monitoring device 201 to measure velocity, acceleration, etc. at a second rate (e.g., a second refresh rate) which is different from the first rate used for the golf club.

Further, while the above referenced embodiments discussed the structural engagement between the monitoring device 201 and the piece of sports equipment or the use of a chip (e.g., an RFID chip) as means of allowing the monitoring device 201 to selectively determine the piece of sports equipment with which the monitoring device 201 has been engaged and, further, select the particular characteristics it will measure and the data it will collect, other methods and means may be used as well.

According to aspects of the disclosure, the monitoring device 201 may be configured to determine the piece of sports equipment with which the monitoring device 201 has been engaged based on the movement of the piece of sports equipment. For example, the monitoring device 201 may be configured to determine the piece of sports equipment with which the monitoring device 201 has been engaged based on "practice" swings of the piece of sports equipment.

According to aspects of the disclosure, the processor 204 may be configured to receive data from components of the monitoring device 201 (e.g., the IMUs in the monitoring device 201). For example, the processor 204 may be configured to receive data from an accelerometer, gyroscope, etc. which indicates the orientation of the piece of sports equipment, the velocity or acceleration of the sports equipment, etc. According to aspects of the disclosure, based on this data, the monitoring device 201 may be configured to determine the piece of sports equipment with which the monitoring device 201 has been engaged and further, select the particular characteristics it will measure and the data it will collect.

For example, if the data indicates that a characteristic is above a predetermined value (or within a predetermined range), the processor 204 may determine the piece of sports equipment with which the monitoring device 201 has been engaged is a first type of sports equipment and further, select the particular characteristics it will measure and the data it will collect accordingly. Further, if the data indicates that a characteristic is below a predetermined value (or within a predetermined range or non-existent), the processor may determine the piece of sports equipment with which the monitoring device 201 has been engaged is a second type of sports equipment and further, select the particular characteristics it will measure and the data it will collect accordingly.

For example, if the processor receives data from the IMUS which indicates the piece of sports equipment was swung in a particular orientation or swing path, then the processor 204 of the monitoring device 201 will assume the piece of sports equipment with which the monitoring device 201 is engaged is a piece of sports equipment that corresponds to such an orientation or swing path. For example, it is noted that orientation and/or swing path profiles for each of respective pieces of sports equipment (e.g., golf clubs, tennis racquets, bats, hockey sticks, etc.) may be saved in memory and as accessible by the processor 204. Therefore, the processor of the monitoring device 201 may compare the measured orientation or swing path with the saved orientations or swing path profiles in the memory and determine which piece of sports equipment the monitoring device 201 is engaged with by matching (or by substantially matching) the measured characteristics with one of the saved profiles. Hence, thereafter, the monitoring device 201 may select the particular characteristics it will measure and the data it will collect accordingly.

Figure 27A:
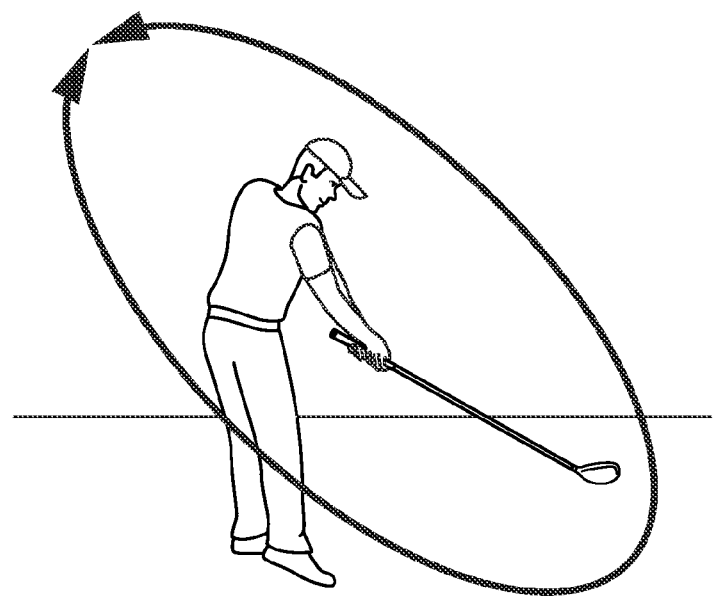
FIGS. 27A-B illustrate swing path profiles of a golf swing and the swing of a baseball bar, respectively.
Figure 27B:
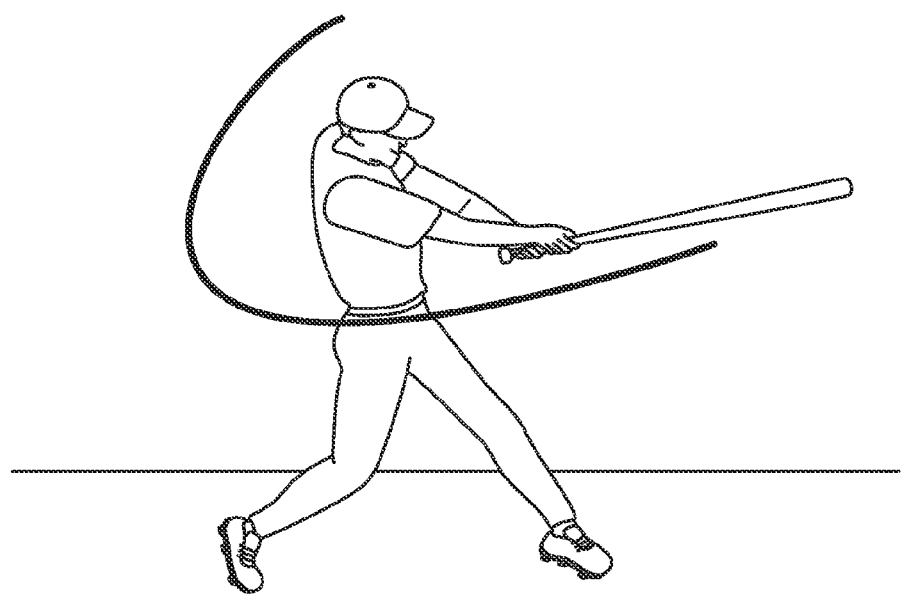

For example, FIGS. 27A and 27B illustrate swing paths for a golf swing and the swing of a baseball bat, respectively. As seen by comparing these swings, they each have different swing paths and orientations throughout the swing. For example, the swing of the baseball bat has an orientation that is relatively horizontal through the middle of the swing path. In contrast the golf swing has an orientation that is relatively vertical through the middle of the swing path. Such data regarding the orientation of the piece of sports equipment throughout the swing path or a portion of the swing path may be determined by the sensors of the monitoring device 201, and then used by the monitoring device 201 to determine the piece of sports equipment with which the monitoring device is engaged in a manner such as discussed above (e.g., comparing the measured characteristics with the saved profiles).

It is noted that in addition to the saved orientations or swing path profiles, velocity and acceleration (and other characteristics) profiles for each of respective pieces of sports equipment (e.g., golf clubs, tennis racquets, bats, hockey sticks, etc.) may be saved in memory and accessible by the processor 204 as well. In this way, such data can also be used to determine the piece of sports equipment with which the monitoring device 201 is engaged with accordingly. For example, the processor of the monitoring device 201 may compare the measured velocity and acceleration (and other characteristics) with the saved velocity and acceleration (and other characteristic) profiles in the memory. For example, the processor may determine if the measured velocity, acceleration (and/or other characteristic) is within a predetermined range of a saved profile. The results of the comparison (e.g., if it is, or is not, within a particular profile) may at least aid in determining the piece of sports equipment with which the monitoring device 201 is engaged. Hence, thereafter, the monitoring device 201 may select the particular characteristics it will measure and the data it will collect.

Similarly, according to additional aspects of the disclosure, the processor 204 may be configured to receive data from each (or more than one) of the IMUs in the monitoring device 201 and compare that data with predetermined values or ranges to determine the data from which IMU to use for a particular purpose. For example, as discussed above with regard to putting and driver signatures in FIGS. 19A-19D, the acceleration and angular velocity for other pieces of sports equipment may have particular graphical ranges or "signatures." Such graphical ranges or "signatures" may be stored in a memory which the processor 204 may access. Therefore, in some embodiments of the disclosure, the processor 204 may be configured to receive data from each (or more than one) of the IMUs in the monitoring device 201 and compare that data with the stored graphical ranges or "signatures." If the data matches a particular graphical range or "signature" associated with a first type of sports equipment, the processor may determine that the swing was the first type of sports equipment and accordingly use data from a first IMU in making particular calculations (or transmitting that data to the remote computer) or select the particular characteristics the monitoring device 201 will measure and the data it will collect. Alternatively, if the data matches a particular graphical range or "signature" associated with a second type of sports equipment, the processor may determine that the swing was associated with the second type of sports equipment and accordingly use data from a second IMU in making particular calculations (or transmitting that data to the remote computer) or select the particular characteristics the monitoring device 201 will measure and the data it will collect. It is noted that while the above embodiment discusses graphical ranges or "signatures" other data could be used instead (e.g., numerical ranges or signatures). Further, it is noted that tolerances may be incorporated into the comparison of the collected data with saved values, ranges, "signatures", etc. such that the collected data does not have to match exactly in order for the type of sports equipment to be identified. For example, either the processor 204 may be configured to account for a predefined tolerance when comparing the data with the saved values, ranges, "signatures", etc. or the saved values, ranges, "signatures", etc. may already include a predefined tolerance. Accordingly, if the receive data from each of the IMUs in the monitoring device 201 does not exactly match the signature of a particular predetermined swing with a predetermined piece of sports equipment, but is still within a tolerance or predetermined range of the particular predetermined swing with a particular piece of sports equipment, then the monitoring device 201 may be configured to identify the piece of sports equipment with which pending swing was produced as the particular piece of sports equipment associated with the signature.

If the data indicates that a characteristic is above a predetermined value (or within a predetermined range), the processor 204 may be configured to use the data from a corresponding, predefined IMU as the determined data (and perhaps discard the data from the other IMU(s)). Conversely, if the data indicates that a characteristic is below that predetermined value (or within a predetermined range), the processor 204 may be configured to use the data from a second corresponding, predefined IMU as the determined data (and perhaps discard the data from the other IMU(s)).

It is noted that the above described aspects of having the processor (or other firmware) receive data from each (or more than one) of the IMUs and then use the data to determine with which type of sports equipment the monitoring device 201 is engaged (and thereby determine which of the particular IMU's data to use and/or transmit or select the particular characteristics the monitoring device 201 will measure and the data it will collect) may be applied to or used in combination with the other features in the other embodiments described herein. For example, in the above described embodiments, which include prongs and detecting switches to determine with which type of club the monitoring device 201 is engaged, the processor (or other firmware) may still collect data from each IMU and then use or transmit such data accordingly. For example, data from each IMU may still be relevant for various characteristics of the golf swing and even though data from one IMU is selected for determining a particular characteristic based on the above described methods, data from other IMUs may still be used for determining other characteristics and/or transmitted to the remote device.

The above discussed embodiments do not preclude other means of allowing the monitoring device 201 to selectively determine the piece of sports equipment with which the monitoring device 201 has been engaged and, further, select the particular characteristics it will measure and the data it will collect. Other methods and means may be used as well.

For example, while the above discussed embodiments describe features which "automatically" determine which of pieces of sports equipment the monitoring device 201 is engaged (i.e., without the user taking an affirmative step to manually choose between the different pieces of sports equipment), this should not be interpreted to mean that embodiments which allow the user to manually determine which piece of sports equipment the monitoring device 201 is engaged with and manually configure the monitoring device 201 to measure particular characteristics and collect particular data accordingly are precluded. Instead, according to aspects of the disclosure, the monitoring device 201 may be configured to receive instructions from the user as to which piece of sports equipment it is engaged. For example, according to an embodiment of the disclosure, the monitoring device 201 could include a switch which the user can manually move between different positions. Further, the processor 204 of the monitoring device 201 could be configured to interpret the different positions of the switch as instructions as to which piece of sports equipment it is engaged.

Alternatively, the processor 204 of the monitoring device 201 could receive instructions from the remote computer 400 discussed above, as to the piece of sports equipment with which it is engaged. It is noted that such instructions could be stored in the memory until the monitoring unit 201 receives other instructions which override such instructions. For example, the particular piece of sports equipment or a particular IMU (e.g., the first IMU instead of the second IMU) whose data is collected and used may be chosen by the user affirmatively instructing the processor 204 via the remote computer 400. Alternatively, particular piece of sports equipment or a particular IMU whose data is collected and used may be chosen/dictated by the particular software application being run by the remote computer. In other words, a particular software application may choose which data or characteristics of the sports equipment is to be measured and/or require that data from first IMU instead of a second IMU to be used to calculate the particular value (even though data from the second IMU may still be collected and stored or used for other purposes). For example, the application directed to determining bat speed may specify that the processor 204 use data from the first IMU instead of the data from the second IMU.

Alternatively, the particular IMU (e.g., the first IMU instead of the second IMU) whose data is collected and used, the piece of sports equipment with which the monitoring device 201 is engaged/the particular characteristics of the swing or stroke to be measured (e.g., based on the type of sports equipment) may be chosen/dictated by the user through voice commands. For example, the remote computer 400 (e.g., a mobile telephone, such as a smart phone as described above) may be positioned near the user when the user is preparing to make a swing or stroke. The remote computer 400 may include a particular software application that transmits instructions to the processor of the monitoring device to use a particular IMU (e.g., the first IMU instead of the second IMU), identify the type of sports equipment with which the monitoring device is engaged and/or measure particular characteristics of the swing or stoke based on the remote computer 400 receiving a predetermined voice command. For example, the remote computer 400 may have voice recognition software which interprets the use's command of "baseball bat", "measure baseball bat speed" of other predetermined phrases as an instruction to transmit data to the remote computer 400 to use a first IMU or identify the type of sports equipment with which the monitoring device is engaged as a baseball bat and/or measure particular characteristics of the swing (e.g., bat speed). Similar embodiments and phrases may be used for other sports equipment, characteristics, or IMUS. Alternatively, the sports equipment itself could be configured to have the voice recognition software and a microphone for receiving the voice commands. Hence, in such an embodiment, the sports equipment itself may be receive the voice commands and interpret them to use a particular IMU or identify the type of sports equipment with which the monitoring device is engaged and/or measure particular characteristics of the swing or stroke.

According to aspects of the disclosure, the remote computer 400 may be configured to receive data from the monitoring device 201 and then associate the data with a particular piece of sports equipment (e.g., by comparing the received data from the monitoring device 201 with swing path, orientation, velocity, acceleration, etc. profiles that are stored on the remote computer similarly to as discussed above). Alternatively, as discussed above, according to aspects of the disclosure, the monitoring device 201 may capture the data associated with the swing and transfer the data collected wherein the data transmission to the remote computer 400 specifies to which piece of sports equipment the data in the transmission relates (e.g., wherein the piece of sporting equipment is selected according to one of the above described embodiments). Further, it is noted that various combinations of the above described embodiments of determining the piece of sports equipment with which the monitoring device 201 has been engaged and, further, selecting the particular characteristics the monitoring device 201 will measure and the data the monitoring device 201 will collect may be used.

It is noted that while the measured characteristics described above have related to rotation, orientation, swing path, velocity, angular velocity, acceleration and angular acceleration, etc. the above described features are not limited to measuring these feature and other characteristics of the swing may be measured as well. Also, it is noted that regardless of how the piece of sports equipment with which the monitoring device 201 has been engaged is selected, once the piece of sports equipment with which the monitoring device 201 has been engaged is selected, data can be determined, processed, transmitted, etc. according to any of the above discussed aspects of the disclosure.

According to aspects of the disclosure, the monitoring device 201 may be activated during insertion of the monitoring device 201 into sports equipment. Further, the monitoring device 201 may be continuously sensing and collecting data. However, according to other aspects of the disclosure, the monitoring device 201 may be selectively activated. For example, the monitoring device 201 may be configured to enter a "sleep" or "hibernation" state when the monitoring device has not been active for a predetermined amount of time (e.g., 1 minute, 5 minutes, 1 or 5 seconds after the monitoring device 201 determines that swing or stroke is completed (as will be described below), etc.). In this "sleep" or "hibernation" state only the components needed for determining activation of the monitoring device 201 may continue to receive power. In other embodiments of the "sleep" or "hibernation" state, components may receive less power than they do in a use state. Further, the monitoring device 201 may be selectively activated manually, or automatically upon the occurrence of an event (e.g., movement of the sports equipment or movement of the sports equipment in a particular fashion).

For example, in an illustrative embodiment of the disclosure, the movement of the sports equipment may act as a trigger to cause the monitoring device 201 to exit the "sleep" or "hibernation" state and/or fully activate (i.e., "wake up"). For example, the monitoring device 201 may be configured to receive data from the IMUs that the sports equipment has been moved and based on the data exit the "sleep" or "hibernation" state and/or fully activate (i.e., "wake up"). According to aspects of the disclosure, the monitoring device 201 may be configured compare the data from the IMUs with a predetermined threshold and only exit the "sleep" or "hibernation" state and/or fully activate (i.e., "wake up") if the data from the IMUs is above the predetermine threshold. For example, the data from the IMUs must be above a predetermined angular velocity or acceleration in order to "wake up" the monitoring device 201. In this way, incidental movement will not "wake up" the monitoring device 201.

In an illustrative embodiment of the disclosure, the predetermined movement of the sports equipment may act as a trigger to cause the monitoring device 201 to exit the "sleep" or "hibernation" state and/or fully activate (i.e., "wake up"). According to aspects of the disclosure, the monitoring device 201 may be configured compare the data from the IMUs with a predetermined range(s) or value(s) (e.g., such as the above discussed graphical or numerical range or signatures which indicate a stroke or swing of the piece of sports equipment) and only exit the "sleep" or "hibernation" state and/or fully activate (i.e., "wake up") if the data from the IMUs is above the predetermined threshold. For example, the predetermined range(s) or value(s) may indicate be a "signature" which indicates a practice swing. Therefore, when the data from the IMUs match (or are within a tolerance or the signature) the monitoring device 201 "wakes up".

In another illustrative embodiment, the user may manually cause the monitoring device 201 to enter to exit the "sleep" or "hibernation" state. For example, the user may use the remote computer 400 (e.g., a smart phone with a software application that configure the smartphone to receive and transmit data to the monitoring device 201) to cause the monitoring device to enter to exit the "sleep" or "hibernation" state. This could be done by inputting data to the smartphone (e.g., voice commands or touching a touch screen) which instructs the monitoring device 201 to enter to exit the "sleep" or "hibernation" state.

According to aspects of the disclosure, similar methods may be used to correlate data to a particular swing and, thereby, indicate individual swings/distinguish between different swings. For example, in embodiments where the monitoring device 201 may be activated and continually receiving data from the IMUs during the entire time the monitoring device 201 is activated, aspects of the disclosure are directed to correlating data for a particular swing (e.g., as distinguished from a practice swing or movement not related to the swing, such as when the sports equipment is being carried to the location of the swing).

According to particular aspects of the disclosure, the pre-shot routine may "zero" the monitoring device 201 (i.e., cause the monitoring device 201 to recognize that the upcoming movement is the beginning of an individual swing). For example, as discussed above, the monitoring device 201 may be configured to receive data from the IMUs that the sports equipment has been moved in a predetermined movement. The monitoring device 201 may be configured to recognize the predetermined range(s) or value(s) as the "signature" which indicates the predetermined movement and determine that any movement after the recognized predetermined movement is part of swing or stroke. Accordingly, only movement of the sports equipment after the predetermined movement will be correlated with the particular swing or stroke. In other words, only movement of the golf club which occurs after the IMUs provide data to the monitoring device 201 that the sports equipment is at rest in the ready position after having completed the predetermined movement will be correlated with the particular swing or stroke.

It is noted that the monitoring device 201 may be configured to account for, or include, a predetermined time after the predetermined movement is completed and after the swing is completed in determining which data is related to the swing or stroke. For example, the monitoring device 201 may be configured to allow for a predetermined time (e.g., 1 or 2 seconds) once the monitoring device 201 has determined that the predetermined movement has been completed (i.e., the IMUS provide data to the monitoring device 201 that the sports equipment is at rest in the ready position after having completed the predetermined movement) before beginning to associate data with the particular stroke. Similarly, the monitoring device 201 may be configured to allow for a predetermined time (e.g., 1 or 2 seconds) once the monitoring device 201 has determined that the swing or stroke has been completed (i.e., the IMUS provide data to the monitoring device 201 that the sports equipment has completed the stroke (e.g., the follow through of the swing or stroke has been completed) as defined by the stored signature of the typical swing or stroke) before ending the association data with the particular stroke.

In some embodiments, the predetermined movement may include one or more practice swings. Further, it is noted that the predetermined movement may be customized to the particular user. For example, the predetermined movement may include one or more practices swing(s) prior to the sports equipment coming to rest in the ready position after having completed the predetermined movement depending on the particular user's habits. Such information regarding the predetermined movement may be stored on in the monitoring device 201. For example, the particular signature of a user's predetermined movement of the sports equipment may be stored to the monitoring device 201 (e.g., uploaded to the memory of the monitoring device 201 via the remote computer 400 or the remote computer 400 could instruct the monitoring device 201 to record data from the IMU for a particular amount during which the user performs the predetermined movement of the sports equipment and then store the recorded data as the signature of the predetermined movement of the sports equipment). According to aspects of the disclosure, the monitoring device 201 may be configured to determine a practice swing and a swing whose signature is within a particular range relative to the signature of an actual swing. For example, a practice swing may be defined as a predetermined amount or range which corresponds to predetermined value (e.g., 70% of the angular velocity of an actual swing or 70% of the radial length of an actual swing). Alternatively, a practice swing may be defined with its own digital signature which identifies the swing as a practice swing as described above.

According to some embodiments of the disclosure, the user may manually correlate data to a particular swing and, thereby, indicate individual swings/distinguish between different swings. For example, the golfer may activate a switch which "zeros" the monitoring device 201 (i.e., cause the monitoring device 201 to recognize that the upcoming movement is the beginning of an individual swing). For example, the user may activate a switch on the sports equipment itself that transmits information to the monitoring device 201 that causes the monitoring device 201 to recognize that the upcoming movement is the beginning of an individual swing. Further, the user may activate a switch on the remote computer 400 (e.g., pressing a button on a smart phone) that causes the monitoring device 201 to recognize that the upcoming movement is the beginning of an individual swing. Further, the golfer may use voice commands to zero the monitoring device 201. For example, the remote computer 400 (e.g., a smart phone) may be configured to receive the voice commands from the user and transmit data to the monitoring device which indicates the beginning and end of the shot. For instance, the remote computer 400 may be configured to interpret the user saying "begin" or "start" as the beginning of the swing and transmit instructions to the remote computer to begin recording data from the IMUs or being associating data from the IMUs as a particular, individual swing. Conversely, the remote computer 400 may be configured to interpret the user saying "done" or "end" as the end of the swing and transmit instructions to the monitoring device to stop recording data from the IMUs or stop associating data from the IMUs as a particular, individual swing.

In some embodiments of the disclosure impact sensors such as described above may be used to determine a recordable swing. For example, if a particular swing has characteristics which resemble both a practice swing and an actual swing (e.g., above a threshold angular velocity), the monitoring device 201 may be configured to receive data from an impact sensor which indicates whether impact with the object (e.g., a baseball, tennis ball, etc.) was made during the swing. In such embodiments, the occurrence of an impact may serve as validating that the swing should not be interpreted as a practice swing, but instead a particular swing for which characteristics of the swing should be measured/determined.

Product/Strategy to Improve Performance Recommendations

As discussed above, according to aspects of the disclosure, data collected from the above described system and metrics determined by the above described system may be uploaded to a network. For example, such data may be uploaded to a network which can interpret the received data and provide recommendations to the golfer. For example, in some embodiments of the disclosure, the collected data and determined metrics may be uploaded to a network which can compare the data and metrics with a predefined set of characteristics in order to recommend products which will aid the golfer in improving various aspects of their games.

By way of example, swing speed data determined by the monitoring device 201 may be uploaded to such a network system. Further, data on shaft of the golf club from which the swing speed data was taken (as identified by one of the above described methods) may also be uploaded to such a network system. The network system may include a database which stores data on swing speeds and a database which stores data on a plurality of shaft stiffnesses. Further, the database may store tables which correlate various swing speeds with ideal shaft stiffness for such swing speeds. For example, the table may correlate a first shaft stiffness for a swing speed of 90 mph, and a second shaft stiffness for a swing speed of 125 mph. The system may be configured to determine whether the shaft used for the golf swing is the type of shaft the table considers the ideal shaft for the determined swing speed. If the system determines that the shaft is not the ideal shaft based on the table data, the system may send a message to the remote computer 400 of the golfer which recommends the ideal shaft based on the table data. For example, if data uploaded to the network showed that the swing speed determined by the monitoring device 201 was 125 mph and a golfer using the first shaft stiffness, then the system would send a message to the remote computer recommending the golfer use a shaft with the second shaft stiffness because their golf swing speed was 125 mph. In this way, the system could aid in improving the golfer's game by providing recommendations regarding the appropriate equipment based on the golfers swing. While the above described example, discusses swing speed and shaft stiffness, it is understood that various other characteristics and products may also be used.

Further, in addition to recommending products to improve the golfer's swing, according to aspects of the disclosure, the system may also recommend strategies to correct the golfers swing directly. For example, the monitoring device 201 could provide rotation data for the club which shows the angle of club face at the point of impact with the golf ball. Further, the network system may include a database which stores data correlating the angle of the club face at the point of impact with the golf ball with the profiled of golf shots (e.g., slices and hooks). If data uploaded to the network showed that the angle of the club face was open as impact, then the system would send a message to the remote computer 400 recommending the golfer adjust their swing to close the club face at the point of impact. In this way, the system could aid in improving the golfer's game by providing recommendations correcting the golfer's swing. While the above described example, discusses angle of the club face at impact with the golf ball, it is understood that various other characteristics and strategies may also be used.

Further, the system may also provide coaching to correct the golfer's swing. For example, as described above, the monitoring device 201 could provide data for the club which indicates the swing path of the golf swing. If data uploaded to the network showed that the swing patch was producing a "sliced" or a "hooked" golf shot, then the system would send instructions to the remote computer 400 describing how the golfer may adjust their swing to correct the slice or hook. For example, the system could provide coaching videos in which coaches provide instructions and describe methods for correcting a slice or hook. Additionally, when the golfer completes a first video, the system may register the completion of the video and provide additional videos (e.g., more advanced correction techniques). Further, the system could provide drills which the golfer can use to correct a slice or hook. Additionally, when the golfer completes a drill, the golfer may communicate completion of the drill to the system and the system may provide additional drills (e.g., more advanced correction drills). Alternatively, the remote computer may be configured to determine when the golfer has completed the drills through the data received from the monitoring device 201. Accordingly, the remote computer 400 may be configured to automatically communicate completion of the drill to the system and the system may provide additional drills (e.g., more advanced correction drills).

While the above described examples discuss the angle of the club face at impact with the golf ball and swing path of the golf swing, it is understood that various other characteristics and strategies may also be used. For example, the monitoring device 201 could provide data on the position/orientation of the golf club shaft or golf club head when the golfer has positioned the golf club at the address position.

As discussed above, according to aspects of the disclosure, data collected from the above described system and metrics determined by the above described system may be uploaded to a network. However, alternatively, instead of uploading such data to a network, the remote computer 400 itself may be configured to compare the data and metrics with a predefined set of characteristics in order to provide coaching or drills which will aid the golfer in improving various aspects of their games. For example, the remote computer 400 (e.g., as configured by a software application) may include a databases which stores data on characteristics of a swing or stroke and, also, stores tables which correlate various characteristics with various coaching videos, drills, etc. Therefore, the remote computer 400 may provide the golfer with various "on board" coaching videos, drills, etc. It is noted that while the above described embodiments relate to golf swings, as described above, monitoring devices and system may be used with other sports equipment as well. Therefore, aspects of the disclosure are directed to providing similar recommendations in other sports based on the received data from the respective pieces of sports equipment. For example, the system may be configured to provide recommendations on: a particular type of tennis racquet based on the speed of a serve or stroke, a particular type of baseball bat based on swing speed, etc. While the above described examples, discusses swing or stroke speed, it is understood that various other characteristics and products may also be used. Further, the system could provide recommendations on strategies to correct the athlete's swing or stroke directly in a manner similar to as described above.

Another embodiment of this disclosure may relate to the use of inductive charging of the monitoring device 1501 while the monitoring device 1501 is installed into golf club 100. Inductive charging involves using an electromagnetic field created by a first electrical current flowing in a first induction coil that "induces" a second electrical current to flow in a second induction coil when the coils are in close proximity to one another. The first and second induction coils may be tuned to resonate at the same frequency to have a more efficient energy transfer.

Figure 28A:
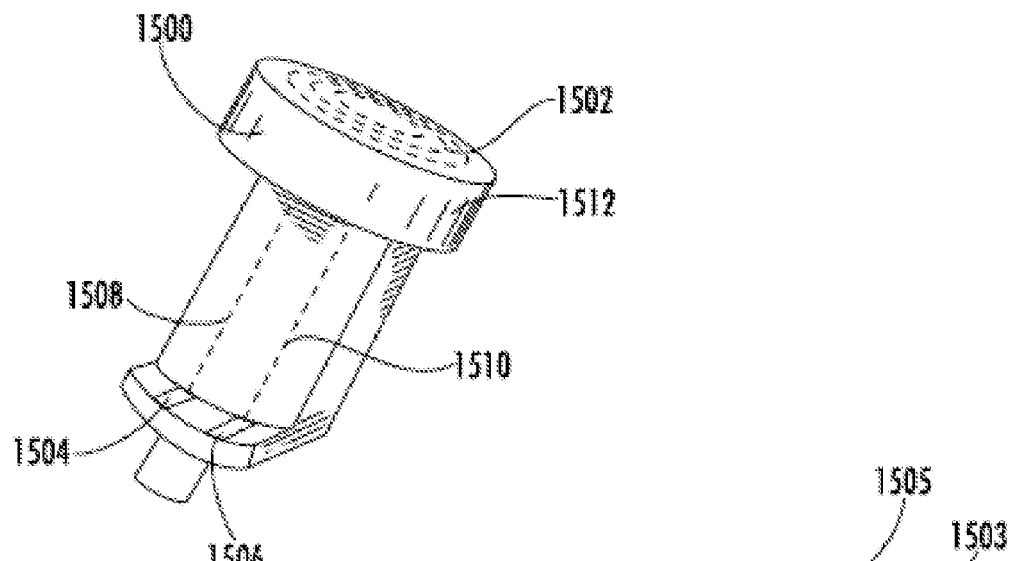
FIGS. 28A-B illustrate a cartridge and monitoring device, respectively, according to aspects of this disclosure.
Figure 28B:
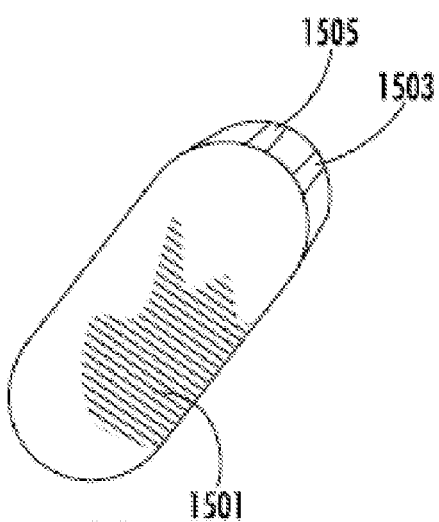

FIGS. 28A and B illustrate a cartridge 1500 and a monitoring device 1501. Cartridge 1500 and monitoring device 1501 may have similar or identical elements to the cartridge 200 and monitoring device 201 (and other cartridges and monitoring devices) described above in addition to the features described herein. Cartridge 1500 may have an induction coil 1502 that when the induction coil 1502 is in proximity to another induction coil carrying a first electrical current, a second electrical current may be induced into the induction coil 1502 to charge a second power source within the monitoring device 1501. The induction coils may be oriented generally parallel (or within +/−10 degrees) to each other when the electromagnetic field is transmitted between them. Alternatively, in some embodiments, the induction coils may not be generally parallel to each other.

The induction coil 1502 may be imbedded within an upper portion of the housing 1512. The induction coil 1502 may be electrically connected to a pair of electrical contacts 1504, 1506 on the cartridge 1500. These electrical contacts 1504, 1506 may transmit an electrical current to a pair of electrical contacts 1503, 1505 of the monitoring device 1501. The electrical contacts 1503, 1503 may transmit an electrical current to the monitoring device 1501 to charge the power source 206, or battery, of the monitoring device 1501.

In some embodiments, the upper portion of the housing 1512 may have a cylindrical shape where the diameter may have a diameter equal to the exterior diameter of the grip 105 of the golf club 100. The cartridge 1500 may further have a plurality of electrical contacts 1504, 1506 on an exterior surface positioned to mate with a plurality of electrical contacts 1503 and 1505 on the exterior surface of the monitoring device 1501.

In addition to the induction coil 1502 of the cartridge 1500, the cartridge 1500 may also include an electrical circuit for converting the electrical current generated in the induction coil 1502 into a usable voltage for charging the power source 206 of the monitoring device 1501. The cartridge 1500 or the monitoring device 1501 may also have a control circuit for monitoring and controlling the recharging process.

The induction coil 1502 may be a flat, single layer spiral coil or may be a different geometric shape. The induction coil 1502 may have an inner diameter within a range of 0.1 to 0.3 inches and may have an outer diameter within a range of 0.3 to 0.58 inches. The induction coil 1502 may include any diameter wire suitable to form a coil within the inner and outer diameters.

Figure 28C:
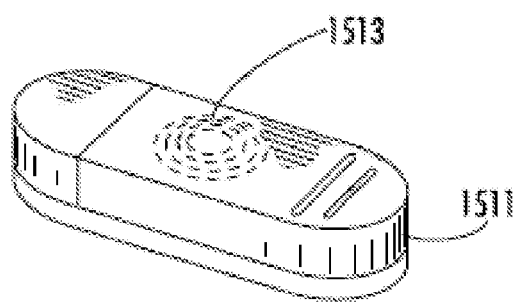
FIG. 28C illustrates a monitoring device according to aspects of this disclosure.

FIG. 28C shows another alternate embodiment of the monitoring device 201. Monitoring device 1511 may be similar to monitoring device 201 (and other monitoring devices described herein) except the monitoring device 1511 may further comprise an induction coil 1513. The induction coil 1513 may be positioned below an exterior surface of the monitoring device 1511. The induction coil 1513 in FIG. 28C may be located below any exterior surface of the monitoring device 1511 or even below a plurality of exterior surfaces. The monitoring device 1511 may also include an electrical circuit for converting current generated from the induction coil 1502 into a usable voltage for charging the power source 206 and also a circuit for monitoring and controlling the recharging process.

Similar to induction coil 1502, induction coil 1513 may be a flat, single layer spiral coil. The induction coil 1513 may have an inner diameter within a range of 0.1 to 0.3 inches and may have an outer diameter within a range of 0.3 to 0.58 inches. The induction coil 1513 may any diameter wire suitable to form a coil within the inner and outer diameters. Additionally, induction coil 1513 may be located beneath any surface of the monitoring device 1511. In other embodiments, the induction coil 1502 may not be a spiral coil and may have any shape capable of inducing an electrical current in a device, such as a cylindrical winding.

Figure 29:
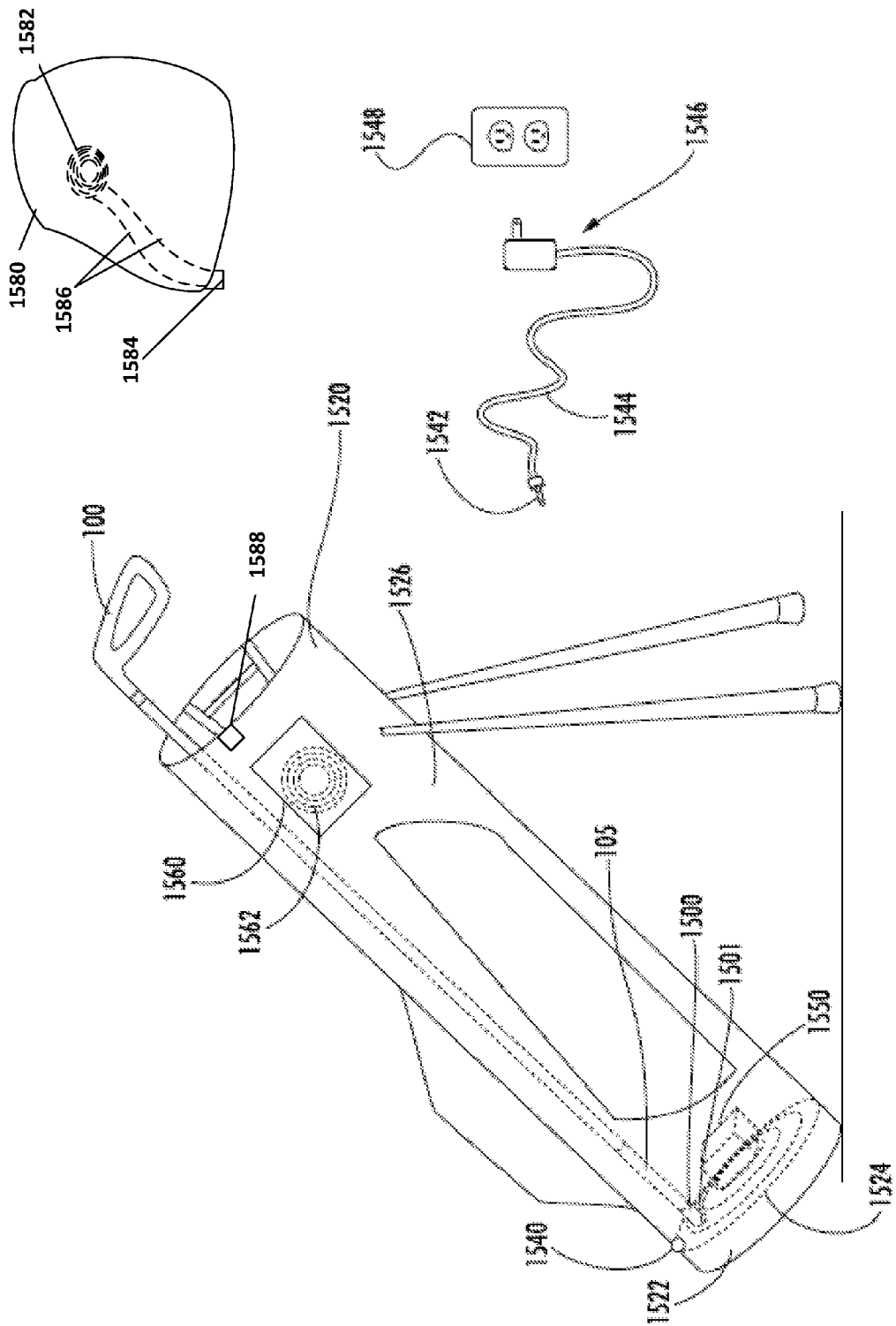
FIG. 29 illustrates a golf bag according to aspects of this disclosure.

FIG. 29 illustrates another embodiment of this disclosure of a golf bag 1520 having a golf bag base 1522 and a container 1526 for holding at least one golf club. The golf bag base 1522 may contain at least one induction coil 1524. When the grip end of the golf club 100 is inserted into the golf bag 1520 and an electrical current is present in the induction coil 1524 of the golf bag 1520, the electromagnetic field from the electrical current in induction coil 1524 may induce an electrical current into the induction coil 1502 of the of the cartridge 1500 to charge the power source 206 or battery within the monitoring device 1501. Alternatively, the electromagnetic field from the electrical current in induction coil 1524 may induce an electrical current into the induction coil 1513 of the monitoring device 1511 to charge the power source 206 or battery within the monitoring device 1511.

A power source or battery 1550 may be contained within the golf bag 1520 and may be electrically connected to the induction coil 1524. The battery 1550 may supply the necessary electrical current to the induction coil 1524 to inductively charge the power source 206 of the monitoring device 1501. The golf bag 1520 may also have a socket 1540 on the exterior of the golf bag 1520 near the golf bag base 1522 that is electrically connected to the induction coil. The socket 1540 may comprise an electrical connector that may connect directly with a mating electrical connector 1542 connected to a cable 1544 that comprises a plug 1546 that can plug into a wall outlet 1548 to provide an electrical current to the golf bag 1520. The cable 1544 may be plugged into the wall outlet 1544 and the socket 1540 to supply the necessary electrical current to the induction coil 1524 to inductively charge the power source 206 of the monitoring device 1501.

In some embodiments, the golf bag 1520 may also comprise a pocket 1560 on a side of the bag 1520 which may be adjacent to the container 1526. The pocket 1560 may contain an induction coil 1562 that may also be connected to the battery 1550 and may also be connected to the socket 1540, which may be electrically connected to the wall outlet 1548. The induction coil 1562 may be used to inductively charge the power source 206 of the monitoring device 1511 if equipped with an induction coil 1513 or the power source 206 of the monitoring device 1501 through the cartridge 1500, when the monitoring device 1501 and cartridge 1500 are removed from the golf club 100. Additionally, the induction coil 1562 may be used to inductively charge a remote computer 400 (e.g., a mobile telephone, such as a smart phone as described above). The pocket 1560 may be sized to hold the monitoring device or remote computer 400 in the correct orientation and proximity to the induction coil 1562. For example, the pocket 1560 may have a height defined in a vertical direction of within a range of 4 to 6 inches, or 3 to 7 inches, a width in a horizontal within a range of 2 inches to 4 inches or 1.5 inches to 5 inches, and a maximum depth or opening at the top of pocket 1560 within a range of 0.5 inches to 3 inches, or less than 2 inches. The pocket 1560 may have a plurality of walls. In some embodiments, at least one of the plurality of walls may contain the induction coil 1562. In such embodiments, the wall including the induction coil 1562 may be more rigid than the other walls. The wall including the induction coil 1562 may have a portion made of a polymer material and the induction coil 1562 may be beneath the surface of the polymer material to keep it protected and not exposed to the interior of the pocket 1560 and/or the interior of the container.

The induction coil 1524 may be oriented generally parallel to a bottom surface of the golf bag base 1522. Alternatively, the induction coil 1524 may be oriented in a generally perpendicular direction to the bottom surface of the golf bag base 1522. The induction coil 1524 may be a flat, single layer spiral coil or may have any geometric shape. The induction coil 1524 may have an outer diameter within a range of 8 inches to 11 inches or within a range of 5 inches to 12 inches. The induction coil 1524 may have an inner diameter within a range of 2 inches 5 inches. The induction coil 1524 may be any diameter wire suitable to form a coil within the inner and outer diameters.

Alternatively, where the golf bag 1520 has individual substantially cylindrical openings to keep the golf clubs organized, the golf bag base 1522 may comprise a plurality of smaller induction coils equal to the number of substantially cylindrical openings. Each of the plurality of induction coils may be located at the bottom of each of the cylindrical openings. In still other embodiments, the golf bag 1520 may contain a designated opening for a club to be charged. The designated opening may be one of the individual substantially cylindrical opening discussed above, or may be an opening separate from the container of the golf bag 1520. For example, in some embodiments the golf bag may have a first container and a second container wherein the second container may be used to inductively charge a device on a golf club as discussed above.

Figure 30:
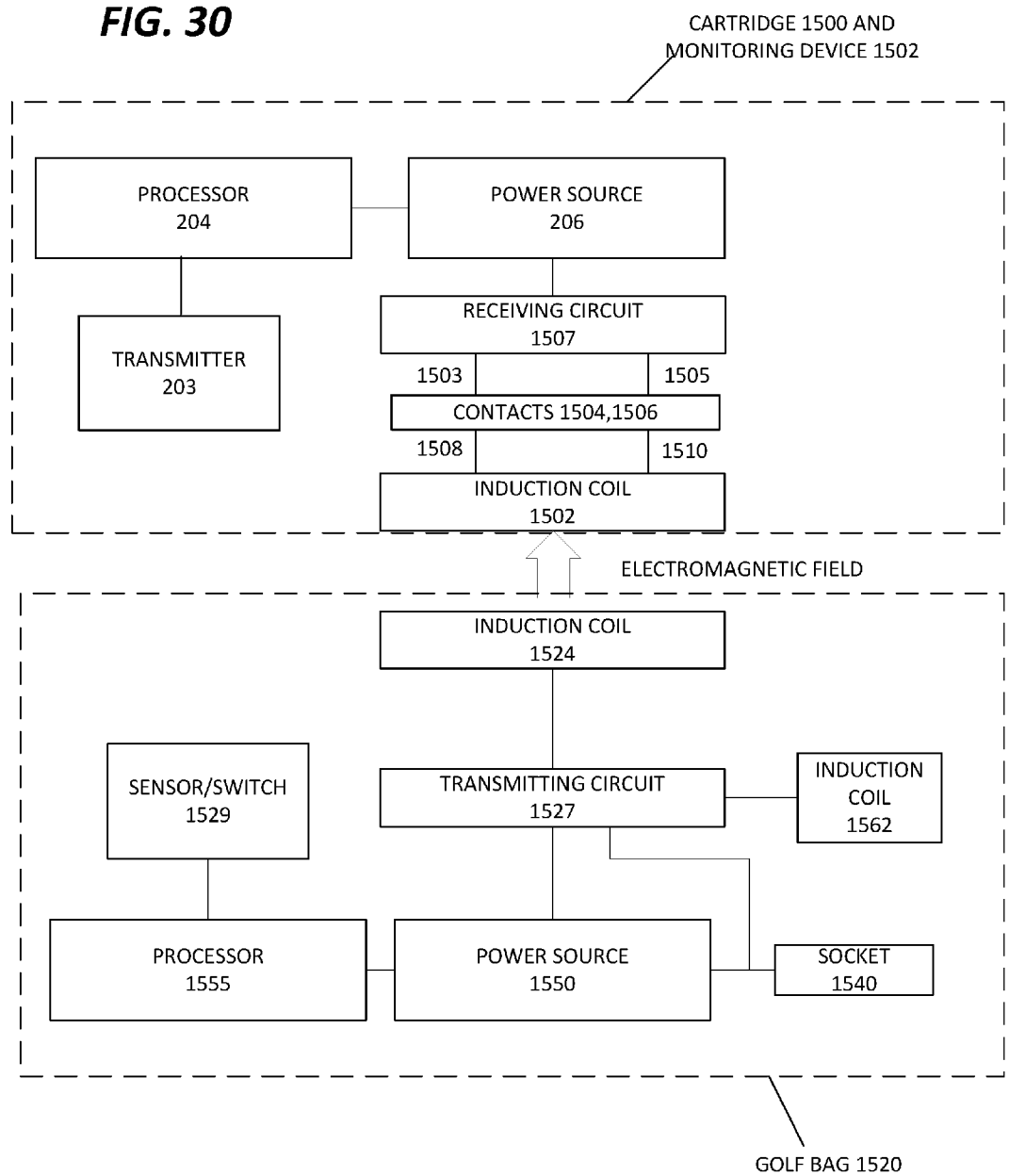
FIG. 30 illustrates a block diagram of a golf bag and cartridge and monitoring device according to aspects of this disclosure.
Figure 31:
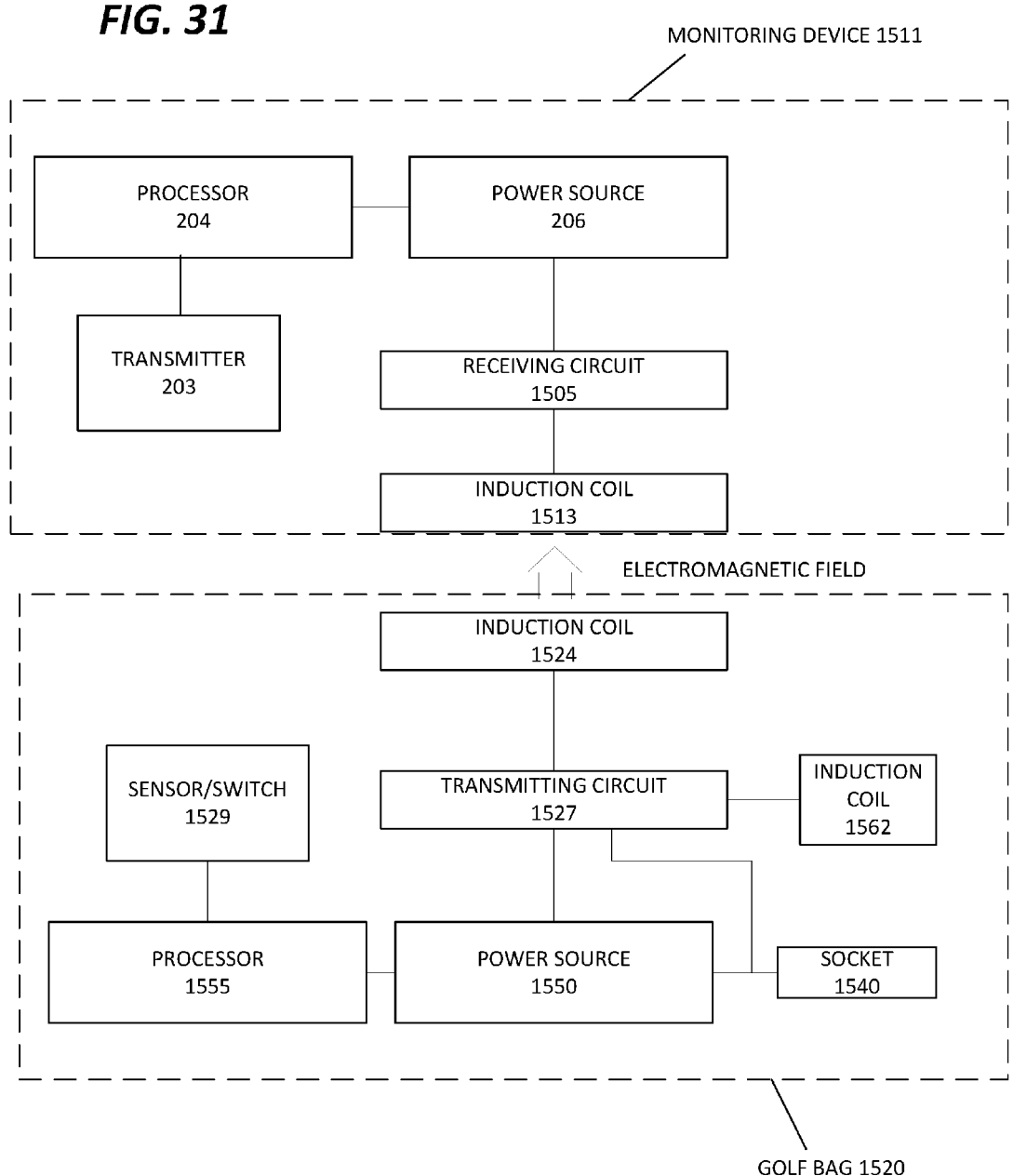
FIG. 31 illustrates a block diagram of a golf bag and monitoring device according to aspects of this disclosure.

FIG. 30 illustrates a block diagram showing the interaction between the cartridge 1500 and monitoring device 1501 and the golf bag 1520. The induction coil 1502 may be electrically connected through a pair of wires 1508, 1510 to a pair of contacts 1504, 1506 which further connect to a pair of contacts 1503, 1505. FIG. 31 illustrates a block diagram of a similar embodiment as FIG. 30, with the difference being that the cartridge 1500 and monitoring device 1501 are replaced by monitoring device 1511. The monitoring device 1501 or the cartridge 1500 may have a receiving circuit 1507. The receiving circuit 1507 may convert the incoming electrical current to a suitable current and voltage to charge the power source 206. Further, the processor 204 of the monitoring device 1501 may assist in controlling the charging process. For example, as discussed above the monitoring device 1501 may enter a "sleep mode" to conserve battery power if the monitoring device 201 is not used for a predetermined amount of time, an induced electrical current may act as a trigger to cause the monitoring device 201 to exit the "sleep mode" and enter a "charging mode." During the charging mode, the processor 204 may check the capacity of the power source 206 to determine if the power source 206 is fully charged. Once the processor 204 determines the power source 206 is fully charged, the processor may instruct the transmitter 203 to communicate to a sensor 1529 on the golf bag 1520 that the power source 206 is fully charged and exit the "charging mode" and enter the "sleep mode." This instruction may cause a processor 1555 on the golf bag 1520 to "turn off" the electrical current within the induction coil 1524.

Additionally, the golf bag 1520 may further include a transmitting circuit 1527 to ensure the proper amperage and voltage is present in induction coil 1524 and induction coil 1562. As discussed above, a processor 1555 on the golf bag 1520 may control the flow of the electrical current through the induction coil 1524 and the induction coil 1562. The processor 1555 may communicate with a sensor 1529 that may detect an event that would cause the processor 1555 to either turn on or turn off the electrical current in the induction coils 1524, 1562. For example, the sensor 1529 may sense when a golf club 100 equipped with a monitoring device 1501 has been inserted into the container 1526 of the golf bag 1520. Once the sensor 1529 detects that a golf club 100 equipped with a monitoring device 1501 has been inserted into the container 1526, the sensor 1529 may communicate with the processor 1555, which may initiate a current into the induction coils 1524, 1562, which may begin the charging process. For example in some embodiments the sensor 1529 may be a mechanical switch that is engaged with grip end 105 of the golf club 100 when the golf club 100 is inserted into the golf bag 1520. Alternatively, the sensor 1529 may be pressure activated, optically activated, mechanically activated or RFID activated. The sensor/switch 1529 may be located on an upper surface of the golf bag base 1522 or in any suitable location. As another alternate option, the sensor 1529 may receive a signal from the monitoring device 1501 to instruct the processor 1555 to initiate the charging mode. As another alternative, the charging mode may be initiated manually by the user via a switch located on the golf bag 1520. Further, when the golf bag 1520 is connected to the external power source like the wall outlet 1548, the golf bag 1520 may automatically enter a charging mode such that an electrical current is present in the induction coil 1524 and/or induction coil 1562.

Additionally, the golf bag 1520 may have a cover 1580 that may also comprise an induction coil 1582 within the cover 1580. The induction coil 1582 may be electrically connected to the battery 1550 through a socket or plug 1584 on the cover 1580 that connects to a corresponding socket or plug 1588 located at an end of the golf bag opposite the golf bag base 1522. A set of wires 1586 may connect the socket or plug 1584 to the induction coil 1582. The cover 1580 may be attached to the golf bag 1520 to enclose a golf club 100 or plurality of golf clubs contained in the golf bag 1520. When the socket or plug 1584 is connected to the socket or plug 1588, an electrical current may be present in the induction coil 1582 that may induce an electrical current in the induction coil 1502 of the cartridge 1500 to charge the power source 206 or battery within the monitoring device 1501 while the cartridge 1500 and monitoring device 1502 are installed into the golf club head of the golf club 100. Alternatively, when the socket or plug 1584 is connected to the socket or plug 1588, an electrical current may be present in the induction coil 1582 that may induce an electrical current in the induction coil 1513 to charge the power source 206 or battery within the monitoring device 1511 while the monitoring device 1511 is installed into the golf club head of the golf club 100.

Figure 32:
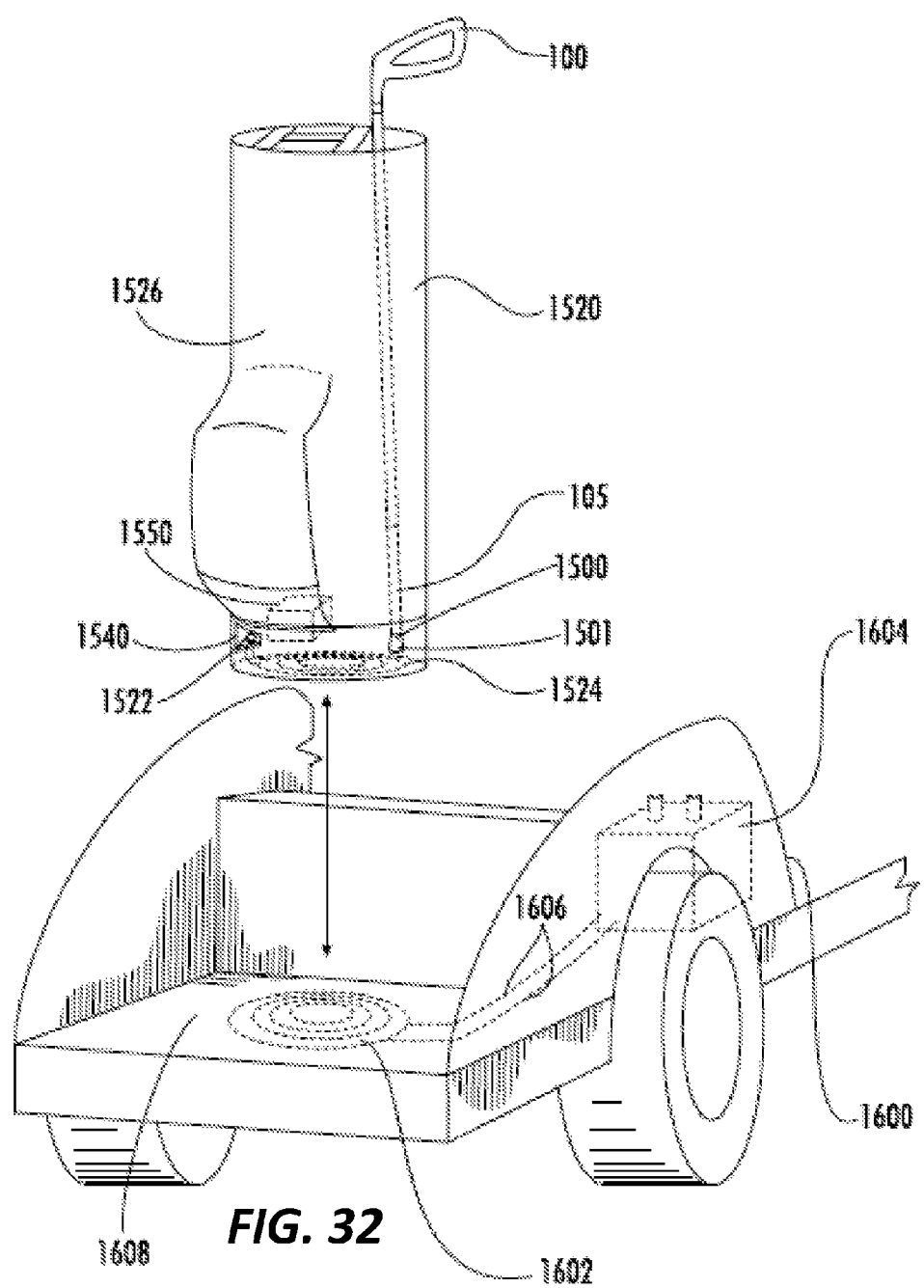
FIG. 32 illustrates an apparatus for transporting a golf bag according to aspects of this disclosure.
Figure 33:
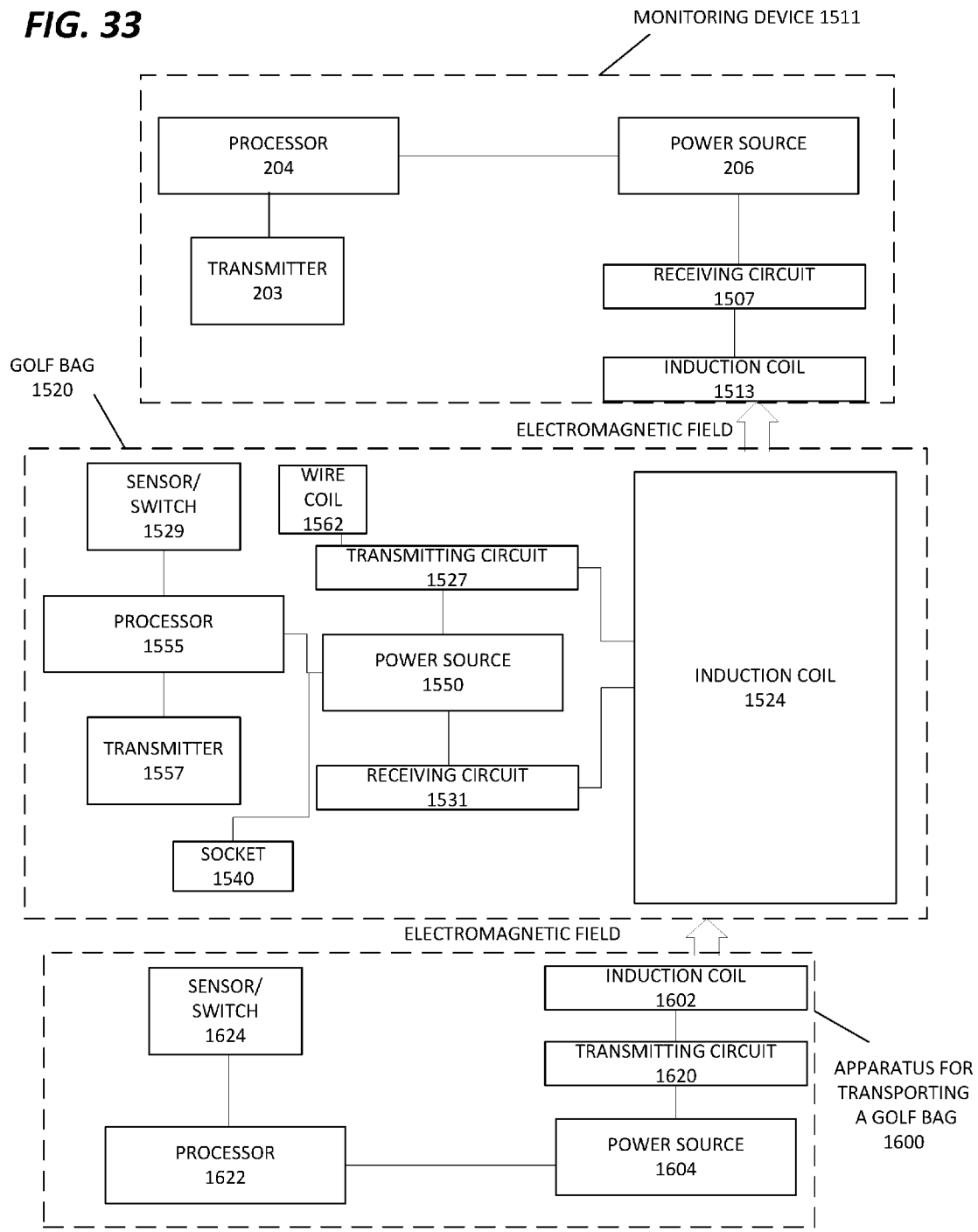
FIG. 33 illustrates a block diagram of an apparatus for transporting a golf bag, a golf bag and a monitoring device according to aspects of this disclosure.

FIGS. 32 and 33 illustrate still another embodiment of this disclosure. The golf bag 1520 may have a power source or battery 1550 positioned within the golf bag 1520 that may be inductively charged from an induction coil 1602 of an apparatus for transporting a golf bag 1600. Thus, the golf bag 1520 may both receive and transmit an inductive charge. As discussed above, the golf bag base 1522 may comprise an induction coil 1524. The golf bag 1520 may further comprise a processor 1555 to control the charging process, such that when the battery 1550 is being charged from an electrical current induced into the induction coil 1524 from an electrical current flowing in induction coil 1602 and reaches a predetermined condition, the processor 1555 may change the induction coil 1524 from a receive mode to a transmit mode to allow the induction coil 1524 to charge the battery of a receiving device. The predetermined condition may be a battery charge capacity greater than 60 percent or greater than 70 percent, or a fully charged state. In addition, the predetermined condition may further comprise the detection of a golf club 100 containing a monitoring device 1501 being placed into the golf bag 1520 or a remote computer 400 or monitoring device 1501 being placed within pocket 1560.

The golf bag 1520 may further comprise a receiving circuit 1531 to convert the induced electrical current to a suitable current and voltage to charge the power source 1550. Additionally, when the golf bag 1520 transitions from receive mode to a transmit mode, the processor 1555 may instruct the apparatus for transporting a golf bag 1600 to "turn off" the electrical current in its induction coil 1602 as to not interfere with the charging process of the monitoring device. The processor 1555 may instruct the apparatus for transporting a golf bag wirelessly through the transmitter 1557 sent to a sensor/switch 1624 on the apparatus 1600.

The apparatus for transporting a golf bag 1600 may comprise a platform 1608 for supporting the golf bag 1520. The platform 1608 may comprise an induction coil 1602 to transmit an electrical current to induce an electrical current in the induction coil 1524 of the golf bag 1520. The induction coil 1602 may be electrically connected to a battery 1604 on the apparatus for transporting a golf bag 1600 using the wires 1606 or other connection method. The platform 1608 may support the golf bag 1520 in a vertical orientation where the bottom surface of the golf bag base 1522 may contact the upper surface of the platform 1608. Alternatively, the platform 1608 may support the golf bag 1520 in any position a horizontal or angled orientation. In addition, the platform 1608 may comprise a plug 1610 to engage the socket 1540 on the golf bag 1520 to provide electrical power without using the induction coil 1602.

Similar to the golf bag 1520, the apparatus for transporting a golf bag 1600 may further include a transmitting circuit 1620 to ensure the proper amperage and voltage is present in induction coil 1602. A processor 1622 may control the flow of the electrical current through the induction coil 1602. The processor 1622 may communicate with a sensor or switch 1624 that may detect an event that would cause the processor 1622 to either turn on or turn off the electrical current in the induction coil 1602. For example, the sensor 1622 may sense when a golf bag 1520 that is equipped with a battery 1550 that can be inductively charged. Once the sensor 1620 detects that a golf bag 1520 is adjacent or on the platform, the sensor 1620 may communicate with the processor 1622, which may initiate an electrical current into the induction coil 1602 to begin the charging process. For example in some embodiments the sensor 1620 may be a mechanical switch that is engaged when the golf bag 1520 is placed adjacent or on the platform 1608. Alternatively, the sensor 1620 may be pressure activated, optically activated, mechanically activated, or RFID activated. The sensor/switch 1620 may be located on an upper surface of the platform 1608 or in any suitable location. As another alternate option, the sensor 1529 may receive a signal from the golf bag 1520 to instruct the processor 1622 to initiate the charging mode. As another alternative, the charging mode may be initiated manually by the user via a switch located on the apparatus for transporting a golf bag 1600. Further, when the socket 1540 of the golf bag 1520 is connected to the plug 1610 of the apparatus 1600, the golf bag 1520 may automatically enter a charging mode such that an electrical current is present in the induction coil 1524 and/or induction coil 1562.

The apparatus for transporting a golf bag 1600 may be any device used to transport a golf bag 1520 during a round of golf. The apparatus 1600 may or may not also be able to carry a golfer as well during the round of golf. For example, the apparatus 1600 may be a golf cart as shown in FIG. 30, or may be a push/pull cart that may or not be motorized, or may be an apparatus where the golfer may stand while riding such as a GolfBoard™. Alternatively, the apparatus for transporting a golf bag 1600 may even be any device used to transport a golf bag to a golf course.

The platform 1608 may have a portion made of a polymer and may contain the induction coil 1602 such that the induction coil 1602 is not exposed and located underneath the upper surface of the platform 1608.

Figure 34:
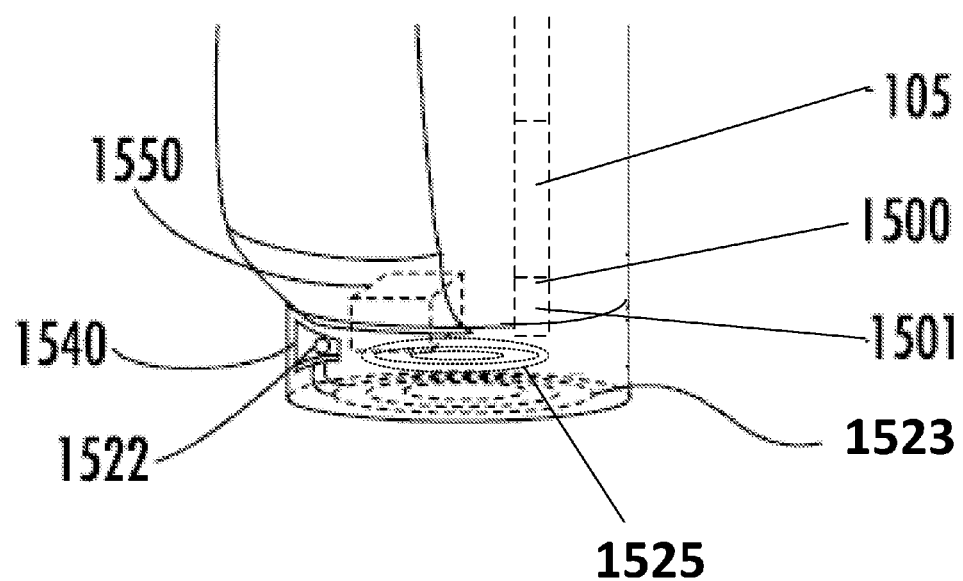
FIG. 34 illustrates an alternate embodiment of a golf bag according to aspects of this disclosure.
Figure 35:
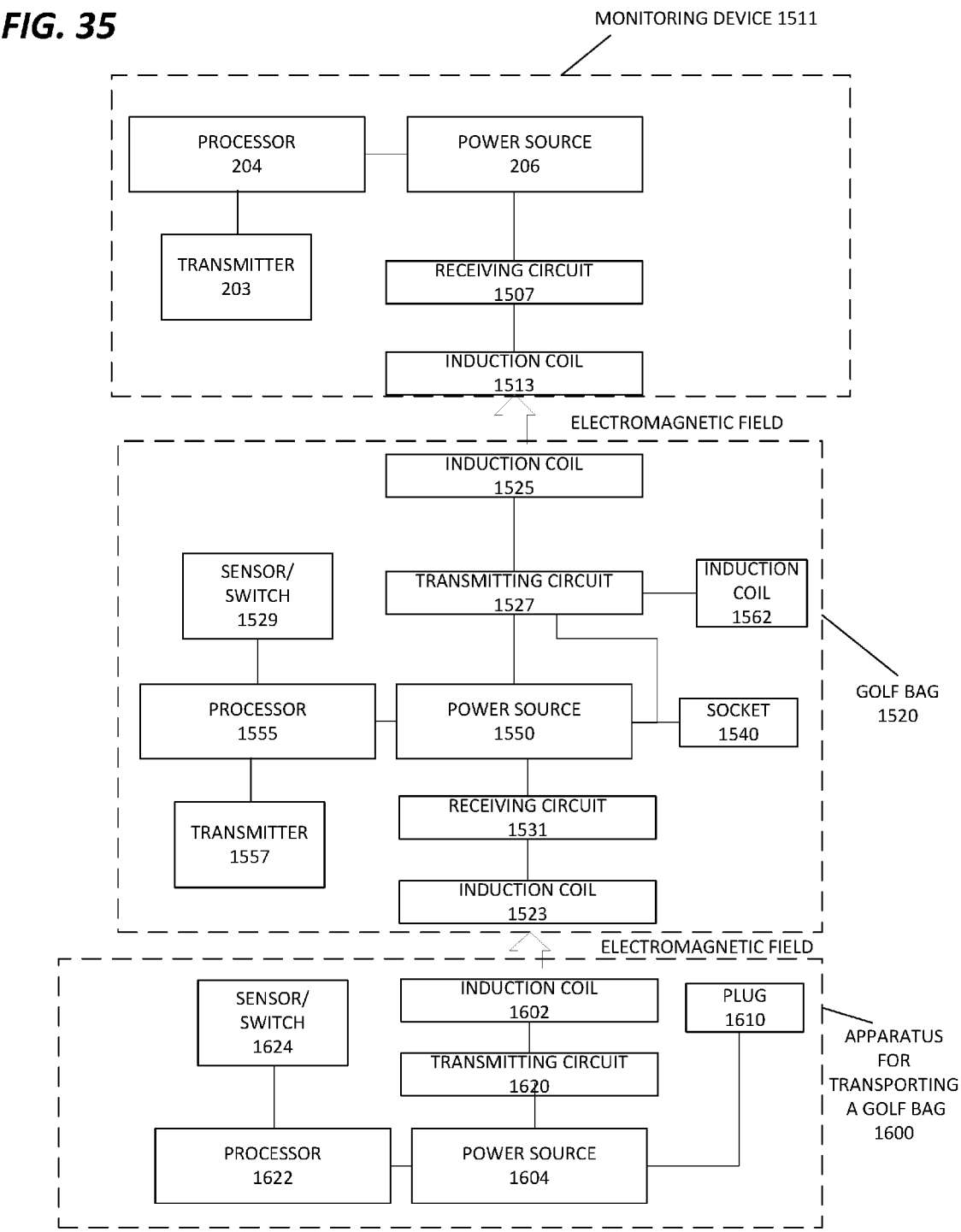
FIG. 35 illustrates a block diagram of an apparatus for transporting a golf bag, a golf bag and a monitoring device according to aspects of this disclosure.

FIGS. 34 and 35 illustrate an alternate embodiment similar to that described above except the golf bag base 1522 may comprise a plurality of induction coils within the golf bag base such that a first induction coil 1523 that may be set up as a receiving induction coil and a second induction coil 1525 that may be set up as a transmitting induction coil. The first or receiver induction coil 1523 may be positioned near the bottom surface of the golf bag base 1522, while the second or transmitting induction coil 1525 may be positioned near the upper surface of the golf bag base 1522. Thus, a first electrical current in the induction coil 1602 may induce a second electrical current into the receiving induction coil 1523 to charge the battery 1550 in the golf bag. Also, a third electrical current when present in the transmitting induction coil 1525 may induce a fourth electrical current into the induction coil 1502 of the cartridge or induction coil 1513 of the monitoring device 1511 to charge the battery 206 of the monitoring device.

Figure 36:
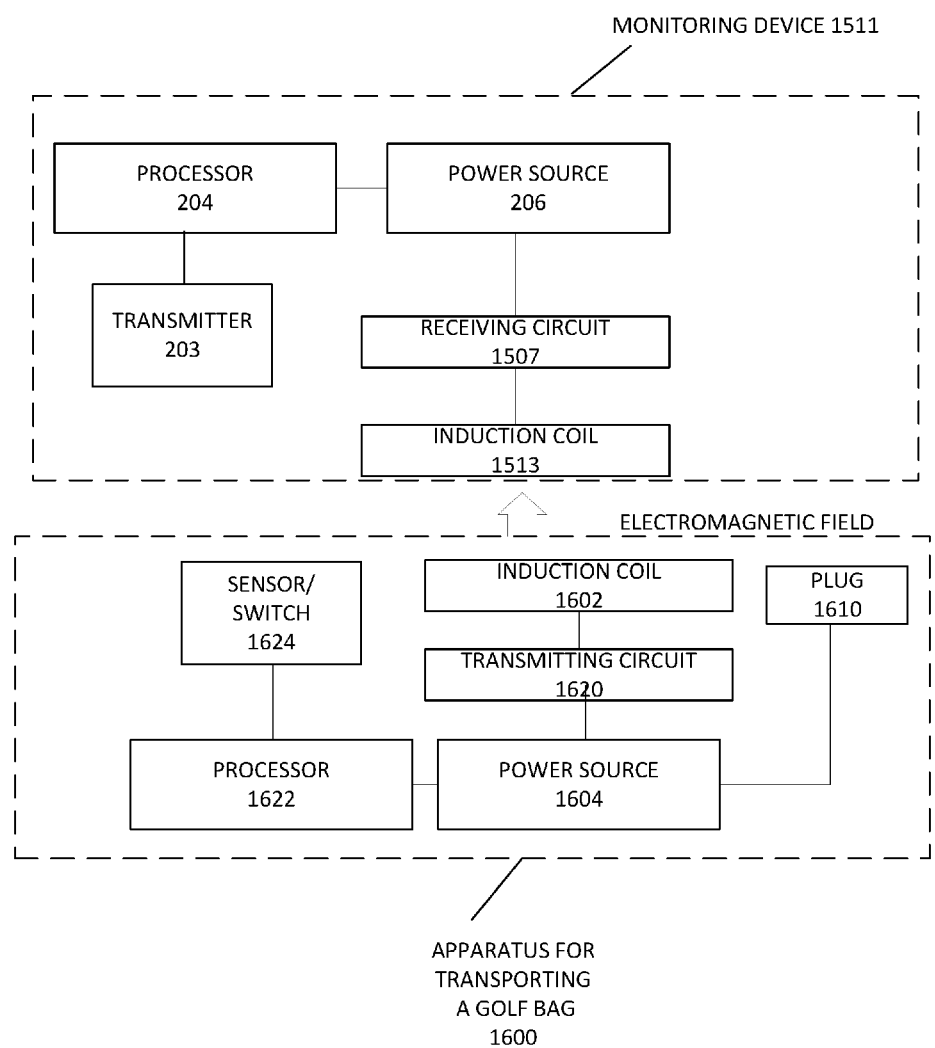
FIG. 36 illustrates a block diagram of an apparatus for transporting a golf bag, and a monitoring device according to aspects of this disclosure.

As still another embodiment illustrated in FIG. 36, the golf bag 1520 may not be involved in the charging process as an electrical current flowing in the induction coil 1602 of the apparatus to transport a golf bag may induce an electrical current within the induction coil 1502 of the cartridge 1500 or the induction coil 1513 of the monitoring device 1511 to charge the battery 206 of the monitoring device.

III. CONCLUSION

The present disclosure is described above and in the accompanying drawings with reference to a variety of example structures, features, elements, and combinations of structures, features, and elements. The purpose served by the disclosure, however, is to provide examples of the various features and concepts related to the disclosure, not to limit the scope of the disclosure. One skilled in the relevant art will recognize that numerous variations and modifications may be made to the embodiments described above without departing from the scope of the present disclosure, as defined by the appended claims. For example, the various features and concepts described above in conjunction with FIGS. 1 through 36 may be used individually and/or in any combination or subcombination without departing from this disclosure.

What is claimed is:

1. An assembly comprising:
   a golf bag comprising:
      a golf bag base having a first induction coil connected to a first power source;
      a container attached to the golf bag base wherein the container is configured to retain a golf club;
   a cartridge having a second induction coil, the cartridge engaged with a grip end of the golf club; and
   a monitoring device having a second power source, the monitoring device engaged with the cartridge;
   wherein when the grip end of the golf club is inserted into the container, a first electrical current flows in the first induction coil to induce a second electrical current into the second induction coil of the cartridge to charge the second power source.

2. The assembly of claim 1, wherein the first power source is a battery contained within the golf bag.

3. The assembly of claim 1, wherein the first power source comprises a plug connected to the golf bag that is connected to an external power source.

4. The assembly of claim 3, wherein the external power source is contained on an apparatus for transporting the golf bag, the apparatus for transporting a golf bag having a platform for supporting the golf bag.

5. The assembly of claim 1, wherein the cartridge comprises a first pair of electrical contacts that are in contact with a second pair of electrical contacts on an exterior of the monitoring device when the monitoring device is secured within the cartridge.

6. The assembly of claim 1, wherein the cartridge has an upper portion having a substantially cylindrical shape, and wherein the upper portion contains the second induction coil.

7. The assembly of claim 1, wherein when the second electrical current is induced into the second induction coil of the cartridge, the first induction coil is substantially parallel to the second induction coil.

8. The assembly of claim 1, wherein the golf bag further comprises a sensor configured to detect when the golf club is inserted into the golf bag and wherein the first electrical current in the first induction coil is configured to activate once the sensor detects the golf club has been inserted into the golf bag.

9. An assembly comprising:
   a golf club having golf club head end and a grip end;
   a golf bag comprising:
      a golf bag base having a first induction coil connected to a first power source;
      a container attached to the golf bag base, the container configured to engage the golf club; and
   a monitoring device engaged with the grip end of the golf club, the monitoring device having a second induction coil and a second power source;
   wherein when the grip end of the golf club is inserted into the container, a first electrical current may flow in the first induction coil and induce a second electrical current into the second induction coil to charge a second power source within the monitoring device.

10. The assembly of claim 9, wherein the first power source is a battery contained within the golf bag.

11. The assembly of claim 9, wherein the first power source is an external power source that is connected to the first induction coil through a cable connected to the golf bag at a first end and connected to an external power source at a second end.

12. The assembly of claim 11, wherein the external power source is contained on an apparatus for transporting the golf bag, the apparatus for transporting the golf bag having a platform for supporting the golf bag and a plug configured to engage a socket on the golf bag.

13. The assembly of claim 9, wherein when the second electrical current is induced into the second induction coil of the monitoring device, the first induction coil is substantially parallel to the second induction coil.

14. The assembly of claim 9, wherein the golf bag further comprises a sensor configured to detect when the golf club is inserted into the golf bag, and wherein the first electrical current in the first induction coil is configured to activate once the sensor detects the golf club has been inserted into the golf bag.

15. An assembly comprising:
an apparatus for transporting a golf bag comprising a platform to support the golf bag, and a first induction coil connected to a first power source;
wherein the golf bag comprises a golf bag base containing a second induction coil; and
wherein when the golf bag base is positioned adjacent the platform, a first electrical current in the first induction coil induces a second electrical current in the second induction coil of the golf bag base to charge a second power source within the golf bag.

16. The assembly of claim 15, wherein the second induction coil is positioned near a bottom surface of the golf bag base, and the golf bag base further comprises a third induction coil positioned near an upper surface of the golf bag base; and the assembly further comprises:
a monitoring device including a fourth induction coil, wherein the monitoring device engages a grip end of a golf club; and
wherein when the grip end of the golf club is inserted into the container of the golf bag, a third electrical current in the third induction coil induces a fourth electrical current into the fourth induction coil of the monitoring device to charge a third power source within the monitoring device.

17. The assembly of claim 15, wherein the second induction coil is positioned near a bottom surface of the golf bag base, and the golf bag base further comprises a third induction coil positioned near an upper surface of the golf bag base; and
the assembly further comprises:
a cartridge having a fourth induction coil;
a monitoring device carried by the cartridge, wherein the cartridge engages a grip end of a golf club; and
wherein when the grip end of the golf club is inserted into the container of the golf bag, a third electrical current in the third induction coil induces a fourth electrical current into the fourth induction coil of the cartridge to charge a third power source within the monitoring device.

18. The assembly of claim 17, wherein the golf bag further comprises a sensor configured to detect when the golf club is inserted into the golf bag, and wherein the third electrical current in the third induction coil is configured to activate once the sensor detects the golf club has been inserted into the golf bag.

* * * * *